(12) United States Patent
Kawahara et al.

(10) Patent No.: US 8,163,804 B2
(45) Date of Patent: *Apr. 24, 2012

(54) COMPOSITION FOR PREVENTING HARMFUL ORGANISMS

(75) Inventors: Nobuyuki Kawahara, Mobara (JP);
Michikazu Nomura, Mobara (JP);
Hidenori Daido, Mobara (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 1085 days.

This patent is subject to a terminal disclaimer.

(21) Appl. No.: 11/989,489

(22) PCT Filed: Jul. 27, 2005

(86) PCT No.: PCT/JP2005/013728
§ 371 (c)(1),
(2), (4) Date: Jan. 25, 2008

(87) PCT Pub. No.: WO2007/013150
PCT Pub. Date: Feb. 1, 2007

(65) Prior Publication Data
US 2009/0162453 A1 Jun. 25, 2009

(51) Int. Cl.
*A01N 37/18* (2006.01)
(52) U.S. Cl. ...................................... 514/615; 424/405
(58) Field of Classification Search .................. None
See application file for complete search history.

(56) References Cited

U.S. PATENT DOCUMENTS
6,548,514 B1  4/2003  Brown
2002/0032238 A1  3/2002  Priepke et al.

FOREIGN PATENT DOCUMENTS
JP   2004-051614 A    2/2004
WO   WO 00/07980 A1   2/2000
WO   WO 00/55120 A1   9/2000
WO   WO01/05769   *   1/2001

OTHER PUBLICATIONS

Patani et al In 96 chem. rev. 3147 (1996) Bioisosterism: A Rational Approachin Drug Design.*
The Pesticide Manual, Thirteenth Edition, 2003, British Crop Protection Council, UK (summary attached).

* cited by examiner

*Primary Examiner* — Neil Levy
(74) *Attorney, Agent, or Firm* — Buchanan Ingersoll & Rooney PC

(57) ABSTRACT

There is a harmful organism that cannot be controlled or is difficult to be controlled with the use of a single agent of a compound represented by the general formula (1) according to the invention, an insecticide, a miticide or a fungicide. Accordingly, an object of the invention is to provide a composition for preventing harmful organisms for efficiently controlling such a harmful organism.
That is, the invention is directed to a composition for preventing harmful organisms, characterized by comprising the compound represented by the general formula (1) and other insecticides, miticides or fungicides as active ingredients,

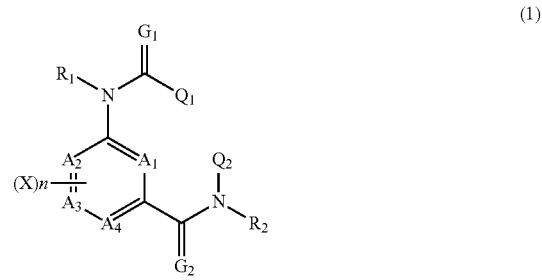

(1)

wherein, in the formula, $A_1$, $A_2$, $A_3$ and $A_4$ independently represent a carbon atom, a nitrogen atom or an oxidized nitrogen atom, $G_1$ and $G_2$ independently represent an oxygen atom or a sulfur atom; $R_1$ and $R_2$ independently represent a hydrogen atom or a $C_1$ to $C_4$ alkyl group; Xs may be the same or different and represent a hydrogen atom, a halogen atom or a trifluoromethyl group; $Q_1$ represents a substituent such as a phenyl group or a heterocyclic group; and $Q_2$ represents a substituent such as a phenyl group or a heterocyclic group.)

4 Claims, No Drawings

COMPOSITION FOR PREVENTING HARMFUL ORGANISMS

TECHNICAL FIELD

The present invention relates to a composition for preventing harmful organisms containing one or two or more compounds selected from compounds represented by the general formula (1), and one or two or more kinds selected from other insecticides, miticides or fungicides as active ingredients,

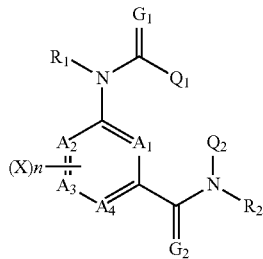

(1)

wherein, in the formula, $A_1$, $A_2$, $A_3$ and $A_4$ independently represent a carbon atom, a nitrogen atom or an oxidized nitrogen atom; $G_1$ and $G_2$ independently represent an oxygen atom or a sulfur atom; $R_1$ and $R_2$ independently represent a hydrogen atom or a C1 to C4 alkyl group; Xs may be the same or different and represent a hydrogen atom, a halogen atom or a trifluoromethyl group;

$Q_1$ represents a phenyl group, a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group, a heterocyclic group (The heterocyclic group herein represents a pyridyl group, a pyridine N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group or a tetrazolyl group.), or a substituted heterocyclic group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group (The heterocyclic group represents the same as those described above.); and $Q_2$ is represented by the general formula (2) or (3),

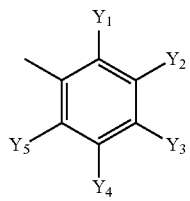

(2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_2$ and $Y_4$ represent a hydrogen atom, a halogen atom or a C1-C4 alkyl group, or

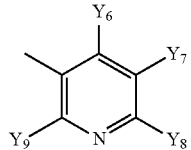

(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group.

BACKGROUND ART

In WO 2000/55120 and U.S. Pat. No. 6,548,514, a compound similar to the compound represented by the general formula (1) for medical use was described. But activity against insects was never described therein. Furthermore, it is obvious that such compounds are not included in the claims of the present invention.

In WO 2000/7980, a compound similar to the compound represented by the general formula (1) for medical use was described. But activity against insects was never described therein. Furthermore, it is obvious that such a compound is not included in the claims of the present invention.

In US Patent Laid-Open No. 2002-032238, a compound similar to the compound represented by the general formula (1) for medical use was described. But activity against insects was never described therein. Furthermore, it is obvious that such a compound is not included in the claims of the present invention.

Furthermore, insecticides, miticides and fungicides that are second active ingredients in the present invention are compounds known in the documents respectively disclosed in Pesticide Manual (The Pesticide Manual Thirteenth Edition) and the like.

However, there is a harmful organism that cannot be controlled or is difficult to be controlled with the use of a single agent of these active compounds.

Patent Document 1: WO 2000/55120
Patent Document 2: U.S. Pat. No. 6,548,514
Patent Document 3: WO 2000/7980
Patent Document 4: US Patent Laid-Open No. 2002-032238
Non-Patent Document 1: Pesticide Manual (The Pesticide Manual Thirteenth Edition, 2003)

DISCLOSURE OF THE INVENTION

There is a harmful organism that cannot be controlled or is difficult to be controlled with the use of a single agent of the compound represented by the general formula (1) according to the present invention, an insecticide, a miticide, or a fungicide. Accordingly, an object of the present invention is to provide a composition for preventing harmful organisms for effectively controlling such a harmful organism.

In order to solve the aforementioned object, the present inventors have repeatedly conducted an extensive study and as a result, have found that one or two more compounds selected from compounds represented by the general formula (1), and one or two or more compounds selected from insecticides, miticides or fungicides are used in combination thereof, whereby it is possible to effectively control a plurality of harmful organisms. Thus, the present invention has been completed.

That is, the present invention relates to the following.

[1] a composition for preventing harmful organisms containing one or two or more compounds selected from compounds represented by the general formula (1), and one or two or more kinds selected from other insecticides, miticides or fungicides as active ingredients,

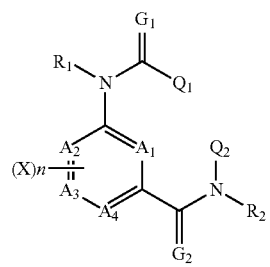

(1)

wherein, in the formula, $A_1$, $A_2$, $A_3$ and $A_4$ independently represent a carbon atom, a nitrogen atom or an oxidized nitrogen atom; $G_1$ and $G_2$ independently represent an oxygen atom or a sulfur atom; $R_1$ and $R_2$ independently represent a hydrogen atom or a C1-C4 alkyl group; Xs may be the same or different and represent a hydrogen atom, a halogen atom or a trifluoromethyl group; $Q_1$ represents a phenyl group, a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group, a heterocyclic group (The heterocyclic group herein represents a pyridyl group, a pyridine N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group or a tetrazolyl group.) or a substituted heterocyclic group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group (The heterocyclic group represents the same as those described above.); and $Q_2$ is represented by the general formula (2) or (3),

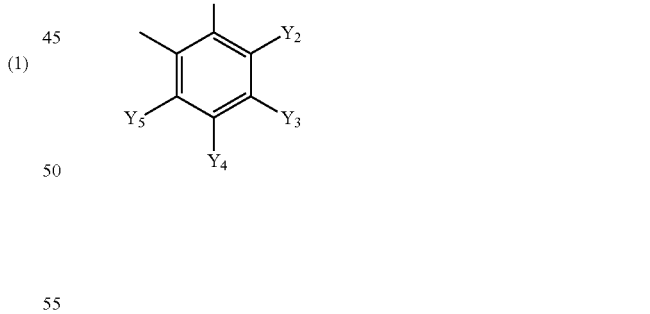

(2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_2$ and $Y_4$ represent a hydrogen atom, a halogen atom or a C1-C4 alkyl group; or

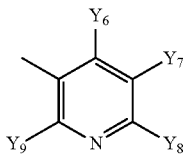

(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group;

[2] the composition for preventing harmful organisms as set forth [1] containing one or two or more compounds selected from compounds represented by the general formula (1a) in which all of $A_1$, $A_2$, $A_3$ and $A_4$ in the general formula (1) are carbon atoms, and one or two or more kinds selected from other insecticides, miticides or fungicides as active ingredients,

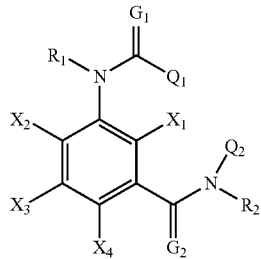

(1a)

wherein, in the formula, $R_1$, $R_2$, $G_1$, $G_2$ and $Q_1$ represent the same as those described in [1]; $Q_2$ is represented by the general formula (2) or (3), (2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C1-C6 perfluoroalkylthio group, a C1-C6 perfluoroalkylsulfinyl group or a C1-C6 perfluoroalkylsulfonyl group; and $Y_2$ and $Y_4$ represent a hydrogen atom, a halogen atom or a C1-C4 alkyl group, or

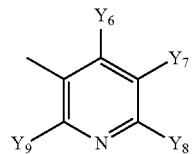

(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C1-C6 perfluoroalkylthio group, a C1-C6 perfluoroalkylsulfinyl group, a C1-C6 perfluoroalkylsulfonyl group; and $Y_7$ represents a hydrogen atom, a halogen atom or a C1-C4 alkyl group;

$X_1$ and $X_2$ are independently a hydrogen atom or a fluorine atom; and $X_3$ and $X_4$ are hydrogen atoms;

[3] the composition for preventing harmful organisms as set forth in [2] containing one or two or more compounds selected from compounds represented by the general formula (1a) in which all of $A_1$, $A_2$, $A_3$ and $A_4$ in the general formula (1) are carbon atoms, and one or two or more kinds selected from other insecticides, miticides or fungicides as active ingredients,

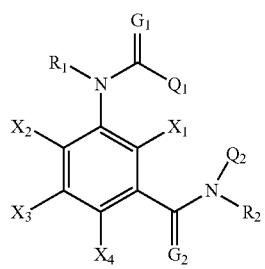

(1a)

wherein, in the formula, $G_1$, $G_2$ and $Q_1$ represent the same as those described in [1]; $Q_2$ is represented by the general formula (2) or (3),

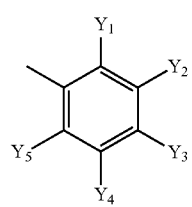

(2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group; and $Y_2$ and $Y_4$ represent a hydrogen atom, a halogen atom or a C1-C4 alkyl group, or

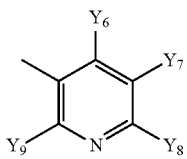
(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; Y represents a C2-C6 perfluoroalkyl group; and $Y_7$ represents a hydrogen atom, a halogen atom or a C1-C4 alkyl group;

$X_1$ and $X_2$ independently represent a hydrogen atom or a fluorine atom; $X_3$ and $X_4$ are hydrogen atoms; and when any one of $R_1$ and $R_2$ is a hydrogen atom, the other one is a C1-C4 alkyl group, or both of $R_1$ and $R_2$ are C1-C4 alkyl groups;

[4] the composition for preventing harmful organisms as set forth in any one of [1] to [3], wherein insecticides, miticides and fungicides are one or two or more compounds selected from azinphos-methyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafenthion, pirimiphos-methyl, fenitrothion, fenthion, phenthoate, flupyrazophos, prothiofos, propaphos, profenofos, oxime, phosalone, phosmet, formothion, phorate, malathion, carbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl, acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, diflubenzuron, teflubenzuron, triflumuron, novaluron, noviflumuron, bistrifluoron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate, endosulfan, chlorfenson, chlorobenzilate, dicofol, bromopropylate, acetoprole, fipronil, ethiprole, pyrethrin, rotenone, nicotine sulphate, BT agent, spinosad, abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, fluazinam, flufenzin, hex-ythiazox, propargite, benzomate, polynactins, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, a compound represented by the general formula (A),

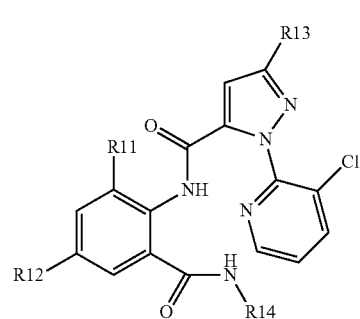
(A)

wherein, in the formula, R11 represents a methyl group or a chloro group; R12 represents a methyl group, a chloro group, a bromo group or a cyano group; R13 represents a chloro group, a bromo group, a trifluoromethyl group or a cyanomethoxy group; and R14 represents a methyl group or an isopropyl group (This compound is disclosed in WO 2003315519, while insecticidal activity and a production method thereof are described), a compound represented by the general formula (B),

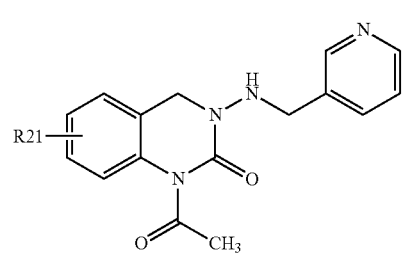
(B)

wherein, in the formula, R21 represents a 1,1,1,2,3,3,3-heptafluoro-2-propyl group or a 1,1,2,2,3,3,3-heptafluoro-1-propyl group (This compound is disclosed in Japanese Patent Laid-open No. 2001-342186, while insecticidal activity and a production method thereof are described), triadimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuarimol, bupirimate, mepanipyrim, cyprodinil, pyrimethanil, metalaxyl, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolarS-methyl, tiadinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, organonickel, guazatine, dodine, quintozene, tolylfluanid, anilazine, nitrothalisopropyl, fenitropan, dimethirimol, benthiazole, harpin protein, flumetover, mandipropamide and penthiopyrad;

[5] the composition for preventing harmful organisms as set forth in [4], wherein insecticides, miticides and fungicides are one or two or more compounds selected from fenitrothion, fenthion, isoxathion, acephate, buprofezin, pyriproxyfen, silafluofen, dinotefuran, imidacloprid, ethofenprox, thiamethoxam, clothianidin, acetamiprid, nitenpyram, thiacloprid, benfuracarb, methomyl, fenobucarb, spinosad, pymetrozine, flonicamid, fipronil, ethiprole, abamectin, a compound represented by the general formula (B),

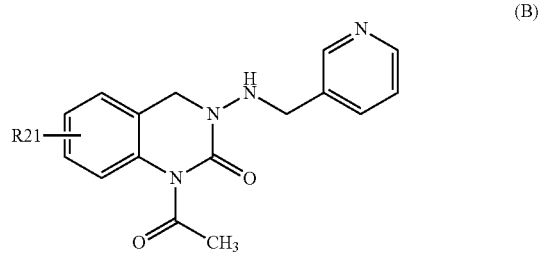

(B)

wherein, in the formula, R21 represents a 1,1,1,2,3,3,3-heptafluoro-2-propyl group or a 1,1,2,2,3,3,3-heptafluoro-1-propyl group (This compound is disclosed in Japanese Patent Laid-open No. 2001-342186, while insecticidal activity and a production method thereof are described), fenpyroximate, pyridaben, hexythiazox, fenbutatin oxide, tebufenpyrad, pyrimidifen, etoxazole, polynactins, milbemectin, acequinocyl, bifenazate, spirodiclofen, dienochlor, spiromesifen, tetradifon, chlorfenapyr, clofentezine, tolfenpyrad, fluacrypyrim, propargite, diafenthiuron, flufenoxuron, penthiopyrad, flusulfamide, iminoctadine acetate, iminocta- dine albesilate, acibenzolar-S-methyl, ferimzone, pyroquilon, orysastrobin, azoxystrobin, carpropamid, diclocymet, probenazole, tiadinil, isoprothiolane, tricyclazole, fthalide, kasugamycin, fenoxanil, mepronil, diclomezine, pencycuron, validamycin, edifenphos, furametpyr, thifluzamide, flutolanil, metominostrobin, iprobenfos and oxolinic acid; and

[6] the composition for preventing harmful organisms as set forth in any one of [1] to [5], wherein one or more compounds of other insecticides, miticides or fungicides are respectively contained in an amount of 0.001 to 95 weight %.

The mixed composition of the present invention is capable of exerting a remarkable control effect even on a harmful organism which failed to bring about a sufficient control effect with the use of a single agent and a plurality of harmful organisms showing chemical resistance and the like so that it can have a remarkable control effect on a harmful organism that cannot be controlled with the use of a single agent and a plurality of harmful organisms showing chemical resistance and the like. Accordingly, the composition for preventing harmful organisms of the present invention can greatly contribute to labor saving in agriculture.

BEST MODE FOR CARRYING OUT THE INVENTION

Wordings used in general formulae such as the general formula (1) and the like of the present invention have the respective meanings as described hereinafter in terms of definitions.

The term "halogen atom" represents a fluorine atom, a chlorine atom, a bromine atom or an iodine atom.

In expression of "Ca-Cb (a and b represent an integer of not less than 1)," for example, "C1-C3" refers to 1 to 3 carbon atoms, "C2-C6" refers to 2 to 6 carbon atoms, and "C1-C4" refers to 1 to 4 carbon atoms.

"n-" refers to normal, "i-" refers to iso, "s-" refers to secondary and "t-" refers to tertiary.

The term "alkyl group which may be substituted" refers to a linear, branched or cyclic alkyl group which may be the same or different and is substituted with a hydrogen atom, a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, di C1-C6 alkylamino groups, a phenyl group which may be substituted, a phenylcarbonyl group which may be substituted, a phenylamino group which may be substituted or a heterocyclic group which may be substituted.

The term "C1-C4 alkylcarbonyl group which may be substituted" refers to a linear, branched or cyclic alkylcarbonyl group having 1 to 4 carbon atoms which may be the same or different and is substituted with a hydrogen atom, a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, di C1-C6 alkylamino groups, a phenyl group which may be substituted, a phenylcarbonyl group which may be substituted, a phenylamino group which may be substituted or a heterocyclic group which may be substituted.

The term "phenyl group which may be substituted" refers to a phenyl group which may be the same or different and is substituted with a hydrogen atom, a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, di C1-C6 alkylamino groups, an acetylamino group, a phenyl group which may be substituted, a phenylcarbonyl group which may be substituted, a phenylamino group which may be substituted or a heterocyclic group which may be substituted.

The term "naphthyl group which may be substituted" refers to a naphthyl group which may be the same or different and is substituted with a hydrogen atom, a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, di C1-C6 alkylamino groups, an acetylamino group, a phenyl group which may be substituted, a phenylcarbonyl group which may be substituted, a phenylamino group which may be substituted or a heterocyclic group which may be substituted.

The term "heterocyclic group which may be substituted" refers to a heterocyclic group which may be the same or different and is substituted with a hydrogen atom, a halogen atom, a hydroxy group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, di C1-C6 alkylamino groups, an acetylamino group, a phenyl group which may be substituted, a phenylcarbonyl group which may be substituted, a phenylamino group which may be substituted or a heterocyclic group which may be substituted.

The term "C1-C3 alkyl group" refers to a linear or branched alkyl group having 1 to 3 carbon atoms such as methyl, ethyl, n-propyl, i-propyl, cyclopropyl or the like, "C1-C4 alkyl group" refers to a linear or branched alkyl group having 1 to 4 carbon atoms such as n-butyl, s-butyl, i-butyl, t-butyl or the like in addition to "C1-C3 alkyl group," and "C1-C6 alkyl group" refers to a linear or branched alkyl group having 1 to 6 carbon atoms such as n-pentyl, 2-pentyl, 3-pentyl, neopentyl, n-hexyl, 2-hexyl, 4-methyl-2-pentyl, 3-methyl-n-pentyl or the like in addition to "C1-C4 alkyl group."

The term "C1-C3 haloalkyl group" refers to a linear or branched alkyl group having 1 to 3 carbon atoms which is substituted with one or more halogen atoms and may be the same or different, such as monofluoromethyl, difluoromethyl, trifluoromethyl, monochloromethyl, dichloromethyl, trichloromethyl, monobromomethyl, dibromomethyl, tribromomethyl, 1-fluoroethyl, 2-fluoroethyl, 2,2-difluoroethyl, 2,2,2-trifluoroethyl, 1-chloroethyl, 2-chloroethyl, 2,2-dichloroethyl, 2,2,2-trichloroethyl, 1-bromoethyl, 2-bromoethyl, 2,2-dibromoethyl, 2,2,2-tribromoethyl, 2-iodoethyl, pentafluoroethyl, 3-fluoro-n-propyl, 3-chloro-n-propyl, 3-bromo-n-propyl, 1,3-difluoro-2-propyl, 1,3-dichloro-2-propyl, 1,1,1-trifluoro-2-propyl, 1-chloro-3-fluoro-2-propyl, 1,1,1,3,3,3-hexafluoro-2-propyl, 1,1,1,3,3,3-hexafluoro-2-chloro-2-propyl, 2,2,3,3,3-pentafluoro-n-propyl, heptafluoro-i-propyl, heptafluoro-n-propyl or the like, and "C1-C4 haloalkyl group" refers to a linear or branched alkyl group having 1 to 4 carbon atoms which is substituted with one or more halogen atoms and may be the same or different, such as 4-fluoro-n-butyl, nonafluoro-n-butyl, nonafluoro-2-butyl or the like in addition to "C1-C3 haloalkyl group."

The term "C2-C4 alkenyl group" refers to an alkenyl group of 2 to 4 carbon atoms having a double bond in the carbon chain such as vinyl, allyl, 2-butenyl, 3-butenyl or the like, and "C2-C4 haloalkenyl group" refers to a linear or branched alkenyl group of 2 to 4 carbon atoms having a double bond in the carbon chain which is substituted with one or more halogen atoms and may be the same or different, such as 3,3-difluoro-2-propenyl, 3,3-dichloro-2-propenyl, 3,3-dibromo-2-propenyl, 2,3-dibromo-2-propenyl, 4,4-difluoro-3-butenyl, 3,4,4-tribromo-3-butenyl or the like.

The term "C2-C4 alkynyl group" refers to a linear or branched alkynyl group of 2 to 4 carbon atoms having a triple bond in the carbon chain such as propargyl, 1-butyn-3-yl, 1-butyne-3-methyl-3-yl or the like, and "C2-C4 haloalkynyl group" refers to a linear or branched alkenyl group of 2 to 4 carbon atoms having a triple bond in the carbon chain which is substituted with one or more halogen atoms and may be the same or different.

The term "C3-C6 cycloalkyl group" refers to a cycloalkyl group of 3 to 6 carbon atoms having a ring structure, such as cyclopropyl, cyclobutyl, cyclopentyl, 2-methylcyclopentyl, 3-methylcyclopentyl, cyclohexyl or the like, and "C3-C6 halocycloalkyl group" refers to a cycloalkyl group of 3 to 6 carbon atoms having a ring structure which is substituted with one or more halogen atoms and may be the same or different, such as 2,2,3,3-tetrafluorocyclobutyl, 2-chlorocyclohexyl, 4-chlorocyclohexyl or the like.

The term "C1-C3 alkoxy group" refers to a linear or branched alkoxy group having 1 to 3 carbon atoms such as methoxy, ethoxy, n-propyloxy, isopropyloxy or the like, "C1-C3 haloalkoxy group" refers to a linear or branched haloalkoxy group having 1 to 3 carbon atoms which is substituted with one or more halogen atoms and may be the same or different, such as monofluoromethoxy, difluoroethoxy, trifluoromethoxy, 1,1,1,3,3,3-hexafluoro-2-propyloxy, 2,2,2-trifluoroethoxy, 2-chloroethoxy, 3-fluoro-n-propyloxy or the like, and "C1-C4 haloalkoxy group" refers to a linear or branched haloalkoxy group having 1 to 4 carbon atoms which is substituted with one or more halogen atoms and may be the same or different, such as 1,1,1,3,3,4,4,4-octafluoro-2-butyloxy or the like, in addition to "C1-C3 haloalkoxy group."

The term "C1-C3 alkylthio group" refers to a linear or branched alkylthio group having 1 to 3 carbon atoms such as methylthio, ethylthio, n-propylthio, i-propylthio, cyclopropylthio or the like, "C1-C4 alkylthio group" refers to a linear or branched alkylthio group having 1 to 4 carbon atoms such as n-butylthio, i-butylthio, s-butylthio, t-butylthio, cyclopropylmethylthio or the like, in addition to "C1-C3 alkylthio group," "C1-C3 haloalkylthio group" refers to a linear or branched alkylthio group having 1 to 3 carbon atoms which is substituted with one or more halogen atoms and may be the same or different, such as trifluoromethylthio, pentafluoroethylthio, 2,2,2-trifluoroethylthio, heptafluoro-n-propylthio, heptafluoro-i-propylthio or the like, and "C1-C4 haloalkylthio group" refers to a linear or branched alkylthio group having 1 to 4 carbon atoms which is substituted with one or more halogen atoms and may be the same or different, such as nonafluoro-n-butylthio, nonafluoro-s-butylthio, 4,4,4-trifluoro-n-butylthio or the like, in addition to "C1-C3 haloalkylthio group."

The term "C1-C3 alkylsulfinyl group" refers to a linear or branched alkylsulfinyl group having 1 to 3 carbon atoms, such as methylsulfinyl, ethylsulfinyl, n-propylsulfinyl, i-propylsulfinyl, cyclopropylsulfinyl or the like, and "C1-C3 haloalkylsulfinyl group" refers to a linear or branched alkylsulfinyl group having 1 to 3 carbon atoms which is substituted with one or more halogen atoms and may be the same or different, such as trifluoromethylsulfinyl, pentafluoroethylsulfinyl, 2,2,2-trifluoroethylsulfinyl, heptafluoro-n-propylsulfinyl, heptafluoro-i-propylsulfinyl or the like.

The term "C1-C3 alkylsulfonyl group" refers to a linear or branched alkylsulfonyl group having 1 to 3 carbon atoms, such as methylsulfonyl, ethylsulfonyl, n-propylsulfonyl, i-propylsulfonyl, cyclopropylsulfonyl or the like, and "C1-C3 haloalkylsulfonyl group" refers to a linear or branched alkylsulfonyl group having 1 to 3 carbon atoms which is substituted with one or more halogen atoms and may be the same or different, such as trifluoromethylsulfonyl, pentafluoroethylsulfonyl, 2,2,2-trifluoroethylsulfonyl, heptafluoro-n-propylsulfonyl, heptafluoro-i-propylsulfonyl or the like.

The term "arylsulfonyl group" refers to an arylsulfonyl group of 6 to 14 carbon atoms having an aromatic ring, such as phenylsulfonyl, p-toluenesulfonyl, 1-naphthylsulfonyl, 2-naphthylsulfonyl, anthrylsulfonyl, phenanthrylsulfonyl, acenaphthylenylsulfonyl or the like.

The term "C1-C4 alkylamino group" refers to a linear, branched or cyclic alkylamino group having 1 to 4 carbon atoms, such as methylamino, ethylamino, n-propylamino, i-propylamino, n-butylamino, cyclopropylamino or the like, and "di C1-C4 alkylamino group" refers to a linear or branched amino group which is substituted with two alkyl groups having 1 to 4 carbon atoms and may be the same or different, such as dimethylamino, diethylamino, N-ethyl-N-methylamino or the like.

The term "C1-C4 alkylcarbonyl group" refers to a linear, branched or cyclic alkylcarbonyl group having 1 to 4 carbon atoms, such as formyl, acetyl, propionyl, isopropylcarbonyl, cyclopropylcarbonyl or the like.

The "C1-C4 haloalkylcarbonyl group" refers to a linear or branched alkylcarbonyl group having 1 to 4 carbon atoms which is substituted with one or more halogen atoms and may be the same or different, such as fluoroacetyl, difluoroacetyl, trifluoroacetyl, chloroacetyl, dichloroacetyl, trichloroacetyl, bromoacetyl, iodoacetyl, 3,3,3-trifluoropropionyl, 2,2,3,3,3-pentafluoropropionyl or the like.

The term "C1-C4 alkylcarbonyloxy group" refers to a linear or branched alkylcarbonyloxy group having 1 to 4 carbon atoms, such as acetoxy, propionyloxy or the like.

The term "C1-C4 alkoxycarbonyl group" refers to a linear or branched alkoxycarbonyl group having 1 to 4 carbon atoms, such as methoxycarbonyl, ethoxycarbonyl, isopropyloxycarbonyl or the like.

The term "C1-C4 perfluoroalkyl group" refers to a linear or branched alkyl group having 1 to 4 carbon atoms which is all substituted with fluorine atoms, such as trifluoromethyl, pentafluoroethyl, heptafluoro-n-propyl, heptafluoro-i-propyl, nonafluoro-n-butyl, nonafluoro-2-butyl, nonafluoro-i-butyl or the like, and "C2-C6 perfluoroalkyl group" refers to a linear or branched alkyl group having 2 to 6 carbon atoms which is all substituted with fluorine atoms, such as pentafluoroethyl, heptafluoro-n-propyl, heptafluoro-i-propyl, nonafluoro-n-butyl, nonafluoro-2-butyl, nonafluoro-i-butyl, perfluoro-n-pentyl, perfluoro-n-hexyl or the like.

The term "C1-C6 perfluoroalkylthio group" refers to a linear or branched alkylthio group having 1 to 6 carbon atoms which is all substituted with fluorine atoms, such as trifluoromethylthio, pentafluoroethylthio, heptafluoro-n-propylthio, heptafluoro-i-propylthio, nonafluoro-n-butylthio, nonafluoro-2-butylthio, nonafluoro-i-butylthio, perfluoro-n-pentylthio, perfluoro-n-hexylthio or the like.

The term "C1-C6 perfluoroalkylsulfinyl group" refers to a linear or branched alkylsulfinyl group having 1 to 6 carbon atoms which is all substituted with fluorine atoms, such as trifluoromethylsulfinyl, pentafluoroethylsulfinyl, heptafluoro-n-propylsulfinyl, heptafluoro-i-propylsulfinyl, nonafluoro-n-butylsulfinyl, nonafluoro-2-butylsulfinyl, nonafluoro-i-butylsulfinyl, perfluoro-n-pentylsulfinyl, perfluoro-n-hexylsulfinyl or the like.

The term "C1-C6 perfluoroalkylsulfonyl group" refers to a linear or branched alkylsulfonyl group having 1 to 6 carbon atoms which is all substituted with fluorine atoms, such as trifluoromethylsulfonyl, pentafluoroethylsulfonyl, heptafluoro-n-propylsulfonyl, heptafluoro-i-propylsulfonyl, nonafluoro-n-butylsulfonyl, nonafluoro-2-butylsulfonyl, nonafluoro-i-butylsulfonyl, perfluoro-n-pentylsulfonyl, perfluoro-n-hexylsulfonyl or the like.

The compound represented by the general formula (1) of the present invention contains one or more asymmetric carbon atoms or asymmetric centers in its structural formula in some cases and has two or more optical isomers in some cases. The present invention also includes all of the respective optical isomers and mixtures comprising of these isomers in any ratio. Furthermore, the compound represented by the general formula (1) of the present invention has two or more geometrical isomers derived from a carbon-carbon double bond in its structural formula in some cases. The present invention also includes all of the respective geometrical isomers and mixtures comprising of these isomers in any ratio.

Preferable examples of the substituents or atoms in the compounds represented by the general formula (1) and the like of the present invention are listed below.

In $A_1$, $A_2$, $A_3$ and $A_4$, it is preferable that $A_1$ is a carbon atom, a nitrogen atom or an oxidized nitrogen atom and all of $A_2$, $A_3$ and $A_4$ are carbon atoms at the same time. it is more preferable that 11 of $A_1$, $A_2$, $A_3$ and $A_4$ are carbon atoms.

$R_1$ is preferably a hydrogen atom or a C1-C4 alkyl group, and further preferably a hydrogen atom, a methyl group or an ethyl group.

$R_2$ is preferably a hydrogen atom or a C1-C4 alkyl group, and further preferably a hydrogen atom, a methyl group or an ethyl group.

$G_1$ and $G_2$ are independently preferably an oxygen atom or a sulfur atom, and further preferably both of $G_1$ and $G_2$ are oxygen atoms.

X is preferably a hydrogen atom or a halogen atom, and further preferably a hydrogen atom or a fluorine atom.

n is preferably 0, 1 or 2, and further preferably 0 or 1.

$X_1$ is preferably a hydrogen atom or a halogen atom, and further preferably a hydrogen atom or a fluorine atom.

$X_2$ is preferably a hydrogen atom or a fluorine atom, and further preferably a hydrogen atom.

$X_3$ and $X_4$ are preferably hydrogen atoms.

$Q_1$ is preferably a phenyl group,
a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group and an acetylamino group, a pyridyl group, or a pyridyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group and an acetylamino group, and further preferably a phenyl group, a substituted phenyl group having one to three substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group, a pyridyl group, or a pyridyl group having one to two substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group.

$Q_2$ is preferably a substituted phenyl group or a substituted pyridyl group represented by the general formula (2) or (3), wherein $Y_1$ and $Y_5$ are independently preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, a cyano group, a methoxy group, an ethoxy group, an n-propyloxy group, a trifluoromethoxy group, a difluoromethoxy group or a pentafluoroethoxy group; and $Y_6$ and $Y_9$ are independently preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group, a cyano group, a trifluoromethylsulfinyl group, a trifluoromethylsulfonyl group, a cyano group, a methoxy group, an ethoxy group, an n-propyloxy group, a trifluoromethoxy group, a difluoromethoxy group or a pentafluoroethoxy group; $Y_2$, $Y_4$ and $Y_7$ are preferably a hydrogen atom, a halogen atom or a methyl group, and further preferably a hydrogen atom; $Y_3$ is preferably a pentafluoroethyl group, a heptafluoro-n-propyl group, a heptafluoro-i-propyl group, a nonafluoro-n-butyl group, a nonafluoro-2-butyl group, a nonafluoro-i-butyl group, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a trifluoromethylsulfonyl group, a pentafluoroethylsulfonyl group, a heptafluoro-n-propylsulfonyl group, a heptafluoro-i-propylsulfonyl group, a nonafluoro-n-butylsulfonyl group or a nonafluoro-2-butylsulfonyl group; and $Y_8$ is preferably a pentafluoroethyl group, a heptafluoro-n-propyl group, a heptafluoro-i-propyl group, a nonafluoro-n-butyl group, a nonafluoro-2-butyl group, a nonafluoro-i-butyl group, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a trifluoromethylsulfonyl group, a pentafluoroethylsulfonyl group, a heptafluoro-n-propylsulfonyl group, a heptafluoro-i-propylsulfonyl group, a nonafluoro-n-butylsulfonyl group, a nonafluoro-2-butylsulfonyl group, a pentafluoroethoxy group or a 1,1,1,3,3,3-hexafluoro-i-propyloxy group.

L is preferably a chlorine atom, a bromine atom or a hydroxy group.

$R_1a$ is preferably a hydrogen atom or a C1 to C4 alkyl group, and further preferably a hydrogen atom, a methyl group or an ethyl group.

$R_2a$ is preferably a hydrogen atom or a C1 to C4 alkyl group, and further preferably a hydrogen atom, a methyl group or an ethyl group.

$G_1a$ and $G_2a$ are independently preferably an oxygen atom or a sulfur atom, and further preferably, both $G_1a$ and $G_2a$ are oxygen atoms.

$X_1a$ is preferably a hydrogen atom or a halogen atom, and further preferably a hydrogen atom or a fluorine atom.

$X_2a$ is preferably a hydrogen atom or a fluorine atom, and further preferably a hydrogen atom.

$X_3a$ and $X_4a$ are preferably hydrogen atoms.

$Y_1a$ and $Y_5a$ are independently preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group or a cyano group.

$Y_2a$ and $Y_4a$ are each preferably a hydrogen atom, a halogen atom or a methyl group, and further preferably a hydrogen atom.

$Q_1a$ is preferably a phenyl group, a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group and an acetylamino group, a pyridyl group, or a pyridyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group and an acetylamino group, and further preferably a phenyl group, a substituted phenyl group having one to three substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group, a pyridyl group, or a pyridyl group having one to two substituents which may be the same or different and are selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group.

$R_a$ and $R_b$ are independently preferably a fluorine atom, a trifluoromethyl group, a pentafluoroethyl group or a heptafluoro-n-propyl group, and further preferably a fluorine atom, a trifluoromethyl group or a pentafluoroethyl group.

$R_c$ is preferably a hydroxy group, a chlorine atom, a bromine atom, an iodine atom, a methoxy group, an ethoxy group, a methylsulfonyloxy group, a trifluoromethylsulfonyloxy group, a phenylsulfonyloxy group, a p-toluenesulfonyloxy group, an acetoxy group or a trifluoroacetoxy group, more preferably a hydroxy group, a chlorine atom, a bromine atom, a methoxy group, a methylsulfonyloxy group, a trifluoromethylsulfonyloxy group, a phenylsulfonyloxy group or a p-toluenesulfonyloxy group, and further preferably a hydroxy group, a chlorine atom or a bromine atom.

$R_c'$ is preferably a hydroxy group.

$R_c''$ is preferably a chlorine atom or a bromine atom.

J, J' and J'' are independently preferably a hydroxy group, a chlorine atom or a bromine atom, and further preferably a chlorine atom.

Typical preparation methods of the compound represented by the general formula (1) according to the present invention are illustrated below. The compound represented by the general formula (1) of the present invention can be prepared according to the methods, but the preparation method paths are not restricted to the following preparation methods.

In the general formulae shown in the following preparation methods, $X_1, X_2, X_3, X_4, Y_1, Y_2, Y_4, Y_5, G_1, G_2, R_1, R_2$ and $Q_1$ may correspond to $X_1a, X_2a, X_3a, X_4a, Y_1a, Y_2a, Y_4a, Y_5a, G_1a, G_2a, R_1a, R_2a$ and $Q_1a$ respectively, or vice versa. Furthermore, $Q_2$ represents the same as those described in [1] or the general formula (2), (3) or (18),

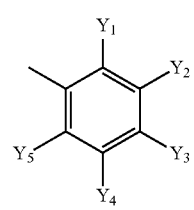

(2)

wherein, in the formula, $Y_1, Y_2, Y_3, Y_4$ and $Y_5$ represent the same as those described above,

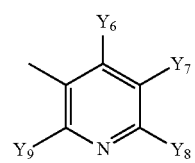

(3)

wherein, in the formula, $Y_6, Y_7, Y_8$ and $Y_9$ represent the same as those described above, or

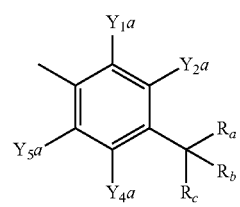

(18)

wherein, in the formula, $Y_1a, Y_2a, Y_4a, Y_5a, R_a, R_b$ and $R_c$ represent the same as those described above.

Preparation Method 1

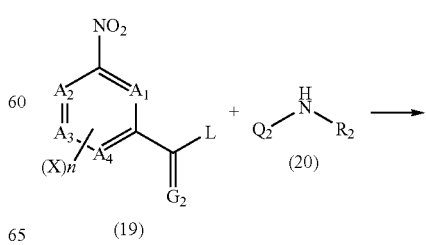

-continued

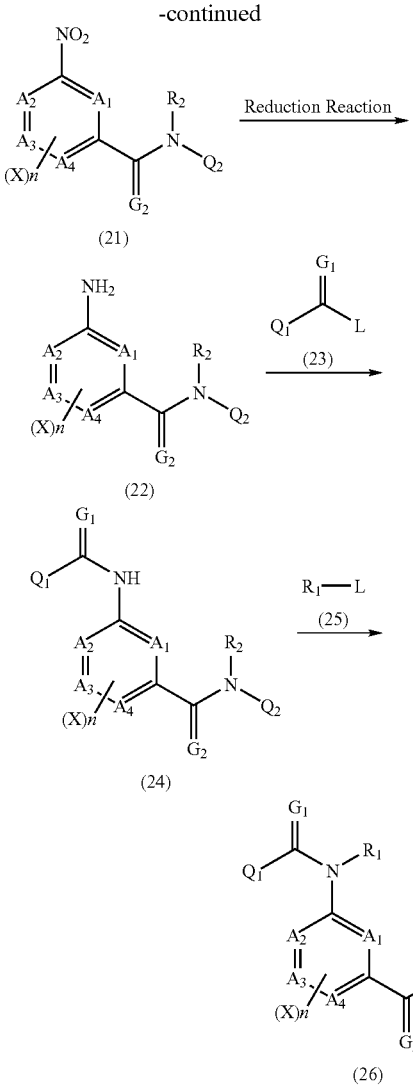

wherein, in the formula, $A_1, A_2, A_3, A_4, G_1, G_2, R_1, R_2, X, n, Q_1$ and $Q_2$ represent the same as those described above; and L represents a functional group having a leaving ability such as a halogen atom, a hydroxyl group or the like.

1-(i) General formula (19)+General formula (20)→General formula (21)

By reacting an m-nitroaromatic carboxylic acid derivative having a leaving group represented by the general formula (19) with an aromatic amine derivative represented by the general formula (20) in an appropriate solvent or without a solvent, an aromatic carboxylic acid amide derivative having a nitro group represented by the general formula (21) can be prepared. In this process, an appropriate base can also be used.

Solvents may not remarkably hinder the progress of the reaction and examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitriles such as acetonitrile and the like; and inert solvents such as 1,3-dimethyl-2-imidazolidinone and the like. These solvents can be used singly or in combination of two or more kinds.

Furthermore, examples of the base include organic bases such as triethylamine, tri-n-butylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as di-potassium monohydrogen phosphate, tri-sodium phosphate and the like; alkali metal hydrides such as sodium hydride and the like; and alkali metal alcoholates such as sodium methoxide, sodium ethoxide and the like. These bases may be suitably selected in the range of 0.01 to 5 mole equivalents, based on the compound represented by the general formula (19) and used accordingly.

The reaction temperature may be suitably selected in the range of −20 degree centigrade to the reflux temperature of a solvent in use, while the reaction time may be properly selected in the range of several minutes to 96 hours.

Of the compounds represented by the general formula (19), an aromatic carboxylic acid halide derivative can be easily prepared from an aromatic carboxylic acid according to a usual method using a halogenating agent. Examples of the halogenating agent include thionyl chloride, thionyl bromide, phosphorus oxychloride, oxalyl chloride, phosphorus trichloride and the like.

On the other hand, the compound represented by the general formula (21) can be prepared from the m-nitroaromatic carboxylic acid derivative and the compound represented by the general formula (20) without using a halogenating agent. As a method thereof, a method suitably using an additive such as 1-hydroxybenzotriazole or the like and employing a condensation agent using N,N'-dicyclohexylcarbodiimide according to a method as described, for example, in Chem. Ber. p. 788 (1970) can be exemplified. Other condensation agents to be used in this case include, for example, 1-ethyl-3-(3-dimethylaminopropyl)carbodiimide, 1,1'-carbonylbis-1H-imidazole and the like.

Furthermore, as other method for preparing the compound represented by the general formula (21), a mixed anhydride procedure using chloroformate esters can be cited. Also, the compound represented by the general formula (21) can be prepared according to a method as described in J. Am. Chem. Soc. p. 5012 (1967). Examples of chloroformate esters to be used in this case include isobutyl chloroformate, isopropyl chloroformate and the like. In addition to chloroformate esters, diethylacetyl chloride, trimethylacetyl chloride and the like can be cited.

Both the method using a condensation agent and mixed anhydride procedure are not restricted to the solvent, reaction temperature and reaction time as described in the above document, and an inert solvent which does not remarkably hinder the suitable progress of the reaction may be used. The reaction temperature and reaction time may be suitably selected as the reaction proceeds.

1-(ii): General Formula (21)→General Formula (22)

An aromatic carboxylic acid amide derivative having a nitro group represented by the general formula (21) can be made into an aromatic carboxylic acid amide derivative having an amino group represented by the general formula (22) by the reduction reaction. As the reduction reaction, a method employing the hydrogenation reaction and a method employing a metallic compound (for example, stannous chloride (anhydride), iron powder, zinc powder and the like) can be cited.

The former method can be carried out in a proper solvent in the presence of a catalyst, in an ordinary pressure or a reduced pressure, in a hydrogen atmosphere. Such a catalyst includes, for example, palladium catalysts such as palladium carbon and the like, nickel catalysts such as Raney nickel and the like, cobalt catalysts, ruthenium catalysts, rhodium catalysts, platinum catalysts and the like. The solvent includes, for example, water; alcohols such as methanol, ethanol and the like; aromatic hydrocarbons such as benzene, toluene and the like; chained ethers or cyclic ethers such as ether, dioxane, tetrahydrofuran and the like; and esters such as ethyl acetate and the like. The pressure may be suitably selected in the range of 0.1 to 10 MPa, the reaction temperature may be suitably selected in the range of −20 degree centigrade to the reflux temperature of a solvent in use, and the reaction time may be properly selected in the range of several minutes to 96 hours. The compound of the general formula (22) can be more effectively prepared.

As the latter method, a method employing stannous chloride (anhydride) as a metallic compound according to the conditions as described in "Organic Syntheses" Coll. Vol. III P. 453 can be cited.

1-(iii): General Formula (22)+General Formula (23) →General formula (24)

By reacting an aromatic carboxylic acid amide derivative having an amino group represented by the general formula (22) with a compound represented by the general formula (23) in an appropriate solvent, a compound represented by the general formula (24) of the present invention can be prepared. In this process, an appropriate base can also be used.

Solvents may not remarkably hinder the progress of the reaction and examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitrites such as acetonitrile and the like; and inert solvents such as 1,3-dimethyl-2-imidazolidinone and the like. These solvents can be used singly or in combination of two or more kinds.

Furthermore, examples of the base include organic bases such as triethylamine, tri-n-butylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as di-potassium monohydrogen phosphate, tri-sodium phosphate and the like; alkali metal hydrides such as sodium hydride and the like; and alkali metal alcoholates such as sodium methoxide, sodium ethoxide and the like. These bases may be suitably selected in the range of 0.01 to 5 mole equivalents based on the compound represented by the general formula (22) and used accordingly. The reaction temperature may be suitably selected in the range of −20 degree centigrade to the reflux temperature of a solvent in use, while the reaction time may be properly selected in the range of several minutes to 96 hours. Furthermore, a method employing a condensation agent and a mixed anhydride procedure as described in 1-(i) can also be used.

1-(iv): General Formula (24)+General Formula (25) →General Formula (26)

By reacting a compound represented by the general formula (24) with an alkyl compound having a leaving group represented by the general formula (25) in a solvent or without a solvent, a compound represented by the general formula (26) of the present invention can be prepared. Examples of the compound represented by the general formula (25) include alkyl halides such as methyl iodide, ethyl iodide, n-propyl bromide and the like. Furthermore, in this process, a suitable base or solvent can be used. As the base or solvent, the bases or solvents cited in 1-(i) can be used. The reaction temperature and reaction time cited in 1-(i) can also be used.

Furthermore, the compound represented by the general formula (26) can also be prepared by an another method comprising reacting an alkylating agent such as dimethyl sulfate, diethyl sulfate or the like with the compound represented by the general formula (24) instead of the compound represented by the general formula (25).

Preparation Method 2

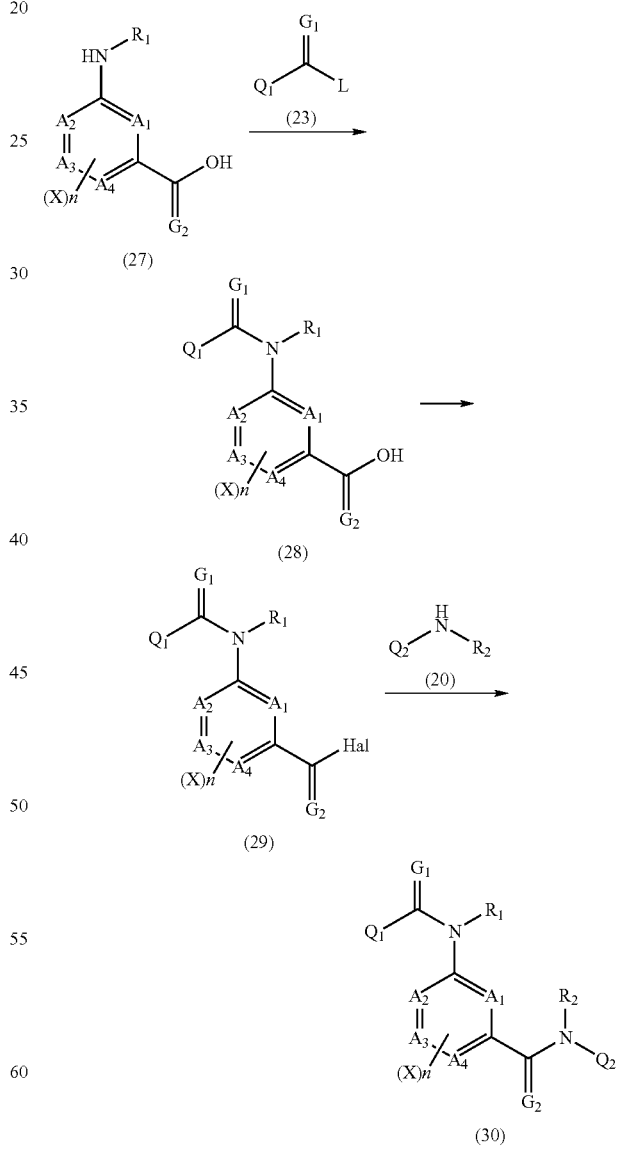

wherein, in the formula, $A_1$, $A_2$, $A_3$, $A_4$, $G_1$, $G_2$, $R_1$, $R_2$, X, n, $Q_1$, $Q_2$, L and Hal represent the same as those described above.

2-(i): General Formula (27)+General Formula (23)→General formula (28)

By reacting carboxylic acids having an amino group represented by the general formula (27) as a starting material with a compound represented by the general formula (23) in accordance with the conditions described in 1-(i), carboxylic acids having an acylamino group represented by the general formula (28) can be prepared.

2-(ii): General Formula (28)→General Formula (29)

A compound represented by the general formula (29) can be prepared by a known usual method comprising reacting a compound represented by the general formula (28) with thionyl chloride, oxalyl chloride, phosgene, phosphorus oxychloride, phosphorus pentachloride, phosphorus trichloride, thionyl bromide, phosphorus tribromide, diethylaminosulfur trifluoride or the like.

2-(iii): General Formula (29)+General Formula (20)→General formula (30)

By reacting a compound represented by the general formula (29) with a compound represented by the general formula (20) according to the conditions described in 1-(i), a compound represented by the general formula (30) can be prepared.

2-(iv): General Formula (28)+General Formula (20)→General formula (30)

By reacting a compound represented by the general formula (28) with a compound represented by the general formula (20) according to the conditions using a condensation agent or a mixed anhydride procedure described in 1-(i), a compound represented by the general formula (30) can be prepared.

Preparation Method 3

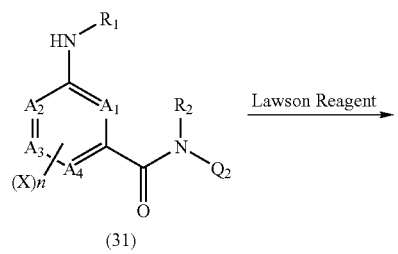

(31)

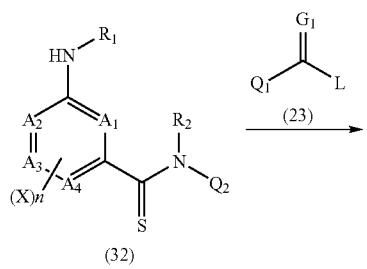

(32)

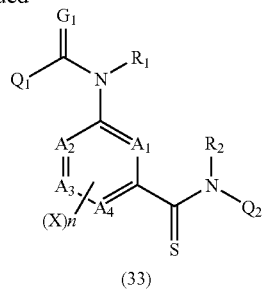

(33)

wherein, in the formula, $A_1$, $A_2$, $A_3$, $A_4$, $G_1$, $R_1$, $R_2$, X, n, $Q_1$, $Q_2$ and L represent the same as those described above.

3-(i): General Formula (31)→General Formula (32)

By reacting a compound represented by the general formula (31) with a Lawson reagent according to the known conditions described in Synthesis p. 463 (1993), Synthesis p. 829 (1984) and the like, a compound represented by the general formula (32) can be prepared. The conditions such as a solvent, reaction temperature and the like are not restricted to those described in the documents.

3-(ii): General Formula (32)+General Formula (23)→General Formula (33)

By reacting a compound represented by the general formula (32) with a compound represented by the general formula (23) according to the conditions described in 1-(i), a compound represented by the general formula (33) can be prepared.

Preparation Method 4

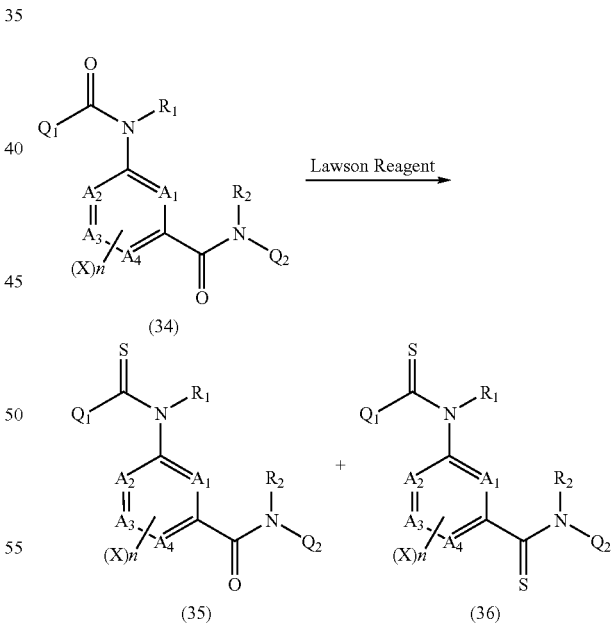

(34)

(35)                     (36)

wherein, in the formula, $A_1$, $A_2$, $A_3$, $A_4$, $R_1$, $R_2$, X, n, $Q_1$ and $Q_2$ represent the same as those described above.

Compounds represented by the general formulae (35) and (36) can be prepared from a compound represented by the general formula (34) according to the conditions described in 3-(i). The conditions such as a solvent, reaction temperature and the like are not restricted to those described in the documents. These two compounds can be easily separated and Preparation Method 5

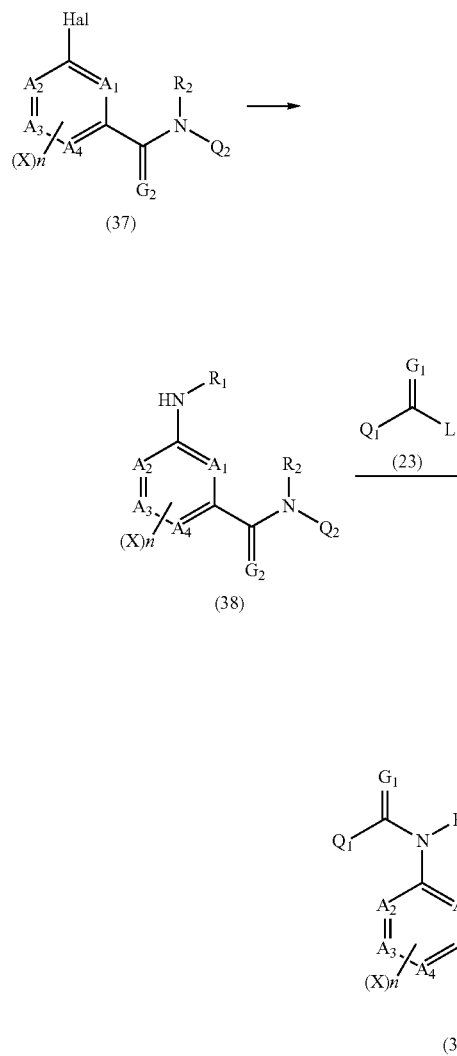

Preparation Method 6

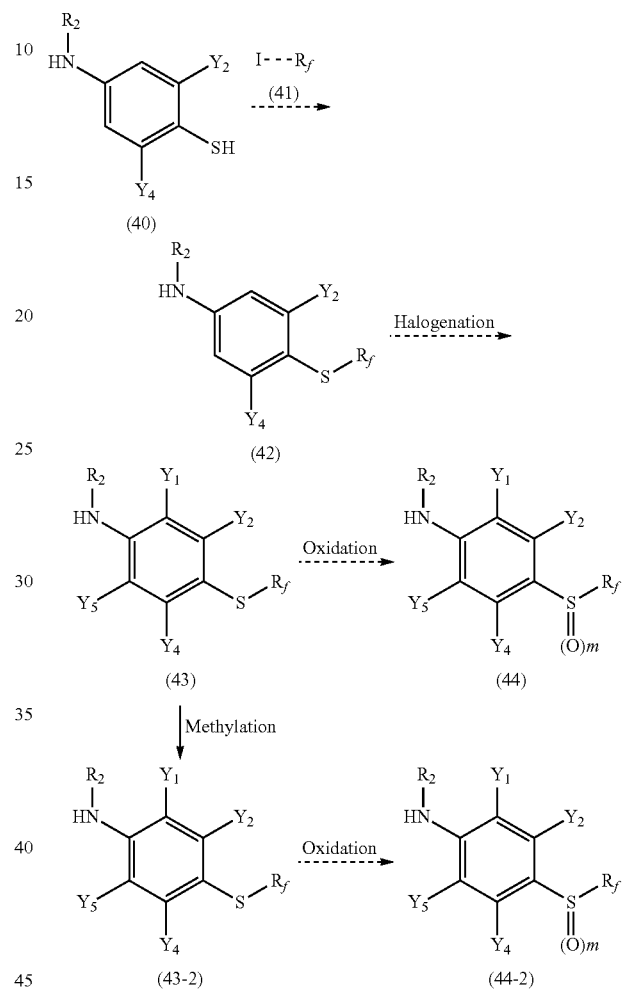

wherein, in the formula, $A_1, A_2, A_3, A_4, G_1, G_2, R_1, R_2, X, n, Q_1, Q_2$ and L represent the same as those described above.

5-(i): General Formula (37)→General Formula (38)

A compound represented by the general formula (38) can be prepared by carrying out an amination reaction using ammonia according to the conditions described, for example, in J. Org. Chem. p. 280 (1958). The conditions such as a reaction solvent and the like are not restricted to those described in the documents, and an inert solvent which does not remarkably hinder the proper progress of the reaction may be used. The reaction temperature and reaction time may be suitably selected as the reaction proceeds. Furthermore, examples of the amination agent include methylamine, ethylamine or the like, in addition to ammonia.

5-(ii): General Formula (38)+General Formula (23) →General formula (39)

By reacting a compound represented by the general formula (38) with a compound represented by the general formula (23) according to the conditions described in 1-(i), a compound represented by the general formula (39) can be prepared.

wherein, in the formula, $R_2$ represents the same as those described above; $Y_1$ and $Y_5$ independently represent a methyl group, a chlorine atom, a bromine atom or an iodine atom; $Y_2$ and $Y_4$ represent the same as those described above; $R_f$ represents a C1-C6 perfluoroalkyl group; and m represents 1 or 2.

6-(i): General Formula (40)+General Formula (41)→General formula (42)

By reacting aminothiophenols represented by the general formula (40) with haloalkyl iodide represented by the general formula (41) in accordance with a method described in J. Fluorine Chem. p. 207 (1994), a compound represented by the general formula (42) can be prepared.

Examples of the haloalkyl iodide represented by the general formula (41) include trifluoromethyl iodide, pentafluoroethyl iodide, heptafluoro-n-propyl iodide, heptafluoroisopropyl iodide, nonafluoro-n-butyl iodide, nonafluoroisopropyl iodide and the like. These may be suitably used in the range of 1 to 10 mole equivalents, based on the compound represented by the general formula (40).

The solvent to be used in this process is not restricted to solvents described in the above documents and may not remarkably hinder the progress of the reaction. Examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitrites such as acetonitrile and the like; and inert solvents such as 1,3-dimethyl-2-imidazolidinone, hexamethylphosphoric triamide and the like. These solvents can be used singly or in combination of two or more kinds. Particularly preferable is a polar solvent. The reaction temperature may be suitably selected in the range of –20 degree centigrade to the reflux temperature of a solvent in use, while the reaction time may be properly selected in the range of several minutes to 96 hours.

6-(ii): General Formula (42)→General Formula (43)

A compound represented by the general formula (43) can be prepared by using a suitable halogenating agent. For example, a method as described in Synth. Commun. p. 1261 (1989) can be cited.

Examples of the halogenating agent include chlorine, bromine, iodine, N-chlorosuccinic acid imide, N-bromosuccinic acid imide, N-iodosuccinic acid imide and the like. These may be suitably used in the range of 1 to 10 mole equivalents, based on a compound represented by the general formula (42).

In this process, an appropriate solvent can also be used, but a solvent in use is not restricted to solvents described in the above documents and may not remarkably hinder the progress of the reaction. Examples thereof include water; aromatic hydrocarbons such as benzene, toluene, xylene and the like; halogenated hydrocarbons such as dichloromethane, chloroform, carbon tetrachloride and the like; chained ethers or cyclic ethers such as diethyl ether, dioxane, tetrahydrofuran, 1,2-dimethoxyethane and the like; esters such as ethyl acetate, butyl acetate and the like; alcohols such as methanol, ethanol and the like; ketones such as acetone, methylisobutyl ketone, cyclohexanone and the like; amides such as dimethylformamide, dimethylacetamide and the like; nitriles such as acetonitrile and the like; and inert solvents such as 1,3-dimethyl-2-imidazolidinone, hexamethylphosphoric triamide and the like. These solvents can be used singly or in combination of two or more kinds. Particularly preferable is a polar solvent. The reaction temperature may be suitably selected in the range of 20 degree centigrade to the reflux temperature of a solvent in use, while the reaction time may be properly selected in the range of several minutes to 96 hours.

6-(iii): General Formula (43)→General formula (44)

A compound represented by the general formula (44) can be prepared by using a suitable oxidant. For example, a method described in Tetrahedron Lett. p. 4955 (1994) can be cited.

Examples of the oxidant include organic peroxides such as m-chloroperbenzoic acid and the like, sodium metaperiodate, hydrogen peroxide, ozone, selenium dioxide, chromic acid, dinitrogen tetraoxide, acyl nitrate, iodine, bromine, N-bromosuccinic acid imide, iodosylbenzyl, t-butyl hypochlorite and the like.

The solvent to be used in this process is not restricted to solvents described in the above documents and may not remarkably hinder the progress of the reaction. These solvents can be used singly or in combination of two or more kinds. Particularly preferable is a polar solvent. The reaction temperature may be suitably selected in the range of –20 degree centigrade to the reflux temperature of a solvent in use, while the reaction time may be properly selected in the range of several minutes to 96 hours.

6-(iv): General Formula (43)→General Formula (43-2)

A compound represented by the general formula (43-2) (wherein, in the formula, any one of $Y_1$ and $Y_5$ must represent a methyl group) can be prepared from a compound represented by the general formula (43) by using a suitable methylating agent. In this process, for example, a method described in Tetrahedron Lett. p. 6237 (2000) can be cited.

6-(v): General Formula (43-2)→General Formula (44-2)

A compound represented by the general formula (44-2) (wherein, in the formula, any one of $Y_1$ and $Y_5$ must represent a methyl group) can be prepared according to the method described in preparation method 6-(iii).

Furthermore, the compound of the present invention can be prepared by suitably selecting a preparation method illustrated in the present invention using an aniline derivative represented by the general formula (43), (44), (43-2) or (44-2).

Preparation Method 7

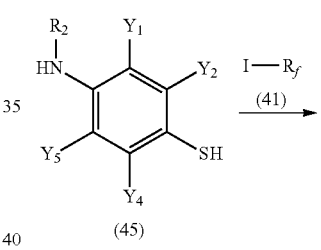

(45)

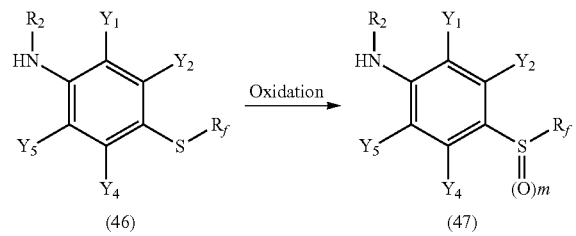

(46)    (47)

wherein, in the formula, $R_2$, $Y_1$, $Y_2$, $Y_4$, $Y_5$, $R_f$ and m represent the same as those described in the preparation method 6.

An aniline derivative represented by the general formula (47) can be prepared using a compound represented by the general formula (45) as a starting raw material according to the preparation method 6. Furthermore, by suitably selecting a preparation method illustrated in the present invention, the compound of the present invention can be prepared.

Preparation Method 8

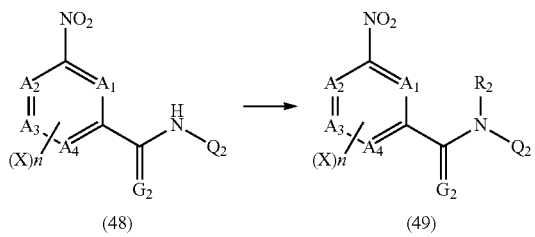

wherein, in the formula, $A_1, A_2, A_3, A_4$, X, n, $G_2$, $R_2$ and $Q_2$ represent the same as those described above.

By reacting a compound represented by the general formula (48) with a suitable reactant using a suitable base in a proper solvent, a compound represented by the general formula (49) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitrites such as acetonitrile, propionitrile and the like; ketones such as acetone, methylisobutyl ketone, cyclohexanone, methylethyl ketone and the like; esters such as ethyl acetate, butyl acetate and the like; alcohols such as methanol, ethanol and the like; and solvents such as 1,3-dimethyl-2-imidazolidinone, sulfolane, dimethylsulfoxide; water and the like. These solvents can be used singly or in combination of two or more kinds.

Examples of the base include organic bases such as triethylamine, tributylamine, pyridine, 4-dimethylaminopyridine and the like; alkali metal hydroxides such as sodium hydroxide, potassium hydroxide and the like; carbonates such as sodium hydrogen carbonate, potassium carbonate and the like; phosphates such as potassium mono-hydrogen phosphate, tri-sodium phosphate and the like; alkali metal hydrides such as sodium hydride and the like; alkali metal alkoxides such as sodium methoxide, sodium ethoxide and the like; organolithiums such as n-butyl lithium and the like; and Grignard reagents such as ethyl magnesium bromide and the like.

These bases may be suitably selected in the range of 0.01 to 5 mole equivalents based on the compound represented by the general formula (48) or may be used as a solvent.

Examples of the reactant include halogenated alkyls such as methyl iodide, ethyl bromide, trifluoromethyl iodide, 2,2,2-trifluoroethyl iodide and the like; halogenated allyls such as allyl iodide and the like; halogenated propargyls such as propargyl bromide and the like; halogenated acyls such as acetyl chloride and the like; acid anhydrides such as trifluoroacetic anhydride and the like; and alkyl sulfuric acids such as dimethyl sulfate, diethyl sulfate and the like.

These reactants may be suitably selected in the range of 1 to 5 mole equivalents, based on the compound represented by the general formula (48) or may be used as a solvent.

The reaction temperature may be suitably selected in the range of −80 degree centigrade to the reflux temperature of a solvent in use, while the reaction time may be properly selected in the range of several minutes to 96 hours.

Preparation Method 9

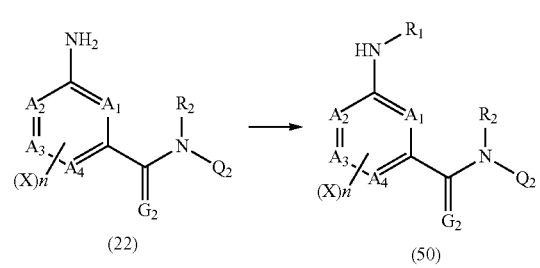

wherein, in the formula, $A_1, A_2, A_3, A_4$, X, n, $G_2$, $R_1$, $R_2$ and $Q_2$ represent the same as those described above.

9-(i): General Formula (22)→General Formula (50)

By reacting a compound represented by the general formula (22) with aldehydes or ketones in an appropriate solvent, adding a suitable catalyst and reacting the resultant in a hydrogen atmosphere, a compound represented by the general formula (50) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of two or more kinds.

Examples of the catalyst include palladium catalysts such as palladium carbon, palladium hydroxide carbon and the like, nickel catalysts such as Raney nickel and the like, cobalt catalysts, platinum catalysts, ruthenium catalysts, rhodium catalysts and the like.

Examples of aldehydes include formaldehyde, acetoaldehyde, propionaldehyde, trifluoroacetoaldehyde, difluoroacetoaldehyde, fluoroacetoaldehyde, chloroacetoaldehyde, dichloroacetoaldehyde, trichloroacetoaldehyde, bromoacetoaldehyde and the like.

Examples of ketones include acetone, perfluoroacetone, methylethyl ketone and the like.

The reaction pressure may be suitably selected in the range of 1 to 100 atm.

The reaction temperature may be suitably selected in the range of −20 degree centigrade to the reflux temperature of a solvent in use, while the reaction time may be properly selected in the range of several minutes to 96 hours.

9-(ii): General Formula (22)→General Formula (50) (Another method 1)

By reacting a compound represented by the general formula (22) with aldehydes or ketones in an appropriate solvent, and applying a suitable reducing agent, a compound represented by the general formula (50) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of two or more kinds.

Examples of the reducing agent include borohydrides such as sodium borohydride, sodium cyanoborohydride, sodium triacetate borohydride and the like.

Examples of aldehydes include formaldehyde, acetoaldehyde, propionaldehyde, trifluoroacetoaldehyde, difluoroacetoaldehyde, fluoroacetoaldehyde, chloroacetoaldehyde, dichloroacetoaldehyde, trichloroacetoaldehyde, bromoacetoaldehyde and the like.

Examples of ketones include acetone, perfluoroacetone, methylethyl ketone and the like.

The reaction temperature may be suitably selected in the range of −20 degree centigrade to the reflux temperature of a solvent in use, while the reaction time may be properly selected in the range of several minutes to 96 hours.

9-(iii): General Formula (22)→General Formula (50) (Another Method 2)

By reacting a compound represented by the general formula (22) with a formylating agent in a proper solvent or without a solvent and applying a reducing agent, it is possible to prepare a compound, wherein, in the general formula (50), $R_1$ is a methyl group.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitrites such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of two or more kinds.

Examples of the formylating agent include anhydrous formic acids such as formaldehyde, formic acid, fluoroformic acid, formyl (2,2-dimethylpropionic acid) and the like; formic acid esters such as phenyl formate and the like; pentafluorobenzaldehyde, oxazole and the like.

Examples of the reducing agent include inorganic acids such as sulfuric acid and the like; organic acids such as formic acid and the like; borohydrides such as sodium borohydride, sodium cyanoborohydride and the like; boronic acid, lithium aluminum hydride and the like.

The reaction temperature may be suitably selected in the range of −20 degree centigrade to the reflux temperature of a solvent in use, while the reaction time may be properly selected in the range of several minutes to 96 hours.

Preparation Method 10

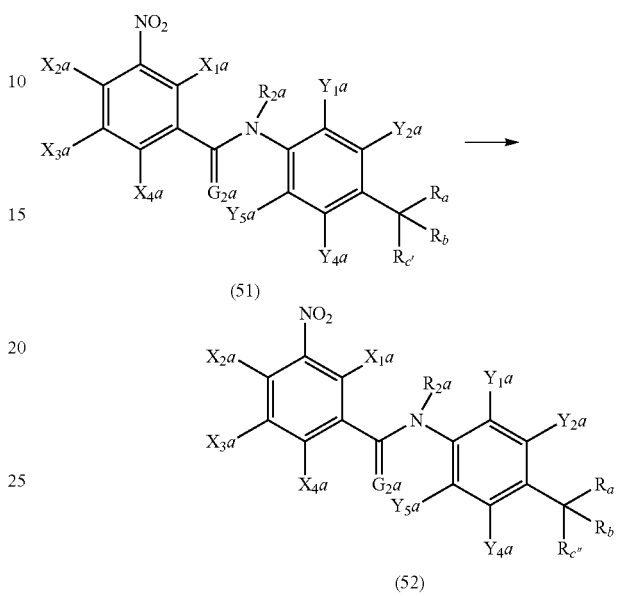

wherein, in the formula, $X_1a$, $X_2a$, $X_3a$, $X_4a$, $Y_1a$, $Y_2a$, $Y_4a$, $Y_5a$, $G_2a$, $R_2a$, $R_a$ and $R_b$ represent the same as those described above; $R_c'$ in the general formula (51) represents a hydroxy group or —O—$R_d$ ($R_d$ represents the same as those described above); and $R_c''$ in the general formula (52) represents a chlorine atom, a bromine atom or an iodine atom.

By reacting a compound represented by the general formula (51) with a suitable halogenating agent in an appropriate solvent or without a solvent, a chlorine compound (a bromine compound or an iodine compound) represented by the general formula (52) can be prepared. In this process, an appropriate additive can also be used.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of two or more kinds.

Examples of the halogenating agent include thionyl chloride, thionyl bromide, phosphorus oxychloride, oxalyl chloride, phosphorus trichloride, phosphorus tribromide, phosphorus pentachloride, Rydon reagents, sulfonyl halides such as methanesulfonyl chloride, p-toluenesulfonyl chloride, benzenesulfonyl chloride and the like, sulfonium halides, sulfonate esters, chlorine, bromine, iodine, hypohalite esters, N-halogenoamines, hydrogen chloride, hydrogen bromide, sodium bromide, potassium bromide, cyanuric chloride, 1,3-dichloro-1,2,4-triazole, titanium (IV) chloride, vanadium (IV) chloride, arsenic (III) chloride, N,N-diethyl-1,2,2-trichlorovinylamine, trichloroacetonitrile, sodium chloride, ammonium bromide, N,N-dimethylchloroforminium chloride, N,N-dimethylchloroforminium bromide, phosphorus trichloride, phosphorus tribromide, N,N-dimethyl phosphoamidine dichloride and the like.

Examples of the additive include metal salts such as zinc chloride, lithium bromide and the like; a phase transfer catalyst; organic bases such as hexamethylphosphoric triamide and the like; inorganic acids such as sulfuric acid and the like; N,N-dimethylformamide and the like.

The halogenating agents may be suitably selected in the range of 0.01 to 10 mole equivalents, based on the compound represented by the general formula (1) or may be used as a solvent.

The reaction temperature may be suitably selected in the range of −80 degree centigrade to the reflux temperature of a solvent in use, while the reaction time may be properly selected in the range of several minutes to 96 hours.

Preparation Method 11

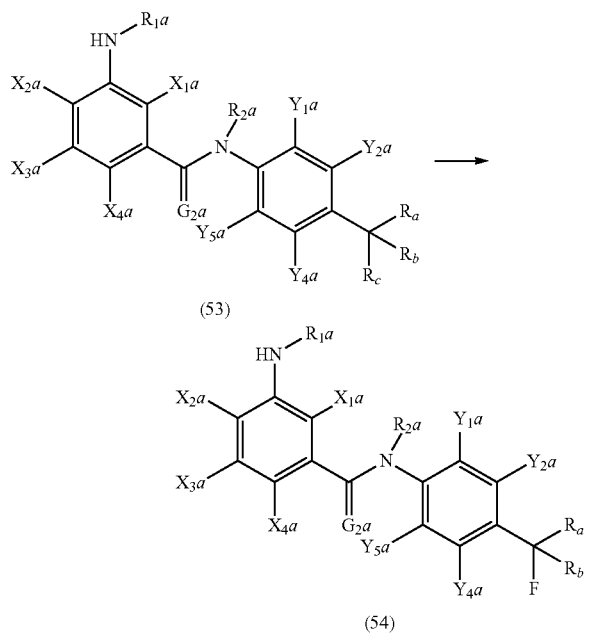

wherein, in the formula, $X_1a$, $X_2a$, $X_3a$, $X_4a$, $Y_1a$, $Y_2a$, $Y_4a$, $Y_5a$, $G_2a$, $R_1a$, $R_2a$, $R_a$, $R_b$ and $R_c$ represent the same as those described above.

By reacting a compound represented by the general formula (53) with a suitable fluorinating agent in an appropriate solvent or without a solvent, a compound represented by the general formula (54) can be prepared.

Solvents may not remarkably hinder the progress of the reaction and examples thereof include aliphatic hydrocarbons such as hexane, cyclohexane, methylcyclohexane and the like; aromatic hydrocarbons such as benzene, xylene, toluene and the like; halogenated hydrocarbons such as dichloromethane, chloroform, carbon tetrachloride, 1,2-dichloroethane and the like; ethers such as diethyl ether, dioxane, tetrahydrofuran, 1,2-dimethoxyethane and the like; amides such as dimethylformamide, dimethylacetamide and the like; nitriles such as acetonitrile, propionitrile and the like; ketones such as acetone, methylisobutyl ketone, cyclohexanone, methylethyl ketone and the like; esters such as ethyl acetate, butyl acetate and the like; alcohols such as 1,3-dimethyl-2-imidazolidinone, sulfolane, dimethylsulfoxide, methanol, ethanol and the like; water and the like. These solvents can be used singly or in combination of two or more kinds.

Examples of the fluorinating agent include 1,1,2,2-tetrafluoroethyldiethylamine, 2-chloro-1,1,2-trifluoroethyldiethylamine, trifluorodiphenylphosphorane, difluorotriphenylphosphorane, fluoroformate esters, sulfur tetrafluoride, potassium fluoride, potassium hydrogen fluoride, cesium fluoride, rubidium fluoride, sodium fluoride, lithium fluoride, antimony (III) fluoride, antimony (V) fluoride, zinc fluoride, cobalt fluoride, lead fluoride, copper fluoride, mercury (II) fluoride, silver fluoride, silver fluoroborate, thallium (I) fluoride, molybdenum (VI) fluoride, arsenic (III) fluoride, bromine fluoride, selenium tetrafluoride, tris(dimethylamino) sulfonium difluorotrimethylsilicate, sodium hexafluorosilicate, quaternary ammonium fluoride, (2-chloroethyl)diethylamine, diethylaminosulfur trifluoride, morpholinosulfur trifluoride, silicon tetrafluoride, hydrogen fluoride, hydrofluoric acid, hydrogen fluoride pyridine complex, hydrogen fluoride triethylamine complex, hydrogen fluoride salt, bis(2-methoxyethyl)aminosulfur trifluoride, 2,2-difluoro-1,3-dimethyl-2-imidazolidinone, iodine pentafluoride, tris(diethylamino)phosphonium-2,2,3,3,4,4-hexafluoro-cyclobutane ylide, triethylammonium hexafluorocyclobutane ylide, hexafluoropropene and the like. These fluorinating agents can be used singly or in combination of two or more kinds. These halogenating agents may be suitably selected in the range of 1 to 10 mole equivalents, based on the compound represented by the general formula (53) or may be suitably used as a solvent.

An additive may also be used and examples thereof include crown ethers such as 18-crown-6 and the like; phase transfer catalysts such as tetraphenylphosphonium salts and the like; inorganic salts such as calcium fluoride, calcium chloride and the like; metal oxides such as mercury oxide and the like; ion exchange resins and the like. The additive can be not only added in the reaction system, but also used as a pretreatment agent of the fluorinating agent.

The reaction temperature may be suitably selected in the range of −80 degree centigrade to the reflux temperature of a solvent in use, while the reaction time may be properly selected in the range of several minutes to 96 hours.

Preparation Method 12

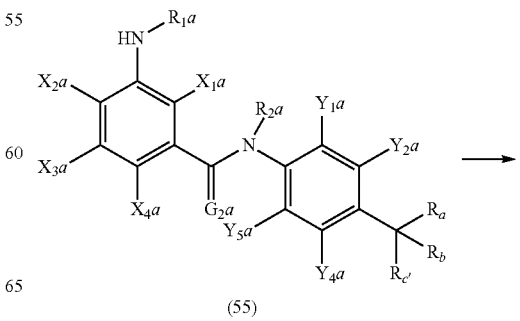

-continued

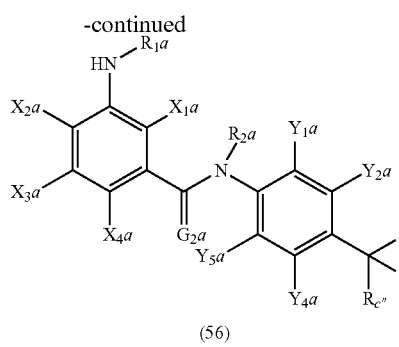

(56)

wherein, in the formula, $X_1a$, $X_2a$, $X_3a$, $X_4a$, $Y_1a$, $Y_2a$, $Y_4a$, $Y_5a$, $G_2a$, $R_1a$, $R_2a$, $R_a$, $R_b$, $R_c'$ and $R_c''$ represent the same as those described above.

A compound represented by the general formula (56) can be prepared from a compound represented by the general formula (55) in accordance with the method described in the preparation method 10.

Preparation Method 13

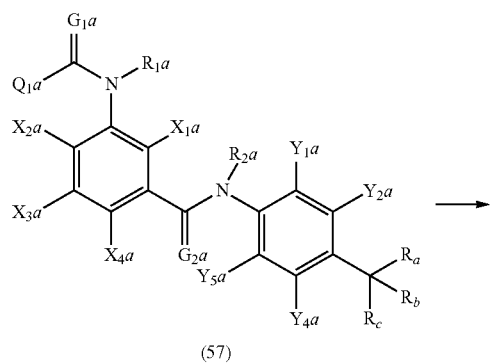

(57)

(58)

wherein, in the formula, $X_1a$, $X_2a$, $X_3a$, $X_4a$, $Y_1a$, $Y_2a$, $Y_4a$, $Y_5a$, $G_1a$, $G_2a$, $R_1a$, $R_2a$, $R_a$, $R_b$, $R_c$ and $Q_1a$ represent the same as those described above.

A compound represented by the general formula (58) can be prepared from a compound represented by the general formula (57) in accordance with the method described in the preparation method 11.

Preparation Method 14

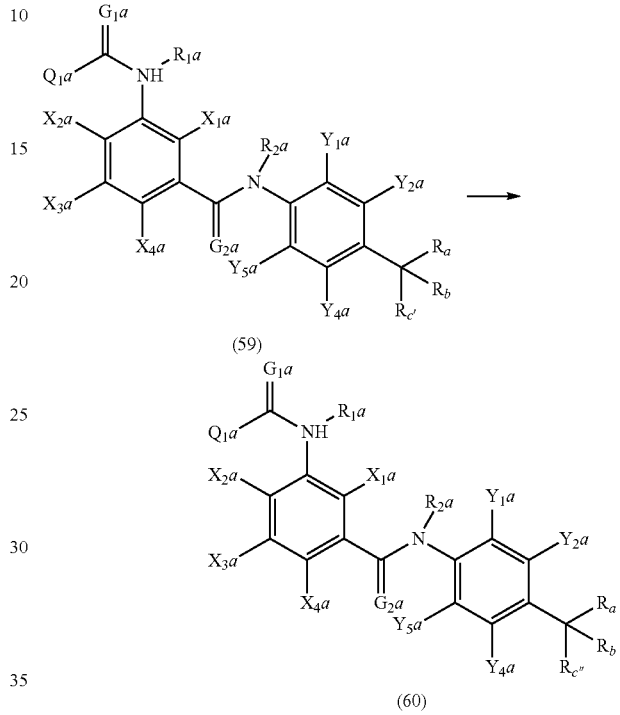

(59)

(60)

wherein, in the formula, $X_1a$, $X_2a$, $X_3a$, $X_4a$, $Y_1a$, $Y_2a$, $Y_4a$, $Y_5a$, $G_1a$, $G_2a$, $R_1a$, $R_2a$, $R_a$, $R_b$, $R_c'$, $R_c''$ and $Q_1a$ represent the same as those described above.

A compound represented by the general formula (60) can be prepared from a compound represented by the general formula (59) in accordance with the method described in the preparation method 10.

In all preparation methods as illustrated above, desired products may be isolated according to a usual method from the reaction system after completion of the reaction, but can be purified, if necessary, by carrying out operations such as recrystallization, column chromatography, distillation and the like. Furthermore, desired products can also be supplied to the next reaction process without isolating them from the reaction system.

Typical compounds of the compound represented by the general formula (1) of the present invention are illustrated in Tables 1 to 5 below, but the present invention is not restricted thereto.

Incidentally, in the tables, "n-" refers to normal, "Me" refers to a methyl group, "Et" refers to an ethyl group, "n-Pr" refers to a normal propyl group, "i-Pr" refers to an isopropyl group, "n-Bu" refers to a normal butyl group, "i-Bu" refers to an isobutyl group, "s-Bu" refers to a secondary butyl group, "t-Bu" refers to a tertiary butyl group, "H" refers to a hydrogen atom, "O" refers to an oxygen atom, "S" refers to a sulfur atom, "C" refers to a carbon atom, "N" refers to a nitrogen atom, "F" refers to a fluorine atom, "Cl" refers to a chlorine atom, "Br" refers to a bromine atom, "I" refers to an iodine atom, "CF₃" refers to a trifluoromethyl group, "MeS" refers to a methylthio group, "MeSO" refers to a methylsulfinyl group, "MeSO₂" refers to a methylsulfonyl group, "MeO" refers to a methoxy group, "NH₂" refers to an amino group, "MeNH" refers to a methylamino group, "Me₂N" refers to a dimethylamino group, and "OH" refers to a hydroxy group.

TABLE 1

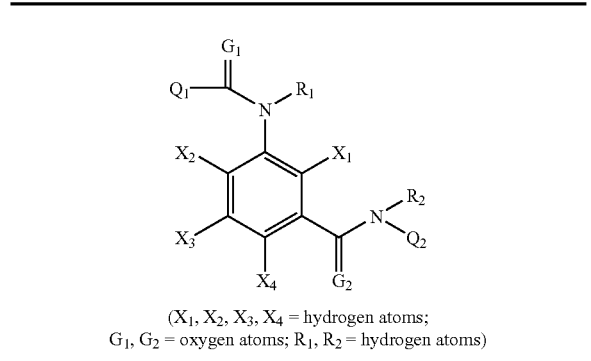

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 1 | phenyl | 2,6-dimethyl-4-(pentafluoroethyl)phenyl |
| 2 | phenyl | 2,6-dichloro-4-(pentafluoroethyl)phenyl |
| 3 | 2-fluorophenyl | 2,6-dichloro-4-(pentafluoroethyl)phenyl |
| 4 | phenyl | 2,6-dibromo-4-(pentafluoroethyl)phenyl |
| 5 | 2-fluorophenyl | 2,6-dibromo-4-(pentafluoroethyl)phenyl |
| 6 | phenyl | 2,6-dichloro-4-(heptafluoroisopropyl)phenyl |
| 7 | phenyl | 2,6-dibromo-4-(heptafluoroisopropyl)phenyl |
| 8 | 2-fluorophenyl | 2,6-dibromo-4-(heptafluoroisopropyl)phenyl |
| 9 | phenyl | 2,6-dimethyl-4-(heptafluoro-n-propyl)phenyl |
| 10 | phenyl | 2,6-dimethyl-4-(heptafluoroisopropyl)phenyl |
| 11 | 2-methylphenyl | 2,6-dimethyl-4-(heptafluoroisopropyl)phenyl |
| 12 | 3-methylphenyl | 2,6-dimethyl-4-(heptafluoroisopropyl)phenyl |
| 13 | 4-methylphenyl | 2,6-dimethyl-4-(heptafluoroisopropyl)phenyl |
| 14 | 2-ethylphenyl | 2,6-dimethyl-4-(heptafluoroisopropyl)phenyl |
| 15 | 3-ethylphenyl | 2,6-dimethyl-4-(heptafluoroisopropyl)phenyl |
| 16 | 4-ethylphenyl | 2,6-dimethyl-4-(heptafluoroisopropyl)phenyl |
| 17 | 2-fluorophenyl | 2,6-dimethyl-4-(heptafluoroisopropyl)phenyl |
| 18 | 3-fluorophenyl | 2,6-dimethyl-4-(heptafluoroisopropyl)phenyl |
| 19 | 4-fluorophenyl | 2,6-dimethyl-4-(heptafluoroisopropyl)phenyl |
| 20 | 2-chlorophenyl | 2,6-dimethyl-4-(heptafluoroisopropyl)phenyl |
| 21 | 3-chlorophenyl | 2,6-dimethyl-4-(heptafluoroisopropyl)phenyl |
| 22 | 4-chlorophenyl | 2,6-dimethyl-4-(heptafluoroisopropyl)phenyl |
| 23 | 2-bromophenyl | 2,6-dimethyl-4-(heptafluoroisopropyl)phenyl |
| 24 | 3-bromophenyl | 2,6-dimethyl-4-(heptafluoroisopropyl)phenyl |
| 25 | 4-bromophenyl | 2,6-dimethyl-4-(heptafluoroisopropyl)phenyl |
| 26 | 2-iodophenyl | 2,6-dimethyl-4-(heptafluoroisopropyl)phenyl |

TABLE 1-continued

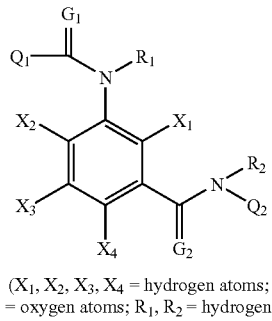

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 27 | 3-iodophenyl | 2,6-dimethyl-4-(heptafluoroisopropyl)phenyl |
| 28 | 4-iodophenyl | 2,6-dimethyl-4-(heptafluoroisopropyl)phenyl |
| 29 | 3-cyanophenyl | 2,6-dimethyl-4-(heptafluoroisopropyl)phenyl |
| 30 | 4-cyanophenyl | 2,6-dimethyl-4-(heptafluoroisopropyl)phenyl |
| 31 | 2-nitrophenyl | 2,6-dimethyl-4-(heptafluoroisopropyl)phenyl |
| 32 | 3-nitrophenyl | 2,6-dimethyl-4-(heptafluoroisopropyl)phenyl |
| 33 | 4-nitrophenyl | 2,6-dimethyl-4-(heptafluoroisopropyl)phenyl |
| 34 | 2-aminophenyl | 2,6-dimethyl-4-(heptafluoroisopropyl)phenyl |
| 35 | 3-aminophenyl | 2,6-dimethyl-4-(heptafluoroisopropyl)phenyl |
| 36 | 4-aminophenyl | 2,6-dimethyl-4-(heptafluoroisopropyl)phenyl |
| 37 | 2-trifluoromethylphenyl | 2,6-dimethyl-4-(heptafluoroisopropyl)phenyl |
| 38 | 3-trifluoromethylphenyl | 2,6-dimethyl-4-(heptafluoroisopropyl)phenyl |
| 39 | 4-trifluoromethylphenyl | 2,6-dimethyl-4-(heptafluoroisopropyl)phenyl |
| 40 | 2-hydroxyphenyl | 2,6-dimethyl-4-(heptafluoroisopropyl)phenyl |
| 41 | 2-methoxyphenyl | 2,6-dimethyl-4-(heptafluoroisopropyl)phenyl |
| 42 | 3-methoxyphenyl | 2,6-dimethyl-4-(heptafluoroisopropyl)phenyl |
| 43 | 4-methoxyphenyl | 2,6-dimethyl-4-(heptafluoroisopropyl)phenyl |
| 44 | 2-phenoxyphenyl | 2,6-dimethyl-4-(heptafluoroisopropyl)phenyl |
| 45 | 4-(1,1-dimethylethyl)phenyl | 2,6-dimethyl-4-(heptafluoroisopropyl)phenyl |
| 46 | 3-(dimethylamino)phenyl | 2,6-dimethyl-4-(heptafluoroisopropyl)phenyl |
| 47 | 4-(dimethylamino)phenyl | 2,6-dimethyl-4-(heptafluoroisopropyl)phenyl |
| 48 | 4-trifluoromethoxyphenyl | 2,6-dimethyl-4-(heptafluoroisopropyl)phenyl |
| 49 | 2-(acetylamino)phenyl | 2,6-dimethyl-4-(heptafluoroisopropyl)phenyl |
| 50 | 3-(acetylamino)phenyl | 2,6-dimethyl-4-(heptafluoroisopropyl)phenyl |
| 51 | 4-(acetylamino)phenyl | 2,6-dimethyl-4-(heptafluoroisopropyl)phenyl |
| 52 | 2-acetoxyphenyl | 2,6-dimethyl-4-(heptafluoroisopropyl)phenyl |
| 53 | 2-(methoxycarbonyl)phenyl | 2,6-dimethyl-4-(heptafluoroisopropyl)phenyl |
| 54 | 4-(methoxycarbonyl)phenyl | 2,6-dimethyl-4-(heptafluoroisopropyl)phenyl |
| 55 | 2-(4-trifluoromethylphenyl)phenyl | 2,6-dimethyl-4-(heptafluoroisopropyl)phenyl |
| 56 | 2,3-dimethylphenyl | 2,6-dimethyl-4-(heptafluoroisopropyl)phenyl |

TABLE 1-continued

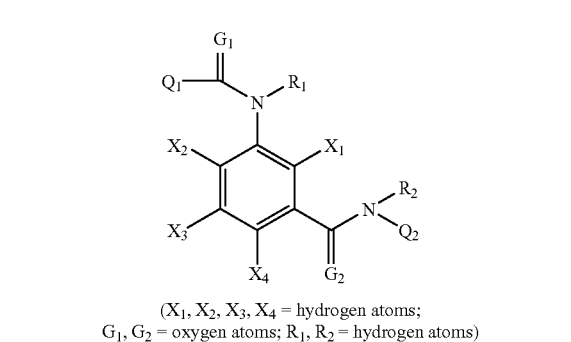

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
| --- | --- | --- |
| 57 | 2,4-dimethylphenyl | 2,6-dimethyl-4-(heptafluoroisopropyl)phenyl |
| 58 | 2,6-dimethylphenyl | 2,6-dimethyl-4-(heptafluoroisopropyl)phenyl |
| 59 | 2,3-difluorophenyl | 2,6-dimethyl-4-(heptafluoroisopropyl)phenyl |
| 60 | 2,4-difluorophenyl | 2,6-dimethyl-4-(heptafluoroisopropyl)phenyl |
| 61 | 2,5-difluorophenyl | 2,6-dimethyl-4-(heptafluoroisopropyl)phenyl |
| 62 | 2,6-difluorophenyl | 2,6-dimethyl-4-(heptafluoroisopropyl)phenyl |
| 63 | 3,4-difluorophenyl | 2,6-dimethyl-4-(heptafluoroisopropyl)phenyl |
| 64 | 3,5-difluorophenyl | 2,6-dimethyl-4-(heptafluoroisopropyl)phenyl |
| 65 | 2,3-dichlorophenyl | 2,6-dimethyl-4-(heptafluoroisopropyl)phenyl |
| 66 | 2,4-dichlorophenyl | 2,6-dimethyl-4-(heptafluoroisopropyl)phenyl |
| 67 | 2,5-dichlorophenyl | 2,6-dimethyl-4-(heptafluoroisopropyl)phenyl |
| 68 | 2,6-dichlorophenyl | 2,6-dimethyl-4-(heptafluoroisopropyl)phenyl |
| 69 | 3,4-dichlorophenyl | 2,6-dimethyl-4-(heptafluoroisopropyl)phenyl |
| 70 | 2,4-dinitrophenyl | 2,6-dimethyl-4-(heptafluoroisopropyl)phenyl |
| 71 | 3,4-dinitrophenyl | 2,6-dimethyl-4-(heptafluoroisopropyl)phenyl |
| 72 | 2,6-dimethoxyphenyl | 2,6-dimethyl-4-(heptafluoroisopropyl)phenyl |
| 73 | 3,5-dimethoxyphenyl | 2,6-dimethyl-4-(heptafluoroisopropyl)phenyl |
| 74 | 3-methyl-4-nitrophenyl | 2,6-dimethyl-4-(heptafluoroisopropyl)phenyl |
| 75 | 5-amino-2-fluorophenyl | 2,6-dimethyl-4-(heptafluoroisopropyl)phenyl |
| 76 | 3-fluoro-2-methylphenyl | 2,6-dimethyl-4-(heptafluoroisopropyl)phenyl |
| 77 | 2-fluoro-5-nitrophenyl | 2,6-dimethyl-4-(heptafluoroisopropyl)phenyl |
| 78 | 4-fluoro-3-nitrophenyl | 2,6-dimethyl-4-(heptafluoroisopropyl)phenyl |
| 79 | 5-fluoro-2-nitrophenyl | 2,6-dimethyl-4-(heptafluoroisopropyl)phenyl |
| 80 | 2-fluoro-6-iodophenyl | 2,6-dimethyl-4-(heptafluoroisopropyl)phenyl |
| 81 | 2-fluoro-5-trifluoromethylphenyl | 2,6-dimethyl-4-(heptafluoroisopropyl)phenyl |
| 82 | 2-chloro-4-nitrophenyl | 2,6-dimethyl-4-(heptafluoroisopropyl)phenyl |
| 83 | 2-chloro-4-fluorophenyl | 2,6-dimethyl-4-(heptafluoroisopropyl)phenyl |
| 84 | 2-chloro-6-fluorophenyl | 2,6-dimethyl-4-(heptafluoroisopropyl)phenyl |
| 85 | 3-chloro-4-fluorophenyl | 2,6-dimethyl-4-(heptafluoroisopropyl)phenyl |
| 86 | 4-chloro-2-fluorophenyl | 2,6-dimethyl-4-(heptafluoroisopropyl)phenyl |
| 87 | 4-chloro-2-nitrophenyl | 2,6-dimethyl-4-(heptafluoroisopropyl)phenyl |
| 88 | 3-methoxy-4-nitrophenyl | 2,6-dimethyl-4-(heptafluoroisopropyl)phenyl |
| 89 | 2-methoxy-4-nitrophenyl | 2,6-dimethyl-4-(heptafluoroisopropyl)phenyl |
| 90 | 2,3,4-trifluorophenyl | 2,6-dimethyl-4-(heptafluoroisopropyl)phenyl |
| 91 | 2,4,6-trimethylphenyl | 2,6-dimethyl-4-(heptafluoroisopropyl)phenyl |
| 92 | 2,3,6-trifluorophenyl | 2,6-dimethyl-4-(heptafluoroisopropyl)phenyl |
| 93 | 2,4,5-trimethoxyphenyl | 2,6-dimethyl-4-(heptafluoroisopropyl)phenyl |
| 94 | 3,4,5-trimethoxyphenyl | 2,6-dimethyl-4-(heptafluoroisopropyl)phenyl |
| 95 | 2,3,4,5,6-pentafluorophenyl | 2,6-dimethyl-4-(heptafluoroisopropyl)phenyl |
| 96 | 2-biphenyl | 2,6-dimethyl-4-(heptafluoroisopropyl)phenyl |
| 97 | 3-biphenyl | 2,6-dimethyl-4-(heptafluoroisopropyl)phenyl |
| 98 | 1-naphthyl | 2,6-dimethyl-4-(heptafluoroisopropyl)phenyl |
| 99 | 2-naphthyl | 2,6-dimethyl-4-(heptafluoroisopropyl)phenyl |
| 100 | pyridin-2-yl | 2,6-dimethyl-4-(heptafluoroisopropyl)phenyl |
| 101 | pyridin-3-yl | 2,6-dimethyl-4-(heptafluoroisopropyl)phenyl |
| 102 | pyridin-4-yl | 2,6-dimethyl-4-(heptafluoroisopropyl)phenyl |
| 103 | 2-methyl pyridin-5-yl | 2,6-dimethyl-4-(heptafluoroisopropyl)phenyl |
| 104 | 3-methyl pyridin-2-yl | 2,6-dimethyl-4-(heptafluoroisopropyl)phenyl |
| 105 | 2-fluoro pyridin-3-yl | 2,6-dimethyl-4-(heptafluoroisopropyl)phenyl |
| 106 | 2-chloro pyridin-3-yl | 2,6-dimethyl-4-(heptafluoroisopropyl)phenyl |
| 107 | 2-chloro pyridin-4-yl | 2,6-dimethyl-4-(heptafluoroisopropyl)phenyl |
| 108 | 2-chloro pyridin-6-yl | 2,6-dimethyl-4-(heptafluoroisopropyl)phenyl |
| 109 | 2-chloro pyridin-5-yl | 2,6-dimethyl-4-(heptafluoroisopropyl)phenyl |
| 110 | 5-chloro pyridin-2-yl | 2,6-dimethyl-4-(heptafluoroisopropyl)phenyl |
| 111 | 4-trifluoromethyl pyridin-3-yl | 2,6-dimethyl-4-(heptafluoroisopropyl)phenyl |
| 112 | 3-hydroxy pyridin-2-yl | 2,6-dimethyl-4-(heptafluoroisopropyl)phenyl |
| 113 | 2-phenoxy pyridin-3-yl | 2,6-dimethyl-4-(heptafluoroisopropyl)phenyl |
| 114 | 2-methylthio pyridin-3-yl | 2,6-dimethyl-4-(heptafluoroisopropyl)phenyl |
| 115 | 2,6-dimethoxy pyridin-3-yl | 2,6-dimethyl-4-(heptafluoroisopropyl)phenyl |
| 116 | 2,3-dichloro pyridin-5-yl | 2,6-dimethyl-4-(heptafluoroisopropyl)phenyl |

TABLE 1-continued

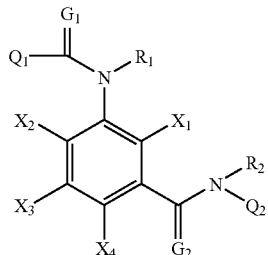

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 117 | 2,5-dichloro pyridin-3-yl | 2,6-dimethyl-4-(heptafluoroisopropyl)phenyl |
| 118 | 2,6-dichloro pyridin-3-yl | 2,6-dimethyl-4-(heptafluoroisopropyl)phenyl |
| 119 | 3,5-dichloro pyridin-4-yl | 2,6-dimethyl-4-(heptafluoroisopropyl)phenyl |
| 120 | pyridine-N-oxid-2-yl | 2,6-dimethyl-4-(heptafluoroisopropyl)phenyl |
| 121 | N-methylpyrrol-2-yl | 2,6-dimethyl-4-(heptafluoroisopropyl)phenyl |
| 122 | pyrazin-2-yl | 2,6-dimethyl-4-(heptafluoroisopropyl)phenyl |
| 123 | 2-methyl pyrazin-5-yl | 2,6-dimethyl-4-(heptafluoroisopropyl)phenyl |
| 124 | 4-trifluoromethyl pyrimidin-5-yl | 2,6-dimethyl-4-(heptafluoroisopropyl)phenyl |
| 125 | furan-2-yl | 2,6-dimethyl-4-(heptafluoroisopropyl)phenyl |
| 126 | furan-3-yl | 2,6-dimethyl-4-(heptafluoroisopropyl)phenyl |
| 127 | 2-tetrahydro furanyl | 2,6-dimethyl-4-(heptafluoroisopropyl)phenyl |
| 128 | 3-tetrahydro furanyl | 2,6-dimethyl-4-(heptafluoroisopropyl)phenyl |
| 129 | benzofuran-2-yl | 2,6-dimethyl-4-(heptafluoroisopropyl)phenyl |
| 130 | tetrahydropyran-2-yl | 2,6-dimethyl-4-(heptafluoroisopropyl)phenyl |
| 131 | 2-methyl-5,6-dihydro-4H pyran-3-yl | 2,6-dimethyl-4-(heptafluoroisopropyl)phenyl |
| 132 | thiophen-2-yl | 2,6-dimethyl-4-(heptafluoroisopropyl)phenyl |
| 133 | thiophen-3-yl | 2,6-dimethyl-4-(heptafluoroisopropyl)phenyl |
| 134 | 3-methyl thiophen-2-yl | 2,6-dimethyl-4-(heptafluoroisopropyl)phenyl |
| 135 | 2-nitrothiophen-4-yl | 2,6-dimethyl-4-(heptafluoroisopropyl)phenyl |
| 136 | 2-methylthiophen-5-yl | 2,6-dimethyl-4-(heptafluoroisopropyl)phenyl |
| 137 | 3-chlorothiophen-2-yl | 2,6-dimethyl-4-(heptafluoroisopropyl)phenyl |
| 138 | 2-chlorothiophen-5-yl | 2,6-dimethyl-4-(heptafluoroisopropyl)phenyl |
| 139 | 3-bromothiophen-2-yl | 2,6-dimethyl-4-(heptafluoroisopropyl)phenyl |
| 140 | 2-bromothiophen-5-yl | 2,6-dimethyl-4-(heptafluoroisopropyl)phenyl |
| 141 | 3-iodothiophen-2-yl | 2,6-dimethyl-4-(heptafluoroisopropyl)phenyl |
| 142 | 3-phenylthiophen-2-yl | 2,6-dimethyl-4-(heptafluoroisopropyl)phenyl |
| 143 | 2,4-dimethyl thiophen-5-yl | 2,6-dimethyl-4-(heptafluoroisopropyl)phenyl |
| 144 | benzothiophen-2-yl | 2,6-dimethyl-4-(heptafluoroisopropyl)phenyl |
| 145 | 4-nitro-1H-pyrrole-2-yl | 2,6-dimethyl-4-(heptafluoroisopropyl)phenyl |
| 146 | 3-ethyl-3H-pyrazol-4-yl | 2,6-dimethyl-4-(heptafluoroisopropyl)phenyl |
| 147 | 1-methyl-3-nitro-1H-pyrazol-4-yl | 2,6-dimethyl-4-(heptafluoroisopropyl)phenyl |
| 148 | 3-chloro-1-methyl-1H-pyrazol-4-yl | 2,6-dimethyl-4-(heptafluoroisopropyl)phenyl |
| 149 | 3-bromo-1-methyl-1H-pyrazol-4-yl | 2,6-dimethyl-4-(heptafluoroisopropyl)phenyl |
| 150 | 1-methyl-3-trifluoromethyl-1H-pyrazol-4-yl | 2,6-dimethyl-4-(heptafluoroisopropyl)phenyl |
| 151 | 1-methyl-5-trifluoromethyl-1H-pyrazol-4-yl | 2,6-dimethyl-4-(heptafluoroisopropyl)phenyl |
| 152 | isoxazol-5-yl | 2,6-dimethyl-4-(heptafluoroisopropyl)phenyl |
| 153 | 4-trifluoro methylthiazol-5-yl | 2,6-dimethyl-4-(heptafluoroisopropyl)phenyl |
| 154 | 2,4-dimethyl thiazol-5-yl | 2,6-dimethyl-4-(heptafluoroisopropyl)phenyl |
| 155 | 2-ethyl-4-methyl thiazol-5-yl | 2,6-dimethyl-4-(heptafluoroisopropyl)phenyl |
| 156 | 2-chloro-4-methyl thiazol-5-yl | 2,6-dimethyl-4-(heptafluoroisopropyl)phenyl |
| 157 | 3-methyl isothiazol-5-yl | 2,6-dimethyl-4-(heptafluoroisopropyl)phenyl |
| 158 | 3,4-dichloro-isothiazol-5-yl | 2,6-dimethyl-4-(heptafluoroisopropyl)phenyl |
| 159 | 3-chlorobenzo thiazol-2-yl | 2,6-dimethyl-4-(heptafluoroisopropyl)phenyl |
| 160 | 2,2-difluoro-benzo[1.3]dioxol-5-yl | 2,6-dimethyl-4-(heptafluoroisopropyl)phenyl |
| 161 | 2,2-difluoro-benzo[1.3]dioxol-4-yl | 2,6-dimethyl-4-(heptafluoroisopropyl)phenyl |
| 162 | 2-phenylquinoline-4-yl | 2,6-dimethyl-4-(heptafluoroisopropyl)phenyl |
| 163 | phenyl | 2-bromo-4-(heptafluoro-isopropyl)-6-methylphenyl |
| 164 | phenyl | 2-ethyl-4-(heptafluoro-isopropyl)-6-methylphenyl |
| 165 | 2-fluorophenyl | 2-ethyl-4-(heptafluoro-isopropyl)-6-methylphenyl |
| 166 | phenyl | 4-(heptafluoroisopropyl)-2-iodo-6-methylphenyl |
| 167 | phenyl | 4-(heptafluoroisopropyl)-2-hydroxy-6-methylphenyl |
| 168 | phenyl | 2-chloro-6-ethyl-4-(heptafluoro isopropyl)phenyl |
| 169 | phenyl | 2-bromo-6-ethyl-4-(heptafluoro isopropyl)phenyl |
| 170 | 2-fluorophenyl | 2-bromo-6-ethyl-4-(heptafluoro isopropyl)phenyl |
| 171 | phenyl | 2-ethyl-4-(heptafluoroisopropyl)-6-iodophenyl |
| 172 | 2-fluorophenyl | 2-ethyl-4-(heptafluoroisopropyl)-6-iodophenyl |
| 173 | 4-nitrophenyl | 2-ethyl-4-(heptafluoroisopropyl)-6-iodophenyl |
| 174 | 4-cyanophenyl | 2-ethyl-4-(heptafluoroisopropyl)-6-iodophenyl |
| 175 | 4-nitrophenyl | 4-(heptafluoroisopropyl)-2-methyl-6-n-propylphenyl |

TABLE 1-continued

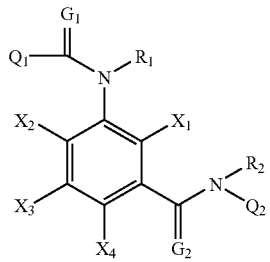

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 176 | phenyl | 4-(heptafluoroisopropyl)-2-isopropyl-6-methylphenyl |
| 177 | 2-fluorophenyl | 4-(heptafluoroisopropyl)-2-isopropyl-6-methylphenyl |
| 178 | phenyl | 2-bromo-4-(heptafluoro-isopropyl)-6-n-propylphenyl |
| 179 | 2-fluorophenyl | 2-bromo-4-(heptafluoro-isopropyl)-6-n-propylphenyl |
| 180 | 4-nitrophenyl | 2-bromo-4-(heptafluoro-isopropyl)-6-n-propylphenyl |
| 181 | 4-cyanophenyl | 2-bromo-4-(heptafluoro-isopropyl)-6-n-propylphenyl |
| 182 | phenyl | 4-(heptafluoroisopropyl)-2-iodo-6-n-propylphenyl |
| 183 | 2-fluorophenyl | 4-(heptafluoroisopropyl)-2-iodo-6-n-propylphenyl |
| 184 | 4-nitrophenyl | 4-(heptafluoroisopropyl)-2-iodo-6-n-propylphenyl |
| 185 | 4-cyanophenyl | 4-(heptafluoroisopropyl)-2-iodo-6-n-propylphenyl |
| 186 | 4-trifluoromethyl phenyl | 4-(heptafluoroisopropyl)-2-iodo-6-n-propylphenyl |
| 187 | phenyl | 2-chloro-4-(heptafluoro-isopropyl)-6-n-butylphenyl |
| 188 | 2-fluorophenyl | 2-chloro-4-(heptafluoro-isopropyl)-6-n-butylphenyl |
| 189 | phenyl | 2-bromo-4-(heptafluoro-isopropyl)-6-n-butylphenyl |
| 190 | 2-fluorophenyl | 2-bromo-4-(heptafluoro-isopropyl)-6-n-butylphenyl |
| 191 | phenyl | 4-(heptafluoroisopropyl)-2-iodo-6-n-butylphenyl |
| 192 | 2-fluorophenyl | 4-(heptafluoroisopropyl)-2-iodo-6-n-butylphenyl |
| 193 | phenyl | 2-(2-butyl)-6-chloro-4-(heptafluoro isopropyl)phenyl |
| 194 | phenyl | 2-bromo-6-(2-butyl)4-(hepta fluoroisopropyl)phenyl |
| 195 | 2-fluorophenyl | 2-bromo-6-(2-butyl)-4-(hepta fluoroisopropyl)phenyl |
| 196 | phenyl | 2-(2-butyl)-4-(heptafluoro-isopropyl)-6-iodophenyl |
| 197 | 2-fluorophenyl | 2-bromo-6-cyano-4-(heptafluoro isopropyl)phenyl |
| 198 | phenyl | 2-bromo-4-(heptafluoro-isopropyl)-6-methylthiophenyl |
| 199 | 2-fluorophenyl | 2-bromo-4-(heptafluoro-isopropyl)-6-methylthiophenyl |
| 200 | phenyl | 2-bromo-4-(heptafluoro-isopropyl)-6-(methylsulfinyl) phenyl |
| 201 | 2-fluorophenyl | 2-chloro-4-(heptafluoro-isopropyl)-6-(methylsulfonyl) phenyl |
| 202 | 2-chloropyridin-3-yl | 2-chloro-4-(heptafluoro-isopropyl)-6-(methylsulfonyl) phenyl |
| 203 | phenyl | 2-bromo-4-(heptafluoro-isopropyl)-6-(methylsulfonyl) phenyl |

TABLE 1-continued

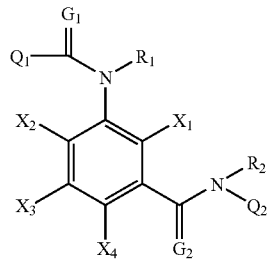

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 204 | 2-fluorophenyl | 2-bromo-4-(heptafluoro-isopropyl)-6-(methylsulfonyl) phenyl |
| 205 | 4-fluorophenyl | 2-bromo-4-(heptafluoro-isopropyl)-6-(methylsulfonyl) phenyl |
| 206 | 4-nitrophenyl | 2-bromo-4-(heptafluoro-isopropyl)-6-(methylsulfonyl) phenyl |
| 207 | 4-cyanophenyl | 2-bromo-4-(heptafluoro-isopropyl)-6-(methylsulfonyl) phenyl |
| 208 | 2-chloropyridin-3-yl | 2-bromo-4-(heptafluoro-isopropyl)-6-(methylsulfonyl) phenyl |
| 209 | phenyl | 4-(heptafluoroisopropyl)-2-methyl thiomethyl-6-trifluoro-methylphenyl |
| 210 | phenyl | 2-bromo-4-(heptafluoro-isopropyl)-6-(trifluoromethyl-thio)phenyl |
| 211 | phenyl | 2,6-dimethyl-4-(nonafluoro-n-butyl)phenyl |
| 212 | phenyl | 2,6-dimethyl-4-(nonafluoro-2-butyl)phenyl |
| 213 | 2-methylphenyl | 2,6-dimethyl-4-(nonafluoro-2-butyl)phenyl |
| 214 | 4-methylphenyl | 2,6-dimethyl-4-(nonafluoro-2-butyl)phenyl |
| 215 | 2-fluorophenyl | 2,6-dimethyl-4-(nonafluoro-2-butyl)phenyl |
| 216 | 3-fluorophenyl | 2,6-dimethyl-4-(nonafluoro-2-butyl)phenyl |
| 217 | 4-fluorophenyl | 2,6-dimethyl-4-(nonafluoro-2-butyl)phenyl |
| 218 | 2-chlorophenyl | 2,6-dimethyl-4-(nonafluoro-2-butyl)phenyl |
| 219 | 4-chlorophenyl | 2,6-dimethyl-4-(nonafluoro-2-butyl)phenyl |
| 220 | 2-bromophenyl | 2,6-dimethyl-4-(nonafluoro-2-butyl)phenyl |
| 221 | 2-iodophenyl | 2,6-dimethyl-4-(nonafluoro-2-butyl)phenyl |
| 222 | 3-cyanophenyl | 2,6-dimethyl-4-(nonafluoro-2-butyl)phenyl |
| 223 | 4-cyanophenyl | 2,6-dimethyl-4-(nonafluoro-2-butyl)phenyl |
| 224 | 2-nitrophenyl | 2,6-dimethyl-4-(nonafluoro-2-butyl)phenyl |
| 225 | 3-nitrophenyl | 2,6-dimethyl-4-(nonafluoro-2-butyl)phenyl |
| 226 | 4-nitrophenyl | 2,6-dimethyl-4-(nonafluoro-2-butyl)phenyl |
| 227 | 2-trifluoromethyl phenyl | 2,6-dimethyl-4-(nonafluoro-2-butyl)phenyl |
| 228 | 4-trifluoromethyl phenyl | 2,6-dimethyl-4-(nonafluoro-2-butyl)phenyl |
| 229 | 4-trifluoromethoxy phenyl | 2,6-dimethyl-4-(nonafluoro-2-butyl)phenyl |
| 230 | 2,3-difluorophenyl | 2,6-dimethyl-4-(nonafluoro-2-butyl)phenyl |

TABLE 1-continued

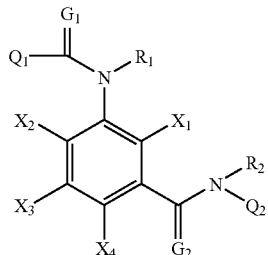

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 231 | 2,4-difluorophenyl | 2,6-dimethyl-4-(nonafluoro-2-butyl)phenyl |
| 232 | 2,5-difluorophenyl | 2,6-dimethyl-4-(nonafluoro-2-butyl)phenyl |
| 233 | 2,6-difluorophenyl | 2,6-dimethyl-4-(nonafluoro-2-butyl)phenyl |
| 234 | 2,4-dichlorophenyl | 2,6-dimethyl-4-(nonafluoro-2-butyl)phenyl |
| 235 | 2,6-dichlorophenyl | 2,6-dimethyl-4-(nonafluoro-2-butyl)phenyl |
| 236 | 3,4-dichlorophenyl | 2,6-dimethyl-4-(nonafluoro-2-butyl)phenyl |
| 237 | 2-chloro-4-nitro phenyl | 2,6-dimethyl-4-(nonafluoro-2-butyl)phenyl |
| 238 | 2-chloro-4-fluoro phenyl | 2,6-dimethyl-4-(nonafluoro-2-butyl)phenyl |
| 239 | 2-chloro-6-fluoro phenyl | 2,6-dimethyl-4-(nonafluoro-2-butyl)phenyl |
| 240 | 4-chloro-2-fluoro phenyl | 2,6-dimethyl-4-(nonafluoro-2-butyl)phenyl |
| 241 | 4-chloro-2-nitrophenyl | 2,6-dimethyl-4-(nonafluoro-2-butyl)phenyl |
| 242 | 2,3,6-trifluoro phenyl | 2,6-dimethyl-4-(nonafluoro-2-butyl)phenyl |
| 243 | pyridin-2-yl | 2,6-dimethyl-4-(nonafluoro-2-butyl)phenyl |
| 244 | pyridin-3-yl | 2,6-dimethyl-4-(nonafluoro-2-butyl)phenyl |
| 245 | 2-fluoropyridin-3-yl | 2,6-dimethyl-4-(nonafluoro-2-butyl)phenyl |
| 246 | 2-chloropyridin-3-yl | 2,6-dimethyl-4-(nonafluoro-2-butyl)phenyl |
| 247 | 2-chloropyridin-5-yl | 2,6-dimethyl-4-(nonafluoro-2-butyl)phenyl |
| 248 | 2-methylthio pyridin-3-yl | 2,6-dimethyl-4-(nonafluoro-2-butyl)phenyl |
| 249 | pyrazin-2-yl | 2,6-dimethyl-4-(nonafluoro-2-butyl)phenyl |
| 250 | furan-2-yl | 2,6-dimethyl-4-(nonafluoro-2-butyl)phenyl |
| 251 | furan-3-yl | 2,6-dimethyl-4-(nonafluoro-2-butyl)phenyl |
| 252 | 2-tetrahydro furanyl | 2,6-dimethyl-4-(nonafluoro-2-butyl)phenyl |
| 253 | benzofuran-2-yl | 2,6-dimethyl-4-(nonafluoro-2-butyl)phenyl |
| 254 | thiophen-2-yl | 2,6-dimethyl-4-(nonafluoro-2-butyl)phenyl |
| 255 | 2,6-difluorophenyl | 2,6-dichloro-4-(trifluoromethylthio)phenyl |
| 256 | phenyl | 2,6-dibromo-4-(trifluoromethylthio)phenyl |
| 257 | 2,6-difluorophenyl | 2,6-dibromo-4-(trifluoromethylthio)phenyl |
| 258 | phenyl | 2,6-dibromo-4-(pentafluoro-ethylthio)phenyl |
| 259 | 2-fluorophenyl | 2,6-dibromo-4-(pentafluoro-ethylthio)phenyl |
| 260 | phenyl | 2,6-dimethyl-4-(heptafluoro-n-propylthio)phenyl |

TABLE 1-continued

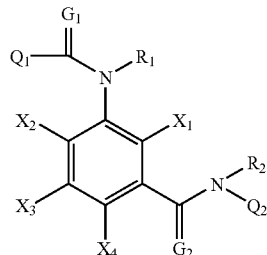

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 261 | 2-fluorophenyl | 2,6-dimethyl-4-(heptafluoro-n-propylthio)phenyl |
| 262 | phenyl | 2,6-dichloro-4-(heptafluoro-n-propylthio)phenyl |
| 263 | phenyl | 2,6-dibromo-4-(heptafluoro-n-propylthio)phenyl |
| 264 | 2-methylphenyl | 2,6-dibromo-4-(heptafluoro-n-propylthio)phenyl |
| 265 | 4-methylphenyl | 2,6-dibromo-4-(heptafluoro-n-propylthio)phenyl |
| 266 | 2-fluorophenyl | 2,6-dibromo-4-(heptafluoro-n-propylthio)phenyl |
| 267 | 3-fluorophenyl | 2,6-dibromo-4-(heptafluoro-n-propylthio)phenyl |
| 268 | 4-fluorophenyl | 2,6-dibromo-4-(heptafluoro-n-propylthio)phenyl |
| 269 | 2-chlorophenyl | 2,6-dibromo-4-(heptafluoro-n-propylthio)phenyl |
| 270 | 4-chlorophenyl | 2,6-dibromo-4-(heptafluoro-n-propylthio)phenyl |
| 271 | 2-bromophenyl | 2,6-dibromo-4-(heptafluoro-n-propylthio)phenyl |
| 272 | 2-iodophenyl | 2,6-dibromo-4-(heptafluoro-n-propylthio)phenyl |
| 273 | 3-cyanophenyl | 2,6-dibromo-4-(heptafluoro-n-propylthio)phenyl |
| 274 | 4-cyanophenyl | 2,6-dibromo-4-(heptafluoro-n-propylthio)phenyl |
| 275 | 2-nitrophenyl | 2,6-dibromo-4-(heptafluoro-n-propylthio)phenyl |
| 276 | 3-nitrophenyl | 2,6-dibromo-4-(heptafluoro-n-propylthio)phenyl |
| 277 | 4-nitrophenyl | 2,6-dibromo-4-(heptafluoro-n-propylthio)phenyl |
| 278 | 2-trifluoromethyl phenyl | 2,6-dibromo-4-(heptafluoro-n-propylthio)phenyl |
| 279 | 4-trifluoromethyl phenyl | 2,6-dibromo-4-(heptafluoro-n-propylthio)phenyl |
| 280 | 4-trifluoromethoxy phenyl | 2,6-dibromo-4-(heptafluoro-n-propylthio)phenyl |
| 281 | 2,3-difluorophenyl | 2,6-dibromo-4-(heptafluoro-n-propylthio)phenyl |
| 282 | 2,4-difluorophenyl | 2,6-dibromo-4-(heptafluoro-n-propylthio)phenyl |
| 283 | 2,5-difluorophenyl | 2,6-dibromo-4-(heptafluoro-n-propylthio)phenyl |
| 284 | 2,6-difluorophenyl | 2,6-dibromo-4-(heptafluoro-n-propylthio)phenyl |
| 285 | 3-aminophenyl | 2,6-dibromo-4-(heptafluoro-n-propylthio)phenyl |
| 286 | 3-(acetylamino) phenyl | 2,6-dibromo-4-(heptafluoro-n-propylthio)phenyl |
| 287 | 3-(methylsulfonyl amino)phenyl | 2,6-dibromo-4-(heptafluoro-n-propylthio)phenyl |
| 288 | 2,4-dinitrophenyl | 2,6-dibromo-4-(heptafluoro-n-propylthio)phenyl |
| 289 | 3,4-dinitrophenyl | 2,6-dibromo-4-(heptafluoro-n-propylthio)phenyl |
| 290 | 3-methyl-4-nitro phenyl | 2,6-dibromo-4-(heptafluoro-n-propylthio)phenyl |

TABLE 1-continued

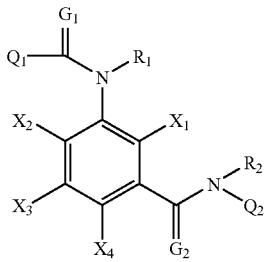

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 291 | 5-amino-2-fluoro phenyl | 2,6-dibromo-4-(heptafluoro-n-propylthio)phenyl |
| 292 | 2-fluoro-5-nitro phenyl | 2,6-dibromo-4-(heptafluoro-n-propylthio)phenyl |
| 293 | 2-fluoro-5-(methyl sulfonylamino) phenyl | 2,6-dibromo-4-(heptafluoro-n-propylthio)phenyl |
| 294 | 2-methoxy-4-nitrophenyl | 2,6-dibromo-4-(heptafluoro-n-propylthio)phenyl |
| 295 | 3-methoxy-4-nitrophenyl | 2,6-dibromo-4-(heptafluoro-n-propylthio)phenyl |
| 296 | 5-(acetylamino)-2 fluorophenyl | 2,6-dibromo-4-(heptafluoro-n-propylthio)phenyl |
| 297 | 2,4-dichlorophenyl | 2,6-dibromo-4-(heptafluoro-n-propylthio)phenyl |
| 298 | 2,6-dichlorophenyl | 2,6-dibromo-4-(heptafluoro-n-propylthio)phenyl |
| 299 | 3,4-dichlorophenyl | 2,6-dibromo-4-(heptafluoro-n-propylthio)phenyl |
| 300 | 2-chloro-4-nitrophenyl | 2,6-dibromo-4-(heptafluoro-n-propylthio)phenyl |
| 301 | 2-chloro-4-fluorophenyl | 2,6-dibromo-4-(heptafluoro-n-propylthio)phenyl |
| 302 | 2-chloro-6-fluorophenyl | 2,6-dibromo-4-(heptafluoro-n-propylthio)phenyl |
| 303 | 4-chloro-2-fluorophenyl | 2,6-dibromo-4-(heptafluoro-n-propylthio)phenyl |
| 304 | 4-chloro-2-nitrophenyl | 2,6-dibromo-4-(heptafluoro-n-propylthio)phenyl |
| 305 | 2,3,6-trifluoro phenyl | 2,6-dibromo-4-(heptafluoro-n-propylthio)phenyl |
| 306 | pyridin-2-yl | 2,6-dibromo-4-(heptafluoro-n-propylthio)phenyl |
| 307 | pyridin-3-yl | 2,6-dibromo-4-(heptafluoro-n-propylthio)phenyl |
| 308 | 2-fluoropyridin-3-yl | 2,6-dibromo-4-(heptafluoro-n-propylthio)phenyl |
| 309 | 2-chloropyridin-3-yl | 2,6-dibromo-4-(heptafluoro-n-propylthio)phenyl |
| 310 | 2-chloropyridin-5-yl | 2,6-dibromo-4-(heptafluoro-n-propylthio)phenyl |
| 311 | 2-methylthio pyridin-3-yl | 2,6-dibromo-4-(heptafluoro-n-propylthio)phenyl |
| 312 | 2,6-dichloro pyridin-3-yl | 2,6-dibromo-4-(heptafluoro-n-propylthio)phenyl |
| 313 | 2,6-dichloro pyridin-4-yl | 2,6-dibromo-4-(heptafluoro-n-propylthio)phenyl |
| 314 | 2-chloro-6-methyl pyridin-3-yl | 2,6-dibromo-4-(heptafluoro-n-propylthio)phenyl |
| 315 | pyridine-N-oxid-2-yl | 2,6-dibromo-4-(heptafluoro-n-propylthio)phenyl |
| 316 | pyrazin-2-yl | 2,6-dibromo-4-(heptafluoro-n-propylthio)phenyl |
| 317 | 1-methyl-3-nitro-1H-pyrazol-4-yl | 2,6-dibromo-4-(heptafluoro-n-propylthio)phenyl |
| 318 | 1-methyl-3-tri fluoromethyl-1H-pyrazol-4-yl | 2,6-dibromo-4-(heptafluoro-n-propylthio)phenyl |
| 319 | 1-methyl-5-tri fluoromethyl-1H-pyrazol-4-yl | 2,6-dibromo-4-(heptafluoro-n-propylthio)phenyl |

TABLE 1-continued

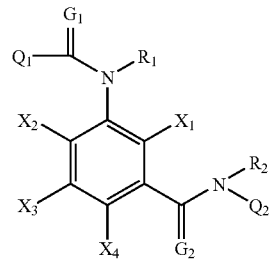

($X_1$, $X_2$, $X_3$, $X_4$ = hydrogen atoms;
$G_1$, $G_2$ = oxygen atoms; $R_1$, $R_2$ = hydrogen atoms)

| Compound No. | $Q_1$ | $Q_2$ |
|---|---|---|
| 320 | 2-tetrahydro furanyl | 2,6-dibromo-4-(heptafluoro-n-propylthio)phenyl |
| 321 | 2-phenylthiazol-4-yl | 2,6-dibromo-4-(heptafluoro-n-propylthio)phenyl |
| 322 | furan-2-yl | 2,6-dibromo-4-(heptafluoro-n-propylthio)phenyl |
| 323 | furan-3-yl | 2,6-dibromo-4-(heptafluoro-n-propylthio)phenyl |
| 324 | 2-tetrahydro furanyl | 2,6-dibromo-4-(heptafluoro-n-propylthio)phenyl |
| 325 | benzofuran-2-yl | 2,6-dibromo-4-(heptafluoro-n-propylthio)phenyl |
| 326 | thiophen-2-yl | 2,6-dibromo-4-(heptafluoro-n-propylthio)phenyl |
| 327 | phenyl | 2,6-diiodo-4-(heptafluoro-n-propylthio)phenyl |
| 328 | 2-fluorophenyl | 2,6-diiodo-4-(heptafluoro-n-propylthio)phenyl |
| 329 | phenyl | 2,6-dichloro-4-(heptafluoro isopropylthio)phenyl |
| 330 | 2-fluorophenyl | 2,6-dichloro-4-(heptafluoro isopropylthio)phenyl |
| 331 | 2-chloropyridin-3-yl | 2,6-dichloro-4-(heptafluoro isopropylthio)phenyl |
| 332 | phenyl | 2,6-dibromo-4-(heptafluoro isopropylthio)phenyl |
| 333 | phenyl | 2,6-dibromo-4-(nonafluoro-n-butylthio)phenyl |
| 334 | 2-fluorophenyl | 2,6-dibromo-4-(nonafluoro-n-butylthio)phenyl |
| 335 | phenyl | 2,6-dibromo-4-(heptafluoro-n-propylsulfinyl)phenyl |
| 336 | 2-methylphenyl | 2,6-dibromo-4-(heptafluoro-n-propylsulfinyl)phenyl |
| 337 | 4-methylphenyl | 2,6-dibromo-4-(heptafluoro-n-propylsulfinyl)phenyl |
| 338 | 2-fluorophenyl | 2,6-dibromo-4-(heptafluoro-n-propylsulfinyl)phenyl |
| 339 | 3-fluorophenyl | 2,6-dibromo-4-(heptafluoro-n-propylsulfinyl)phenyl |
| 340 | 4-fluorophenyl | 2,6-dibromo-4-(heptafluoro-n-propylsulfinyl)phenyl |
| 341 | 2-chlorophenyl | 2,6-dibromo-4-(heptafluoro-n-propylsulfinyl)phenyl |
| 342 | 4-chlorophenyl | 2,6-dibromo-4-(heptafluoro-n-propylsulfinyl)phenyl |
| 343 | 2-bromophenyl | 2,6-dibromo-4-(heptafluoro-n-propylsulfinyl)phenyl |
| 344 | 2-iodophenyl | 2,6-dibromo-4-(heptafluoro-n-propylsulfinyl)phenyl |
| 345 | 3-cyanophenyl | 2,6-dibromo-4-(heptafluoro-n-propylsulfinyl)phenyl |
| 346 | 4-cyanophenyl | 2,6-dibromo-4-(heptafluoro-n-propylsulfinyl)phenyl |
| 347 | 2-nitrophenyl | 2,6-dibromo-4-(heptafluoro-n-propylsulfinyl)phenyl |
| 348 | 3-nitrophenyl | 2,6-dibromo-4-(heptafluoro-n-propylsulfinyl)phenyl |
| 349 | 4-nitrophenyl | 2,6-dibromo-4-(heptafluoro-n-propylsulfinyl)phenyl |

TABLE 1-continued

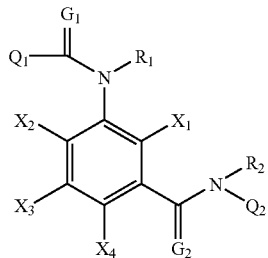

(X₁, X₂, X₃, X₄ = hydrogen atoms;
G₁, G₂ = oxygen atoms; R₁, R₂ = hydrogen atoms)

| Compound No. | Q₁ | Q₂ |
|---|---|---|
| 350 | 2-trifluoromethylphenyl | 2,6-dibromo-4-(heptafluoro-n-propylsulfinyl)phenyl |
| 351 | 4-trifluoromethylphenyl | 2,6-dibromo-4-(heptafluoro-n-propylsulfinyl)phenyl |
| 352 | 4-trifluoromethoxyphenyl | 2,6-dibromo-4-(heptafluoro-n-propylsulfinyl)phenyl |
| 353 | 2,3-difluorophenyl | 2,6-dibromo-4-(heptafluoro-n-propylsulfinyl)phenyl |
| 354 | 2,4-difluorophenyl | 2,6-dibromo-4-(heptafluoro-n-propylsulfinyl)phenyl |
| 355 | 2,5-difluorophenyl | 2,6-dibromo-4-(heptafluoro-n-propylsulfinyl)phenyl |
| 356 | 2,6-difluorophenyl | 2,6-dibromo-4-(heptafluoro-n-propylsulfinyl)phenyl |
| 357 | 2,4-dichlorophenyl | 2,6-dibromo-4-(heptafluoro-n-propylsulfinyl)phenyl |
| 358 | 2,6-dichlorophenyl | 2,6-dibromo-4-(heptafluoro-n-propylsulfinyl)phenyl |
| 359 | 3,4-dichlorophenyl | 2,6-dibromo-4-(heptafluoro-n-propylsulfinyl)phenyl |
| 360 | 2-chloro-4-nitrophenyl | 2,6-dibromo-4-(heptafluoro-n-propylsulfinyl)phenyl |
| 361 | 2-chloro-4-fluorophenyl | 2,6-dibromo-4-(heptafluoro-n-propylsulfinyl)phenyl |
| 362 | 2-chloro-6-fluorophenyl | 2,6-dibromo-4-(heptafluoro-n-propylsulfinyl)phenyl |
| 363 | 4-chloro-2-fluorophenyl | 2,6-dibromo-4-(heptafluoro-n-propylsulfinyl)phenyl |
| 364 | 4-chloro-2-nitrophenyl | 2,6-dibromo-4-(heptafluoro-n-propylsulfinyl)phenyl |
| 365 | 2,3,6-trifluorophenyl | 2,6-dibromo-4-(heptafluoro-n-propylsulfinyl)phenyl |
| 366 | pyridin-2-yl | 2,6-dibromo-4-(heptafluoro-n-propylsulfinyl)phenyl |
| 367 | pyridin-3-yl | 2,6-dibromo-4-(heptafluoro-n-propylsulfinyl)phenyl |
| 368 | 2-fluoropyridin-3-yl | 2,6-dibromo-4-(heptafluoro-n-propylsulfinyl)phenyl |
| 369 | 2-chloropyridin-3-yl | 2,6-dibromo-4-(heptafluoro-n-propylsulfinyl)phenyl |
| 370 | 2-chloropyridin-5-yl | 2,6-dibromo-4-(heptafluoro-n-propylsulfinyl)phenyl |
| 371 | 2-methylthiopyridin-3-yl | 2,6-dibromo-4-(heptafluoro-n-propylsulfinyl)phenyl |
| 372 | pyrazin-2-yl | 2,6-dibromo-4-(heptafluoro-n-propylsulfinyl)phenyl |
| 373 | furan-2-yl | 2,6-dibromo-4-(heptafluoro-n-propylsulfinyl)phenyl |
| 374 | thiophen-2-yl | 2,6-dibromo-4-(heptafluoro-n-propylsulfinyl)phenyl |
| 375 | 2,6-difluorophenyl | 2,6-dichloro-4-(trifluoromethylsulfonyl)phenyl |
| 376 | phenyl | 2,6-dibromo-4-(trifluoromethylsulfonyl)phenyl |
| 377 | 2,6-difluorophenyl | 2,6-dibromo-4-(trifluoromethylsulfonyl)phenyl |
| 378 | 2-fluorophenyl | 2,6-dichloro-4-(heptafluoroisopropylsulfonyl)phenyl |
| 379 | phenyl | 2,6-dichloro-4-(heptafluoroisopropylsulfonyl)phenyl |
| 380 | phenyl | 2,6-dibromo-4-(heptafluoro-n-propylsulfonyl)phenyl |
| 381 | 2-methylphenyl | 2,6-dibromo-4-(heptafluoro-n-propylsulfonyl)phenyl |
| 382 | 4-methylphenyl | 2,6-dibromo-4-(heptafluoro-n-propylsulfonyl)phenyl |
| 383 | 2-fluorophenyl | 2,6-dibromo-4-(heptafluoro-n-propylsulfonyl)phenyl |
| 384 | 3-fluorophenyl | 2,6-dibromo-4-(heptafluoro-n-propylsulfonyl)phenyl |
| 385 | 4-fluorophenyl | 2,6-dibromo-4-(heptafluoro-n-propylsulfonyl)phenyl |
| 386 | 2-chlorophenyl | 2,6-dibromo-4-(heptafluoro-n-propylsulfonyl)phenyl |
| 387 | 4-chlorophenyl | 2,6-dibromo-4-(heptafluoro-n-propylsulfonyl)phenyl |
| 388 | 2-bromophenyl | 2,6-dibromo-4-(heptafluoro-n-propylsulfonyl)phenyl |
| 389 | 2-iodophenyl | 2,6-dibromo-4-(heptafluoro-n-propylsulfonyl)phenyl |
| 390 | 3-cyanophenyl | 2,6-dibromo-4-(heptafluoro-n-propylsulfonyl)phenyl |
| 391 | 4-cyanophenyl | 2,6-dibromo-4-(heptafluoro-n-propylsulfonyl)phenyl |
| 392 | 2-nitrophenyl | 2,6-dibromo-4-(heptafluoro-n-propylsulfonyl)phenyl |
| 393 | 3-nitrophenyl | 2,6-dibromo-4-(heptafluoro-n-propylsulfonyl)phenyl |
| 394 | 4-nitrophenyl | 2,6-dibromo-4-(heptafluoro-n-propylsulfonyl)phenyl |
| 395 | 2-trifluoromethylphenyl | 2,6-dibromo-4-(heptafluoro-n-propylsulfonyl)phenyl |
| 396 | 4-trifluoromethylphenyl | 2,6-dibromo-4-(heptafluoro-n-propylsulfonyl)phenyl |
| 397 | 4-trifluoromethoxyphenyl | 2,6-dibromo-4-(heptafluoro-n-propylsulfonyl)phenyl |
| 398 | 2,3-difluorophenyl | 2,6-dibromo-4-(heptafluoro-n-propylsulfonyl)phenyl |
| 399 | 2,4-difluorophenyl | 2,6-dibromo-4-(heptafluoro-n-propylsulfonyl)phenyl |
| 400 | 2,5-difluorophenyl | 2,6-dibromo-4-(heptafluoro-n-propylsulfonyl)phenyl |
| 401 | 2,6-difluorophenyl | 2,6-dibromo-4-(heptafluoro-n-propylsulfonyl)phenyl |
| 402 | 2,4-dichlorophenyl | 2,6-dibromo-4-(heptafluoro-n-propylsulfonyl)phenyl |
| 403 | 2,6-dichlorophenyl | 2,6-dibromo-4-(heptafluoro-n-propylsulfonyl)phenyl |
| 404 | 3,4-dichlorophenyl | 2,6-dibromo-4-(heptafluoro-n-propylsulfonyl)phenyl |
| 405 | 2-chloro-4-nitrophenyl | 2,6-dibromo-4-(heptafluoro-n-propylsulfonyl)phenyl |
| 406 | 2-chloro-4-fluorophenyl | 2,6-dibromo-4-(heptafluoro-n-propylsulfonyl)phenyl |
| 407 | 2-chloro-6-fluorophenyl | 2,6-dibromo-4-(heptafluoro-n-propylsulfonyl)phenyl |
| 408 | 4-chloro-2-fluorophenyl | 2,6-dibromo-4-(heptafluoro-n-propylsulfonyl)phenyl |
| 409 | 4-chloro-2-nitrophenyl | 2,6-dibromo-4-(heptafluoro-n-propylsulfonyl)phenyl |

TABLE 1-continued

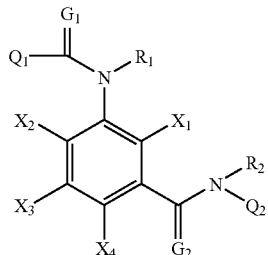

(X₁, X₂, X₃, X₄ = hydrogen atoms;
G₁, G₂ = oxygen atoms; R₁, R₂ = hydrogen atoms)

| Compound No. | Q₁ | Q₂ |
|---|---|---|
| 410 | 2,3,6-trifluoro phenyl | 2,6-dibromo-4-(heptafluoro-n-propylsulfonyl)phenyl |
| 411 | pyridin-2-yl | 2,6-dibromo-4-(heptafluoro-n-propylsulfonyl)phenyl |
| 412 | pyridin-3-yl | 2,6-dibromo-4-(heptafluoro-n-propylsulfonyl)phenyl |
| 413 | 2-fluoropyridin-3-yl | 2,6-dibromo-4-(heptafluoro-n-propylsulfonyl)phenyl |
| 414 | 2-chloropyridin-3-yl | 2,6-dibromo-4-(heptafluoro-n-propylsulfonyl)phenyl |
| 415 | 2-chloropyridin-5-yl | 2,6-dibromo-4-(heptafluoro-n-propylsulfonyl)phenyl |
| 416 | 2-methylthio pyridin-3-yl | 2,6-dibromo-4-(heptafluoro-n-propylsulfonyl)phenyl |
| 417 | pyrazin-2-yl | 2,6-dibromo-4-(heptafluoro-n-propylsulfonyl)phenyl |
| 418 | furan-2-yl | 2,6-dibromo-4-(heptafluoro-n-propylsulfonyl)phenyl |
| 419 | thiophen-2-yl | 2,6-dibromo-4-(heptafluoro-n-propylsulfonyl)phenyl |
| 420 | phenyl | 2,6-dimethyl-4-(heptafluoro-n-propylthio)phenyl |
| 421 | 2-methylphenyl | 2,6-dimethyl-4-(heptafluoro-n-propylthio)phenyl |
| 422 | 4-methylphenyl | 2,6-dimethyl-4-(heptafluoro-n-propylthio)phenyl |
| 423 | 2-fluorophenyl | 2,6-dimethyl-4-(heptafluoro-n-propylthio)phenyl |
| 424 | 3-fluorophenyl | 2,6-dimethyl-4-(heptafluoro-n-propylthio)phenyl |
| 425 | 4-fluorophenyl | 2,6-dimethyl-4-(heptafluoro-n-propylthio)phenyl |
| 426 | 2-chlorophenyl | 2,6-dimethyl-4-(heptafluoro-n-propylthio)phenyl |
| 427 | 4-chlorophenyl | 2,6-dimethyl-4-(heptafluoro-n-propylthio)phenyl |
| 428 | 2-bromophenyl | 2,6-dimethyl-4-(heptafluoro-n-propylthio)phenyl |
| 429 | 2-iodophenyl | 2,6-dimethyl-4-(heptafluoro-n-propylthio)phenyl |
| 430 | 3-cyanophenyl | 2,6-dimethyl-4-(heptafluoro-n-propylthio)phenyl |
| 431 | 4-cyanophenyl | 2,6-dimethyl-4-(heptafluoro-n-propylthio)phenyl |
| 432 | 2-nitrophenyl | 2,6-dimethyl-4-(heptafluoro-n-propylthio)phenyl |
| 433 | 3-nitrophenyl | 2,6-dimethyl-4-(heptafluoro-n-propylthio)phenyl |
| 434 | 4-nitrophenyl | 2,6-dimethyl-4-(heptafluoro-n-propylthio)phenyl |
| 435 | 2-trifluoromethyl phenyl | 2,6-dimethyl-4-(heptafluoro-n-propylthio)phenyl |
| 436 | 4-trifluoromethyl phenyl | 2,6-dimethyl-4-(heptafluoro-n-propylthio)phenyl |
| 437 | 4-trifluoromethoxy phenyl | 2,6-dimethyl-4-(heptafluoro-n-propylthio)phenyl |
| 438 | 2,3-difluorophenyl | 2,6-dimethyl-4-(heptafluoro-n-propylthio)phenyl |
| 439 | 2,4-difluorophenyl | 2,6-dimethyl-4-(heptafluoro-n-propylthio)phenyl |

TABLE 1-continued

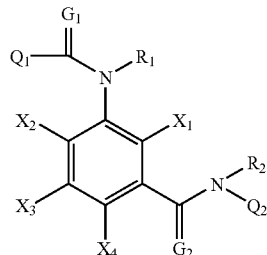

(X₁, X₂, X₃, X₄ = hydrogen atoms;
G₁, G₂ = oxygen atoms; R₁, R₂ = hydrogen atoms)

| Compound No. | Q₁ | Q₂ |
|---|---|---|
| 440 | 2,5-difluorophenyl | 2,6-dimethyl-4-(heptafluoro-n-propylthio)phenyl |
| 441 | 2,6-difluorophenyl | 2,6-dimethyl-4-(heptafluoro-n-propylthio)phenyl |
| 442 | 2,4-dichlorophenyl | 2,6-dimethyl-4-(heptafluoro-n-propylthio)phenyl |
| 443 | 2,6-dichlorophenyl | 2,6-dimethyl-4-(heptafluoro-n-propylthio)phenyl |
| 444 | 3,4-dichlorophenyl | 2,6-dimethyl-4-(heptafluoro-n-propylthio)phenyl |
| 445 | 2-chloro-4-nitro phenyl | 2,6-dimethyl-4-(heptafluoro-n-propylthio)phenyl |
| 446 | 2-chloro-4-fluoro phenyl | 2,6-dimethyl-4-(heptafluoro-n-propylthio)phenyl |
| 447 | 2-chloro-6-fluoro phenyl | 2,6-dimethyl-4-(heptafluoro-n-propylthio)phenyl |
| 448 | 4-chloro-2-fluoro phenyl | 2,6-dimethyl-4-(heptafluoro-n-propylthio)phenyl |
| 449 | 4-chloro-2-nitro phenyl | 2,6-dimethyl-4-(heptafluoro-n-propylthio)phenyl |
| 450 | 2,3,6-trifluoro phenyl | 2,6-dimethyl-4-(heptafluoro-n-propylthio)phenyl |
| 451 | pyridin-2-yl | 2,6-dimethyl-4-(heptafluoro-n-propylthio)phenyl |
| 452 | pyridin-3-yl | 2,6-dimethyl-4-(heptafluoro-n-propylthio)phenyl |
| 453 | 2-fluoropyridin-3-yl | 2,6-dimethyl-4-(heptafluoro-n-propylthio)phenyl |
| 454 | 2-chloropyridin-3-yl | 2,6-dimethyl-4-(heptafluoro-n-propylthio)phenyl |
| 455 | 2-chloropyridin-5-yl | 2,6-dimethyl-4-(heptafluoro-n-propylthio)phenyl |
| 456 | 2-methylthio pyridin-3-yl | 2,6-dimethyl-4-(heptafluoro-n-propylthio)phenyl |
| 457 | pyrazin-2-yl | 2,6-dimethyl-4-(heptafluoro-n-propylthio)phenyl |
| 458 | furan-2-yl | 2,6-dimethyl-4-(heptafluoro-n-propylthio)phenyl |
| 459 | thiophen-2-yl | 2,6-dimethyl-4-(heptafluoro-n-propylthio)phenyl |
| 460 | 2,6-difuorophenyl | 2,6-dichloro-4-(trifluoromethylsulfonyl)phenyl |
| 461 | phenyl | 2-bromo-6-(heptafluoroiso-propyloxy)-4-methylpyridin-3-yl |
| 462 | 2-fluorophenyl | 2-bromo-6-(heptafluoroiso-propyloxy)-4-methylpyridin-3-yl |
| 463 | phenyl | 2,4-dimethyl-6-(2,2,2-trifluoro-1-trifluoromethylethoxy)pyridin-3-yl |
| 464 | phenyl | 2-chloro-4-methyl-6-(2,2,2-trifluoro-1-trifluoromethylethoxy)pyridin-3-yl |
| 465 | phenyl | 2-bromo-4-methyl-6-(2,2,2-trifluoro-1-trifluoromethylethoxy)pyridin-3-yl |
| 466 | 2-fluorophenyl | 2-bromo-4-methyl-6-(2,2,2-trifluoro-1-trifluoromethylethoxy)pyridin-3-yl |
| 467 | phenyl | 2-iodo-4-methyl-6-(2,2,2-trifluoro-1-trifluoromethylethoxy)pyridin-3-yl |

TABLE 2

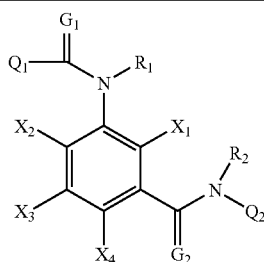

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 601 | phenyl | F | H | H | H | 2,6-dimethyl-4-(heptafluoro isopropyl)phenyl |
| 602 | 2-methylphenyl | F | H | H | H | 2,6-dimethyl-4-(heptafluoro isopropyl)phenyl |
| 603 | 3-methylphenyl | F | H | H | H | 2,6-dimethyl-4-(heptafluoro isopropyl)phenyl |
| 604 | 4-methylphenyl | F | H | H | H | 2,6-dimethyl-4-(heptafluoro isopropyl)phenyl |
| 605 | 2-nitrophenyl | F | H | H | H | 2,6-dimethyl-4-(heptafluoro isopropyl)phenyl |
| 606 | 3-nitrophenyl | F | H | H | H | 2,6-dimethyl-4-(heptafluoro isopropyl)phenyl |
| 607 | 4-nitrophenyl | F | H | H | H | 2,6-dimethyl-4-(heptafluoro isopropyl)phenyl |
| 608 | 3-cyanophenyl | F | H | H | H | 2,6-dimethyl-4-(heptafluoro isopropyl)phenyl |
| 609 | 4-cyanophenyl | F | H | H | H | 2,6-dimethyl-4-(heptafluoro isopropyl)phenyl |
| 610 | 2-fluorophenyl | F | H | H | H | 2,6-dimethyl-4-(heptafluoro isopropyl)phenyl |
| 611 | 3-fluorophenyl | F | H | H | H | 2,6-dimethyl-4-(heptafluoro isopropyl)phenyl |
| 612 | 4-fluorophenyl | F | H | H | H | 2,6-dimethyl-4-(heptafluoro isopropyl)phenyl |
| 613 | 2-chlorophenyl | F | H | H | H | 2,6-dimethyl-4-(heptafluoro isopropyl)phenyl |
| 614 | 4-chlorophenyl | F | H | H | H | 2,6-dimethyl-4-(heptafluoro isopropyl)phenyl |
| 615 | 2-bromophenyl | F | H | H | H | 2,6-dimethyl-4-(heptafluoro isopropyl)phenyl |
| 616 | 2-iodophenyl | F | H | H | H | 2,6-dimethyl-4-(heptafluoro isopropyl)phenyl |
| 617 | 2-trifluoromethyl phenyl | F | H | H | H | 2,6-dimethyl-4-(heptafluoro isopropyl)phenyl |
| 618 | 4-trifluoromethyl phenyl | F | H | H | H | 2,6-dimethyl-4-(heptafluoro isopropyl)phenyl |
| 619 | 4-trifluoromethoxy phenyl | F | H | H | H | 2,6-dimethyl-4-(heptafluoro isopropyl)phenyl |
| 620 | 4-(dimethylamino) phenyl | F | H | H | H | 2,6-dimethyl-4-(heptafluoro isopropyl)phenyl |
| 621 | 2,3-difluorophenyl | F | H | H | H | 2,6-dimethyl-4-(heptafluoro isopropyl)phenyl |
| 622 | 2,4-difluorophenyl | F | H | H | H | 2,6-dimethyl-4-(heptafluoro isopropyl)phenyl |
| 623 | 2,5-difluorophenyl | F | H | H | H | 2,6-dimethyl-4-(heptafluoro isopropyl)phenyl |
| 624 | 2,6-difluorophenyl | F | H | H | H | 2,6-dimethyl-4-(heptafluoro isopropyl)phenyl |
| 625 | 2,4-dichlorophenyl | F | H | H | H | 2,6-dimethyl-4-(heptafluoro isopropyl)phenyl |
| 626 | 2,6-dichlorophenyl | F | H | H | H | 2,6-dimethyl-4-(heptafluoro isopropyl)phenyl |
| 627 | 3,4-dichlorophenyl | F | H | H | H | 2,6-dimethyl-4-(heptafluoro isopropyl)phenyl |
| 628 | 2-fluoro-4-nitro phenyl | F | H | H | H | 2,6-dimethyl-4-(heptafluoro isopropyl)phenyl |
| 629 | 4-fluoro-2-nitro phenyl | F | H | H | H | 2,6-dimethyl-4-(heptafluoro isopropyl)phenyl |
| 630 | 2-chloro-4-fluoro phenyl | F | H | H | H | 2,6-dimethyl-4-(heptafluoro isopropyl)phenyl |
| 631 | 4-chloro-2-fluoro phenyl | F | H | H | H | 2,6-dimethyl-4-(heptafluoro isopropyl)phenyl |
| 632 | 2-chloro-6-fluoro phenyl | F | H | H | H | 2,6-dimethyl-4-(heptafluoro isopropyl)phenyl |
| 633 | 2-chloro-4-nitro phenyl | F | H | H | H | 2,6-dimethyl-4-(heptafluoro isopropyl)phenyl |

TABLE 2-continued

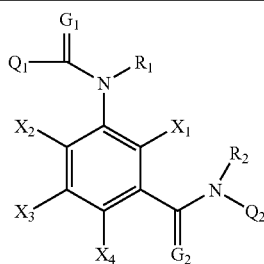

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 634 | 4-chloro-2-nitrophenyl | F | H | H | H | 2,6-dimethyl-4-(heptafluoroisopropyl)phenyl |
| 635 | 2,3,6-trifluorophenyl | F | H | H | H | 2,6-dimethyl-4-(heptafluoroisopropyl)phenyl |
| 636 | pyridin-2-yl | F | H | H | H | 2,6-dimethyl-4-(heptafluoroisopropyl)phenyl |
| 637 | pyridin-3-yl | F | H | H | H | 2,6-dimethyl-4-(heptafluoroisopropyl)phenyl |
| 638 | 2-fluoropyridin-3-yl | F | H | H | H | 2,6-dimethyl-4-(heptafluoroisopropyl)phenyl |
| 639 | 2-chloropyridin-3-yl | F | H | H | H | 2,6-dimethyl-4-(heptafluoroisopropyl)phenyl |
| 640 | 2-chloropyridin-5-yl | F | H | H | H | 2,6-dimethyl-4-(heptafluoroisopropyl)phenyl |
| 641 | 2-methylthiopyridin-3-yl | F | H | H | H | 2,6-dimethyl-4-(heptafluoroisopropyl)phenyl |
| 642 | pyrazin-2-yl | F | H | H | H | 2,6-dimethyl-4-(heptafluoroisopropyl)phenyl |
| 643 | furan-2-yl | F | H | H | H | 2,6-dimethyl-4-(heptafluoroisopropyl)phenyl |
| 644 | furan-3-yl | F | H | H | H | 2,6-dimethyl-4-(heptafluoroisopropyl)phenyl |
| 645 | 2-tetrahydrofuranyl | F | H | H | H | 2,6-dimethyl-4-(heptafluoroisopropyl)phenyl |
| 646 | benzofuran-2-yl | F | H | H | H | 2,6-dimethyl-4-(heptafluoroisopropyl)phenyl |
| 647 | thiophen-2-yl | F | H | H | H | 2,6-dimethyl-4-(heptafluoroisopropyl)phenyl |
| 648 | 2-methyl-5,6-dihydro-4H-pyran-3-yl | F | H | H | H | 2,6-dimethyl-4-(heptafluoroisopropyl)phenyl |
| 649 | phenyl | H | Cl | H | H | 2,6-dimethyl-4-(heptafluoroisopropyl)phenyl |
| 650 | phenyl | H | F | H | H | 2,6-dimethyl-4-(heptafluoroisopropyl)phenyl |
| 651 | 4-nitrophenyl | H | F | H | H | 2,6-dimethyl-4-(heptafluoroisopropyl)phenyl |
| 652 | 4-cyanophenyl | H | F | H | H | 2,6-dimethyl-4-(heptafluoroisopropyl)phenyl |
| 653 | 2-fluorophenyl | H | F | H | H | 2,6-dimethyl-4-(heptafluoroisopropyl)phenyl |
| 654 | 4-fluorophenyl | H | F | H | H | 2,6-dimethyl-4-(heptafluoroisopropyl)phenyl |
| 655 | 4-trifluoromethylphenyl | H | F | H | H | 2,6-dimethyl-4-(heptafluoroisopropyl)phenyl |
| 656 | 2,4-difluorophenyl | H | F | H | H | 2,6-dimethyl-4-(heptafluoroisopropyl)phenyl |
| 657 | 2-chloropyridin-3-yl | H | F | H | H | 2,6-dimethyl-4-(heptafluoroisopropyl)phenyl |
| 658 | phenyl | H | H | $CF_3$ | H | 2,6-dimethyl-4-(heptafluoroisopropyl)phenyl |
| 659 | phenyl | H | H | H | F | 2,6-dimethyl-4-(heptafluoroisopropyl)phenyl |
| 660 | phenyl | H | H | H | Cl | 2,6-dimethyl-4-(heptafluoroisopropyl)phenyl |
| 661 | phenyl | H | H | H | Br | 2,6-dimethyl-4-(heptafluoroisopropyl)phenyl |
| 662 | phenyl | H | H | H | I | 2,6-dimethyl-4-(heptafluoroisopropyl)phenyl |
| 663 | phenyl | F | H | H | F | 2,6-dimethyl-4-(heptafluoroisopropyl)phenyl |
| 664 | phenyl | H | Br | H | Br | 2,6-dimethyl-4-(heptafluoroisopropyl)phenyl |
| 665 | phenyl | F | H | H | H | 2,6-dimethyl-4-(nonafluoro-2-butyl)phenyl |
| 666 | 2-methylphenyl | F | H | H | H | 2,6-dimethyl-4-(nonafluoro-2-butyl)phenyl |

TABLE 2-continued

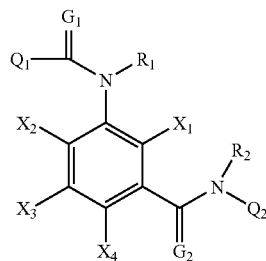

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 667 | 4-methylphenyl | F | H | H | H | 2,6-dimethyl-4-(nonafluoro-2-butyl)phenyl |
| 668 | 2-fluorophenyl | F | H | H | H | 2,6-dimethyl-4-(nonafluoro-2-butyl)phenyl |
| 669 | 3-fluorophenyl | F | H | H | H | 2,6-dimethyl-4-(nonafluoro-2-butyl)phenyl |
| 670 | 4-fluorophenyl | F | H | H | H | 2,6-dimethyl-4-(nonafluoro-2-butyl)phenyl |
| 671 | 2-chlorophenyl | F | H | H | H | 2,6-dimethyl-4-(nonafluoro-2-butyl)phenyl |
| 672 | 4-chlorophenyl | F | H | H | H | 2,6-dimethyl-4-(nonafluoro-2-butyl)phenyl |
| 673 | 2-bromophenyl | F | H | H | H | 2,6-dimethyl-4-(nonafluoro-2-butyl)phenyl |
| 674 | 2-iodophenyl | F | H | H | H | 2,6-dimethyl-4-(nonafluoro-2-butyl)phenyl |
| 675 | 3-cyanophenyl | F | H | H | H | 2,6-dimethyl-4-(nonafluoro-2-butyl)phenyl |
| 676 | 4-cyanophenyl | F | H | H | H | 2,6-dimethyl-4-(nonafluoro-2-butyl)phenyl |
| 677 | 2-nitrophenyl | F | H | H | H | 2,6-dimethyl-4-(nonafluoro-2-butyl)phenyl |
| 678 | 3-nitrophenyl | F | H | H | H | 2,6-dimethyl-4-(nonafluoro-2-butyl)phenyl |
| 679 | 4-nitrophenyl | F | H | H | H | 2,6-dimethyl-4-(nonafluoro-2-butyl)phenyl |
| 680 | 2-trifluoromethyl phenyl | F | H | H | H | 2,6-dimethyl-4-(nonafluoro-2-butyl)phenyl |
| 681 | 4-trifluoromethyl phenyl | F | H | H | H | 2,6-dimethyl-4-(nonafluoro-2-butyl)phenyl |
| 682 | 4-trifluoromethoxy phenyl | F | H | H | H | 2,6-dimethyl-4-(nonafluoro-2-butyl)phenyl |
| 683 | 2,3-difluorophenyl | F | H | H | H | 2,6-dimethyl-4-(nonafluoro-2-butyl)phenyl |
| 684 | 2,4-difluorophenyl | F | H | H | H | 2,6-dimethyl-4-(nonafluoro-2-butyl)phenyl |
| 685 | 2,5-difluorophenyl | F | H | H | H | 2,6-dimethyl-4-(nonafluoro-2-butyl)phenyl |
| 686 | 2,6-difluorophenyl | F | H | H | H | 2,6-dimethyl-4-(nonafluoro-2-butyl)phenyl |
| 687 | 2,4-dichlorophenyl | F | H | H | H | 2,6-dimethyl-4-(nonafluoro-2-butyl)phenyl |
| 688 | 2,6-dichlorophenyl | F | H | H | H | 2,6-dimethyl-4-(nonafluoro-2-butyl)phenyl |
| 689 | 3,4-dichlorophenyl | F | H | H | H | 2,6-dimethyl-4-(nonafluoro-2-butyl)phenyl |
| 690 | 2-chloro-4-nitro phenyl | F | H | H | H | 2,6-dimethyl-4-(nonafluoro-2-butyl)phenyl |
| 691 | 2-chloro-4-fluoro phenyl | F | H | H | H | 2,6-dimethyl-4-(nonafluoro-2-butyl)phenyl |
| 692 | 2-chloro-6-fluoro phenyl | F | H | H | H | 2,6-dimethyl-4-(nonafluoro-2-butyl)phenyl |
| 693 | 4-chloro-2-fluoro phenyl | F | H | H | H | 2,6-dimethyl-4-(nonafluoro-2-butyl)phenyl |
| 694 | 4-chloro-2-nitro phenyl | F | H | H | H | 2,6-dimethyl-4-(nonafluoro-2-butyl)phenyl |
| 695 | 2,3,6-trifluoro phenyl | F | H | H | H | 2,6-dimethyl-4-(nonafluoro-2-butyl)phenyl |
| 696 | pyridin-2-yl | F | H | H | H | 2,6-dimethyl-4-(nonafluoro-2-butyl)phenyl |
| 697 | pyridin-3-yl | F | H | H | H | 2,6-dimethyl-4-(nonafluoro-2-butyl)phenyl |
| 698 | 2-fluoropyridin-3-yl | F | H | H | H | 2,6-dimethyl-4-(nonafluoro-2-butyl)phenyl |
| 699 | 2-chloropyridin-3-yl | F | H | H | H | 2,6-dimethyl-4-(nonafluoro-2-butyl)phenyl |

TABLE 2-continued

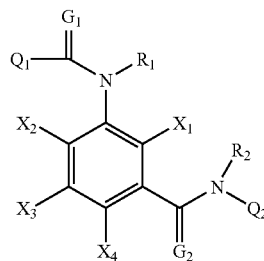

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 700 | 2-chloropyridin-5-yl | F | H | H | H | 2,6-dimethyl-4-(nonafluoro-2-butyl)phenyl |
| 701 | 2-methylthio pyridin-3-yl | F | H | H | H | 2,6-dimethyl-4-(nonafluoro-2-butyl)phenyl |
| 702 | pyrazin-2-yl | F | H | H | H | 2,6-dimethyl-4-(nonafluoro-2-butyl)phenyl |
| 703 | furan-2-yl | F | H | H | H | 2,6-dimethyl-4-(nonafluoro-2-butyl)phenyl |
| 704 | furan-3-yl | F | H | H | H | 2,6-dimethyl-4-(nonafluoro-2-butyl)phenyl |
| 705 | 2-tetrahydrofuranyl | F | H | H | H | 2,6-dimethyl-4-(nonafluoro-2-butyl)phenyl |
| 706 | benzofuran-2-yl | F | H | H | H | 2,6-dimethyl-4-(nonafluoro-2-butyl)phenyl |
| 707 | thiophen-2-yl | F | H | H | H | 2,6-dimethyl-4-(nonafluoro-2-butyl)phenyl |
| 708 | phenyl | F | H | H | H | 2,6-dibromo-4-(heptafluoro-n-propylthio)phenyl |
| 709 | 2-methylphenyl | F | H | H | H | 2,6-dibromo-4-(heptafluoro-n-propylthio)phenyl |
| 710 | 4-methylphenyl | F | H | H | H | 2,6-dibromo-4-(heptafluoro-n-propylthio)phenyl |
| 711 | 2-fluorophenyl | F | H | H | H | 2,6-dibromo-4-(heptafluoro-n-propylthio)phenyl |
| 712 | 3-fluorophenyl | F | H | H | H | 2,6-dibromo-4-(heptafluoro-n-propylthio)phenyl |
| 713 | 4-fluorophenyl | F | H | H | H | 2,6-dibromo-4-(heptafluoro-n-propylthio)phenyl |
| 714 | 2-chlorophenyl | F | H | H | H | 2,6-dibromo-4-(heptafluoro-n-propylthio)phenyl |
| 715 | 4-chlorophenyl | F | H | H | H | 2,6-dibromo-4-(heptafluoro-n-propylthio)phenyl |
| 716 | 2-bromophenyl | F | H | H | H | 2,6-dibromo-4-(heptafluoro-n-propylthio)phenyl |
| 717 | 2-iodophenyl | F | H | H | H | 2,6-dibromo-4-(heptafluoro-n-propylthio)phenyl |
| 718 | 3-cyanophenyl | F | H | H | H | 2,6-dibromo-4-(heptafluoro-n-propylthio)phenyl |
| 719 | 4-cyanophenyl | F | H | H | H | 2,6-dibromo-4-(heptafluoro-n-propylthio)phenyl |
| 720 | 2-nitrophenyl | F | H | H | H | 2,6-dibromo-4-(heptafluoro-n-propylthio)phenyl |
| 721 | 3-nitrophenyl | F | H | H | H | 2,6-dibromo-4-(heptafluoro-n-propylthio)phenyl |
| 722 | 4-nitrophenyl | F | H | H | H | 2,6-dibromo-4-(heptafluoro-n-propylthio)phenyl |
| 723 | 2-trifluoromethyl phenyl | F | H | H | H | 2,6-dibromo-4-(heptafluoro-n-propylthio)phenyl |
| 724 | 4-trifluoromethyl phenyl | F | H | H | H | 2,6-dibromo-4-(heptafluoro-n-propylthio)phenyl |
| 725 | 4-trifluoromethoxy phenyl | F | H | H | H | 2,6-dibromo-4-(heptafluoro-n-propylthio)phenyl |
| 726 | 2,3-difluorophenyl | F | H | H | H | 2,6-dibromo-4-(heptafluoro-n-propylthio)phenyl |
| 727 | 2,4-difluorophenyl | F | H | H | H | 2,6-dibromo-4-(heptafluoro-n-propylthio)phenyl |
| 728 | 2,5-difluorophenyl | F | H | H | H | 2,6-dibromo-4-(heptafluoro-n-propylthio)phenyl |
| 729 | 2,6-difluorophenyl | F | H | H | H | 2,6-dibromo-4-(heptafluoro-n-propylthio)phenyl |
| 730 | 2,4-dichlorophenyl | F | H | H | H | 2,6-dibromo-4-(heptafluoro-n-propylthio)phenyl |
| 731 | 2,6-dichlorophenyl | F | H | H | H | 2,6-dibromo-4-(heptafluoro-n-propylthio)phenyl |
| 732 | 3,4-dichlorophenyl | F | H | H | H | 2,6-dibromo-4-(heptafluoro-n-propylthio)phenyl |

TABLE 2-continued

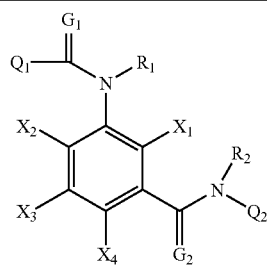

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 733 | 2-chloro-4-nitro phenyl | F | H | H | H | 2,6-dibromo-4-(heptafluoro-n-propylthio)phenyl |
| 734 | 2-chloro-4-fluoro phenyl | F | H | H | H | 2,6-dibromo-4-(heptafluoro-n-propylthio)phenyl |
| 735 | 2-chloro-6-fluoro phenyl | F | H | H | H | 2,6-dibromo-4-(heptafluoro-n-propylthio)phenyl |
| 736 | 4-chloro-2-fluoro phenyl | F | H | H | H | 2,6-dibromo-4-(heptafluoro-n-propylthio)phenyl |
| 737 | 4-chloro-2-nitro phenyl | F | H | H | H | 2,6-dibromo-4-(heptafluoro-n-propylthio)phenyl |
| 738 | 2,3,6-trifluoro phenyl | F | H | H | H | 2,6-dibromo-4-(heptafluoro-n-propylthio)phenyl |
| 739 | pyridin-2-yl | F | H | H | H | 2,6-dibromo-4-(heptafluoro-n-propylthio)phenyl |
| 740 | pyridin-3-yl | F | H | H | H | 2,6-dibromo-4-(heptafluoro-n-propylthio)phenyl |
| 741 | 2-fluoropyridin-3-yl | F | H | H | H | 2,6-dibromo-4-(heptafluoro-n-propylthio)phenyl |
| 742 | 2-chloropyridin-3-yl | F | H | H | H | 2,6-dibromo-4-(heptafluoro-n-propylthio)phenyl |
| 743 | 2-chloropyridin-5-yl | F | H | H | H | 2,6-dibromo-4-(heptafluoro-n-propylthio)phenyl |
| 744 | 2-methylthio pyridin-3-yl | F | H | H | H | 2,6-dibromo-4-(heptafluoro-n-propylthio)phenyl |
| 745 | pyrazin-2-yl | F | H | H | H | 2,6-dibromo-4-(heptafluoro-n-propylthio)phenyl |
| 746 | furan-2-yl | F | H | H | H | 2,6-dibromo-4-(heptafluoro-n-propylthio)phenyl |
| 747 | furan-3-yl | F | H | H | H | 2,6-dibromo-4-(heptafluoro-n-propylthio)phenyl |
| 748 | 2-tetrahydrofuranyl | F | H | H | H | 2,6-dibromo-4-(heptafluoro-n-propylthio)phenyl |
| 749 | benzofuran-2-yl | F | H | H | H | 2,6-dibromo-4-(heptafluoro-n-propylthio)phenyl |
| 750 | thiophen-2-yl | F | H | H | H | 2,6-dibromo-4-(heptafluoro-n-propylthio)phenyl |
| 751 | phenyl | F | H | H | H | 2,6-dibromo-4-(heptafluoro-n-propylsulfinyl)phenyl |
| 752 | 2-methylphenyl | F | H | H | H | 2,6-dibromo-4-(heptafluoro-n-propylsulfinyl)phenyl |
| 753 | 4-methylphenyl | F | H | H | H | 2,6-dibromo-4-(heptafluoro-n-propylsulfinyl)phenyl |
| 754 | 2-fluorophenyl | F | H | H | H | 2,6-dibromo-4-(heptafluoro-n-propylsulfinyl)phenyl |
| 755 | 3-fluorophenyl | F | H | H | H | 2,6-dibromo-4-(heptafluoro-n-propylsulfinyl)phenyl |
| 756 | 4-fluorophenyl | F | H | H | H | 2,6-dibromo-4-(heptafluoro-n-propylsulfinyl)phenyl |
| 757 | 2-chlorophenyl | F | H | H | H | 2,6-dibromo-4-(heptafluoro-n-propylsulfinyl)phenyl |
| 758 | 4-chlorophenyl | F | H | H | H | 2,6-dibromo-4-(heptafluoro-n-propylsulfinyl)phenyl |
| 759 | 2-bromophenyl | F | H | H | H | 2,6-dibromo-4-(heptafluoro-n-propylsulfinyl)phenyl |
| 760 | 2-iodophenyl | F | H | H | H | 2,6-dibromo-4-(heptafluoro-n-propylsulfinyl)phenyl |
| 761 | 3-cyanophenyl | F | H | H | H | 2,6-dibromo-4-(heptafluoro-n-propylsulfinyl)phenyl |
| 762 | 4-cyanophenyl | F | H | H | H | 2,6-dibromo-4-(heptafluoro-n-propylsulfinyl)phenyl |
| 763 | 2-nitrophenyl | F | H | H | H | 2,6-dibromo-4-(heptafluoro-n-propylsulfinyl)phenyl |
| 764 | 3-nitrophenyl | F | H | H | H | 2,6-dibromo-4-(heptafluoro-n-propylsulfinyl)phenyl |
| 765 | 4-nitrophenyl | F | H | H | H | 2,6-dibromo-4-(heptafluoro-n-propylsulfinyl)phenyl |

TABLE 2-continued

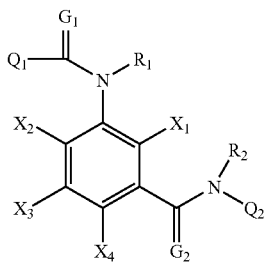

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 766 | 2-trifluoromethyl phenyl | F | H | H | H | 2,6-dibromo-4-(heptafluoro-n-propylsulfinyl)phenyl |
| 767 | 4-trifluoromethyl phenyl | F | H | H | H | 2,6-dibromo-4-(heptafluoro-n-propylsulfinyl)phenyl |
| 768 | 4-trifluoromethoxy phenyl | F | H | H | H | 2,6-dibromo-4-(heptafluoro-n-propylsulfinyl)phenyl |
| 769 | 2,3-difluorophenyl | F | H | H | H | 2,6-dibromo-4-(heptafluoro-n-propylsulfinyl)phenyl |
| 770 | 2,4-difluorophenyl | F | H | H | H | 2,6-dibromo-4-(heptafluoro-n-propylsulfinyl)phenyl |
| 771 | 2,5-difluorophenyl | F | H | H | H | 2,6-dibromo-4-(heptafluoro-n-propylsulfinyl)phenyl |
| 772 | 2,6-difluorophenyl | F | H | H | H | 2,6-dibromo-4-(heptafluoro-n-propylsulfinyl)phenyl |
| 773 | 2,4-dichlorophenyl | F | H | H | H | 2,6-dibromo-4-(heptafluoro-n-propylsulfinyl)phenyl |
| 774 | 2,6-dichlorophenyl | F | H | H | H | 2,6-dibromo-4-(heptafluoro-n-propylsulfinyl)phenyl |
| 775 | 3,4-dichlorophenyl | F | H | H | H | 2,6-dibromo-4-(heptafluoro-n-propylsulfinyl)phenyl |
| 776 | 2-chloro-4-nitro phenyl | F | H | H | H | 2,6-dibromo-4-(heptafluoro-n-propylsulfinyl)phenyl |
| 777 | 2-chloro-4-fluoro phenyl | F | H | H | H | 2,6-dibromo-4-(heptafluoro-n-propylsulfinyl)phenyl |
| 778 | 2-chloro-6-fluoro phenyl | F | H | H | H | 2,6-dibromo-4-(heptafluoro-n-propylsulfinyl)phenyl |
| 779 | 4-chloro-2-fluoro phenyl | F | H | H | H | 2,6-dibromo-4-(heptafluoro-n-propylsulfinyl)phenyl |
| 780 | 4-chloro-2-nitro phenyl | F | H | H | H | 2,6-dibromo-4-(heptafluoro-n-propylsulfinyl)phenyl |
| 781 | 2,3,6-trifluoro phenyl | F | H | H | H | 2,6-dibromo-4-(heptafluoro-n-propylsulfinyl)phenyl |
| 782 | pyridin-2-yl | F | H | H | H | 2,6-dibromo-4-(heptafluoro-n-propylsulfinyl)phenyl |
| 783 | pyridin-3-yl | F | H | H | H | 2,6-dibromo-4-(heptafluoro-n-propylsulfinyl)phenyl |
| 784 | 2-fluoropyridin-3-yl | F | H | H | H | 2,6-dibromo-4-(heptafluoro-n-propylsulfinyl)phenyl |
| 785 | 2-chloropyridin-3-yl | F | H | H | H | 2,6-dibromo-4-(heptafluoro-n-propylsulfinyl)phenyl |
| 786 | 2-chloropyridin-5-yl | F | H | H | H | 2,6-dibromo-4-(heptafluoro-n-propylsulfinyl)phenyl |
| 787 | 2-methylthio pyridin-3-yl | F | H | H | H | 2,6-dibromo-4-(heptafluoro-n-propylsulfinyl)phenyl |
| 788 | pyrazin-2-yl | F | H | H | H | 2,6-dibromo-4-(heptafluoro-n-propylsulfinyl)phenyl |
| 789 | furan-2-yl | F | H | H | H | 2,6-dibromo-4-(heptafluoro-n-propylsulfinyl)phenyl |
| 790 | thiophen-2-yl | F | H | H | H | 2,6-dibromo-4-(heptafluoro-n-propylsulfinyl)phenyl |
| 791 | phenyl | F | H | H | H | 2,6-dimethyl-4-(heptafluoro-n-propylthio)phenyl |
| 792 | 2-methylphenyl | F | H | H | H | 2,6-dimethyl-4-(heptafluoro-n-propylthio)phenyl |
| 793 | 4-methylphenyl | F | H | H | H | 2,6-dimethyl-4-(heptafluoro-n-propylthio)phenyl |
| 794 | 2-fluorophenyl | F | H | H | H | 2,6-dimethyl-4-(heptafluoro-n-propylthio)phenyl |
| 795 | 3-fluorophenyl | F | H | H | H | 2,6-dimethyl-4-(heptafluoro-n-propylthio)phenyl |
| 796 | 4-fluorophenyl | F | H | H | H | 2,6-dimethyl-4-(heptafluoro-n-propylthio)phenyl |
| 797 | 2-chlorophenyl | F | H | H | H | 2,6-dimethyl-4-(heptafluoro-n-propylthio)phenyl |
| 798 | 4-chlorophenyl | F | H | H | H | 2,6-dimethyl-4-(heptafluoro-n-propylthio)phenyl |

TABLE 2-continued

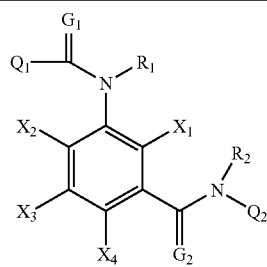

(G$_1$, G$_2$ = oxygen atoms; R$_1$, R$_2$ = hydrogen atoms)

| Compound No. | Q$_1$ | X$_1$ | X$_2$ | X$_3$ | X$_4$ | Q$_2$ |
|---|---|---|---|---|---|---|
| 799 | 2-bromophenyl | F | H | H | H | 2,6-dimethyl-4-(heptafluoro-n-propylthio)phenyl |
| 800 | 2-iodophenyl | F | H | H | H | 2,6-dimethyl-4-(heptafluoro-n-propylthio)phenyl |
| 801 | 3-cyanophenyl | F | H | H | H | 2,6-dimethyl-4-(heptafluoro-n-propylthio)phenyl |
| 802 | 4-cyanophenyl | F | H | H | H | 2,6-dimethyl-4-(heptafluoro-n-propylthio)phenyl |
| 803 | 2-nitrophenyl | F | H | H | H | 2,6-dimethyl-4-(heptafluoro-n-propylthio)phenyl |
| 804 | 3-nitrophenyl | F | H | H | H | 2,6-dimethyl-4-(heptafluoro-n-propylthio)phenyl |
| 805 | 4-nitrophenyl | F | H | H | H | 2,6-dimethyl-4-(heptafluoro-n-propylthio)phenyl |
| 806 | 2-trifluoromethyl phenyl | F | H | H | H | 2,6-dimethyl-4-(heptafluoro-n-propylthio)phenyl |
| 807 | 4-trifluoromethyl phenyl | F | H | H | H | 2,6-dimethyl-4-(heptafluoro-n-propylthio)phenyl |
| 808 | 4-trifluoromethoxy phenyl | F | H | H | H | 2,6-dimethyl-4-(heptafluoro-n-propylthio)phenyl |
| 809 | 2,3-difluorophenyl | F | H | H | H | 2,6-dimethyl-4-(heptafluoro-n-propylthio)phenyl |
| 810 | 2,4-difluorophenyl | F | H | H | H | 2,6-dimethyl-4-(heptafluoro-n-propylthio)phenyl |
| 811 | 2,5-difluorophenyl | F | H | H | H | 2,6-dimethyl-4-(heptafluoro-n-propylthio)phenyl |
| 812 | 2,6-difluorophenyl | F | H | H | H | 2,6-dimethyl-4-(heptafluoro-n-propylthio)phenyl |
| 813 | 2,4-dichlorophenyl | F | H | H | H | 2,6-dimethyl-4-(heptafluoro-n-propylthio)phenyl |
| 814 | 2,6-dichlorophenyl | F | H | H | H | 2,6-dimethyl-4-(heptafluoro-n-propylthio)phenyl |
| 815 | 3,4-dichlorophenyl | F | H | H | H | 2,6-dimethyl-4-(heptafluoro-n-propylthio)phenyl |
| 816 | 2-chloro-4-nitro phenyl | F | H | H | H | 2,6-dimethyl-4-(heptafluoro-n-propylthio)phenyl |
| 817 | 2-chloro-4-fluoro phenyl | F | H | H | H | 2,6-dimethyl-4-(heptafluoro-n-propylthio)phenyl |
| 818 | 2-chloro-6-fluoro phenyl | F | H | H | H | 2,6-dimethyl-4-(heptafluoro-n-propylthio)phenyl |
| 819 | 4-chloro-2-fluoro phenyl | F | H | H | H | 2,6-dimethyl-4-(heptafluoro-n-propylthio)phenyl |
| 820 | 4-chloro-2-nitro phenyl | F | H | H | H | 2,6-dimethyl-4-(heptafluoro-n-propylthio)phenyl |
| 821 | 2,3,6-trifluoro phenyl | F | H | H | H | 2,6-dimethyl-4-(heptafluoro-n-propylthio)phenyl |
| 822 | pyridin-2-yl | F | H | H | H | 2,6-dimethyl-4-(heptafluoro-n-propylthio)phenyl |
| 823 | pyridin-3-yl | F | H | H | H | 2,6-dimethyl-4-(heptafluoro-n-propylthio)phenyl |
| 824 | 2-fluoropyridin-3-yl | F | H | H | H | 2,6-dimethyl-4-(heptafluoro-n-propylthio)phenyl |
| 825 | 2-chloropyridin-3-yl | F | H | H | H | 2,6-dimethyl-4-(heptafluoro-n-propylthio)phenyl |
| 826 | 2-chloropyridin-5-yl | F | H | H | H | 2,6-dimethyl-4-(heptafluoro-n-propylthio)phenyl |
| 827 | 2-methylthio pyridin-3-yl | F | H | H | H | 2,6-dimethyl-4-(heptafluoro-n-propylthio)phenyl |
| 828 | pyrazin-2-yl | F | H | H | H | 2,6-dimethyl-4-(heptafluoro-n-propylthio)phenyl |
| 829 | furan-2-yl | F | H | H | H | 2,6-dimethyl-4-(heptafluoro-n-propylthio)phenyl |
| 830 | thiophen-2-yl | F | H | H | H | 2,6-dimethyl-4-(heptafluoro-n-propylthio)phenyl |
| 831 | phenyl | Cl | H | H | H | 2,6-dibromo-4-(heptafluoro-n-propylthio)phenyl |

TABLE 2-continued

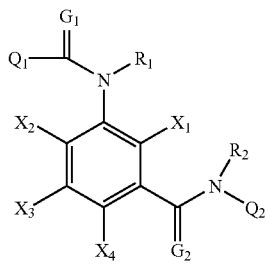

($G_1$, $G_2$ = oxygen atoms; $R_1$, $R_2$ = hydrogen atoms)

| Compound No. | $Q_1$ | $X_1$ | $X_2$ | $X_3$ | $X_4$ | $Q_2$ |
|---|---|---|---|---|---|---|
| 832 | 2-fluorophenyl | Cl | H | H | H | 2,6-dibromo-4-(heptafluoro-n-propylthio)phenyl |
| 833 | 2-chloropyridin-3-yl | Cl | H | H | H | 2,6-dibromo-4-(heptafluoro-n-propylthio)phenyl |

TABLE 3

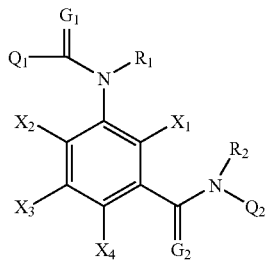

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1001 | phenyl | Me | H | H | H | 2,6-dimethyl-4-(heptafluoro isopropyl)phenyl |
| 1002 | 2-methylphenyl | Me | H | H | H | 2,6-dimethyl-4-(heptafluoro isopropyl)phenyl |
| 1003 | 4-methylphenyl | Me | H | H | H | 2,6-dimethyl-4-(heptafluoro isopropyl)phenyl |
| 1004 | 2-fluorophenyl | Me | H | H | H | 2,6-dimethyl-4-(heptafluoro isopropyl)phenyl |
| 1005 | 3-fluorophenyl | Me | H | H | H | 2,6-dimethyl-4-(heptafluoro isopropyl)phenyl |
| 1006 | 4-fluorophenyl | Me | H | H | H | 2,6-dimethyl-4-(heptafluoro isopropyl)phenyl |
| 1007 | 2-chlorophenyl | Me | H | H | H | 2,6-dimethyl-4-(heptafluoro isopropyl)phenyl |
| 1008 | 4-chlorophenyl | Me | H | H | H | 2,6-dimethyl-4-(heptafluoro isopropyl)phenyl |
| 1009 | 2-bromophenyl | Me | H | H | H | 2,6-dimethyl-4-(heptafluoro isopropyl)phenyl |
| 1010 | 2-iodophenyl | Me | H | H | H | 2,6-dimethyl-4-(heptafluoro isopropyl)phenyl |
| 1011 | 3-cyanophenyl | Me | H | H | H | 2,6-dimethyl-4-(heptafluoro isopropyl)phenyl |
| 1012 | 4-cyanophenyl | Me | H | H | H | 2,6-dimethyl-4-(heptafluoro isopropyl)phenyl |
| 1013 | 2-nitrophenyl | Me | H | H | H | 2,6-dimethyl-4-(heptafluoro isopropyl)phenyl |
| 1014 | 3-nitrophenyl | Me | H | H | H | 2,6-dimethyl-4-(heptafluoro isopropyl)phenyl |
| 1015 | 4-nitrophenyl | Me | H | H | H | 2,6-dimethyl-4-(heptafluoro isopropyl)phenyl |
| 1016 | 2-trifluoromethyl phenyl | Me | H | H | H | 2,6-dimethyl-4-(heptafluoro isopropyl)phenyl |
| 1017 | 4-trifluoromethyl phenyl | Me | H | H | H | 2,6-dimethyl-4-(heptafluoro isopropyl)phenyl |
| 1018 | 4-trifluoromethoxy phenyl | Me | H | H | H | 2,6-dimethyl-4-(heptafluoro isopropyl)phenyl |

TABLE 3-continued

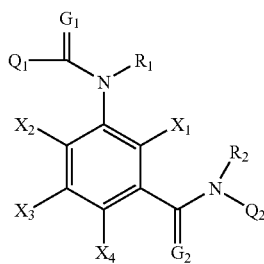

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1019 | 2,3-difluorophenyl | Me | H | H | H | 2,6-dimethyl-4-(heptafluoro isopropyl)phenyl |
| 1020 | 2,4-difluorophenyl | Me | H | H | H | 2,6-dimethyl-4-(heptafluoro isopropyl)phenyl |
| 1021 | 2,5-difluorophenyl | Me | H | H | H | 2,6-dimethyl-4-(heptafluoro isopropyl)phenyl |
| 1022 | 2,6-difluorophenyl | Me | H | H | H | 2,6-dimethyl-4-(heptafluoro isopropyl)phenyl |
| 1023 | 2,4-dichlorophenyl | Me | H | H | H | 2,6-dimethyl-4-(heptafluoro isopropyl)phenyl |
| 1024 | 2,6-dichlorophenyl | Me | H | H | H | 2,6-dimethyl-4-(heptafluoro isopropyl)phenyl |
| 1025 | 3,4-dichlorophenyl | Me | H | H | H | 2,6-dimethyl-4-(heptafluoro isopropyl)phenyl |
| 1026 | 2-chloro-4-nitro phenyl | Me | H | H | H | 2,6-dimethyl-4-(heptafluoro isopropyl)phenyl |
| 1027 | 2-chloro-4-fluoro phenyl | Me | H | H | H | 2,6-dimethyl-4-(heptafluoro isopropyl)phenyl |
| 1028 | 2-chloro-6-fluoro phenyl | Me | H | H | H | 2,6-dimethyl-4-(heptafluoro isopropyl)phenyl |
| 1029 | 4-chloro-2-fluoro phenyl | Me | H | H | H | 2,6-dimethyl-4-(heptafluoro isopropyl)phenyl |
| 1030 | 4-chloro-2-nitro phenyl | Me | H | H | H | 2,6-dimethyl-4-(heptafluoro isopropyl)phenyl |
| 1031 | 2,3,6-trifluoro phenyl | Me | H | H | H | 2,6-dimethyl-4-(heptafluoro isopropyl)phenyl |
| 1032 | 3-(acetylamino) phenyl | Me | H | H | H | 2,6-dimethyl-4-(heptafluoro isopropyl)phenyl |
| 1033 | pyridin-2-yl | Me | H | H | H | 2,6-dimethyl-4-(heptafluoro isopropyl)phenyl |
| 1034 | pyridin-3-yl | Me | H | H | H | 2,6-dimethyl-4-(heptafluoro isopropyl)phenyl |
| 1035 | 2-fluoropyridin-3-yl | Me | H | H | H | 2,6-dimethyl-4-(heptafluoro isopropyl)phenyl |
| 1036 | 2-chloropyridin-3-yl | Me | H | H | H | 2,6-dimethyl-4-(heptafluoro isopropyl)phenyl |
| 1037 | 2-chloropyridin-5-yl | Me | H | H | H | 2,6-dimethyl-4-(heptafluoro isopropyl)phenyl |
| 1038 | 2-trifluoromethyl pyridin-3-yl | Me | H | H | H | 2,6-dimethyl-4-(heptafluoro isopropyl)phenyl |
| 1039 | 2-methylthio pyridin-3-yl | Me | H | H | H | 2,6-dimethyl-4-(heptafluoro isopropyl)phenyl |
| 1040 | pyrazin-2-yl | Me | H | H | H | 2,6-dimethyl-4-(heptafluoro isopropyl)phenyl |
| 1041 | furan-2-yl | Me | H | H | H | 2,6-dimethyl-4-(heptafluoro isopropyl)phenyl |
| 1042 | furan-3-yl | Me | H | H | H | 2,6-dimethyl-4-(heptafluoro isopropyl)phenyl |
| 1043 | 2-tetrahydrofuranyl | Me | H | H | H | 2,6-dimethyl-4-(heptafluoro isopropyl)phenyl |
| 1044 | benzofuran-2-yl | Me | H | H | H | 2,6-dimethyl-4-(heptafluoro isopropyl)phenyl |
| 1045 | thiophen-2-yl | Me | H | H | H | 2,6-dimethyl-4-(heptafluoro isopropyl)phenyl |
| 1046 | phenyl | Me | H | H | H | 2-bromo-4-(heptafluoroisopropyl)-6-(methylsulfonyl)phenyl |
| 1047 | 2-methylphenyl | Me | H | H | H | 2-bromo-4-(heptafluoroisopropyl)-6-(methylsulfonyl)phenyl |
| 1048 | 4-methylphenyl | Me | H | H | H | 2-bromo-4-(heptafluoroisopropyl)-6-(methylsulfonyl)phenyl |
| 1049 | 2-fluorophenyl | Me | H | H | H | 2-bromo-4-(heptafluoroisopropyl)-6-(methylsulfonyl)phenyl |
| 1050 | 3-fluorophenyl | Me | H | H | H | 2-bromo-4-(heptafluoroisopropyl)-6-(methylsulfonyl)phenyl |
| 1051 | 4-fluorophenyl | Me | H | H | H | 2-bromo-4-(heptafluoroisopropyl)-6-(methylsulfonyl)phenyl |

TABLE 3-continued

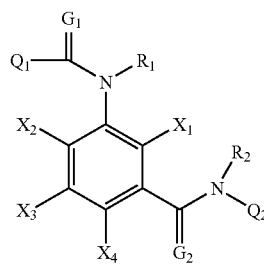

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1052 | 2-chlorophenyl | Me | H | H | H | 2-bromo-4-(heptafluoroisopropyl)-6-(methylsulfonyl)phenyl |
| 1053 | 4-chlorophenyl | Me | H | H | H | 2-bromo-4-(heptafluoroisopropyl)-6-(methylsulfonyl)phenyl |
| 1054 | 2-bromophenyl | Me | H | H | H | 2-bromo-4-(heptafluoroisopropyl)-6-(methylsulfonyl)phenyl |
| 1055 | 2-iodophenyl | Me | H | H | H | 2-bromo-4-(heptafluoroisopropyl)-6-(methylsulfonyl)phenyl |
| 1056 | 3-cyanophenyl | Me | H | H | H | 2-bromo-4-(heptafluoroisopropyl)-6-(methylsulfonyl)phenyl |
| 1057 | 4-cyanophenyl | Me | H | H | H | 2-bromo-4-(heptafluoroisopropyl)-6-(methylsulfonyl)phenyl |
| 1058 | 2-nitrophenyl | Me | H | H | H | 2-bromo-4-(heptafluoroisopropyl)-6-(methylsulfonyl)phenyl |
| 1059 | 3-nitrophenyl | Me | H | H | H | 2-bromo-4-(heptafluoroisopropyl)-6-(methylsulfonyl)phenyl |
| 1060 | 4-nitrophenyl | Me | H | H | H | 2-bromo-4-(heptafluoroisopropyl)-6-(methylsulfonyl)phenyl |
| 1061 | 2-trifluoromethyl phenyl | Me | H | H | H | 2-bromo-4-(heptafluoroisopropyl)-6-(methylsulfonyl)phenyl |
| 1062 | 4-trifluoromethyl phenyl | Me | H | H | H | 2-bromo-4-(heptafluoroisopropyl)-6-(methylsulfonyl)phenyl |
| 1063 | 4-trifluoromethoxy phenyl | Me | H | H | H | 2-bromo-4-(heptafluoroisopropyl)-6-(methylsulfonyl)phenyl |
| 1064 | 2,3-difluorophenyl | Me | H | H | H | 2-bromo-4-(heptafluoroisopropyl)-6-(methylsulfonyl)phenyl |
| 1065 | 2,4-difluorophenyl | Me | H | H | H | 2-bromo-4-(heptafluoroisopropyl)-6-(methylsulfonyl)phenyl |
| 1066 | 2,5-difluorophenyl | Me | H | H | H | 2-bromo-4-(heptafluoroisopropyl)-6-(methylsulfonyl)phenyl |
| 1067 | 2,6-difluorophenyl | Me | H | H | H | 2-bromo-4-(heptafluoroisopropyl)-6-(methylsulfonyl)phenyl |
| 1068 | 2,4-dichlorophenyl | Me | H | H | H | 2-bromo-4-(heptafluoroisopropyl)-6-(methylsulfonyl)phenyl |
| 1069 | 2,6-dichlorophenyl | Me | H | H | H | 2-bromo-4-(heptafluoroisopropyl)-6-(methylsulfonyl)phenyl |
| 1070 | 3,4-dichlorophenyl | Me | H | H | H | 2-bromo-4-(heptafluoroisopropyl)-6-(methylsulfonyl)phenyl |
| 1071 | 2-chloro-4-nitro phenyl | Me | H | H | H | 2-bromo-4-(heptafluoroisopropyl)-6-(methylsulfonyl)phenyl |
| 1072 | 2-chloro-4-fluoro phenyl | Me | H | H | H | 2-bromo-4-(heptafluoroisopropyl)-6-(methylsulfonyl)phenyl |
| 1073 | 2-chloro-6-fluoro phenyl | Me | H | H | H | 2-bromo-4-(heptafluoroisopropyl)-6-(methylsulfonyl)phenyl |
| 1074 | 4-chloro-2-fluoro phenyl | Me | H | H | H | 2-bromo-4-(heptafluoroisopropyl)-6-(methylsulfonyl)phenyl |
| 1075 | 4-chloro-2-nitro phenyl | Me | H | H | H | 2-bromo-4-(heptafluoroisopropyl)-6-(methylsulfonyl)phenyl |
| 1076 | 2,3,6-trifluoro phenyl | Me | H | H | H | 2-bromo-4-(heptafluoroisopropyl)-6-(methylsulfonyl)phenyl |
| 1077 | pyridin-2-yl | Me | H | H | H | 2-bromo-4-(heptafluoroisopropyl)-6-(methylsulfonyl)phenyl |
| 1078 | pyridin-3-yl | Me | H | H | H | 2-bromo-4-(heptafluoroisopropyl)-6-(methylsulfonyl)phenyl |
| 1079 | 2-fluoropyridin-3-yl | Me | H | H | H | 2-bromo-4-(heptafluoroisopropyl)-6-(methylsulfonyl)phenyl |
| 1080 | 2-chloropyridin-3-yl | Me | H | H | H | 2-bromo-4-(heptafluoroisopropyl)-6-(methylsulfonyl)phenyl |
| 1081 | 2-chloropyridin-5-yl | Me | H | H | H | 2-bromo-4-(heptafluoroisopropyl)-6-(methylsulfonyl)phenyl |
| 1082 | 2-methylthio pyridin-3-yl | Me | H | H | H | 2-bromo-4-(heptafluoroisopropyl)-6-(methylsulfonyl)phenyl |
| 1083 | pyrazin-2-yl | Me | H | H | H | 2-bromo-4-(heptafluoroisopropyl)-6-(methylsulfonyl)phenyl |
| 1084 | furan-2-yl | Me | H | H | H | 2-bromo-4-(heptafluoroisopropyl)-6-(methylsulfonyl)phenyl |

TABLE 3-continued

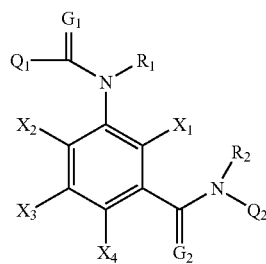

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1085 | thiophen-2-yl | Me | H | H | H | 2-bromo-4-(heptafluoroisopropyl)-6-(methylsulfonyl)phenyl |
| 1086 | phenyl | Me | H | H | H | 2-n-propyl-6-iodo-4-(heptafluoroisopropyl)phenyl |
| 1087 | 2-methylphenyl | Me | H | H | H | 2-n-propyl-6-iodo-4-(heptafluoroisopropyl)phenyl |
| 1088 | 4-methylphenyl | Me | H | H | H | 2-n-propyl-6-iodo-4-(heptafluoroisopropyl)phenyl |
| 1089 | 2-fluorophenyl | Me | H | H | H | 2-n-propyl-6-iodo-4-(heptafluoroisopropyl)phenyl |
| 1090 | 3-fluorophenyl | Me | H | H | H | 2-n-propyl-6-iodo-4-(heptafluoroisopropyl)phenyl |
| 1091 | 4-fluorophenyl | Me | H | H | H | 2-n-propyl-6-iodo-4-(heptafluoroisopropyl)phenyl |
| 1092 | 2-chlorophenyl | Me | H | H | H | 2-n-propyl-6-iodo-4-(heptafluoroisopropyl)phenyl |
| 1093 | 4-chlorophenyl | Me | H | H | H | 2-n-propyl-6-iodo-4-(heptafluoroisopropyl)phenyl |
| 1094 | 2-bromophenyl | Me | H | H | H | 2-n-propyl-6-iodo-4-(heptafluoroisopropyl)phenyl |
| 1095 | 2-iodophenyl | Me | H | H | H | 2-n-propyl-6-iodo-4-(heptafluoroisopropyl)phenyl |
| 1096 | 3-cyanophenyl | Me | H | H | H | 2-n-propyl-6-iodo-4-(heptafluoroisopropyl)phenyl |
| 1097 | 4-cyanophenyl | Me | H | H | H | 2-n-propyl-6-iodo-4-(heptafluoroisopropyl)phenyl |
| 1098 | 2-nitrophenyl | Me | H | H | H | 2-n-propyl-6-iodo-4-(heptafluoroisopropyl)phenyl |
| 1099 | 3-nitrophenyl | Me | H | H | H | 2-n-propyl-6-iodo-4-(heptafluoroisopropyl)phenyl |
| 1100 | 4-nitrophenyl | Me | H | H | H | 2-n-propyl-6-iodo-4-(heptafluoroisopropyl)phenyl |
| 1101 | 2-trifluoromethyl phenyl | Me | H | H | H | 2-n-propyl-6-iodo-4-(heptafluoroisopropyl)phenyl |
| 1102 | 4-trifluoromethyl phenyl | Me | H | H | H | 2-n-propyl-6-iodo-4-(heptafluoroisopropyl)phenyl |
| 1103 | 4-trifluoromethoxy phenyl | Me | H | H | H | 2-n-propyl-6-iodo-4-(heptafluoroisopropyl)phenyl |
| 1104 | 2,3-difluorophenyl | Me | H | H | H | 2-n-propyl-6-iodo-4-(heptafluoroisopropyl)phenyl |
| 1105 | 2,4-difluorophenyl | Me | H | H | H | 2-n-propyl-6-iodo-4-(heptafluoroisopropyl)phenyl |
| 1106 | 2,5-difluorophenyl | Me | H | H | H | 2-n-propyl-6-iodo-4-(heptafluoroisopropyl)phenyl |
| 1107 | 2,6-difluorophenyl | Me | H | H | H | 2-n-propyl-6-iodo-4-(heptafluoroisopropyl)phenyl |
| 1108 | 2,4-dichlorophenyl | Me | H | H | H | 2-n-propyl-6-iodo-4-(heptafluoroisopropyl)phenyl |
| 1109 | 2,6-dichlorophenyl | Me | H | H | H | 2-n-propyl-6-iodo-4-(heptafluoroisopropyl)phenyl |
| 1110 | 3,4-dichlorophenyl | Me | H | H | H | 2-n-propyl-6-iodo-4-(heptafluoroisopropyl)phenyl |
| 1111 | 2-chloro-4-nitro phenyl | Me | H | H | H | 2-n-propyl-6-iodo-4-(heptafluoroisopropyl)phenyl |
| 1112 | 2-chloro-4-fluoro phenyl | Me | H | H | H | 2-n-propyl-6-iodo-4-(heptafluoroisopropyl)phenyl |
| 1113 | 2-chloro-6-fluoro phenyl | Me | H | H | H | 2-n-propyl-6-iodo-4-(heptafluoroisopropyl)phenyl |
| 1114 | 4-chloro-2-fluoro phenyl | Me | H | H | H | 2-n-propyl-6-iodo-4-(heptafluoroisopropyl)phenyl |
| 1115 | 4-chloro-2-nitro phenyl | Me | H | H | H | 2-n-propyl-6-iodo-4-(heptafluoroisopropyl)phenyl |
| 1116 | 2,3,6-trifluoro phenyl | Me | H | H | H | 2-n-propyl-6-iodo-4-(heptafluoroisopropyl)phenyl |
| 1117 | pyridin-2-yl | Me | H | H | H | 2-n-propyl-6-iodo-4-(heptafluoroisopropyl)phenyl |

TABLE 3-continued

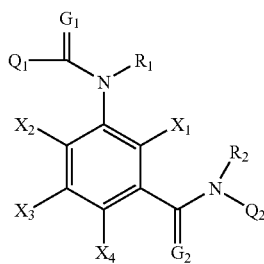

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1118 | pyridin-3-yl | Me | H | H | H | 2-n-propyl-6-iodo-4-(heptafluoroisopropyl)phenyl |
| 1119 | 2-fluoropyridin-3-yl | Me | H | H | H | 2-n-propyl-6-iodo-4-(heptafluoroisopropyl)phenyl |
| 1120 | 2-chloropyridin-3-yl | Me | H | H | H | 2-n-propyl-6-iodo-4-(heptafluoroisopropyl)phenyl |
| 1121 | 2-chloropyridin-5-yl | Me | H | H | H | 2-n-propyl-6-iodo-4-(heptafluoroisopropyl)phenyl |
| 1122 | 2-methylthio pyridin-3-yl | Me | H | H | H | 2-n-propyl-6-iodo-4-(heptafluoroisopropyl)phenyl |
| 1123 | pyrazin-2-yl | Me | H | H | H | 2-n-propyl-6-iodo-4-(heptafluoroisopropyl)phenyl |
| 1124 | furan-2-yl | Me | H | H | H | 2-n-propyl-6-iodo-4-(heptafluoroisopropyl)phenyl |
| 1125 | 2-fluorophenyl | Me | H | H | H | 2,6-dimethyl-4-(heptafluoro-n-propylthio)phenyl |
| 1126 | phenyl | Me | H | H | H | 2,6-dibromo-4-(heptafluoro-n-propylthio)phenyl |
| 1127 | 2-methylphenyl | Me | H | H | H | 2,6-dibromo-4-(heptafluoro-n-propylthio)phenyl |
| 1128 | 4-methylphenyl | Me | H | H | H | 2,6-dibromo-4-(heptafluoro-n-propylthio)phenyl |
| 1129 | 2-fluorophenyl | Me | H | H | H | 2,6-dibromo-4-(heptafluoro-n-propylthio)phenyl |
| 1130 | 3-fluorophenyl | Me | H | H | H | 2,6-dibromo-4-(heptafluoro-n-propylthio)phenyl |
| 1131 | 4-fluorophenyl | Me | H | H | H | 2,6-dibromo-4-(heptafluoro-n-propylthio)phenyl |
| 1132 | 2-chlorophenyl | Me | H | H | H | 2,6-dibromo-4-(heptafluoro-n-propylthio)phenyl |
| 1133 | 4-chlorophenyl | Me | H | H | H | 2,6-dibromo-4-(heptafluoro-n-propylthio)phenyl |
| 1134 | 2-bromophenyl | Me | H | H | H | 2,6-dibromo-4-(heptafluoro-n-propylthio)phenyl |
| 1135 | 2-iodophenyl | Me | H | H | H | 2,6-dibromo-4-(heptafluoro-n-propylthio)phenyl |
| 1136 | 3-cyanophenyl | Me | H | H | H | 2,6-dibromo-4-(heptafluoro-n-propylthio)phenyl |
| 1137 | 4-cyanophenyl | Me | H | H | H | 2,6-dibromo-4-(heptafluoro-n-propylthio)phenyl |
| 1138 | 2-nitrophenyl | Me | H | H | H | 2,6-dibromo-4-(heptafluoro-n-propylthio)phenyl |
| 1139 | 3-nitrophenyl | Me | H | H | H | 2,6-dibromo-4-(heptafluoro-n-propylthio)phenyl |
| 1140 | 4-nitrophenyl | Me | H | H | H | 2,6-dibromo-4-(heptafluoro-n-propylthio)phenyl |
| 1141 | 2-trifluoromethyl phenyl | Me | H | H | H | 2,6-dibromo-4-(heptafluoro-n-propylthio)phenyl |
| 1142 | 4-trifluoromethyl phenyl | Me | H | H | H | 2,6-dibromo-4-(heptafluoro-n-propylthio)phenyl |
| 1143 | 4-trifluoromethoxy phenyl | Me | H | H | H | 2,6-dibromo-4-(heptafluoro-n-propylthio)phenyl |
| 1144 | 2,3-difluorophenyl | Me | H | H | H | 2,6-dibromo-4-(heptafluoro-n-propylthio)phenyl |
| 1145 | 2,4-difluorophenyl | Me | H | H | H | 2,6-dibromo-4-(heptafluoro-n-propylthio)phenyl |
| 1146 | 2,5-difluorophenyl | Me | H | H | H | 2,6-dibromo-4-(heptafluoro-n-propylthio)phenyl |
| 1147 | 2,6-difluorophenyl | Me | H | H | H | 2,6-dibromo-4-(heptafluoro-n-propylthio)phenyl |
| 1148 | 2,4-dichlorophenyl | Me | H | H | H | 2,6-dibromo-4-(heptafluoro-n-propylthio)phenyl |
| 1149 | 2,6-dichlorophenyl | Me | H | H | H | 2,6-dibromo-4-(heptafluoro-n-propylthio)phenyl |
| 1150 | 3,4-dichlorophenyl | Me | H | H | H | 2,6-dibromo-4-(heptafluoro-n-propylthio)phenyl |

TABLE 3-continued

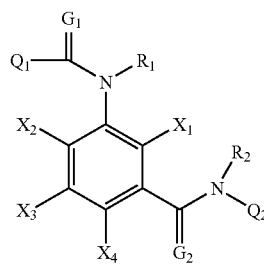

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1151 | 2-chloro-4-nitrophenyl | Me | H | H | H | 2,6-dibromo-4-(heptafluoro-n-propylthio)phenyl |
| 1152 | 2-chloro-4-fluorophenyl | Me | H | H | H | 2,6-dibromo-4-(heptafluoro-n-propylthio)phenyl |
| 1153 | 2-chloro-6-fluorophenyl | Me | H | H | H | 2,6-dibromo-4-(heptafluoro-n-propylthio)phenyl |
| 1154 | 4-chloro-2-fluorophenyl | Me | H | H | H | 2,6-dibromo-4-(heptafluoro-n-propylthio)phenyl |
| 1155 | 4-chloro-2-nitrophenyl | Me | H | H | H | 2,6-dibromo-4-(heptafluoro-n-propylthio)phenyl |
| 1156 | 2,3,6-trifluorophenyl | Me | H | H | H | 2,6-dibromo-4-(heptafluoro-n-propylthio)phenyl |
| 1157 | pyridin-2-yl | Me | H | H | H | 2,6-dibromo-4-(heptafluoro-n-propylthio)phenyl |
| 1158 | pyridin-3-yl | Me | H | H | H | 2,6-dibromo-4-(heptafluoro-n-propylthio)phenyl |
| 1159 | 2-fluoropyridin-3-yl | Me | H | H | H | 2,6-dibromo-4-(heptafluoro-n-propylthio)phenyl |
| 1160 | 2-chloropyridin-3-yl | Me | H | H | H | 2,6-dibromo-4-(heptafluoro-n-propylthio)phenyl |
| 1161 | 2-chloropyridin-5-yl | Me | H | H | H | 2,6-dibromo-4-(heptafluoro-n-propylthio)phenyl |
| 1162 | 2-methylthiopyridin-3-yl | Me | H | H | H | 2,6-dibromo-4-(heptafluoro-n-propylthio)phenyl |
| 1163 | pyrazin-2-yl | Me | H | H | H | 2,6-dibromo-4-(heptafluoro-n-propylthio)phenyl |
| 1164 | furan-2-yl | Me | H | H | H | 2,6-dibromo-4-(heptafluoro-n-propylthio)phenyl |
| 1165 | thiophen-2-yl | Me | H | H | H | 2,6-dibromo-4-(heptafluoro-n-propylthio)phenyl |
| 1166 | phenyl | Me | H | H | H | 2,6-dibromo-4-(heptafluoro-n-propylsulfinyl)phenyl |
| 1167 | 2-methylphenyl | Me | H | H | H | 2,6-dibromo-4-(heptafluoro-n-propylsulfinyl)phenyl |
| 1168 | 4-methylphenyl | Me | H | H | H | 2,6-dibromo-4-(heptafluoro-n-propylsulfinyl)phenyl |
| 1169 | 2-fluorophenyl | Me | H | H | H | 2,6-dibromo-4-(heptafluoro-n-propylsulfinyl)phenyl |
| 1170 | 3-fluorophenyl | Me | H | H | H | 2,6-dibromo-4-(heptafluoro-n-propylsulfinyl)phenyl |
| 1171 | 4-fluorophenyl | Me | H | H | H | 2,6-dibromo-4-(heptafluoro-n-propylsulfinyl)phenyl |
| 1172 | 2-chlorophenyl | Me | H | H | H | 2,6-dibromo-4-(heptafluoro-n-propylsulfinyl)phenyl |
| 1173 | 4-chlorophenyl | Me | H | H | H | 2,6-dibromo-4-(heptafluoro-n-propylsulfinyl)phenyl |
| 1174 | 2-bromophenyl | Me | H | H | H | 2,6-dibromo-4-(heptafluoro-n-propylsulfinyl)phenyl |
| 1175 | 2-iodophenyl | Me | H | H | H | 2,6-dibromo-4-(heptafluoro-n-propylsulfinyl)phenyl |
| 1176 | 3-cyanophenyl | Me | H | H | H | 2,6-dibromo-4-(heptafluoro-n-propylsulfinyl)phenyl |
| 1177 | 4-cyanophenyl | Me | H | H | H | 2,6-dibromo-4-(heptafluoro-n-propylsulfinyl)phenyl |
| 1178 | 2-nitrophenyl | Me | H | H | H | 2,6-dibromo-4-(heptafluoro-n-propylsulfinyl)phenyl |
| 1179 | 3-nitrophenyl | Me | H | H | H | 2,6-dibromo-4-(heptafluoro-n-propylsulfinyl)phenyl |
| 1180 | 4-nitrophenyl | Me | H | H | H | 2,6-dibromo-4-(heptafluoro-n-propylsulfinyl)phenyl |
| 1181 | 2-trifluoromethylphenyl | Me | H | H | H | 2,6-dibromo-4-(heptafluoro-n-propylsulfinyl)phenyl |
| 1182 | 4-trifluoromethylphenyl | Me | H | H | H | 2,6-dibromo-4-(heptafluoro-n-propylsulfinyl)phenyl |
| 1183 | 4-trifluoromethoxyphenyl | Me | H | H | H | 2,6-dibromo-4-(heptafluoro-n-propylsulfinyl)phenyl |

TABLE 3-continued

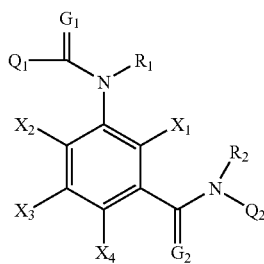

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1184 | 2,3-difluorophenyl | Me | H | H | H | 2,6-dibromo-4-(heptafluoro-n-propylsulfinyl)phenyl |
| 1185 | 2,4-difluorophenyl | Me | H | H | H | 2,6-dibromo-4-(heptafluoro-n-propylsulfinyl)phenyl |
| 1186 | 2,5-difluorophenyl | Me | H | H | H | 2,6-dibromo-4-(heptafluoro-n-propylsulfinyl)phenyl |
| 1187 | 2,6-difluorophenyl | Me | H | H | H | 2,6-dibromo-4-(heptafluoro-n-propylsulfinyl)phenyl |
| 1188 | 2,4-dichlorophenyl | Me | H | H | H | 2,6-dibromo-4-(heptafluoro-n-propylsulfinyl)phenyl |
| 1189 | 2,6-dichlorophenyl | Me | H | H | H | 2,6-dibromo-4-(heptafluoro-n-propylsulfinyl)phenyl |
| 1190 | 3,4-dichlorophenyl | Me | H | H | H | 2,6-dibromo-4-(heptafluoro-n-propylsulfinyl)phenyl |
| 1191 | 2-chloro-4-nitro phenyl | Me | H | H | H | 2,6-dibromo-4-(heptafluoro-n-propylsulfinyl)phenyl |
| 1192 | 2-chloro-4-fluoro phenyl | Me | H | H | H | 2,6-dibromo-4-(heptafluoro-n-propylsulfinyl)phenyl |
| 1193 | 2-chloro-6-fluoro phenyl | Me | H | H | H | 2,6-dibromo-4-(heptafluoro-n-propylsulfinyl)phenyl |
| 1194 | 4-chloro-2-fluoro phenyl | Me | H | H | H | 2,6-dibromo-4-(heptafluoro-n-propylsulfinyl)phenyl |
| 1195 | 4-chloro-2-nitro phenyl | Me | H | H | H | 2,6-dibromo-4-(heptafluoro-n-propylsulfinyl)phenyl |
| 1196 | 2,3,6-trifluoro phenyl | Me | H | H | H | 2,6-dibromo-4-(heptafluoro-n-propylsulfinyl)phenyl |
| 1197 | pyridin-2-yl | Me | H | H | H | 2,6-dibromo-4-(heptafluoro-n-propylsulfinyl)phenyl |
| 1198 | pyridin-3-yl | Me | H | H | H | 2,6-dibromo-4-(heptafluoro-n-propylsulfinyl)phenyl |
| 1199 | 2-fluoropyridin-3-yl | Me | H | H | H | 2,6-dibromo-4-(heptafluoro-n-propylsulfinyl)phenyl |
| 1200 | 2-chloropyridin-3-yl | Me | H | H | H | 2,6-dibromo-4-(heptafluoro-n-propylsulfinyl)phenyl |
| 1201 | 2-chloropyridin-5-yl | Me | H | H | H | 2,6-dibromo-4-(heptafluoro-n-propylsulfinyl)phenyl |
| 1202 | 2-methylthio pyridin-3-yl | Me | H | H | H | 2,6-dibromo-4-(heptafluoro-n-propylsulfinyl)phenyl |
| 1203 | pyrazin-2-yl | Me | H | H | H | 2,6-dibromo-4-(heptafluoro-n-propylsulfinyl)phenyl |
| 1204 | furan-2-yl | Me | H | H | H | 2,6-dibromo-4-(heptafluoro-n-propylsulfinyl)phenyl |
| 1205 | thiophen-2-yl | Me | H | H | H | 2,6-dibromo-4-(heptafluoro-n-propylsulfinyl)phenyl |
| 1206 | 2-fluorophenyl | Et | H | H | H | 2,6-dimethyl-4-(heptafluoro isopropyl)phenyl |
| 1207 | pyridin-3-yl | Et | H | H | H | 2,6-dimethyl-4-(heptafluoro isopropyl)phenyl |
| 1208 | phenyl | Me | H | F | H | 2,6-dimethyl-4-(heptafluoro isopropyl)phenyl |
| 1209 | 2-methylphenyl | Me | H | F | H | 2,6-dimethyl-4-(heptafluoro isopropyl)phenyl |
| 1210 | 3-methylphenyl | Me | H | F | H | 2,6-dimethyl-4-(heptafluoro isopropyl)phenyl |
| 1211 | 4-methylphenyl | Me | H | F | H | 2,6-dimethyl-4-(heptafluoro isopropyl)phenyl |
| 1212 | 2-nitrophenyl | Me | H | F | H | 2,6-dimethyl-4-(heptafluoro isopropyl)phenyl |
| 1213 | 3-nitrophenyl | Me | H | F | H | 2,6-dimethyl-4-(heptafluoro isopropyl)phenyl |
| 1214 | 4-nitrophenyl | Me | H | F | H | 2,6-dimethyl-4-(heptafluoro isopropyl)phenyl |
| 1215 | 2-cyanophenyl | Me | H | F | H | 2,6-dimethyl-4-(heptafluoro isopropyl)phenyl |
| 1216 | 3-cyanophenyl | Me | H | F | H | 2,6-dimethyl-4-(heptafluoro isopropyl)phenyl |

TABLE 3-continued

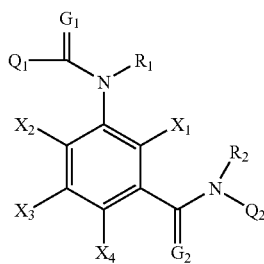

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1217 | 4-cyanophenyl | Me | H | F | H | 2,6-dimethyl-4-(heptafluoro isopropyl)phenyl |
| 1218 | 2-fluorophenyl | Me | H | F | H | 2,6-dimethyl-4-(heptafluoro isopropyl)phenyl |
| 1219 | 3-fluorophenyl | Me | H | F | H | 2,6-dimethyl-4-(heptafluoro isopropyl)phenyl |
| 1220 | 4-fluorophenyl | Me | H | F | H | 2,6-dimethyl-4-(heptafluoro isopropyl)phenyl |
| 1221 | 2-chlorophenyl | Me | H | F | H | 2,6-dimethyl-4-(heptafluoro isopropyl)phenyl |
| 1222 | 4-chlorophenyl | Me | H | F | H | 2,6-dimethyl-4-(heptafluoro isopropyl)phenyl |
| 1223 | 2-bromophenyl | Me | H | F | H | 2,6-dimethyl-4-(heptafluoro isopropyl)phenyl |
| 1224 | 2-iodophenyl | Me | H | F | H | 2,6-dimethyl-4-(heptafluoro isopropyl)phenyl |
| 1225 | 2-trifluoromethyl phenyl | Me | H | F | H | 2,6-dimethyl-4-(heptafluoro isopropyl)phenyl |
| 1226 | 4-trifluoromethyl phenyl | Me | H | F | H | 2,6-dimethyl-4-(heptafluoro isopropyl)phenyl |
| 1227 | 4-trifluoromethoxy phenyl | Me | H | F | H | 2,6-dimethyl-4-(heptafluoro isopropyl)phenyl |
| 1228 | 2,3-difluorophenyl | Me | H | F | H | 2,6-dimethyl-4-(heptafluoro isopropyl)phenyl |
| 1229 | 2,4-difluorophenyl | Me | H | F | H | 2,6-dimethyl-4-(heptafluoro isopropyl)phenyl |
| 1230 | 2,5-difluorophenyl | Me | H | F | H | 2,6-dimethyl-4-(heptafluoro isopropyl)phenyl |
| 1231 | 2,6-difluorophenyl | Me | H | F | H | 2,6-dimethyl-4-(heptafluoro isopropyl)phenyl |
| 1232 | 2,4-dichlorophenyl | Me | H | F | H | 2,6-dimethyl-4-(heptafluoro isopropyl)phenyl |
| 1233 | 2,6-dichlorophenyl | Me | H | F | H | 2,6-dimethyl-4-(heptafluoro isopropyl)phenyl |
| 1234 | 3,4-dichlorophenyl | Me | H | F | H | 2,6-dimethyl-4-(heptafluoro isopropyl)phenyl |
| 1235 | 2-fluoro-4-nitro phenyl | Me | H | F | H | 2,6-dimethyl-4-(heptafluoro isopropyl)phenyl |
| 1236 | 4-fluoro-2-nitro phenyl | Me | H | F | H | 2,6-dimethyl-4-(heptafluoro isopropyl)phenyl |
| 1237 | 2-chloro-4-fluoro phenyl | Me | H | F | H | 2,6-dimethyl-4-(heptafluoro isopropyl)phenyl |
| 1238 | 4-chloro-2-fluoro phenyl | Me | H | F | H | 2,6-dimethyl-4-(heptafluoro isopropyl)phenyl |
| 1239 | 2-chloro-6-fluoro phenyl | Me | H | F | H | 2,6-dimethyl-4-(heptafluoro isopropyl)phenyl |
| 1240 | 2-chloro-4-nitro phenyl | Me | H | F | H | 2,6-dimethyl-4-(heptafluoro isopropyl)phenyl |
| 1241 | 4-chloro-2-nitro phenyl | Me | H | F | H | 2,6-dimethyl-4-(heptafluoro isopropyl)phenyl |
| 1242 | 2,3,6-trifluoro phenyl | Me | H | F | H | 2,6-dimethyl-4-(heptafluoro isopropyl)phenyl |
| 1243 | pyridin-2-yl | Me | H | F | H | 2,6-dimethyl-4-(heptafluoro isopropyl)phenyl |
| 1244 | pyridin-3-yl | Me | H | F | H | 2,6-dimethyl-4-(heptafluoro isopropyl)phenyl |
| 1245 | 2-chloropyridin-3-yl | Me | H | F | H | 2,6-dimethyl-4-(heptafluoro isopropyl)phenyl |
| 1246 | 2-fluoropyridin-3-yl | Me | H | F | H | 2,6-dimethyl-4-(heptafluoro isopropyl)phenyl |
| 1247 | 2-chloropyridin-5-yl | Me | H | F | H | 2,6-dimethyl-4-(heptafluoro isopropyl)phenyl |
| 1248 | 2-methylthio pyridin-3-yl | Me | H | F | H | 2,6-dimethyl-4-(heptafluoro isopropyl)phenyl |
| 1249 | pyrazin-2-yl | Me | H | F | H | 2,6-dimethyl-4-(heptafluoro isopropyl)phenyl |

TABLE 3-continued

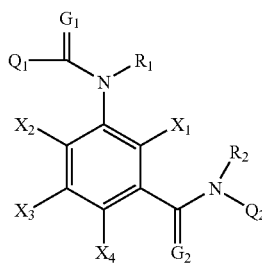

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1250 | furan-2-yl | Me | H | F | H | 2,6-dimethyl-4-(heptafluoro isopropyl)phenyl |
| 1251 | furan-3-yl | Me | H | F | H | 2,6-dimethyl-4-(heptafluoro isopropyl)phenyl |
| 1252 | 2-tetrahydrofuranyl | Me | H | F | H | 2,6-dimethyl-4-(heptafluoro isopropyl)phenyl |
| 1253 | benzofuran-2-yl | Me | H | F | H | 2,6-dimethyl-4-(heptafluoro isopropyl)phenyl |
| 1254 | thiophen-2-yl | Me | H | F | H | 2,6-dimethyl-4-(heptafluoro isopropyl)phenyl |
| 1255 | phenyl | Me | H | F | H | 2,6-dimethyl-4-(nonafluoro-2-butyl)phenyl |
| 1256 | 2-methylphenyl | Me | H | F | H | 2,6-dimethyl-4-(nonafluoro-2-butyl)phenyl |
| 1257 | 3-methylphenyl | Me | H | F | H | 2,6-dimethyl-4-(nonafluoro-2-butyl)phenyl |
| 1258 | 4-methylphenyl | Me | H | F | H | 2,6-dimethyl-4-(nonafluoro-2-butyl)phenyl |
| 1259 | 2-nitrophenyl | Me | H | F | H | 2,6-dimethyl-4-(nonafluoro-2-butyl)phenyl |
| 1260 | 3-nitrophenyl | Me | H | F | H | 2,6-dimethyl-4-(nonafluoro-2-butyl)phenyl |
| 1261 | 4-nitrophenyl | Me | H | F | H | 2,6-dimethyl-4-(nonafluoro-2-butyl)phenyl |
| 1262 | 2-cyanophenyl | Me | H | F | H | 2,6-dimethyl-4-(nonafluoro-2-butyl)phenyl |
| 1263 | 3-cyanophenyl | Me | H | F | H | 2,6-dimethyl-4-(nonafluoro-2-butyl)phenyl |
| 1264 | 4-cyanophenyl | Me | H | F | H | 2,6-dimethyl-4-(nonafluoro-2-butyl)phenyl |
| 1265 | 2-fluorophenyl | Me | H | F | H | 2,6-dimethyl-4-(nonafluoro-2-butyl)phenyl |
| 1266 | 3-fluorophenyl | Me | H | F | H | 2,6-dimethyl-4-(nonafluoro-2-butyl)phenyl |
| 1267 | 4-fluorophenyl | Me | H | F | H | 2,6-dimethyl-4-(nonafluoro-2-butyl)phenyl |
| 1268 | 2-chlorophenyl | Me | H | F | H | 2,6-dimethyl-4-(nonafluoro-2-butyl)phenyl |
| 1269 | 4-chlorophenyl | Me | H | F | H | 2,6-dimethyl-4-(nonafluoro-2-butyl)phenyl |
| 1270 | 2-bromophenyl | Me | H | F | H | 2,6-dimethyl-4-(nonafluoro-2-butyl)phenyl |
| 1271 | 2-iodophenyl | Me | H | F | H | 2,6-dimethyl-4-(nonafluoro-2-butyl)phenyl |
| 1272 | 2-trifluoromethyl phenyl | Me | H | F | H | 2,6-dimethyl-4-(nonafluoro-2-butyl)phenyl |
| 1273 | 4-trifluoromethyl phenyl | Me | H | F | H | 2,6-dimethyl-4-(nonafluoro-2-butyl)phenyl |
| 1274 | 4-trifluoromethoxy phenyl | Me | H | F | H | 2,6-dimethyl-4-(nonafluoro-2-butyl)phenyl |
| 1275 | 2,3-difluorophenyl | Me | H | F | H | 2,6-dimethyl-4-(nonafluoro-2-butyl)phenyl |
| 1276 | 2,4-difluorophenyl | Me | H | F | H | 2,6-dimethyl-4-(nonafluoro-2-butyl)phenyl |
| 1277 | 2,5-difluorophenyl | Me | H | F | H | 2,6-dimethyl-4-(nonafluoro-2-butyl)phenyl |
| 1278 | 2,6-difluorophenyl | Me | H | F | H | 2,6-dimethyl-4-(nonafluoro-2-butyl)phenyl |
| 1279 | 2,4-dichlorophenyl | Me | H | F | H | 2,6-dimethyl-4-(nonafluoro-2-butyl)phenyl |
| 1280 | 2,6-dichlorophenyl | Me | H | F | H | 2,6-dimethyl-4-(nonafluoro-2-butyl)phenyl |
| 1281 | 3,4-dichlorophenyl | Me | H | F | H | 2,6-dimethyl-4-(nonafluoro-2-butyl)phenyl |
| 1282 | 2-fluoro-4-nitro phenyl | Me | H | F | H | 2,6-dimethyl-4-(nonafluoro-2-butyl)phenyl |

TABLE 3-continued

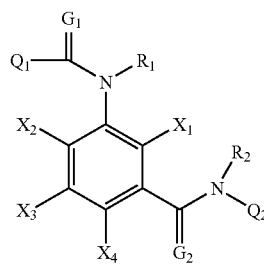

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1283 | 4-fluoro-2-nitro phenyl | Me | H | F | H | 2,6-dimethyl-4-(nonafluoro-2-butyl)phenyl |
| 1284 | 2-chloro-4-fluoro phenyl | Me | H | F | H | 2,6-dimethyl-4-(nonafluoro-2-butyl)phenyl |
| 1285 | 4-chloro-2-fluoro phenyl | Me | H | F | H | 2,6-dimethyl-4-(nonafluoro-2-butyl)phenyl |
| 1286 | 2-chloro-6-fluoro phenyl | Me | H | F | H | 2,6-dimethyl-4-(nonafluoro-2-butyl)phenyl |
| 1287 | 2-chloro-4-nitro phenyl | Me | H | F | H | 2,6-dimethyl-4-(nonafluoro-2-butyl)phenyl |
| 1288 | 4-chloro-2-nitro phenyl | Me | H | F | H | 2,6-dimethyl-4-(nonafluoro-2-butyl)phenyl |
| 1289 | 2,3,6-trifluoro phenyl | Me | H | F | H | 2,6-dimethyl-4-(nonafluoro-2-butyl)phenyl |
| 1290 | pyridine-2-yl | Me | H | F | H | 2,6-dimethyl-4-(nonafluoro-2-butyl)phenyl |
| 1291 | pyridine-3-yl | Me | H | F | H | 2,6-dimethyl-4-(nonafluoro-2-butyl)phenyl |
| 1292 | 2-fluoropyridine-3-yl | Me | H | F | H | 2,6-dimethyl-4-(nonafluoro-2-butyl)phenyl |
| 1293 | 2-chloropyridine-3-yl | Me | H | F | H | 2,6-dimethyl-4-(nonafluoro-2-butyl)phenyl |
| 1294 | 2-chloropyridine-5-yl | Me | H | F | H | 2,6-dimethyl-4-(nonafluoro-2-butyl)phenyl |
| 1295 | 2-methylthio pyridine-3-yl | Me | H | F | H | 2,6-dimethyl-4-(nonafluoro-2-butyl)phenyl |
| 1296 | pyrazine-2-yl | Me | H | F | H | 2,6-dimethyl-4-(nonafluoro-2-butyl)phenyl |
| 1297 | furan-2-yl | Me | H | F | H | 2,6-dimethyl-4-(nonafluoro-2-butyl)phenyl |
| 1298 | furan-3-yl | Me | H | F | H | 2,6-dimethyl-4-(nonafluoro-2-butyl)phenyl |
| 1299 | 2-tetrahydrofuranyl | Me | H | F | H | 2,6-dimethyl-4-(nonafluoro-2-butyl)phenyl |
| 1300 | benzofuran-2-yl | Me | H | F | H | 2,6-dimethyl-4-(nonafluoro-2-butyl)phenyl |
| 1301 | thiophen-2-yl | Me | H | F | H | 2,6-dimethyl-4-(nonafluoro-2-butyl)phenyl |
| 1302 | phenyl | Me | H | F | H | 2-bromo-4-(heptafluoroisopropyl)-6-(methylsulfonyl)phenyl |
| 1303 | 2-methylphenyl | Me | H | F | H | 2-bromo-4-(heptafluoroisopropyl)-6-(methylsulfonyl)phenyl |
| 1304 | 4-methylphenyl | Me | H | F | H | 2-bromo-4-(heptafluoroisopropyl)-6-(methylsulfonyl)phenyl |
| 1305 | 2-fluorophenyl | Me | H | F | H | 2-bromo-4-(heptafluoroisopropyl)-6-(methylsulfonyl)phenyl |
| 1306 | 3-fluorophenyl | Me | H | F | H | 2-bromo-4-(heptafluoroisopropyl)-6-(methylsulfonyl)phenyl |
| 1307 | 4-fluorophenyl | Me | H | F | H | 2-bromo-4-(heptafluoroisopropyl)-6-(methylsulfonyl)phenyl |
| 1308 | 2-chlorophenyl | Me | H | F | H | 2-bromo-4-(heptafluoroisopropyl)-6-(methylsulfonyl)phenyl |
| 1309 | 4-chlorophenyl | Me | H | F | H | 2-bromo-4-(heptafluoroisopropyl)-6-(methylsulfonyl)phenyl |
| 1310 | 2-bromophenyl | Me | H | F | H | 2-bromo-4-(heptafluoroisopropyl)-6-(methylsulfonyl)phenyl |
| 1311 | 2-iodophenyl | Me | H | F | H | 2-bromo-4-(heptafluoroisopropyl)-6-(methylsulfonyl)phenyl |
| 1312 | 3-cyanophenyl | Me | H | F | H | 2-bromo-4-(heptafluoroisopropyl)-6-(methylsulfonyl)phenyl |
| 1313 | 4-cyanophenyl | Me | H | F | H | 2-bromo-4-(heptafluoroisopropyl)-6-(methylsulfonyl)phenyl |
| 1314 | 2-nitrophenyl | Me | H | F | H | 2-bromo-4-(heptafluoroisopropyl)-6-(methylsulfonyl)phenyl |
| 1315 | 3-nitrophenyl | Me | H | F | H | 2-bromo-4-(heptafluoroisopropyl)-6-(methylsulfonyl)phenyl |

TABLE 3-continued

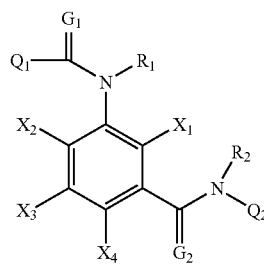

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1316 | 4-nitrophenyl | Me | H | F | H | 2-bromo-4-(heptafluoroisopropyl)-6-(methylsulfonyl)phenyl |
| 1317 | 2-trifluoromethyl phenyl | Me | H | F | H | 2-bromo-4-(heptafluoroisopropyl)-6-(methylsulfonyl)phenyl |
| 1318 | 4-trifluoromethyl phenyl | Me | H | F | H | 2-bromo-4-(heptafluoroisopropyl)-6-(methylsulfonyl)phenyl |
| 1319 | 4-trifluoromethoxy phenyl | Me | H | F | H | 2-bromo-4-(heptafluoroisopropyl)-6-(methylsulfonyl)phenyl |
| 1320 | 2,3-difluorophenyl | Me | H | F | H | 2-bromo-4-(heptafluoroisopropyl)-6-(methylsulfonyl)phenyl |
| 1321 | 2,4-difluorophenyl | Me | H | F | H | 2-bromo-4-(heptafluoroisopropyl)-6-(methylsulfonyl)phenyl |
| 1322 | 2,5-difluorophenyl | Me | H | F | H | 2-bromo-4-(heptafluoroisopropyl)-6-(methylsulfonyl)phenyl |
| 1323 | 2,6-difluorophenyl | Me | H | F | H | 2-bromo-4-(heptafluoroisopropyl)-6-(methylsulfonyl)phenyl |
| 1324 | 2,4-dichlorophenyl | Me | H | F | H | 2-bromo-4-(heptafluoroisopropyl)-6-(methylsulfonyl)phenyl |
| 1325 | 2,6-dichlorophenyl | Me | H | F | H | 2-bromo-4-(heptafluoroisopropyl)-6-(methylsulfonyl)phenyl |
| 1326 | 3,4-dichlorophenyl | Me | H | F | H | 2-bromo-4-(heptafluoroisopropyl)-6-(methylsulfonyl)phenyl |
| 1327 | 2-chloro-4-nitro phenyl | Me | H | F | H | 2-bromo-4-(heptafluoroisopropyl)-6-(methylsulfonyl)phenyl |
| 1328 | 2-chloro-4-fluoro phenyl | Me | H | F | H | 2-bromo-4-(heptafluoroisopropyl)-6-(methylsulfonyl)phenyl |
| 1329 | 2-chloro-6-fluoro phenyl | Me | H | F | H | 2-bromo-4-(heptafluoroisopropyl)-6-(methylsulfonyl)phenyl |
| 1330 | 4-chloro-2-fluoro phenyl | Me | H | F | H | 2-bromo-4-(heptafluoroisopropyl)-6-(methylsulfonyl)phenyl |
| 1331 | 4-chloro-2-nitro phenyl | Me | H | F | H | 2-bromo-4-(heptafluoroisopropyl)-6-(methylsulfonyl)phenyl |
| 1332 | 2,3,6-trifluoro phenyl | Me | H | F | H | 2-bromo-4-(heptafluoroisopropyl)-6-(methylsulfonyl)phenyl |
| 1333 | pyridin-2-yl | Me | H | F | H | 2-bromo-4-(heptafluoroisopropyl)-6-(methylsulfonyl)phenyl |
| 1334 | pyridin-3-yl | Me | H | F | H | 2-bromo-4-(heptafluoroisopropyl)-6-(methylsulfonyl)phenyl |
| 1335 | 2-fluoropyridin-3-yl | Me | H | F | H | 2-bromo-4-(heptafluoroisopropyl)-6-(methylsulfonyl)phenyl |
| 1336 | 2-chloropyridin-3-yl | Me | H | F | H | 2-bromo-4-(heptafluoroisopropyl)-6-(methylsulfonyl)phenyl |
| 1337 | 2-chloropyridin-5-yl | Me | H | F | H | 2-bromo-4-(heptafluoroisopropyl)-6-(methylsulfonyl)phenyl |
| 1338 | 2-methylthio pyridin-3-yl | Me | H | F | H | 2-bromo-4-(heptafluoroisopropyl)-6-(methylsulfonyl)phenyl |
| 1339 | pyrazin-2-yl | Me | H | F | H | 2-bromo-4-(heptafluoroisopropyl)-6-(methylsulfonyl)phenyl |
| 1340 | furan-2-yl | Me | H | F | H | 2-bromo-4-(heptafluoroisopropyl)-6-(methylsulfonyl)phenyl |
| 1341 | thiophen-2-yl | Me | H | F | H | 2-bromo-4-(heptafluoroisopropyl)-6-(methylsulfonyl)phenyl |
| 1342 | phenyl | Me | H | F | H | 2-n-propyl-6-iodo-4-(heptafluoro isopropyl)phenyl |
| 1343 | 2-methylphenyl | Me | H | F | H | 2-n-propyl-6-iodo-4-(heptafluoro isopropyl)phenyl |
| 1344 | 4-methylphenyl | Me | H | F | H | 2-n-propyl-6-iodo-4-(heptafluoro isopropyl)phenyl |
| 1345 | 2-fluorophenyl | Me | H | F | H | 2-n-propyl-6-iodo-4-(heptafluoro isopropyl)phenyl |
| 1346 | 3-fluorophenyl | Me | H | F | H | 2-n-propyl-6-iodo-4-(heptafluoro isopropyl)phenyl |
| 1347 | 4-fluorophenyl | Me | H | F | H | 2-n-propyl-6-iodo-4-(heptafluoro isopropyl)phenyl |
| 1348 | 2-chlorophenyl | Me | H | F | H | 2-n-propyl-6-iodo-4-(heptafluoro isopropyl)phenyl |

TABLE 3-continued

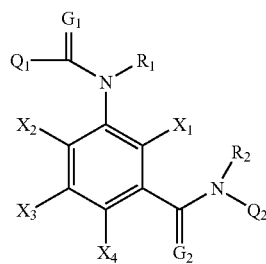

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1349 | 4-chlorophenyl | Me | H | F | H | 2-n-propyl-6-iodo-4-(heptafluoro isopropyl)phenyl |
| 1350 | 2-bromophenyl | Me | H | F | H | 2-n-propyl-6-iodo-4-(heptafluoro isopropyl)phenyl |
| 1351 | 2-iodophenyl | Me | H | F | H | 2-n-propyl-6-iodo-4-(heptafluoro isopropyl)phenyl |
| 1352 | 3-cyanophenyl | Me | H | F | H | 2-n-propyl-6-iodo-4-(heptafluoro isopropyl)phenyl |
| 1353 | 4-cyanophenyl | Me | H | F | H | 2-n-propyl-6-iodo-4-(heptafluoro isopropyl)phenyl |
| 1354 | 2-nitrophenyl | Me | H | F | H | 2-n-propyl-6-iodo-4-(heptafluoro isopropyl)phenyl |
| 1355 | 3-nitrophenyl | Me | H | F | H | 2-n-propyl-6-iodo-4-(heptafluoro isopropyl)phenyl |
| 1356 | 4-nitrophenyl | Me | H | F | H | 2-n-propyl-6-iodo-4-(heptafluoro isopropyl)phenyl |
| 1357 | 2-trifluoromethyl phenyl | Me | H | F | H | 2-n-propyl-6-iodo-4-(heptafluoro isopropyl)phenyl |
| 1358 | 4-trifluoromethyl phenyl | Me | H | F | H | 2-n-propyl-6-iodo-4-(heptafluoro isopropyl)phenyl |
| 1359 | 4-trifluoromethoxy phenyl | Me | H | F | H | 2-n-propyl-6-iodo-4-(heptafluoro isopropyl)phenyl |
| 1360 | 2,3-difluorophenyl | Me | H | F | H | 2-n-propyl-6-iodo-4-(heptafluoro isopropyl)phenyl |
| 1361 | 2,4-difluorophenyl | Me | H | F | H | 2-n-propyl-6-iodo-4-(heptafluoro isopropyl)phenyl |
| 1362 | 2,5-difluorophenyl | Me | H | F | H | 2-n-propyl-6-iodo-4-(heptafluoro isopropyl)phenyl |
| 1363 | 2,6-difluorophenyl | Me | H | F | H | 2-n-propyl-6-iodo-4-(heptafluoro isopropyl)phenyl |
| 1364 | 2,4-dichlorophenyl | Me | H | F | H | 2-n-propyl-6-iodo-4-(heptafluoro isopropyl)phenyl |
| 1365 | 2,6-dichlorophenyl | Me | H | F | H | 2-n-propyl-6-iodo-4-(heptafluoro isopropyl)phenyl |
| 1366 | 3,4-dichlorophenyl | Me | H | F | H | 2-n-propyl-6-iodo-4-(heptafluoro isopropyl)phenyl |
| 1367 | 2-chloro-4-nitro phenyl | Me | H | F | H | 2-n-propyl-6-iodo-4-(heptafluoro isopropyl)phenyl |
| 1368 | 2-chloro-4-fluoro phenyl | Me | H | F | H | 2-n-propyl-6-iodo-4-(heptafluoro isopropyl)phenyl |
| 1369 | 2-chloro-6-fluoro phenyl | Me | H | F | H | 2-n-propyl-6-iodo-4-(heptafluoro isopropyl)phenyl |
| 1370 | 4-chloro-2-fluoro phenyl | Me | H | F | H | 2-n-propyl-6-iodo-4-(heptafluoro isopropyl)phenyl |
| 1371 | 4-chloro-2-nitro phenyl | Me | H | F | H | 2-n-propyl-6-iodo-4-(heptafluoro isopropyl)phenyl |
| 1372 | 2,3,6-trifluoro phenyl | Me | H | F | H | 2-n-propyl-6-iodo-4-(heptafluoro isopropyl)phenyl |
| 1373 | pyridin-2-yl | Me | H | F | H | 2-n-propyl-6-iodo-4-(heptafluoro isopropyl)phenyl |
| 1374 | pyridin-3-yl | Me | H | F | H | 2-n-propyl-6-iodo-4-(heptafluoro isopropyl)phenyl |
| 1375 | 2-fluoropyridin-3-yl | Me | H | F | H | 2-n-propyl-6-iodo-4-(heptafluoro isopropyl)phenyl |
| 1376 | 2-chloropyridin-3-yl | Me | H | F | H | 2-n-propyl-6-iodo-4-(heptafluoro isopropyl)phenyl |
| 1377 | 2-chloropyridin-5-yl | Me | H | F | H | 2-n-propyl-6-iodo-4-(heptafluoro isopropyl)phenyl |
| 1378 | 2-methylthio pyridin-3-yl | Me | H | F | H | 2-n-propyl-6-iodo-4-(heptafluoro isopropyl)phenyl |
| 1379 | pyrazin-2-yl | Me | H | F | H | 2-n-propyl-6-iodo-4-(heptafluoro isopropyl)phenyl |
| 1380 | furan-2-yl | Me | H | F | H | 2-n-propyl-6-iodo-4-(heptafluoro isopropyl)phenyl |
| 1381 | thiophen-2-yl | Me | H | F | H | 2-n-propyl-6-iodo-4-(heptafluoro isopropyl)phenyl |

TABLE 3-continued

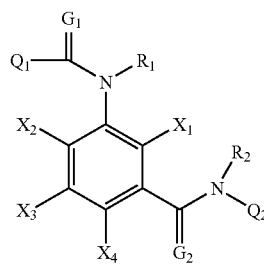

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1382 | phenyl | Me | H | F | H | 2,6-dibromo-4-(heptafluoro-n-propylthio)phenyl |
| 1383 | 2-methylphenyl | Me | H | F | H | 2,6-dibromo-4-(heptafluoro-n-propylthio)phenyl |
| 1384 | 4-methylphenyl | Me | H | F | H | 2,6-dibromo-4-(heptafluoro-n-propylthio)phenyl |
| 1385 | 2-fluorophenyl | Me | H | F | H | 2,6-dibromo-4-(heptafluoro-n-propylthio)phenyl |
| 1386 | 3-fluorophenyl | Me | H | F | H | 2,6-dibromo-4-(heptafluoro-n-propylthio)phenyl |
| 1387 | 4-fluorophenyl | Me | H | F | H | 2,6-dibromo-4-(heptafluoro-n-propylthio)phenyl |
| 1388 | 2-chlorophenyl | Me | H | F | H | 2,6-dibromo-4-(heptafluoro-n-propylthio)phenyl |
| 1389 | 4-chlorophenyl | Me | H | F | H | 2,6-dibromo-4-(heptafluoro-n-propylthio)phenyl |
| 1390 | 2-bromophenyl | Me | H | F | H | 2,6-dibromo-4-(heptafluoro-n-propylthio)phenyl |
| 1391 | 2-iodophenyl | Me | H | F | H | 2,6-dibromo-4-(heptafluoro-n-propylthio)phenyl |
| 1392 | 3-cyanophenyl | Me | H | F | H | 2,6-dibromo-4-(heptafluoro-n-propylthio)phenyl |
| 1393 | 4-cyanophenyl | Me | H | F | H | 2,6-dibromo-4-(heptafluoro-n-propylthio)phenyl |
| 1394 | 2-nitrophenyl | Me | H | F | H | 2,6-dibromo-4-(heptafluoro-n-propylthio)phenyl |
| 1395 | 3-nitrophenyl | Me | H | F | H | 2,6-dibromo-4-(heptafluoro-n-propylthio)phenyl |
| 1396 | 4-nitrophenyl | Me | H | F | H | 2,6-dibromo-4-(heptafluoro-n-propylthio)phenyl |
| 1397 | 2-trifluoromethyl phenyl | Me | H | F | H | 2,6-dibromo-4-(heptafluoro-n-propylthio)phenyl |
| 1398 | 4-trifluoromethyl phenyl | Me | H | F | H | 2,6-dibromo-4-(heptafluoro-n-propylthio)phenyl |
| 1399 | 4-trifluoromethoxy phenyl | Me | H | F | H | 2,6-dibromo-4-(heptafluoro-n-propylthio)phenyl |
| 1400 | 2,3-difluorophenyl | Me | H | F | H | 2,6-dibromo-4-(heptafluoro-n-propylthio)phenyl |
| 1401 | 2,4-difluorophenyl | Me | H | F | H | 2,6-dibromo-4-(heptafluoro-n-propylthio)phenyl |
| 1402 | 2,5-difluorophenyl | Me | H | F | H | 2,6-dibromo-4-(heptafluoro-n-propylthio)phenyl |
| 1403 | 2,6-difluorophenyl | Me | H | F | H | 2,6-dibromo-4-(heptafluoro-n-propylthio)phenyl |
| 1404 | 2,4-dichlorophenyl | Me | H | F | H | 2,6-dibromo-4-(heptafluoro-n-propylthio)phenyl |
| 1405 | 2,6-dichlorophenyl | Me | H | F | H | 2,6-dibromo-4-(heptafluoro-n-propylthio)phenyl |
| 1406 | 3,4-dichlorophenyl | Me | H | F | H | 2,6-dibromo-4-(heptafluoro-n-propylthio)phenyl |
| 1407 | 2-chloro-4-nitro phenyl | Me | H | F | H | 2,6-dibromo-4-(heptafluoro-n-propylthio)phenyl |
| 1408 | 2-chloro-4-fluoro phenyl | Me | H | F | H | 2,6-dibromo-4-(heptafluoro-n-propylthio)phenyl |
| 1409 | 2-chloro-6-fluoro phenyl | Me | H | F | H | 2,6-dibromo-4-(heptafluoro-n-propylthio)phenyl |
| 1410 | 4-chloro-2-fluoro phenyl | Me | H | F | H | 2,6-dibromo-4-(heptafluoro-n-propylthio)phenyl |
| 1411 | 4-chloro-2-nitro phenyl | Me | H | F | H | 2,6-dibromo-4-(heptafluoro-n-propylthio)phenyl |
| 1412 | 2,3,6-trifluoro phenyl | Me | H | F | H | 2,6-dibromo-4-(heptafluoro-n-propylthio)phenyl |
| 1413 | pyridin-2-yl | Me | H | F | H | 2,6-dibromo-4-(heptafluoro-n-propylthio)phenyl |
| 1414 | pyridin-3-yl | Me | H | F | H | 2,6-dibromo-4-(heptafluoro-n-propylthio)phenyl |

TABLE 3-continued

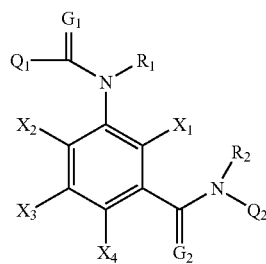

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1415 | 2-fluoropyridin-3-yl | Me | H | F | H | 2,6-dibromo-4-(heptafluoro-n-propylthio)phenyl |
| 1416 | 2-chloropyridin-3-yl | Me | H | F | H | 2,6-dibromo-4-(heptafluoro-n-propylthio)phenyl |
| 1417 | 2-chloropyridin-5-yl | Me | H | F | H | 2,6-dibromo-4-(heptafluoro-n-propylthio)phenyl |
| 1418 | 2-methylthio pyridin-3-yl | Me | H | F | H | 2,6-dibromo-4-(heptafluoro-n-propylthio)phenyl |
| 1419 | pyrazin-2-yl | Me | H | F | H | 2,6-dibromo-4-(heptafluoro-n-propylthio)phenyl |
| 1420 | furan-2-yl | Me | H | F | H | 2,6-dibromo-4-(heptafluoro-n-propylthio)phenyl |
| 1421 | thiophen-2-yl | Me | H | F | H | 2,6-dibromo-4-(heptafluoro-n-propylthio)phenyl |
| 1422 | phenyl | Me | H | F | H | 2,6-dibromo-4-(heptafluoro-n-propylsulfinyl)phenyl |
| 1423 | 2-methylphenyl | Me | H | F | H | 2,6-dibromo-4-(heptafluoro-n-propylsulfinyl)phenyl |
| 1424 | 4-methylphenyl | Me | H | F | H | 2,6-dibromo-4-(heptafluoro-n-propylsulfinyl)phenyl |
| 1425 | 2-fluorophenyl | Me | H | F | H | 2,6-dibromo-4-(heptafluoro-n-propylsulfinyl)phenyl |
| 1426 | 3-fluorophenyl | Me | H | F | H | 2,6-dibromo-4-(heptafluoro-n-propylsulfinyl)phenyl |
| 1427 | 4-fluorophenyl | Me | H | F | H | 2,6-dibromo-4-(heptafluoro-n-propylsulfinyl)phenyl |
| 1428 | 2-chlorophenyl | Me | H | F | H | 2,6-dibromo-4-(heptafluoro-n-propylsulfinyl)phenyl |
| 1429 | 4-chlorophenyl | Me | H | F | H | 2,6-dibromo-4-(heptafluoro-n-propylsulfinyl)phenyl |
| 1430 | 2-bromophenyl | Me | H | F | H | 2,6-dibromo-4-(heptafluoro-n-propylsulfinyl)phenyl |
| 1431 | 2-iodophenyl | Me | H | F | H | 2,6-dibromo-4-(heptafluoro-n-propylsulfinyl)phenyl |
| 1432 | 3-cyanophenyl | Me | H | F | H | 2,6-dibromo-4-(heptafluoro-n-propylsulfinyl)phenyl |
| 1433 | 4-cyanophenyl | Me | H | F | H | 2,6-dibromo-4-(heptafluoro-n-propylsulfinyl)phenyl |
| 1434 | 2-nitrophenyl | Me | H | F | H | 2,6-dibromo-4-(heptafluoro-n-propylsulfinyl)phenyl |
| 1435 | 3-nitrophenyl | Me | H | F | H | 2,6-dibromo-4-(heptafluoro-n-propylsulfinyl)phenyl |
| 1436 | 4-nitrophenyl | Me | H | F | H | 2,6-dibromo-4-(heptafluoro-n-propylsulfinyl)phenyl |
| 1437 | 2-trifluoromethyl phenyl | Me | H | F | H | 2,6-dibromo-4-(heptafluoro-n-propylsulfinyl)phenyl |
| 1438 | 4-trifluoromethyl phenyl | Me | H | F | H | 2,6-dibromo-4-(heptafluoro-n-propylsulfinyl)phenyl |
| 1439 | 4-trifluoromethoxy phenyl | Me | H | F | H | 2,6-dibromo-4-(heptafluoro-n-propylsulfinyl)phenyl |
| 1440 | 2,3-difluorophenyl | Me | H | F | H | 2,6-dibromo-4-(heptafluoro-n-propylsulfinyl)phenyl |
| 1441 | 2,4-difluorophenyl | Me | H | F | H | 2,6-dibromo-4-(heptafluoro-n-propylsulfinyl)phenyl |
| 1442 | 2,5-difluorophenyl | Me | H | F | H | 2,6-dibromo-4-(heptafluoro-n-propylsulfinyl)phenyl |
| 1443 | 2,6-difluorophenyl | Me | H | F | H | 2,6-dibromo-4-(heptafluoro-n-propylsulfinyl)phenyl |
| 1444 | 2,4-dichlorophenyl | Me | H | F | H | 2,6-dibromo-4-(heptafluoro-n-propylsulfinyl)phenyl |
| 1445 | 2,6-dichlorophenyl | Me | H | F | H | 2,6-dibromo-4-(heptafluoro-n-propylsulfinyl)phenyl |
| 1446 | 3,4-dichlorophenyl | Me | H | F | H | 2,6-dibromo-4-(heptafluoro-n-propylsulfinyl)phenyl |
| 1447 | 2-chloro-4-nitro phenyl | Me | H | F | H | 2,6-dibromo-4-(heptafluoro-n-propylsulfinyl)phenyl |

TABLE 3-continued

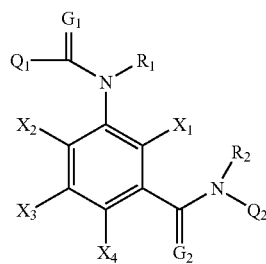

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1448 | 2-chloro-4-fluorophenyl | Me | H | F | H | 2,6-dibromo-4-(heptafluoro-n-propylsulfinyl)phenyl |
| 1449 | 2-chloro-6-fluorophenyl | Me | H | F | H | 2,6-dibromo-4-(heptafluoro-n-propylsulfinyl)phenyl |
| 1450 | 4-chloro-2-fluorophenyl | Me | H | F | H | 2,6-dibromo-4-(heptafluoro-n-propylsulfinyl)phenyl |
| 1451 | 4-chloro-2-nitrophenyl | Me | H | F | H | 2,6-dibromo-4-(heptafluoro-n-propylsulfinyl)phenyl |
| 1452 | 2,3,6-trifluorophenyl | Me | H | F | H | 2,6-dibromo-4-(heptafluoro-n-propylsulfinyl)phenyl |
| 1453 | pyridin-2-yl | Me | H | F | H | 2,6-dibromo-4-(heptafluoro-n-propylsulfinyl)phenyl |
| 1454 | pyridin-3-yl | Me | H | F | H | 2,6-dibromo-4-(heptafluoro-n-propylsulfinyl)phenyl |
| 1455 | 2-fluoropyridin-3-yl | Me | H | F | H | 2,6-dibromo-4-(heptafluoro-n-propylsulfinyl)phenyl |
| 1456 | 2-chloropyridin-3-yl | Me | H | F | H | 2,6-dibromo-4-(heptafluoro-n-propylsulfinyl)phenyl |
| 1457 | 2-chloropyridin-5-yl | Me | H | F | H | 2,6-dibromo-4-(heptafluoro-n-propylsulfinyl)phenyl |
| 1458 | 2-methylthiopyridin-3-yl | Me | H | F | H | 2,6-dibromo-4-(heptafluoro-n-propylsulfinyl)phenyl |
| 1459 | pyrazin-2-yl | Me | H | F | H | 2,6-dibromo-4-(heptafluoro-n-propylsulfinyl)phenyl |
| 1460 | furan-2-yl | Me | H | F | H | 2,6-dibromo-4-(heptafluoro-n-propylsulfinyl)phenyl |
| 1461 | thiophen-2-yl | Me | H | F | H | 2,6-dibromo-4-(heptafluoro-n-propylsulfinyl)phenyl |
| 1462 | phenyl | Et | H | F | H | 2,6-dimethyl-4-(heptafluoroisopropyl)phenyl |
| 1463 | phenyl | Me | H | H | F | 2,6-dimethyl-4-(heptafluoroisopropyl)phenyl |
| 1464 | 4-nitrophenyl | Me | H | H | F | 2,6-dimethyl-4-(heptafluoroisopropyl)phenyl |
| 1465 | 4-cyanophenyl | Me | H | H | F | 2,6-dimethyl-4-(heptafluoroisopropyl)phenyl |
| 1466 | phenyl | Me | H | H | F | 2-bromo-4-(heptafluoroisopropyl)-6-(methylsulfonyl)phenyl |
| 1467 | 4-nitrophenyl | Me | H | H | F | 2-bromo-4-(heptafluoroisopropyl)-6-(methylsulfonyl)phenyl |
| 1468 | 4-cyanophenyl | Me | H | H | F | 2-bromo-4-(heptafluoroisopropyl)-6-(methylsulfonyl)phenyl |
| 1469 | phenyl | Me | H | H | F | 2-n-propyl-6-iodo-4-(heptafluoroisopropyl)phenyl |
| 1470 | 4-nitrophenyl | Me | H | H | F | 2-n-propyl-6-iodo-4-(heptafluoroisopropyl)phenyl |
| 1471 | 4-cyanophenyl | Me | H | H | F | 2-n-propyl-6-iodo-4-(heptafluoroisopropyl)phenyl |
| 1472 | phenyl | Me | H | H | F | 2,6-dibromo-4-(heptafluoro-n-propylthio)phenyl |
| 1473 | 4-nitrophenyl | Me | H | H | F | 2,6-dibromo-4-(heptafluoro-n-propylthio)phenyl |
| 1474 | 4-cyanophenyl | Me | H | H | F | 2,6-dibromo-4-(heptafluoro-n-propylthio)phenyl |
| 1475 | phenyl | Me | H | H | F | 2,6-dibromo-4-(heptafluoro-n-propylsulfonyl)phenyl |
| 1476 | 4-nitrophenyl | Me | H | H | F | 2,6-dibromo-4-(heptafluoro-n-propylsulfonyl)phenyl |
| 1477 | 4-cyanophenyl | Me | H | H | F | 2,6-dibromo-4-(heptafluoro-n-propylsulfonyl)phenyl |
| 1478 | phenyl | H | Me | H | H | 2,6-dimethyl-4-(heptafluoroisopropyl)phenyl |
| 1479 | phenyl | H | Me | H | H | 2-bromo-4-(heptafluoroisopropyl)-6-methylphenyl |
| 1480 | phenyl | H | Me | H | H | 2,6-dibromo-4-(heptafluoro-n-propylthio)phenyl |

TABLE 3-continued

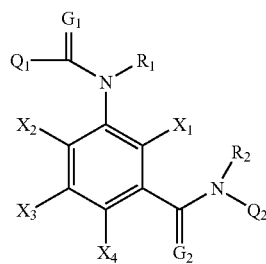

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1481 | 2-fluorophenyl | H | Me | H | H | 2,6-dibromo-4-(heptafluoro-n-propylthio)phenyl |
| 1482 | phenyl | H | Et | H | H | 2,6-dimethyl-4-(heptafluoro isopropyl)phenyl |
| 1483 | phenyl | H | i-Pr | H | H | 2,6-dimethyl-4-(heptafluoro isopropyl)phenyl |
| 1484 | phenyl | H | acetyl | H | H | 2,6-dimethyl-4-(heptafluoro isopropyl)phenyl |
| 1485 | phenyl | H | Me | F | H | 2,6-dimethyl-4-(heptafluoro isopropyl)phenyl |
| 1486 | 2-fluorophenyl | H | Me | F | H | 2,6-dimethyl-4-(heptafluoro isopropyl)phenyl |
| 1487 | phenyl | Me | Me | H | H | 2,6-dimethyl-4-(heptafluoro isopropyl)phenyl |
| 1488 | 2-methylphenyl | Me | Me | H | H | 2,6-dimethyl-4-(heptafluoro isopropyl)phenyl |
| 1489 | 4-methylphenyl | Me | Me | H | H | 2,6-dimethyl-4-(heptafluoro isopropyl)phenyl |
| 1490 | 2-fluorophenyl | Me | Me | H | H | 2,6-dimethyl-4-(heptafluoro isopropyl)phenyl |
| 1491 | 3-fluorophenyl | Me | Me | H | H | 2,6-dimethyl-4-(heptafluoro isopropyl)phenyl |
| 1492 | 4-fluorophenyl | Me | Me | H | H | 2,6-dimethyl-4-(heptafluoro isopropyl)phenyl |
| 1493 | 2-chlorophenyl | Me | Me | H | H | 2,6-dimethyl-4-(heptafluoro isopropyl)phenyl |
| 1494 | 4-chlorophenyl | Me | Me | H | H | 2,6-dimethyl-4-(heptafluoro isopropyl)phenyl |
| 1495 | 2-bromophenyl | Me | Me | H | H | 2,6-dimethyl-4-(heptafluoro isopropyl)phenyl |
| 1496 | 2-iodophenyl | Me | Me | H | H | 2,6-dimethyl-4-(heptafluoro isopropyl)phenyl |
| 1497 | 3-cyanophenyl | Me | Me | H | H | 2,6-dimethyl-4-(heptafluoro isopropyl)phenyl |
| 1498 | 4-cyanophenyl | Me | Me | H | H | 2,6-dimethyl-4-(heptafluoro isopropyl)phenyl |
| 1499 | 2-nitrophenyl | Me | Me | H | H | 2,6-dimethyl-4-(heptafluoro isopropyl)phenyl |
| 1500 | 3-nitrophenyl | Me | Me | H | H | 2,6-dimethyl-4-(heptafluoro isopropyl)phenyl |
| 1501 | 4-nitrophenyl | Me | Me | H | H | 2,6-dimethyl-4-(heptafluoro isopropyl)phenyl |
| 1502 | 2-trifluoromethyl phenyl | Me | Me | H | H | 2,6-dimethyl-4-(heptafluoro isopropyl)phenyl |
| 1503 | 4-trifluoromethyl phenyl | Me | Me | H | H | 2,6-dimethyl-4-(heptafluoro isopropyl)phenyl |
| 1504 | 4-trifluoromethoxy phenyl | Me | Me | H | H | 2,6-dimethyl-4-(heptafluoro isopropyl)phenyl |
| 1505 | 2,3-difluorophenyl | Me | Me | H | H | 2,6-dimethyl-4-(heptafluoro isopropyl)phenyl |
| 1506 | 2,4-difluorophenyl | Me | Me | H | H | 2,6-dimethyl-4-(heptafluoro isopropyl)phenyl |
| 1507 | 2,5-difluorophenyl | Me | Me | H | H | 2,6-dimethyl-4-(heptafluoro isopropyl)phenyl |
| 1508 | 2,6-difluorophenyl | Me | Me | H | H | 2,6-dimethyl-4-(heptafluoro isopropyl)phenyl |
| 1509 | 2,4-dichlorophenyl | Me | Me | H | H | 2,6-dimethyl-4-(heptafluoro isopropyl)phenyl |
| 1510 | 2,6-dichlorophenyl | Me | Me | H | H | 2,6-dimethyl-4-(heptafluoro isopropyl)phenyl |
| 1511 | 3,4-dichlorophenyl | Me | Me | H | H | 2,6-dimethyl-4-(heptafluoro isopropyl)phenyl |
| 1512 | 2-chloro-4-nitro phenyl | Me | Me | H | H | 2,6-dimethyl-4-(heptafluoro isopropyl)phenyl |
| 1513 | 2-chloro-4-fluoro phenyl | Me | Me | H | H | 2,6-dimethyl-4-(heptafluoro isopropyl)phenyl |

TABLE 3-continued

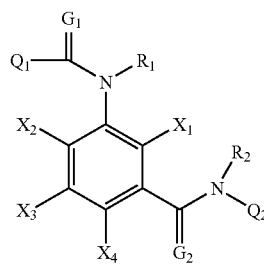

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1514 | 2-chloro-6-fluoro phenyl | Me | Me | H | H | 2,6-dimethyl-4-(heptafluoro isopropyl)phenyl |
| 1515 | 4-chloro-2-fluoro phenyl | Me | Me | H | H | 2,6-dimethyl-4-(heptafluoro isopropyl)phenyl |
| 1516 | 4-chloro-2-nitro phenyl | Me | Me | H | H | 2,6-dimethyl-4-(heptafluoro isopropyl)phenyl |
| 1517 | 2,3,6-trifluoro phenyl | Me | Me | H | H | 2,6-dimethyl-4-(heptafluoro isopropyl)phenyl |
| 1518 | pyridin-2-yl | Me | Me | H | H | 2,6-dimethyl-4-(heptafluoro isopropyl)phenyl |
| 1519 | pyridin-3-yl | Me | Me | H | H | 2,6-dimethyl-4-(heptafluoro isopropyl)phenyl |
| 1520 | 2-fluoropyridin-3-yl | Me | Me | H | H | 2,6-dimethyl-4-(heptafluoro isopropyl)phenyl |
| 1521 | 2-chloropyridin-3-yl | Me | Me | H | H | 2,6-dimethyl-4-(heptafluoro isopropyl)phenyl |
| 1522 | 2-chloropyridin-5-yl | Me | Me | H | H | 2,6-dimethyl-4-(heptafluoro isopropyl)phenyl |
| 1523 | 2-methylthio pyridin-3-yl | Me | Me | H | H | 2,6-dimethyl-4-(heptafluoro isopropyl)phenyl |
| 1524 | pyrazin-2-yl | Me | Me | H | H | 2,6-dimethyl-4-(heptafluoro isopropyl)phenyl |
| 1525 | furan-2-yl | Me | Me | H | H | 2,6-dimethyl-4-(heptafluoro isopropyl)phenyl |
| 1526 | thiophen-2-yl | Me | Me | H | H | 2,6-dimethyl-4-(heptafluoro isopropyl)phenyl |
| 1527 | phenyl | Me | Me | H | H | 2-bromo-4-(heptafluoroisopropyl)-6-(methylsulfonyl)phenyl |
| 1528 | 2-methylphenyl | Me | Me | H | H | 2-bromo-4-(heptafluoroisopropyl)-6-(methylsulfonyl)phenyl |
| 1529 | 4-methylphenyl | Me | Me | H | H | 2-bromo-4-(heptafluoroisopropyl)-6-(methylsulfonyl)phenyl |
| 1530 | 2-fluorophenyl | Me | Me | H | H | 2-bromo-4-(heptafluoroisopropyl)-6-(methylsulfonyl)phenyl |
| 1531 | 3-fluorophenyl | Me | Me | H | H | 2-bromo-4-(heptafluoroisopropyl)-6-(methylsulfonyl)phenyl |
| 1532 | 4-fluorophenyl | Me | Me | H | H | 2-bromo-4-(heptafluoroisopropyl)-6-(methylsulfonyl)phenyl |
| 1533 | 2-chlorophenyl | Me | Me | H | H | 2-bromo-4-(heptafluoroisopropyl)-6-(methylsulfonyl)phenyl |
| 1534 | 4-chlorophenyl | Me | Me | H | H | 2-bromo-4-(heptafluoroisopropyl)-6-(methylsulfonyl)phenyl |
| 1535 | 2-bromophenyl | Me | Me | H | H | 2-bromo-4-(heptafluoroisopropyl)-6-(methylsulfonyl)phenyl |
| 1536 | 2-iodophenyl | Me | Me | H | H | 2-bromo-4-(heptafluoroisopropyl)-6-(methylsulfonyl)phenyl |
| 1537 | 3-cyanophenyl | Me | Me | H | H | 2-bromo-4-(heptafluoroisopropyl)-6-(methylsulfonyl)phenyl |
| 1538 | 4-cyanophenyl | Me | Me | H | H | 2-bromo-4-(heptafluoroisopropyl)-6-(methylsulfonyl)phenyl |
| 1539 | 2-nitrophenyl | Me | Me | H | H | 2-bromo-4-(heptafluoroisopropyl)-6-(methylsulfonyl)phenyl |
| 1540 | 3-nitrophenyl | Me | Me | H | H | 2-bromo-4-(heptafluoroisopropyl)-6-(methylsulfonyl)phenyl |
| 1541 | 4-nitrophenyl | Me | Me | H | H | 2-bromo-4-(heptafluoroisopropyl)-6-(methylsulfonyl)phenyl |
| 1542 | 2-trifluoromethyl phenyl | Me | Me | H | H | 2-bromo-4-(heptafluoroisopropyl)-6-(methylsulfonyl)phenyl |
| 1543 | 4-trifluoromethyl phenyl | Me | Me | H | H | 2-bromo-4-(heptafluoroisopropyl)-6-(methylsulfonyl)phenyl |
| 1544 | 4-trifluoromethoxy phenyl | Me | Me | H | H | 2-bromo-4-(heptafluoroisopropyl)-6-(methylsulfonyl)phenyl |
| 1545 | 2,3-difluorophenyl | Me | Me | H | H | 2-bromo-4-(heptafluoroisopropyl)-6-(methylsulfonyl)phenyl |
| 1546 | 2,4-difluorophenyl | Me | Me | H | H | 2-bromo-4-(heptafluoroisopropyl)-6-(methylsulfonyl)phenyl |

TABLE 3-continued

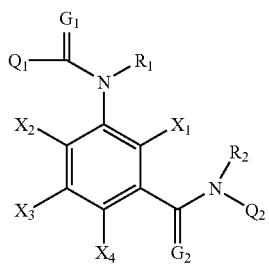

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1547 | 2,5-difluorophenyl | Me | Me | H | H | 2-bromo-4-(heptafluoroisopropyl)-6-(methylsulfonyl)phenyl |
| 1548 | 2,6-difluorophenyl | Me | Me | H | H | 2-bromo-4-(heptafluoroisopropyl)-6-(methylsulfonyl)phenyl |
| 1549 | 2,4-dichlorophenyl | Me | Me | H | H | 2-bromo-4-(heptafluoroisopropyl)-6-(methylsulfonyl)phenyl |
| 1550 | 2,6-dichlorophenyl | Me | Me | H | H | 2-bromo-4-(heptafluoroisopropyl)-6-(methylsulfonyl)phenyl |
| 1551 | 3,4-dichlorophenyl | Me | Me | H | H | 2-bromo-4-(heptafluoroisopropyl)-6-(methylsulfonyl)phenyl |
| 1552 | 2-chloro-4-nitro phenyl | Me | Me | H | H | 2-bromo-4-(heptafluoroisopropyl)-6-(methylsulfonyl)phenyl |
| 1553 | 2-chloro-4-fluoro phenyl | Me | Me | H | H | 2-bromo-4-(heptafluoroisopropyl)-6-(methylsulfonyl)phenyl |
| 1554 | 2-chloro-6-fluoro phenyl | Me | Me | H | H | 2-bromo-4-(heptafluoroisopropyl)-6-(methylsulfonyl)phenyl |
| 1555 | 4-chloro-2-fluoro phenyl | Me | Me | H | H | 2-bromo-4-(heptafluoroisopropyl)-6-(methylsulfonyl)phenyl |
| 1556 | 4-chloro-2-nitro phenyl | Me | Me | H | H | 2-bromo-4-(heptafluoroisopropyl)-6-(methylsulfonyl)phenyl |
| 1557 | 2,3,6-trifluoro phenyl | Me | Me | H | H | 2-bromo-4-(heptafluoroisopropyl)-6-(methylsulfonyl)phenyl |
| 1558 | pyridin-2-yl | Me | Me | H | H | 2-bromo-4-(heptafluoroisopropyl)-6-(methylsulfonyl)phenyl |
| 1559 | pyridin-3-yl | Me | Me | H | H | 2-bromo-4-(heptafluoroisopropyl)-6-(methylsulfonyl)phenyl |
| 1560 | 2-fluoropyridin-3-yl | Me | Me | H | H | 2-bromo-4-(heptafluoroisopropyl)-6-(methylsulfonyl)phenyl |
| 1561 | 2-chloropyridin-3-yl | Me | Me | H | H | 2-bromo-4-(heptafluoroisopropyl)-6-(methylsulfonyl)phenyl |
| 1562 | 2-chloropyridin-5-yl | Me | Me | H | H | 2-bromo-4-(heptafluoroisopropyl)-6-(methylsulfonyl)phenyl |
| 1563 | 2-methylthio pyridin-3-yl | Me | Me | H | H | 2-bromo-4-(heptafluoroisopropyl)-6-(methylsulfonyl)phenyl |
| 1564 | pyrazin-2-yl | Me | Me | H | H | 2-bromo-4-(heptafluoroisopropyl)-6-(methylsulfonyl)phenyl |
| 1565 | furan-2-yl | Me | Me | H | H | 2-bromo-4-(heptafluoroisopropyl)-6-(methylsulfonyl)phenyl |
| 1566 | thiophen-2-yl | Me | Me | H | H | 2-bromo-4-(heptafluoroisopropyl)-6-(methylsulfonyl)phenyl |
| 1567 | phenyl | Me | Me | H | H | 2-n-propyl-6-iodo-4-(heptafluoroisopropyl)phenyl |
| 1568 | 2-methylphenyl | Me | Me | H | H | 2-n-propyl-6-iodo-4-(heptafluoroisopropyl)phenyl |
| 1569 | 4-methylphenyl | Me | Me | H | H | 2-n-propyl-6-iodo-4-(heptafluoroisopropyl)phenyl |
| 1570 | 2-fluorophenyl | Me | Me | H | H | 2-n-propyl-6-iodo-4-(heptafluoroisopropyl)phenyl |
| 1571 | 3-fluorophenyl | Me | Me | H | H | 2-n-propyl-6-iodo-4-(heptafluoroisopropyl)phenyl |
| 1572 | 4-fluorophenyl | Me | Me | H | H | 2-n-propyl-6-iodo-4-(heptafluoroisopropyl)phenyl |
| 1573 | 2-chlorophenyl | Me | Me | H | H | 2-n-propyl-6-iodo-4-(heptafluoroisopropyl)phenyl |
| 1574 | 4-chlorophenyl | Me | Me | H | H | 2-n-propyl-6-iodo-4-(heptafluoroisopropyl)phenyl |
| 1575 | 2-bromophenyl | Me | Me | H | H | 2-n-propyl-6-iodo-4-(heptafluoroisopropyl)phenyl |
| 1576 | 2-iodophenyl | Me | Me | H | H | 2-n-propyl-6-iodo-4-(heptafluoroisopropyl)phenyl |
| 1577 | 3-cyanophenyl | Me | Me | H | H | 2-n-propyl-6-iodo-4-(heptafluoroisopropyl)phenyl |
| 1578 | 4-cyanophenyl | Me | Me | H | H | 2-n-propyl-6-iodo-4-(heptafluoroisopropyl)phenyl |
| 1579 | 2-nitrophenyl | Me | Me | H | H | 2-n-propyl-6-iodo-4-(heptafluoroisopropyl)phenyl |

TABLE 3-continued

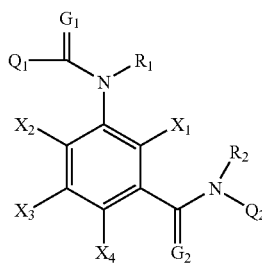

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1580 | 3-nitrophenyl | Me | Me | H | H | 2-n-propyl-6-iodo-4-(heptafluoro isopropyl)phenyl |
| 1581 | 4-nitrophenyl | Me | Me | H | H | 2-n-propyl-6-iodo-4-(heptafluoro isopropyl)phenyl |
| 1582 | 2-trifluoromethyl phenyl | Me | Me | H | H | 2-n-propyl-6-iodo-4-(heptafluoro isopropyl)phenyl |
| 1583 | 4-trifluoromethyl phenyl | Me | Me | H | H | 2-n-propyl-6-iodo-4-(heptafluoro isopropyl)phenyl |
| 1584 | 4-trifluoromethoxy phenyl | Me | Me | H | H | 2-n-propyl-6-iodo-4-(heptafluoro isopropyl)phenyl |
| 1585 | 2,3-difluorophenyl | Me | Me | H | H | 2-n-propyl-6-iodo-4-(heptafluoro isopropyl)phenyl |
| 1586 | 2,4-difluorophenyl | Me | Me | H | H | 2-n-propyl-6-iodo-4-(heptafluoro isopropyl)phenyl |
| 1587 | 2,5-difluorophenyl | Me | Me | H | H | 2-n-propyl-6-iodo-4-(heptafluoro isopropyl)phenyl |
| 1588 | 2,6-difluorophenyl | Me | Me | H | H | 2-n-propyl-6-iodo-4-(heptafluoro isopropyl)phenyl |
| 1589 | 2,4-dichlorophenyl | Me | Me | H | H | 2-n-propyl-6-iodo-4-(heptafluoro isopropyl)phenyl |
| 1590 | 2,6-dichlorophenyl | Me | Me | H | H | 2-n-propyl-6-iodo-4-(heptafluoro isopropyl)phenyl |
| 1591 | 3,4-dichlorophenyl | Me | Me | H | H | 2-n-propyl-6-iodo-4-(heptafluoro isopropyl)phenyl |
| 1592 | 2-chloro-4-nitro phenyl | Me | Me | H | H | 2-n-propyl-6-iodo-4-(heptafluoro isopropyl)phenyl |
| 1593 | 2-chloro-4-fluoro phenyl | Me | Me | H | H | 2-n-propyl-6-iodo-4-(heptafluoro isopropyl)phenyl |
| 1594 | 2-chloro-6-fluoro phenyl | Me | Me | H | H | 2-n-propyl-6-iodo-4-(heptafluoro isopropyl)phenyl |
| 1595 | 4-chloro-2-fluoro phenyl | Me | Me | H | H | 2-n-propyl-6-iodo-4-(heptafluoro isopropyl)phenyl |
| 1596 | 4-chloro-2-nitro phenyl | Me | Me | H | H | 2-n-propyl-6-iodo-4-(heptafluoro isopropyl)phenyl |
| 1597 | 2,3,6-trifluoro phenyl | Me | Me | H | H | 2-n-propyl-6-iodo-4-(heptafluoro isopropyl)phenyl |
| 1598 | pyridin-2-yl | Me | Me | H | H | 2-n-propyl-6-iodo-4-(heptafluoro isopropyl)phenyl |
| 1599 | pyridin-3-yl | Me | Me | H | H | 2-n-propyl-6-iodo-4-(heptafluoro isopropyl)phenyl |
| 1600 | 2-fluoropyridin-3-yl | Me | Me | H | H | 2-n-propyl-6-iodo-4-(heptafluoro isopropyl)phenyl |
| 1601 | 2-chloropyridin-3-yl | Me | Me | H | H | 2-n-propyl-6-iodo-4-(heptafluoro isopropyl)phenyl |
| 1602 | 2-chloropyridin-5-yl | Me | Me | H | H | 2-n-propyl-6-iodo-4-(heptafluoro isopropyl)phenyl |
| 1603 | 2-methylthio pyridin-3-yl | Me | Me | H | H | 2-n-propyl-6-iodo-4-(heptafluoro isopropyl)phenyl |
| 1604 | pyrazin-2-yl | Me | Me | H | H | 2-n-propyl-6-iodo-4-(heptafluoro isopropyl)phenyl |
| 1605 | furan-2-yl | Me | Me | H | H | 2-n-propyl-6-iodo-4-(heptafluoro isopropyl)phenyl |
| 1606 | thiophen-2-yl | Me | Me | H | H | 2-n-propyl-6-iodo-4-(heptafluoro isopropyl)phenyl |
| 1607 | phenyl | Me | Me | H | H | 2,6-dibromo-4-(heptafluoro-n-propylthio)phenyl |
| 1608 | 2-methylphenyl | Me | Me | H | H | 2,6-dibromo-4-(heptafluoro-n-propylthio)phenyl |
| 1609 | 3-methylphenyl | Me | Me | H | H | 2,6-dibromo-4-(heptafluoro-n-propylthio)phenyl |
| 1610 | 4-methylphenyl | Me | Me | H | H | 2,6-dibromo-4-(heptafluoro-n-propylthio)phenyl |
| 1611 | 2-nitrophenyl | Me | Me | H | H | 2,6-dibromo-4-(heptafluoro-n-propylthio)phenyl |
| 1612 | 3-nitrophenyl | Me | Me | H | H | 2,6-dibromo-4-(heptafluoro-n-propylthio)phenyl |

TABLE 3-continued

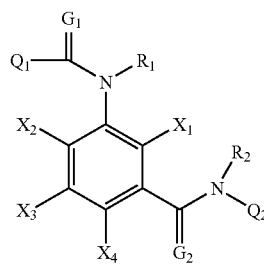

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1613 | 4-nitrophenyl | Me | Me | H | H | 2,6-dibromo-4-(heptafluoro-n-propylthio)phenyl |
| 1614 | 2-cyanophenyl | Me | Me | H | H | 2,6-dibromo-4-(heptafluoro-n-propylthio)phenyl |
| 1615 | 3-cyanophenyl | Me | Me | H | H | 2,6-dibromo-4-(heptafluoro-n-propylthio)phenyl |
| 1616 | 4-cyanophenyl | Me | Me | H | H | 2,6-dibromo-4-(heptafluoro-n-propylthio)phenyl |
| 1617 | 2-fluorophenyl | Me | Me | H | H | 2,6-dibromo-4-(heptafluoro-n-propylthio)phenyl |
| 1618 | 3-fluorophenyl | Me | Me | H | H | 2,6-dibromo-4-(heptafluoro-n-propylthio)phenyl |
| 1619 | 4-fluorophenyl | Me | Me | H | H | 2,6-dibromo-4-(heptafluoro-n-propylthio)phenyl |
| 1620 | 2-chlorophenyl | Me | Me | H | H | 2,6-dibromo-4-(heptafluoro-n-propylthio)phenyl |
| 1621 | 4-chlorophenyl | Me | Me | H | H | 2,6-dibromo-4-(heptafluoro-n-propylthio)phenyl |
| 1622 | 2-bromophenyl | Me | Me | H | H | 2,6-dibromo-4-(heptafluoro-n-propylthio)phenyl |
| 1623 | 2-iodophenyl | Me | Me | H | H | 2,6-dibromo-4-(heptafluoro-n-propylthio)phenyl |
| 1624 | 2-trifluoromethyl phenyl | Me | Me | H | H | 2,6-dibromo-4-(heptafluoro-n-propylthio)phenyl |
| 1625 | 4-trifluoromethyl phenyl | Me | Me | H | H | 2,6-dibromo-4-(heptafluoro-n-propylthio)phenyl |
| 1626 | 4-trifluoromethoxy phenyl | Me | Me | H | H | 2,6-dibromo-4-(heptafluoro-n-propylthio)phenyl |
| 1627 | 2,3-difluorophenyl | Me | Me | H | H | 2,6-dibromo-4-(heptafluoro-n-propylthio)phenyl |
| 1628 | 2,4-difluorophenyl | Me | Me | H | H | 2,6-dibromo-4-(heptafluoro-n-propylthio)phenyl |
| 1629 | 2,5-difluorophenyl | Me | Me | H | H | 2,6-dibromo-4-(heptafluoro-n-propylthio)phenyl |
| 1630 | 2,6-difluorophenyl | Me | Me | H | H | 2,6-dibromo-4-(heptafluoro-n-propylthio)phenyl |
| 1631 | 2,4-dichlorophenyl | Me | Me | H | H | 2,6-dibromo-4-(heptafluoro-n-propylthio)phenyl |
| 1632 | 2,6-dichlorophenyl | Me | Me | H | H | 2,6-dibromo-4-(heptafluoro-n-propylthio)phenyl |
| 1633 | 3,4-dichlorophenyl | Me | Me | H | H | 2,6-dibromo-4-(heptafluoro-n-propylthio)phenyl |
| 1634 | 2-fluoro-4-nitro phenyl | Me | Me | H | H | 2,6-dibromo-4-(heptafluoro-n-propylthio)phenyl |
| 1635 | 4-fluoro-2-nitro phenyl | Me | Me | H | H | 2,6-dibromo-4-(heptafluoro-n-propylthio)phenyl |
| 1636 | 2-chloro-4-fluoro phenyl | Me | Me | H | H | 2,6-dibromo-4-(heptafluoro-n-propylthio)phenyl |
| 1637 | 4-chloro-2-fluoro phenyl | Me | Me | H | H | 2,6-dibromo-4-(heptafluoro-n-propylthio)phenyl |
| 1638 | 2-chloro-6-fluoro phenyl | Me | Me | H | H | 2,6-dibromo-4-(heptafluoro-n-propylthio)phenyl |
| 1639 | 2-chloro-4-nitro phenyl | Me | Me | H | H | 2,6-dibromo-4-(heptafluoro-n-propylthio)phenyl |
| 1640 | 4-chloro-2-nitro phenyl | Me | Me | H | H | 2,6-dibromo-4-(heptafluoro-n-propylthio)phenyl |
| 1641 | 2,3,6-trifluoro phenyl | Me | Me | H | H | 2,6-dibromo-4-(heptafluoro-n-propylthio)phenyl |
| 1642 | pyridin-2-yl | Me | Me | H | H | 2,6-dibromo-4-(heptafluoro-n-propylthio)phenyl |
| 1643 | pyridin-3-yl | Me | Me | H | H | 2,6-dibromo-4-(heptafluoro-n-propylthio)phenyl |
| 1644 | 2-fluoropyridin-3-yl | Me | Me | H | H | 2,6-dibromo-4-(heptafluoro-n-propylthio)phenyl |
| 1645 | 2-chloropyridin-3-yl | Me | Me | H | H | 2,6-dibromo-4-(heptafluoro-n-propylthio)phenyl |

TABLE 3-continued

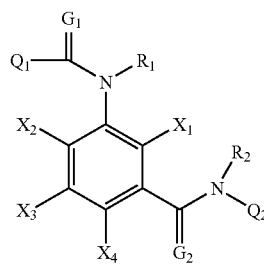

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1646 | 2-chloropyridin-5-yl | Me | Me | H | H | 2,6-dibromo-4-(heptafluoro-n-propylthio)phenyl |
| 1647 | 2-methylthio pyridin-3-yl | Me | Me | H | H | 2,6-dibromo-4-(heptafluoro-n-propylthio)phenyl |
| 1648 | pyrazin-2-yl | Me | Me | H | H | 2,6-dibromo-4-(heptafluoro-n-propylthio)phenyl |
| 1649 | furan-2-yl | Me | Me | H | H | 2,6-dibromo-4-(heptafluoro-n-propylthio)phenyl |
| 1650 | furan-3-yl | Me | Me | H | H | 2,6-dibromo-4-(heptafluoro-n-propylthio)phenyl |
| 1651 | 2-tetrahydrofuranyl | Me | Me | H | H | 2,6-dibromo-4-(heptafluoro-n-propylthio)phenyl |
| 1652 | benzofuran-2-yl | Me | Me | H | H | 2,6-dibromo-4-(heptafluoro-n-propylthio)phenyl |
| 1653 | thiophen-2-yl | Me | Me | H | H | 2,6-dibromo-4-(heptafluoro-n-propylthio)phenyl |
| 1654 | 3,4-dinitrophenyl | Me | Me | H | H | 2,6-dibromo-4-(heptafluoro-n-propylthio)phenyl |
| 1655 | 3-methoxy-4-nitro phenyl | Me | Me | H | H | 2,6-dibromo-4-(heptafluoro-n-propylthio)phenyl |
| 1656 | 2,3,4-trifluoro phenyl | Me | Me | H | H | 2,6-dibromo-4-(heptafluoro-n-propylthio)phenyl |
| 1657 | phenyl | Me | Me | H | H | 2,6-dibromo-4-(heptafluoro-n-propylsulfinyl)phenyl |
| 1658 | 2-methylphenyl | Me | Me | H | H | 2,6-dibromo-4-(heptafluoro-n-propylsulfinyl)phenyl |
| 1659 | 4-methylphenyl | Me | Me | H | H | 2,6-dibromo-4-(heptafluoro-n-propylsulfinyl)phenyl |
| 1660 | 2-fluorophenyl | Me | Me | H | H | 2,6-dibromo-4-(heptafluoro-n-propylsulfinyl)phenyl |
| 1661 | 3-fluorophenyl | Me | Me | H | H | 2,6-dibromo-4-(heptafluoro-n-propylsulfinyl)phenyl |
| 1662 | 4-fluorophenyl | Me | Me | H | H | 2,6-dibromo-4-(heptafluoro-n-propylsulfinyl)phenyl |
| 1663 | 2-chlorophenyl | Me | Me | H | H | 2,6-dibromo-4-(heptafluoro-n-propylsulfinyl)phenyl |
| 1664 | 4-chlorophenyl | Me | Me | H | H | 2,6-dibromo-4-(heptafluoro-n-propylsulfinyl)phenyl |
| 1665 | 2-bromophenyl | Me | Me | H | H | 2,6-dibromo-4-(heptafluoro-n-propylsulfinyl)phenyl |
| 1666 | 2-iodophenyl | Me | Me | H | H | 2,6-dibromo-4-(heptafluoro-n-propylsulfinyl)phenyl |
| 1667 | 3-cyanophenyl | Me | Me | H | H | 2,6-dibromo-4-(heptafluoro-n-propylsulfinyl)phenyl |
| 1668 | 4-cyanophenyl | Me | Me | H | H | 2,6-dibromo-4-(heptafluoro-n-propylsulfinyl)phenyl |
| 1669 | 2-nitrophenyl | Me | Me | H | H | 2,6-dibromo-4-(heptafluoro-n-propylsulfinyl)phenyl |
| 1670 | 3-nitrophenyl | Me | Me | H | H | 2,6-dibromo-4-(heptafluoro-n-propylsulfinyl)phenyl |
| 1671 | 4-nitrophenyl | Me | Me | H | H | 2,6-dibromo-4-(heptafluoro-n-propylsulfinyl)phenyl |
| 1672 | 2-trifluoromethyl phenyl | Me | Me | H | H | 2,6-dibromo-4-(heptafluoro-n-propylsulfinyl)phenyl |
| 1673 | 4-trifluoromethyl phenyl | Me | Me | H | H | 2,6-dibromo-4-(heptafluoro-n-propylsulfinyl)phenyl |
| 1674 | 4-trifluoromethoxy phenyl | Me | Me | H | H | 2,6-dibromo-4-(heptafluoro-n-propylsulfinyl)phenyl |
| 1675 | 2,3-difluorophenyl | Me | Me | H | H | 2,6-dibromo-4-(heptafluoro-n-propylsulfinyl)phenyl |
| 1676 | 2,4-difluorophenyl | Me | Me | H | H | 2,6-dibromo-4-(heptafluoro-n-propylsulfinyl)phenyl |
| 1677 | 2,5-difluorophenyl | Me | Me | H | H | 2,6-dibromo-4-(heptafluoro-n-propylsulfinyl)phenyl |
| 1678 | 2,6-difluorophenyl | Me | Me | H | H | 2,6-dibromo-4-(heptafluoro-n-propylsulfinyl)phenyl |

TABLE 3-continued

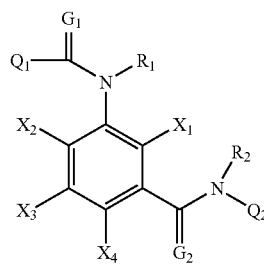

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1679 | 2,4-dichlorophenyl | Me | Me | H | H | 2,6-dibromo-4-(heptafluoro-n-propylsulfinyl)phenyl |
| 1680 | 2,6-dichlorophenyl | Me | Me | H | H | 2,6-dibromo-4-(heptafluoro-n-propylsulfinyl)phenyl |
| 1681 | 3,4-dichlorophenyl | Me | Me | H | H | 2,6-dibromo-4-(heptafluoro-n-propylsulfinyl)phenyl |
| 1682 | 2-chloro-4-nitro phenyl | Me | Me | H | H | 2,6-dibromo-4-(heptafluoro-n-propylsulfinyl)phenyl |
| 1683 | 2-chloro-4-fluoro phenyl | Me | Me | H | H | 2,6-dibromo-4-(heptafluoro-n-propylsulfinyl)phenyl |
| 1684 | 2-chloro-6-fluoro phenyl | Me | Me | H | H | 2,6-dibromo-4-(heptafluoro-n-propylsulfinyl)phenyl |
| 1685 | 4-chloro-2-fluoro phenyl | Me | Me | H | H | 2,6-dibromo-4-(heptafluoro-n-propylsulfinyl)phenyl |
| 1686 | 4-chloro-2-nitro phenyl | Me | Me | H | H | 2,6-dibromo-4-(heptafluoro-n-propylsulfinyl)phenyl |
| 1687 | 2,3,6-trifluoro phenyl | Me | Me | H | H | 2,6-dibromo-4-(heptafluoro-n-propylsulfinyl)phenyl |
| 1688 | pyridin-2-yl | Me | Me | H | H | 2,6-dibromo-4-(heptafluoro-n-propylsulfinyl)phenyl |
| 1689 | pyridin-3-yl | Me | Me | H | H | 2,6-dibromo-4-(heptafluoro-n-propylsulfinyl)phenyl |
| 1690 | 2-fluoropyridin-3-yl | Me | Me | H | H | 2,6-dibromo-4-(heptafluoro-n-propylsulfinyl)phenyl |
| 1691 | 2-chloropyridin-3-yl | Me | Me | H | H | 2,6-dibromo-4-(heptafluoro-n-propylsulfinyl)phenyl |
| 1692 | 2-chloropyridin-5-yl | Me | Me | H | H | 2,6-dibromo-4-(heptafluoro-n-propylsulfinyl)phenyl |
| 1693 | 2-methylthio pyridin-3-yl | Me | Me | H | H | 2,6-dibromo-4-(heptafluoro-n-propylsulfinyl)phenyl |
| 1694 | pyrazin-2-yl | Me | Me | H | H | 2,6-dibromo-4-(heptafluoro-n-propylsulfinyl)phenyl |
| 1695 | furan-2-yl | Me | Me | H | H | 2,6-dibromo-4-(heptafluoro-n-propylsulfinyl)phenyl |
| 1696 | thiophen-2-yl | Me | Me | H | H | 2,6-dibromo-4-(heptafluoro-n-propylsulfinyl)phenyl |
| 1697 | phenyl | Me | Me | F | H | 2,6-dimethyl-4-(heptafluoro isopropyl)phenyl |
| 1698 | 2-methylphenyl | Me | Me | F | H | 2,6-dimethyl-4-(heptafluoro isopropyl)phenyl |
| 1699 | 4-methylphenyl | Me | Me | F | H | 2,6-dimethyl-4-(heptafluoro isopropyl)phenyl |
| 1700 | 2-fluorophenyl | Me | Me | F | H | 2,6-dimethyl-4-(heptafluoro isopropyl)phenyl |
| 1701 | 3-fluorophenyl | Me | Me | F | H | 2,6-dimethyl-4-(heptafluoro isopropyl)phenyl |
| 1702 | 4-fluorophenyl | Me | Me | F | H | 2,6-dimethyl-4-(heptafluoro isopropyl)phenyl |
| 1703 | 2-chlorophenyl | Me | Me | F | H | 2,6-dimethyl-4-(heptafluoro isopropyl)phenyl |
| 1704 | 4-chlorophenyl | Me | Me | F | H | 2,6-dimethyl-4-(heptafluoro isopropyl)phenyl |
| 1705 | 2-bromophenyl | Me | Me | F | H | 2,6-dimethyl-4-(heptafluoro isopropyl)phenyl |
| 1706 | 2-iodophenyl | Me | Me | F | H | 2,6-dimethyl-4-(heptafluoro isopropyl)phenyl |
| 1707 | 3-cyanophenyl | Me | Me | F | H | 2,6-dimethyl-4-(heptafluoro isopropyl)phenyl |
| 1708 | 4-cyanophenyl | Me | Me | F | H | 2,6-dimethyl-4-(heptafluoro isopropyl)phenyl |
| 1709 | 2-nitrophenyl | Me | Me | F | H | 2,6-dimethyl-4-(heptafluoro isopropyl)phenyl |
| 1710 | 3-nitrophenyl | Me | Me | F | H | 2,6-dimethyl-4-(heptafluoro isopropyl)phenyl |
| 1711 | 4-nitrophenyl | Me | Me | F | H | 2,6-dimethyl-4-(heptafluoro isopropyl)phenyl |

TABLE 3-continued

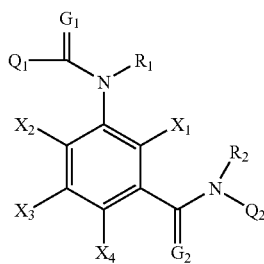

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1712 | 2-trifluoromethyl phenyl | Me | Me | F | H | 2,6-dimethyl-4-(heptafluoro isopropyl)phenyl |
| 1713 | 4-trifluoromethyl phenyl | Me | Me | F | H | 2,6-dimethyl-4-(heptafluoro isopropyl)phenyl |
| 1714 | 4-trifluoromethoxy phenyl | Me | Me | F | H | 2,6-dimethyl-4-(heptafluoro isopropyl)phenyl |
| 1715 | 2,3-difluorophenyl | Me | Me | F | H | 2,6-dimethyl-4-(heptafluoro isopropyl)phenyl |
| 1716 | 2,4-difluorophenyl | Me | Me | F | H | 2,6-dimethyl-4-(heptafluoro isopropyl)phenyl |
| 1717 | 2,5-difluorophenyl | Me | Me | F | H | 2,6-dimethyl-4-(heptafluoro isopropyl)phenyl |
| 1718 | 2,6-difluorophenyl | Me | Me | F | H | 2,6-dimethyl-4-(heptafluoro isopropyl)phenyl |
| 1719 | 2,4-dichlorophenyl | Me | Me | F | H | 2,6-dimethyl-4-(heptafluoro isopropyl)phenyl |
| 1720 | 2,6-dichlorophenyl | Me | Me | F | H | 2,6-dimethyl-4-(heptafluoro isopropyl)phenyl |
| 1721 | 3,4-dichlorophenyl | Me | Me | F | H | 2,6-dimethyl-4-(heptafluoro isopropyl)phenyl |
| 1722 | 2-chloro-4-nitro phenyl | Me | Me | F | H | 2,6-dimethyl-4-(heptafluoro isopropyl)phenyl |
| 1723 | 2-chloro-4-fluoro phenyl | Me | Me | F | H | 2,6-dimethyl-4-(heptafluoro isopropyl)phenyl |
| 1724 | 2-chloro-6-fluoro phenyl | Me | Me | F | H | 2,6-dimethyl-4-(heptafluoro isopropyl)phenyl |
| 1725 | 4-chloro-2-fluoro phenyl | Me | Me | F | H | 2,6-dimethyl-4-(heptafluoro isopropyl)phenyl |
| 1726 | 4-chloro-2-nitro phenyl | Me | Me | F | H | 2,6-dimethyl-4-(heptafluoro isopropyl)phenyl |
| 1727 | 2,3,6-trifluoro phenyl | Me | Me | F | H | 2,6-dimethyl-4-(heptafluoro isopropyl)phenyl |
| 1728 | pyridin-2-yl | Me | Me | F | H | 2,6-dimethyl-4-(heptafluoro isopropyl)phenyl |
| 1729 | pyridin-3-yl | Me | Me | F | H | 2,6-dimethyl-4-(heptafluoro isopropyl)phenyl |
| 1730 | 2-fluoropyridin-3-yl | Me | Me | F | H | 2,6-dimethyl-4-(heptafluoro isopropyl)phenyl |
| 1731 | 2-chloropyridin-3-yl | Me | Me | F | H | 2,6-dimethyl-4-(heptafluoro isopropyl)phenyl |
| 1732 | 2-chloropyridin-5-yl | Me | Me | F | H | 2,6-dimethyl-4-(heptafluoro isopropyl)phenyl |
| 1733 | 2-methylthio pyridin-3-yl | Me | Me | F | H | 2,6-dimethyl-4-(heptafluoro isopropyl)phenyl |
| 1734 | pyrazin-2-yl | Me | Me | F | H | 2,6-dimethyl-4-(heptafluoro isopropyl)phenyl |
| 1735 | furan-2-yl | Me | Me | F | H | 2,6-dimethyl-4-(heptafluoro isopropyl)phenyl |
| 1736 | thiophen-2-yl | Me | Me | F | H | 2,6-dimethyl-4-(heptafluoro isopropyl)phenyl |
| 1737 | phenyl | Me | Me | F | H | 2-bromo-4-(heptafluoroisopropyl)-6-(methylsulfonyl)phenyl |
| 1738 | 2-methylphenyl | Me | Me | F | H | 2-bromo-4-(heptafluoroisopropyl)-6-(methylsulfonyl)phenyl |
| 1739 | 4-methylphenyl | Me | Me | F | H | 2-bromo-4-(heptafluoroisopropyl)-6-(methylsulfonyl)phenyl |
| 1740 | 2-fluorophenyl | Me | Me | F | H | 2-bromo-4-(heptafluoroisopropyl)-6-(methylsulfonyl)phenyl |
| 1741 | 3-fluorophenyl | Me | Me | F | H | 2-bromo-4-(heptafluoroisopropyl)-6-(methylsulfonyl)phenyl |
| 1742 | 4-fluorophenyl | Me | Me | F | H | 2-bromo-4-(heptafluoroisopropyl)-6-(methylsulfonyl)phenyl |
| 1743 | 2-chlorophenyl | Me | Me | F | H | 2-bromo-4-(heptafluoroisopropyl)-6-(methylsulfonyl)phenyl |
| 1744 | 4-chlorophenyl | Me | Me | F | H | 2-bromo-4-(heptafluoroisopropyl)-6-(methylsulfonyl)phenyl |

TABLE 3-continued

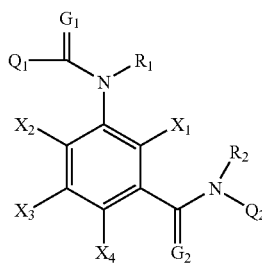

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
| --- | --- | --- | --- | --- | --- | --- |
| 1745 | 2-bromophenyl | Me | Me | F | H | 2-bromo-4-(heptafluoroisopropyl)-6-(methylsulfonyl)phenyl |
| 1746 | 2-iodophenyl | Me | Me | F | H | 2-bromo-4-(heptafluoroisopropyl)-6-(methylsulfonyl)phenyl |
| 1747 | 3-cyanophenyl | Me | Me | F | H | 2-bromo-4-(heptafluoroisopropyl)-6-(methylsulfonyl)phenyl |
| 1748 | 4-cyanophenyl | Me | Me | F | H | 2-bromo-4-(heptafluoroisopropyl)-6-(methylsulfonyl)phenyl |
| 1749 | 2-nitrophenyl | Me | Me | F | H | 2-bromo-4-(heptafluoroisopropyl)-6-(methylsulfonyl)phenyl |
| 1750 | 3-nitrophenyl | Me | Me | F | H | 2-bromo-4-(heptafluoroisopropyl)-6-(methylsulfonyl)phenyl |
| 1751 | 4-nitrophenyl | Me | Me | F | H | 2-bromo-4-(heptafluoroisopropyl)-6-(methylsulfonyl)phenyl |
| 1752 | 2-trifluoromethyl phenyl | Me | Me | F | H | 2-bromo-4-(heptafluoroisopropyl)-6-(methylsulfonyl)phenyl |
| 1753 | 4-trifluoromethyl phenyl | Me | Me | F | H | 2-bromo-4-(heptafluoroisopropyl)-6-(methylsulfonyl)phenyl |
| 1754 | 4-trifluoromethoxy phenyl | Me | Me | F | H | 2-bromo-4-(heptafluoroisopropyl)-6-(methylsulfonyl)phenyl |
| 1755 | 2,3-difluorophenyl | Me | Me | F | H | 2-bromo-4-(heptafluoroisopropyl)-6-(methylsulfonyl)phenyl |
| 1756 | 2,4-difluorophenyl | Me | Me | F | H | 2-bromo-4-(heptafluoroisopropyl)-6-(methylsulfonyl)phenyl |
| 1757 | 2,5-difluorophenyl | Me | Me | F | H | 2-bromo-4-(heptafluoroisopropyl)-6-(methylsulfonyl)phenyl |
| 1758 | 2,6-difluorophenyl | Me | Me | F | H | 2-bromo-4-(heptafluoroisopropyl)-6-(methylsulfonyl)phenyl |
| 1759 | 2,4-dichlorophenyl | Me | Me | F | H | 2-bromo-4-(heptafluoroisopropyl)-6-(methylsulfonyl)phenyl |
| 1760 | 2,6-dichlorophenyl | Me | Me | F | H | 2-bromo-4-(heptafluoroisopropyl)-6-(methylsulfonyl)phenyl |
| 1761 | 3,4-dichlorophenyl | Me | Me | F | H | 2-bromo-4-(heptafluoroisopropyl)-6-(methylsulfonyl)phenyl |
| 1762 | 2-chloro-4-nitro phenyl | Me | Me | F | H | 2-bromo-4-(heptafluoroisopropyl)-6-(methylsulfonyl)phenyl |
| 1763 | 2-chloro-4-fluoro phenyl | Me | Me | F | H | 2-bromo-4-(heptafluoroisopropyl)-6-(methylsulfonyl)phenyl |
| 1764 | 2-chloro-6-fluoro phenyl | Me | Me | F | H | 2-bromo-4-(heptafluoroisopropyl)-6-(methylsulfonyl)phenyl |
| 1765 | 4-chloro-2-fluoro phenyl | Me | Me | F | H | 2-bromo-4-(heptafluoroisopropyl)-6-(methylsulfonyl)phenyl |
| 1766 | 4-chloro-2-nitro phenyl | Me | Me | F | H | 2-bromo-4-(heptafluoroisopropyl)-6-(methylsulfonyl)phenyl |
| 1767 | 2,3,6-trifluoro phenyl | Me | Me | F | H | 2-bromo-4-(heptafluoroisopropyl)-6-(methylsulfonyl)phenyl |
| 1768 | pyridin-2-yl | Me | Me | F | H | 2-bromo-4-(heptafluoroisopropyl)-6-(methylsulfonyl)phenyl |
| 1769 | pyridin-3-yl | Me | Me | F | H | 2-bromo-4-(heptafluoroisopropyl)-6-(methylsulfonyl)phenyl |
| 1770 | 2-fluoropyridin-3-yl | Me | Me | F | H | 2-bromo-4-(heptafluoroisopropyl)-6-(methylsulfonyl)phenyl |
| 1771 | 2-chloropyridin-3-yl | Me | Me | F | H | 2-bromo-4-(heptafluoroisopropyl)-6-(methylsulfonyl)phenyl |
| 1772 | 2-chloropyridin-5-yl | Me | Me | F | H | 2-bromo-4-(heptafluoroisopropyl)-6-(methylsulfonyl)phenyl |
| 1773 | 2-methylthio pyridin-3-yl | Me | Me | F | H | 2-bromo-4-(heptafluoroisopropyl)-6-(methylsulfonyl)phenyl |
| 1774 | pyrazin-2-yl | Me | Me | F | H | 2-bromo-4-(heptafluoroisopropyl)-6-(methylsulfonyl)phenyl |
| 1775 | furan-2-yl | Me | Me | F | H | 2-bromo-4-(heptafluoroisopropyl)-6-(methylsulfonyl)phenyl |
| 1776 | thiophen-2-yl | Me | Me | F | H | 2-bromo-4-(heptafluoroisopropyl)-6-(methylsulfonyl)phenyl |
| 1777 | phenyl | Me | Me | F | H | 2-n-propyl-6-iodo-4-(heptafluoro isopropyl)phenyl |

TABLE 3-continued

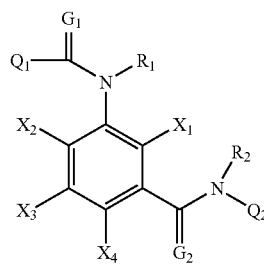

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1778 | 2-methylphenyl | Me | Me | F | H | 2-n-propyl-6-iodo-4-(heptafluoroisopropyl)phenyl |
| 1779 | 4-methylphenyl | Me | Me | F | H | 2-n-propyl-6-iodo-4-(heptafluoroisopropyl)phenyl |
| 1780 | 2-fluorophenyl | Me | Me | F | H | 2-n-propyl-6-iodo-4-(heptafluoroisopropyl)phenyl |
| 1781 | 3-fluorophenyl | Me | Me | F | H | 2-n-propyl-6-iodo-4-(heptafluoroisopropyl)phenyl |
| 1782 | 4-fluorophenyl | Me | Me | F | H | 2-n-propyl-6-iodo-4-(heptafluoroisopropyl)phenyl |
| 1783 | 2-chlorophenyl | Me | Me | F | H | 2-n-propyl-6-iodo-4-(heptafluoroisopropyl)phenyl |
| 1784 | 4-chlorophenyl | Me | Me | F | H | 2-n-propyl-6-iodo-4-(heptafluoroisopropyl)phenyl |
| 1785 | 2-bromophenyl | Me | Me | F | H | 2-n-propyl-6-iodo-4-(heptafluoroisopropyl)phenyl |
| 1786 | 2-iodophenyl | Me | Me | F | H | 2-n-propyl-6-iodo-4-(heptafluoroisopropyl)phenyl |
| 1787 | 3-cyanophenyl | Me | Me | F | H | 2-n-propyl-6-iodo-4-(heptafluoroisopropyl)phenyl |
| 1788 | 4-cyanophenyl | Me | Me | F | H | 2-n-propyl-6-iodo-4-(heptafluoroisopropyl)phenyl |
| 1789 | 2-nitrophenyl | Me | Me | F | H | 2-n-propyl-6-iodo-4-(heptafluoroisopropyl)phenyl |
| 1790 | 3-nitrophenyl | Me | Me | F | H | 2-n-propyl-6-iodo-4-(heptafluoroisopropyl)phenyl |
| 1791 | 4-nitrophenyl | Me | Me | F | H | 2-n-propyl-6-iodo-4-(heptafluoroisopropyl)phenyl |
| 1792 | 2-trifluoromethylphenyl | Me | Me | F | H | 2-n-propyl-6-iodo-4-(heptafluoroisopropyl)phenyl |
| 1793 | 4-trifluoromethylphenyl | Me | Me | F | H | 2-n-propyl-6-iodo-4-(heptafluoroisopropyl)phenyl |
| 1794 | 4-trifluoromethoxyphenyl | Me | Me | F | H | 2-n-propyl-6-iodo-4-(heptafluoroisopropyl)phenyl |
| 1795 | 2,3-difluorophenyl | Me | Me | F | H | 2-n-propyl-6-iodo-4-(heptafluoroisopropyl)phenyl |
| 1796 | 2,4-difluorophenyl | Me | Me | F | H | 2-n-propyl-6-iodo-4-(heptafluoroisopropyl)phenyl |
| 1797 | 2,5-difluorophenyl | Me | Me | F | H | 2-n-propyl-6-iodo-4-(heptafluoroisopropyl)phenyl |
| 1798 | 2,6-difluorophenyl | Me | Me | F | H | 2-n-propyl-6-iodo-4-(heptafluoroisopropyl)phenyl |
| 1799 | 2,4-dichlorophenyl | Me | Me | F | H | 2-n-propyl-6-iodo-4-(heptafluoroisopropyl)phenyl |
| 1800 | 2,6-dichlorophenyl | Me | Me | F | H | 2-n-propyl-6-iodo-4-(heptafluoroisopropyl)phenyl |
| 1801 | 3,4-dichlorophenyl | Me | Me | F | H | 2-n-propyl-6-iodo-4-(heptafluoroisopropyl)phenyl |
| 1802 | 2-chloro-4-nitrophenyl | Me | Me | F | H | 2-n-propyl-6-iodo-4-(heptafluoroisopropyl)phenyl |
| 1803 | 2-chloro-4-fluorophenyl | Me | Me | F | H | 2-n-propyl-6-iodo-4-(heptafluoroisopropyl)phenyl |
| 1804 | 2-chloro-6-fluorophenyl | Me | Me | F | H | 2-n-propyl-6-iodo-4-(heptafluoroisopropyl)phenyl |
| 1805 | 4-chloro-2-fluorophenyl | Me | Me | F | H | 2-n-propyl-6-iodo-4-(heptafluoroisopropyl)phenyl |
| 1806 | 4-chloro-2-nitrophenyl | Me | Me | F | H | 2-n-propyl-6-iodo-4-(heptafluoroisopropyl)phenyl |
| 1807 | 2,3,6-trifluorophenyl | Me | Me | F | H | 2-n-propyl-6-iodo-4-(heptafluoroisopropyl)phenyl |
| 1808 | pyridin-2-yl | Me | Me | F | H | 2-n-propyl-6-iodo-4-(heptafluoroisopropyl)phenyl |
| 1809 | pyridin-3-yl | Me | Me | F | H | 2-n-propyl-6-iodo-4-(heptafluoroisopropyl)phenyl |
| 1810 | 2-fluoropyridin-3-yl | Me | Me | F | H | 2-n-propyl-6-iodo-4-(heptafluoroisopropyl)phenyl |

TABLE 3-continued

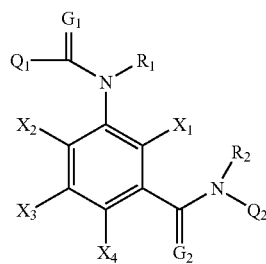

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1811 | 2-chloropyridin-3-yl | Me | Me | F | H | 2-n-propyl-6-iodo-4-(heptafluoro isopropyl)phenyl |
| 1812 | 2-chloropyridin-5-yl | Me | Me | F | H | 2-n-propyl-6-iodo-4-(heptafluoro isopropyl)phenyl |
| 1813 | 2-methylthio pyridin-3-yl | Me | Me | F | H | 2-n-propyl-6-iodo-4-(heptafluoro isopropyl)phenyl |
| 1814 | pyrazin-2-yl | Me | Me | F | H | 2-n-propyl-6-iodo-4-(heptafluoro isopropyl)phenyl |
| 1815 | furan-2-yl | Me | Me | F | H | 2-n-propyl-6-iodo-4-(heptafluoro isopropyl)phenyl |
| 1816 | thiophen-2-yl | Me | Me | F | H | 2-n-propyl-6-iodo-4-(heptafluoro isopropyl)phenyl |
| 1817 | phenyl | Me | Me | F | H | 2,6-dibromo-4-(heptafluoro-n-propylthio)phenyl |
| 1818 | 2-methylphenyl | Me | Me | F | H | 2,6-dibromo-4-(heptafluoro-n-propylthio)phenyl |
| 1819 | 4-methylphenyl | Me | Me | F | H | 2,6-dibromo-4-(heptafluoro-n-propylthio)phenyl |
| 1820 | 2-fluorophenyl | Me | Me | F | H | 2,6-dibromo-4-(heptafluoro-n-propylthio)phenyl |
| 1821 | 3-fluorophenyl | Me | Me | F | H | 2,6-dibromo-4-(heptafluoro-n-propylthio)phenyl |
| 1822 | 4-fluorophenyl | Me | Me | F | H | 2,6-dibromo-4-(heptafluoro-n-propylthio)phenyl |
| 1823 | 2-chlorophenyl | Me | Me | F | H | 2,6-dibromo-4-(heptafluoro-n-propylthio)phenyl |
| 1824 | 4-chlorophenyl | Me | Me | F | H | 2,6-dibromo-4-(heptafluoro-n-propylthio)phenyl |
| 1825 | 2-bromophenyl | Me | Me | F | H | 2,6-dibromo-4-(heptafluoro-n-propylthio)phenyl |
| 1826 | 2-iodophenyl | Me | Me | F | H | 2,6-dibromo-4-(heptafluoro-n-propylthio)phenyl |
| 1827 | 3-cyanophenyl | Me | Me | F | H | 2,6-dibromo-4-(heptafluoro-n-propylthio)phenyl |
| 1828 | 4-cyanophenyl | Me | Me | F | H | 2,6-dibromo-4-(heptafluoro-n-propylthio)phenyl |
| 1829 | 2-nitrophenyl | Me | Me | F | H | 2,6-dibromo-4-(heptafluoro-n-propylthio)phenyl |
| 1830 | 3-nitrophenyl | Me | Me | F | H | 2,6-dibromo-4-(heptafluoro-n-propylthio)phenyl |
| 1831 | 4-nitrophenyl | Me | Me | F | H | 2,6-dibromo-4-(heptafluoro-n-propylthio)phenyl |
| 1832 | 2-trifluoromethyl phenyl | Me | Me | F | H | 2,6-dibromo-4-(heptafluoro-n-propylthio)phenyl |
| 1833 | 4-trifluoromethyl phenyl | Me | Me | F | H | 2,6-dibromo-4-(heptafluoro-n-propylthio)phenyl |
| 1834 | 4-trifluoromethoxy phenyl | Me | Me | F | H | 2,6-dibromo-4-(heptafluoro-n-propylthio)phenyl |
| 1835 | 2,3-difluorophenyl | Me | Me | F | H | 2,6-dibromo-4-(heptafluoro-n-propylthio)phenyl |
| 1836 | 2,4-difluorophenyl | Me | Me | F | H | 2,6-dibromo-4-(heptafluoro-n-propylthio)phenyl |
| 1837 | 2,5-difluorophenyl | Me | Me | F | H | 2,6-dibromo-4-(heptafluoro-n-propylthio)phenyl |
| 1838 | 2,6-difluorophenyl | Me | Me | F | H | 2,6-dibromo-4-(heptafluoro-n-propylthio)phenyl |
| 1839 | 2,4-dichlorophenyl | Me | Me | F | H | 2,6-dibromo-4-(heptafluoro-n-propylthio)phenyl |
| 1840 | 2,6-dichlorophenyl | Me | Me | F | H | 2,6-dibromo-4-(heptafluoro-n-propylthio)phenyl |
| 1841 | 3,4-dichlorophenyl | Me | Me | F | H | 2,6-dibromo-4-(heptafluoro-n-propylthio)phenyl |
| 1842 | 2-chloro-4-nitro phenyl | Me | Me | F | H | 2,6-dibromo-4-(heptafluoro-n-propylthio)phenyl |
| 1843 | 2-chloro-4-fluoro phenyl | Me | Me | F | H | 2,6-dibromo-4-(heptafluoro-n-propylthio)phenyl |

TABLE 3-continued

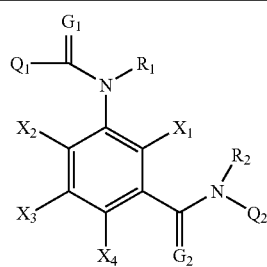

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1844 | 2-chloro-6-fluoro phenyl | Me | Me | F | H | 2,6-dibromo-4-(heptafluoro-n-propylthio)phenyl |
| 1845 | 4-chloro-2-fluoro phenyl | Me | Me | F | H | 2,6-dibromo-4-(heptafluoro-n-propylthio)phenyl |
| 1846 | 4-chloro-2-nitro phenyl | Me | Me | F | H | 2,6-dibromo-4-(heptafluoro-n-propylthio)phenyl |
| 1847 | 2,3,6-trifluoro phenyl | Me | Me | F | H | 2,6-dibromo-4-(heptafluoro-n-propylthio)phenyl |
| 1848 | pyridin-2-yl | Me | Me | F | H | 2,6-dibromo-4-(heptafluoro-n-propylthio)phenyl |
| 1849 | pyridin-3-yl | Me | Me | F | H | 2,6-dibromo-4-(heptafluoro-n-propylthio)phenyl |
| 1850 | 2-fluoropyridin-3-yl | Me | Me | F | H | 2,6-dibromo-4-(heptafluoro-n-propylthio)phenyl |
| 1851 | 2-chloropyridin-3-yl | Me | Me | F | H | 2,6-dibromo-4-(heptafluoro-n-propylthio)phenyl |
| 1852 | 2-chloropyridin-5-yl | Me | Me | F | H | 2,6-dibromo-4-(heptafluoro-n-propylthio)phenyl |
| 1853 | 2-methylthio pyridin-3-yl | Me | Me | F | H | 2,6-dibromo-4-(heptafluoro-n-propylthio)phenyl |
| 1854 | pyrazin-2-yl | Me | Me | F | H | 2,6-dibromo-4-(heptafluoro-n-propylthio)phenyl |
| 1855 | furan-2-yl | Me | Me | F | H | 2,6-dibromo-4-(heptafluoro-n-propylthio)phenyl |
| 1856 | thiophen-2-yl | Me | Me | F | H | 2,6-dibromo-4-(heptafluoro-n-propylthio)phenyl |
| 1857 | phenyl | Me | Me | F | H | 2,6-dibromo-4-(heptafluoro-n-propylsulfinyl)phenyl |
| 1858 | 2-methylphenyl | Me | Me | F | H | 2,6-dibromo-4-(heptafluoro-n-propylsulfinyl)phenyl |
| 1859 | 4-methylphenyl | Me | Me | F | H | 2,6-dibromo-4-(heptafluoro-n-propylsulfinyl)phenyl |
| 1860 | 2-fluorophenyl | Me | Me | F | H | 2,6-dibromo-4-(heptafluoro-n-propylsulfinyl)phenyl |
| 1861 | 3-fluorophenyl | Me | Me | F | H | 2,6-dibromo-4-(heptafluoro-n-propylsulfinyl)phenyl |
| 1862 | 4-fluorophenyl | Me | Me | F | H | 2,6-dibromo-4-(heptafluoro-n-propylsulfinyl)phenyl |
| 1863 | 2-chlorophenyl | Me | Me | F | H | 2,6-dibromo-4-(heptafluoro-n-propylsulfinyl)phenyl |
| 1864 | 4-chlorophenyl | Me | Me | F | H | 2,6-dibromo-4-(heptafluoro-n-propylsulfinyl)phenyl |
| 1865 | 2-bromophenyl | Me | Me | F | H | 2,6-dibromo-4-(heptafluoro-n-propylsulfinyl)phenyl |
| 1866 | 2-iodophenyl | Me | Me | F | H | 2,6-dibromo-4-(heptafluoro-n-propylsulfinyl)phenyl |
| 1867 | 3-cyanophenyl | Me | Me | F | H | 2,6-dibromo-4-(heptafluoro-n-propylsulfinyl)phenyl |
| 1868 | 4-cyanophenyl | Me | Me | F | H | 2,6-dibromo-4-(heptafluoro-n-propylsulfinyl)phenyl |
| 1869 | 2-nitrophenyl | Me | Me | F | H | 2,6-dibromo-4-(heptafluoro-n-propylsulfinyl)phenyl |
| 1870 | 3-nitrophenyl | Me | Me | F | H | 2,6-dibromo-4-(heptafluoro-n-propylsulfinyl)phenyl |
| 1871 | 4-nitrophenyl | Me | Me | F | H | 2,6-dibromo-4-(heptafluoro-n-propylsulfinyl)phenyl |
| 1872 | 2-trifluoromethyl phenyl | Me | Me | F | H | 2,6-dibromo-4-(heptafluoro-n-propylsulfinyl)phenyl |
| 1873 | 4-trifluoromethyl phenyl | Me | Me | F | H | 2,6-dibromo-4-(heptafluoro-n-propylsulfinyl)phenyl |
| 1874 | 4-trifluoromethoxy phenyl | Me | Me | F | H | 2,6-dibromo-4-(heptafluoro-n-propylsulfinyl)phenyl |
| 1875 | 2,3-difluorophenyl | Me | Me | F | H | 2,6-dibromo-4-(heptafluoro-n-propylsulfinyl)phenyl |
| 1876 | 2,4-difluorophenyl | Me | Me | F | H | 2,6-dibromo-4-(heptafluoro-n-propylsulfinyl)phenyl |

TABLE 3-continued

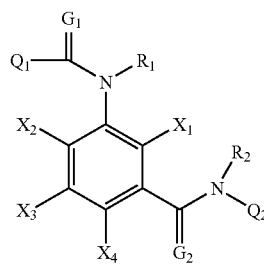

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1877 | 2,5-difluorophenyl | Me | Me | F | H | 2,6-dibromo-4-(heptafluoro-n-propylsulfinyl)phenyl |
| 1878 | 2,6-difluorophenyl | Me | Me | F | H | 2,6-dibromo-4-(heptafluoro-n-propylsulfinyl)phenyl |
| 1879 | 2,4-dichlorophenyl | Me | Me | F | H | 2,6-dibromo-4-(heptafluoro-n-propylsulfinyl)phenyl |
| 1880 | 2,6-dichlorophenyl | Me | Me | F | H | 2,6-dibromo-4-(heptafluoro-n-propylsulfinyl)phenyl |
| 1881 | 3,4-dichlorophenyl | Me | Me | F | H | 2,6-dibromo-4-(heptafluoro-n-propylsulfinyl)phenyl |
| 1882 | 2-chloro-4-nitro phenyl | Me | Me | F | H | 2,6-dibromo-4-(heptafluoro-n-propylsulfinyl)phenyl |
| 1883 | 2-chloro-4-fluoro phenyl | Me | Me | F | H | 2,6-dibromo-4-(heptafluoro-n-propylsulfinyl)phenyl |
| 1884 | 2-chloro-6-fluoro phenyl | Me | Me | F | H | 2,6-dibromo-4-(heptafluoro-n-propylsulfinyl)phenyl |
| 1885 | 4-chloro-2-fluoro phenyl | Me | Me | F | H | 2,6-dibromo-4-(heptafluoro-n-propylsulfinyl)phenyl |
| 1886 | 4-chloro-2-nitro phenyl | Me | Me | F | H | 2,6-dibromo-4-(heptafluoro-n-propylsulfinyl)phenyl |
| 1887 | 2,3,6-trifluoro phenyl | Me | Me | F | H | 2,6-dibromo-4-(heptafluoro-n-propylsulfinyl)phenyl |
| 1888 | pyridin-2-yl | Me | Me | F | H | 2,6-dibromo-4-(heptafluoro-n-propylsulfinyl)phenyl |
| 1889 | pyridin-3-yl | Me | Me | F | H | 2,6-dibromo-4-(heptafluoro-n-propylsulfinyl)phenyl |
| 1890 | 2-fluoropyridin-3-yl | Me | Me | F | H | 2,6-dibromo-4-(heptafluoro-n-propylsulfinyl)phenyl |
| 1891 | 2-chloropyridin-3-yl | Me | Me | F | H | 2,6-dibromo-4-(heptafluoro-n-propylsulfinyl)phenyl |
| 1892 | 2-chloropyridin-5-yl | Me | Me | F | H | 2,6-dibromo-4-(heptafluoro-n-propylsulfinyl)phenyl |
| 1893 | 2-methylthio pyridin-3-yl | Me | Me | F | H | 2,6-dibromo-4-(heptafluoro-n-propylsulfinyl)phenyl |
| 1894 | pyrazin-2-yl | Me | Me | F | H | 2,6-dibromo-4-(heptafluoro-n-propylsulfinyl)phenyl |
| 1895 | furan-2-yl | Me | Me | F | H | 2,6-dibromo-4-(heptafluoro-n-propylsulfinyl)phenyl |
| 1896 | thiophen-2-yl | Me | Me | F | H | 2,6-dibromo-4-(heptafluoro-n-propylsulfinyl)phenyl |
| 1897 | 2-fluorophenyl | Me | H | H | H | 2,6-dibromo-4-(pentafluoroethyl)phenyl |
| 1898 | 2-fluorophenyl | Me | H | H | H | 2-bromo-4-(heptafluoro isopropyl)-6-methylphenyl |
| 1899 | 2-fluorophenyl | Me | H | H | H | 2-ethyl-4-(heptafluoro isopropyl)-6-methylphenyl |
| 1900 | 2-fluorophenyl | Me | H | H | H | 4-(heptafluoroisopropyl)-2-iodo-6-methylphenyl |
| 1901 | 2-fluorophenyl | Me | H | H | H | 2-chloro-6-ethyl-4-(heptafluoro isopropyl)phenyl |
| 1902 | 2-fluorophenyl | Me | H | H | H | 2-bromo-6-ethyl-4-(heptafluoro isopropyl)phenyl |
| 1903 | 2-fluorophenyl | Me | H | H | H | 2-ethyl-4-(heptafluoro isopropyl)-6-iodophenyl |
| 1904 | 2-fluorophenyl | Me | H | H | H | 4-(heptafluoroisopropyl)-2-isopropyl-6-methylphenyl |
| 1905 | 2-fluorophenyl | Me | H | H | H | 2-bromo-4-(heptafluoroisopropyl)-6-n-propylphenyl |
| 1906 | 2-fluorophenyl | Me | H | H | H | 2-bromo-4-(heptafluoroisopropyl)-6-(trifluoromethylthio)phenyl |
| 1907 | 2-fluorophenyl | Me | H | H | H | 2,6-dibromo-4-(trifluoro methylthio)phenyl |
| 1908 | 2-fluorophenyl | Me | H | H | H | 2,6-dibromo-4-(pentafluoro ethylthio)phenyl |
| 1909 | 2-fluorophenyl | Me | H | H | H | 2,6-dibromo-4-(nonafluoro-n-butylthio)phenyl |

TABLE 3-continued

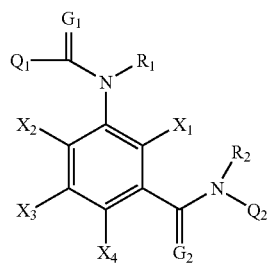

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1910 | 2-fluorophenyl | Me | H | H | H | 2,6-dichloro-4-(heptafluoro isopropylsulfonyl)phenyl |
| 1911 | 2-fluorophenyl | Me | H | H | H | 2,6-dibromo-4-(heptafluoro-n-propylsulfonyl)phenyl |
| 1912 | 2-fluorophenyl | Me | H | H | H | 2-bromo-6-(heptafluoroisopropyl oxy)-4-methylpyridin-3-yl |
| 1913 | 2-fluorophenyl | Me | H | H | H | 2,4-dimethyl-6-(2,2,2-trifluoro-1-trifluoromethylethoxy)pyridin-3-yl |
| 1914 | 2-fluorophenyl | Me | H | H | H | 2-chloro-4-methyl-6-(2,2,2-trifluoro-1-trifluoromethyl ethoxy)pyridin-3-yl |
| 1915 | 2-fluorophenyl | Me | H | H | H | 2-bromo-4-methyl-6-(2,2,2-trifluoro-1-trifluoromethyl ethoxy)pyridin-3-yl |
| 1916 | 2-fluorophenyl | Me | H | H | H | 2-iodo-4-methyl-6-(2,2,2-trifluoro-1-trifluoromethyl ethoxy)pyridin-3-yl |
| 1917 | 2-fluorophenyl | Me | H | F | H | 2,6-dibromo-4-(pentafluoro ethyl)phenyl |
| 1918 | 2-fluorophenyl | Me | H | F | H | 2-bromo-4-(heptafluoroisopropyl)-6-methylphenyl |
| 1919 | 2-fluorophenyl | Me | H | F | H | 2-ethyl-4-(heptafluoroisopropyl)-6-methylphenyl |
| 1920 | 2-fluorophenyl | Me | H | F | H | 4-(heptafluoroisopropyl)-2-iodo-6-methylphenyl |
| 1921 | 2-fluorophenyl | Me | H | F | H | 2-chloro-6-ethyl-4-(heptafluoro isopropyl)phenyl |
| 1922 | 2-fluorophenyl | Me | H | F | H | 2-bromo-6-ethyl-4-(heptafluoro isopropyl)phenyl |
| 1923 | 2-fluorophenyl | Me | H | F | H | 2-ethyl-4-(heptafluoro isopropyl)-6-iodophenyl |
| 1924 | 2-fluorophenyl | Me | H | F | H | 4-(heptafluoroisopropyl)-2-isopropyl-6-methylphenyl |
| 1925 | 2-fluorophenyl | Me | H | F | H | 2-bromo-4-(heptafluoroisopropyl)-6-n-propylphenyl |
| 1926 | 2-fluorophenyl | Me | H | F | H | 2-bromo-4-(heptafluoroisopropyl)-6-(trifluoromethylthio)phenyl |
| 1927 | 2-fluorophenyl | Me | H | F | H | 2,6-dibromo-4-(trifluoro methylthio)phenyl |
| 1928 | 2-fluorophenyl | Me | H | F | H | 2,6-dibromo-4-(pentafluoro ethylthio)phenyl |
| 1929 | 2-fluorophenyl | Me | H | F | H | 2,6-dibromo-4-(nonafluoro-n-butylthio)phenyl |
| 1930 | 2-fluorophenyl | Me | H | F | H | 2,6-dichloro-4-(heptafluoro isopropylsulfonyl)phenyl |
| 1931 | 2-fluorophenyl | Me | H | F | H | 2,6-dibromo-4-(heptafluoro-n-propylsulfonyl)phenyl |
| 1932 | 2-fluorophenyl | Me | H | F | H | 2-bromo-6-(heptafluoroisopropyl oxy)-4-methylpyridin-3-yl |
| 1933 | 2-fluorophenyl | Me | H | F | H | 2,4-dimethyl-6-(2,2,2-trifluoro-1-trifluoromethylethoxy)pyridin-3-yl |
| 1934 | 2-fluorophenyl | Me | H | F | H | 2-chloro-4-methyl-6-(2,2,2-trifluoro-1-trifluoromethyl ethoxy)pyridin-3-yl |
| 1935 | 2-fluorophenyl | Me | H | F | H | 2-bromo-4-methyl-6-(2,2,2-trifluoro-1-trifluoromethyl ethoxy)pyridin-3-yl |
| 1936 | 2-fluorophenyl | Me | H | F | H | 2-iodo-4-methyl-6-(2,2,2-trifluoro-1-trifluoromethyl ethoxy)pyridin-3-yl |
| 1937 | 2-fluorophenyl | Me | Me | H | H | 2,6-dibromo-4-(pentafluoro ethyl)phenyl |
| 1938 | 2-fluorophenyl | Me | Me | H | H | 2-bromo-4-(heptafluoroisopropyl)-6-methylphenyl |

TABLE 3-continued

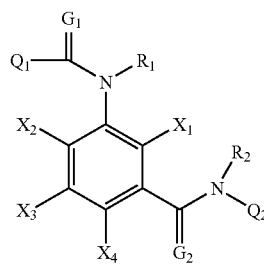

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1939 | 2-fluorophenyl | Me | Me | H | H | 2-ethyl-4-(heptafluoroisopropyl)-6-methylphenyl |
| 1940 | 2-fluorophenyl | Me | Me | H | H | 4-(heptafluoroisopropyl)-2-iodo-6-methylphenyl |
| 1941 | 2-fluorophenyl | Me | Me | H | H | 2-chloro-6-ethyl-4-(heptafluoroisopropyl)phenyl |
| 1942 | 2-fluorophenyl | Me | Me | H | H | 2-bromo-6-ethyl-4-(heptafluoroisopropyl)phenyl |
| 1943 | 2-fluorophenyl | Me | Me | H | H | 2-ethyl-4-(heptafluoroisopropyl)-6-iodophenyl |
| 1944 | 2-fluorophenyl | Me | Me | H | H | 4-(heptafluoroisopropyl)-2-isopropyl-6-methylphenyl |
| 1945 | 2-fluorophenyl | Me | Me | H | H | 2-bromo-4-(heptafluoroisopropyl)-6-n-propylphenyl |
| 1946 | 2-fluorophenyl | Me | Me | H | H | 2-bromo-4-(heptafluoroisopropyl)-6-(trifluoromethylthio)phenyl |
| 1947 | 2-fluorophenyl | Me | Me | H | H | 2,6-dibromo-4-(trifluoromethylthio)phenyl |
| 1948 | 2-fluorophenyl | Me | Me | H | H | 2,6-dibromo-4-(pentafluoroethylthio)phenyl |
| 1949 | 2-fluorophenyl | Me | Me | H | H | 2,6-dibromo-4-(nonafluoro-n-butylthio)phenyl |
| 1950 | 2-fluorophenyl | Me | Me | H | H | 2,6-dichloro-4-(heptafluoroisopropylsulfonyl)phenyl |
| 1951 | 2-fluorophenyl | Me | Me | H | H | 2,6-dibromo-4-(heptafluoro-n-propylsulfonyl)phenyl |
| 1952 | 2-fluorophenyl | Me | Me | H | H | 2-bromo-6-(heptafluoroisopropyloxy)-4-methylpyridin-3-yl |
| 1953 | 2-fluorophenyl | Me | Me | H | H | 2,4-dimethyl-6-(2,2,2-trifluoro-1-trifluoromethylethoxy)pyridin-3-yl |
| 1954 | 2-fluorophenyl | Me | Me | H | H | 2-chloro-4-methyl-6-(2,2,2-trifluoro-1-trifluoromethylethoxy)pyridin-3-yl |
| 1955 | 2-fluorophenyl | Me | Me | H | H | 2-bromo-4-methyl-6-(2,2,2-trifluoro-1-trifluoromethylethoxy)pyridin-3-yl |
| 1956 | 2-fluorophenyl | Me | Me | H | H | 2-iodo-4-methyl-6-(2,2,2-trifluoro-1-trifluoromethylethoxy)pyridin-3-yl |
| 1957 | 2-fluorophenyl | Me | Me | F | H | 2,6-dibromo-4-(pentafluoroethyl)phenyl |
| 1958 | 2-fluorophenyl | Me | Me | F | H | 2-bromo-4-(heptafluoroisopropyl)-6-methylphenyl |
| 1959 | 2-fluorophenyl | Me | Me | F | H | 2-ethyl-4-(heptafluoroisopropyl)-6-methylphenyl |
| 1960 | 2-fluorophenyl | Me | Me | F | H | 4-(heptafluoroisopropyl)-2-iodo-6-methylphenyl |
| 1961 | 2-fluorophenyl | Me | Me | F | H | 2-chloro-6-ethyl-4-(heptafluoroisopropyl)phenyl |
| 1962 | 2-fluorophenyl | Me | Me | F | H | 2-bromo-6-ethyl-4-(heptafluoroisopropyl)phenyl |
| 1963 | 2-fluorophenyl | Me | Me | F | H | 2-ethyl-4-(heptafluoroisopropyl)-6-iodophenyl |
| 1964 | 2-fluorophenyl | Me | Me | F | H | 4-(heptafluoroisopropyl)-2-isopropyl-6-methylphenyl |
| 1965 | 2-fluorophenyl | Me | Me | F | H | 2-bromo-4-(heptafluoroisopropyl)-6-n-propylphenyl |
| 1966 | 2-fluorophenyl | Me | Me | F | H | 2-bromo-4-(heptafluoroisopropyl)-6-(trifluoromethylthio)phenyl |
| 1967 | 2-fluorophenyl | Me | Me | F | H | 2,6-dibromo-4-(trifluoromethylthio)phenyl |
| 1968 | 2-fluorophenyl | Me | Me | F | H | 2,6-dibromo-4-(pentafluoroethylthio)phenyl |
| 1969 | 2-fluorophenyl | Me | Me | F | H | 2,6-dibromo-4-(nonafluoro-n-butylthio)phenyl |

TABLE 3-continued

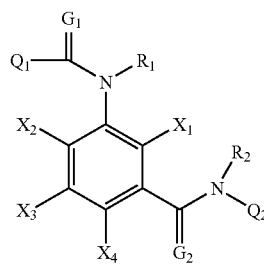

($X_3$, $X_4$ = hydrogen atoms; $G_1$, $G_2$ = oxygen atoms)

| Compound No. | $Q_1$ | $R_1$ | $R_2$ | $X_1$ | $X_2$ | $Q_2$ |
|---|---|---|---|---|---|---|
| 1970 | 2-fluorophenyl | Me | Me | F | H | 2,6-dichloro-4-(heptafluoro isopropylsulfonyl)phenyl |
| 1971 | 2-fluorophenyl | Me | Me | F | H | 2,6-dibromo-4-(heptafluoro-n-propylsulfonyl)phenyl |
| 1972 | 2-fluorophenyl | Me | Me | F | H | 2-bromo-6-(heptafluoroisopropyloxy)-4-methylpyridin-3-yl |
| 1973 | 2-fluorophenyl | Me | Me | F | H | 2,4-dimethyl-6-(2,2,2-trifluoro-1-trifluoromethylethoxy)pyridin-3-yl |
| 1974 | 2-fluorophenyl | Me | Me | F | H | 2-chloro-4-methyl-6-(2,2,2-trifluoro-1-trifluoromethylethoxy)pyridin-3-yl |
| 1975 | 2-fluorophenyl | Me | Me | F | H | 2-bromo-4-methyl-6-(2,2,2-trifluoro-1-trifluoromethylethoxy)pyridin-3-yl |
| 1976 | 2-fluorophenyl | Me | Me | F | H | 2-iodo-4-methyl-6-(2,2,2-trifluoro-1-trifluoromethylethoxy)pyridin-3-yl |

TABLE 4

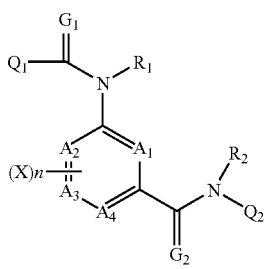

($A_3$, $A_4$, = carbon atoms; X, $R_2$ = hydrogen atoms; $G_1$, $G_2$ = oxygen atoms; n = 0)

| Compound No. | $Q_1$ | $R_1$ | $A_1$ | $A_2$ | $Q_2$ |
|---|---|---|---|---|---|
| 2001 | phenyl | H | N | C | 2,6-dimethyl-4-heptafluoroisopropylphenyl |
| 2002 | 2-methylphenyl | H | N | C | 2,6-dimethyl-4-heptafluoroisopropylphenyl |
| 2003 | 4-methylphenyl | H | N | C | 2,6-dimethyl-4-heptafluoroisopropylphenyl |
| 2004 | 2-fluorophenyl | H | N | C | 2,6-dimethyl-4-heptafluoroisopropylphenyl |
| 2005 | 3-fluorophenyl | H | N | C | 2,6-dimethyl-4-heptafluoroisopropylphenyl |
| 2006 | 4-fluorophenyl | H | N | C | 2,6-dimethyl-4-heptafluoroisopropylphenyl |

TABLE 4-continued

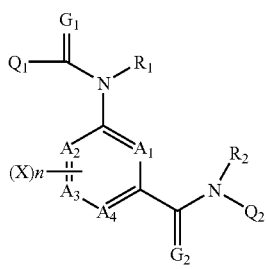

($A_3$, $A_4$, = carbon atoms; X, $R_2$ = hydrogen atoms; $G_1$, $G_2$ = oxygen atoms; n = 0)

| Compound No. | $Q_1$ | $R_1$ | $A_1$ | $A_2$ | $Q_2$ |
|---|---|---|---|---|---|
| 2007 | 2-chlorophenyl | H | N | C | 2,6-dimethyl-4-heptafluoroisopropylphenyl |
| 2008 | 4-chlorophenyl | H | N | C | 2,6-dimethyl-4-heptafluoroisopropylphenyl |
| 2009 | 2-bromophenyl | H | N | C | 2,6-dimethyl-4-heptafluoroisopropylphenyl |
| 2010 | 2-iodophenyl | H | N | C | 2,6-dimethyl-4-heptafluoroisopropylphenyl |
| 2011 | 3-cyanophenyl | H | N | C | 2,6-dimethyl-4-heptafluoroisopropylphenyl |
| 2012 | 4-cyanophenyl | H | N | C | 2,6-dimethyl-4-heptafluoroisopropylphenyl |

TABLE 4-continued

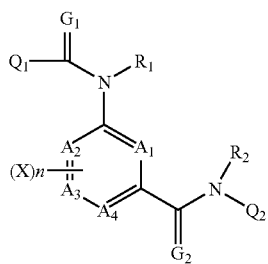

(A$_3$, A$_4$, = carbon atoms; X, R$_2$ = hydrogen atoms; G$_1$, G$_2$ = oxygen atoms; n = 0)

| Compound No. | Q$_1$ | R$_1$ | A$_1$ | A$_2$ | Q$_2$ |
|---|---|---|---|---|---|
| 2013 | 2-nitrophenyl | H | N | C | 2,6-dimethyl-4-heptafluoro isopropylphenyl |
| 2014 | 3-nitrophenyl | H | N | C | 2,6-dimethyl-4-heptafluoro isopropylphenyl |
| 2015 | 4-nitrophenyl | H | N | C | 2,6-dimethyl-4-heptafluoro isopropylphenyl |
| 2016 | 2-trifluoromethyl phenyl | H | N | C | 2,6-dimethyl-4-heptafluoro isopropylphenyl |
| 2017 | 4-trifluoromethyl phenyl | H | N | C | 2,6-dimethyl-4-heptafluoro isopropylphenyl |
| 2018 | 4-trifluoromethoxy phenyl | H | N | C | 2,6-dimethyl-4-heptafluoro isopropylphenyl |
| 2019 | 2,3-difluorophenyl | H | N | C | 2,6-dimethyl-4-heptafluoro isopropylphenyl |
| 2020 | 2,4-difluorophenyl | H | N | C | 2,6-dimethyl-4-heptafluoro isopropylphenyl |
| 2021 | 2,5-difluorophenyl | H | N | C | 2,6-dimethyl-4-heptafluoro isopropylphenyl |
| 2022 | 2,6-difluorophenyl | H | N | C | 2,6-dimethyl-4-heptafluoro isopropylphenyl |
| 2023 | 2,4-dichlorophenyl | H | N | C | 2,6-dimethyl-4-heptafluoro isopropylphenyl |
| 2024 | 2,6-dichlorophenyl | H | N | C | 2,6-dimethyl-4-heptafluoro isopropylphenyl |
| 2025 | 3,4-dichlorophenyl | H | N | C | 2,6-dimethyl-4-heptafluoro isopropylphenyl |
| 2026 | 2-chloro-4-nitro phenyl | H | N | C | 2,6-dimethyl-4-heptafluoro isopropylphenyl |
| 2027 | 2-chloro-4-fluoro phenyl | H | N | C | 2,6-dimethyl-4-heptafluoro isopropylphenyl |
| 2028 | 2-chloro-6-fluoro phenyl | H | N | C | 2,6-dimethyl-4-heptafluoro isopropylphenyl |
| 2029 | 4-chloro-2-fluoro phenyl | H | N | C | 2,6-dimethyl-4-heptafluoro isopropylphenyl |
| 2030 | 4-chloro-2-nitro phenyl | H | N | C | 2,6-dimethyl-4-heptafluoro isopropylphenyl |
| 2031 | 2,3,6-trifluoro phenyl | H | N | C | 2,6-dimethyl-4-heptafluoro isopropylphenyl |
| 2032 | pyridin-2-yl | H | N | C | 2,6-dimethyl-4-heptafluoro isopropylphenyl |
| 2033 | pyridin-3-yl | H | N | C | 2,6-dimethyl-4-heptafluoro isopropylphenyl |
| 2034 | pyridin-4-yl | H | N | C | 2,6-dimethyl-4-heptafluoro isopropylphenyl |
| 2035 | 2-fluoropyridin-3-yl | H | N | C | 2,6-dimethyl-4-heptafluoro isopropylphenyl |
| 2036 | 2-chloropyridin-3-yl | H | N | C | 2,6-dimethyl-4-heptafluoro isopropylphenyl |
| 2037 | 2-chloropyridin-5-yl | H | N | C | 2,6-dimethyl-4-heptafluoro isopropylphenyl |
| 2038 | 2-methylthio pyridin-3-yl | H | N | C | 2,6-dimethyl-4-heptafluoro isopropylphenyl |
| 2039 | pyrazin-2-yl | H | N | C | 2,6-dimethyl-4-heptafluoro isopropylphenyl |
| 2040 | furan-2-yl | H | N | C | 2,6-dimethyl-4-heptafluoro isopropylphenyl |
| 2041 | thiophen-2-yl | H | N | C | 2,6-dimethyl-4-heptafluoro isopropylphenyl |
| 2042 | phenyl | H | N | C | 2,6-dibromo-4-(heptafluoro-n-propylthio)phenyl |
| 2043 | 2-methylphenyl | H | N | C | 2,6-dibromo-4-(heptafluoro-n-propylthio)phenyl |
| 2044 | 4-methylphenyl | H | N | C | 2,6-dibromo-4-(heptafluoro-n-propylthio)phenyl |
| 2045 | 2-fluorophenyl | H | N | C | 2,6-dibromo-4-(heptafluoro-n-propylthio)phenyl |
| 2046 | 3-fluorophenyl | H | N | C | 2,6-dibromo-4-(heptafluoro-n-propylthio)phenyl |
| 2047 | 4-fluorophenyl | H | N | C | 2,6-dibromo-4-(heptafluoro-n-propylthio)phenyl |
| 2048 | 2-chlorophenyl | H | N | C | 2,6-dibromo-4-(heptafluoro-n-propylthio)phenyl |
| 2049 | 4-chlorophenyl | H | N | C | 2,6-dibromo-4-(heptafluoro-n-propylthio)phenyl |
| 2050 | 2-bromophenyl | H | N | C | 2,6-dibromo-4-(heptafluoro-n-propylthio)phenyl |

TABLE 4-continued

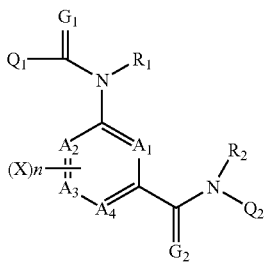

(A₃, A₄, = carbon atoms; X, R₂ = hydrogen atoms; G₁, G₂ = oxygen atoms; n = 0)

| Compound No. | Q₁ | R₁ | A₁ | A₂ | Q₂ |
|---|---|---|---|---|---|
| 2051 | 2-iodophenyl | H | N | C | 2,6-dibromo-4-(heptafluoro-n-propylthio)phenyl |
| 2052 | 3-cyanophenyl | H | N | C | 2,6-dibromo-4-(heptafluoro-n-propylthio)phenyl |
| 2053 | 4-cyanophenyl | H | N | C | 2,6-dibromo-4-(heptafluoro-n-propylthio)phenyl |
| 2054 | 2-nitrophenyl | H | N | C | 2,6-dibromo-4-(heptafluoro-n-propylthio)phenyl |
| 2055 | 3-nitrophenyl | H | N | C | 2,6-dibromo-4-(heptafluoro-n-propylthio)phenyl |
| 2056 | 4-nitrophenyl | H | N | C | 2,6-dibromo-4-(heptafluoro-n-propylthio)phenyl |
| 2057 | 2-trifluoromethyl phenyl | H | N | C | 2,6-dibromo-4-(heptafluoro-n-propylthio)phenyl |
| 2058 | 4-trifluoromethyl phenyl | H | N | C | 2,6-dibromo-4-(heptafluoro-n-propylthio)phenyl |
| 2059 | 4-trifluoromethoxy phenyl | H | N | C | 2,6-dibromo-4-(heptafluoro-n-propylthio)phenyl |
| 2060 | 2,3-difluorophenyl | H | N | C | 2,6-dibromo-4-(heptafluoro-n-propylthio)phenyl |
| 2061 | 2,4-difluorophenyl | H | N | C | 2,6-dibromo-4-(heptafluoro-n-propylthio)phenyl |
| 2062 | 2,5-difluorophenyl | H | N | C | 2,6-dibromo-4-(heptafluoro-n-propylthio)phenyl |
| 2063 | 2,6-difluorophenyl | H | N | C | 2,6-dibromo-4-(heptafluoro-n-propylthio)phenyl |
| 2064 | 2,4-dichlorophenyl | H | N | C | 2,6-dibromo-4-(heptafluoro-n-propylthio)phenyl |
| 2065 | 2,6-dichlorophenyl | H | N | C | 2,6-dibromo-4-(heptafluoro-n-propylthio)phenyl |
| 2066 | 3,4-dichlorophenyl | H | N | C | 2,6-dibromo-4-(heptafluoro-n-propylthio)phenyl |
| 2067 | 2-chloro-4-nitro phenyl | H | N | C | 2,6-dibromo-4-(heptafluoro-n-propylthio)phenyl |
| 2068 | 2-chloro-4-fluoro phenyl | H | N | C | 2,6-dibromo-4-(heptafluoro-n-propylthio)phenyl |
| 2069 | 2-chloro-6-fluoro phenyl | H | N | C | 2,6-dibromo-4-(heptafluoro-n-propylthio)phenyl |
| 2070 | 4-chloro-2-fluoro phenyl | H | N | C | 2,6-dibromo-4-(heptafluoro-n-propylthio)phenyl |
| 2071 | 4-chloro-2-nitro phenyl | H | N | C | 2,6-dibromo-4-(heptafluoro-n-propylthio)phenyl |
| 2072 | 2,3,6-trifluoro phenyl | H | N | C | 2,6-dibromo-4-(heptafluoro-n-propylthio)phenyl |
| 2073 | pyridin-2-yl | H | N | C | 2,6-dibromo-4-(heptafluoro-n-propylthio)phenyl |
| 2074 | pyridin-3-yl | H | N | C | 2,6-dibromo-4-(heptafluoro-n-propylthio)phenyl |
| 2075 | 2-fluoropyridin-3-yl | H | N | C | 2,6-dibromo-4-(heptafluoro-n-propylthio)phenyl |
| 2076 | 2-chloropyridin-3-yl | H | N | C | 2,6-dibromo-4-(heptafluoro-n-propylthio)phenyl |
| 2077 | 2-chloropyridin-5-yl | H | N | C | 2,6-dibromo-4-(heptafluoro-n-propylthio)phenyl |
| 2078 | 2-methylthio pyridin-3-yl | H | N | C | 2,6-dibromo-4-(heptafluoro-n-propylthio)phenyl |
| 2079 | pyrazin-2-yl | H | N | C | 2,6-dibromo-4-(heptafluoro-n-propylthio)phenyl |
| 2080 | furan-2-yl | H | N | C | 2,6-dibromo-4-(heptafluoro-n-propylthio)phenyl |
| 2081 | thiophen-2-yl | H | N | C | 2,6-dibromo-4-(heptafluoro-n-propylthio)phenyl |
| 2082 | phenyl | Me | N | C | 2,6-dimethyl-4-heptafluoro isopropylphenyl |
| 2083 | 2-methylphenyl | Me | N | C | 2,6-dimethyl-4-heptafluoro isopropylphenyl |
| 2084 | 4-methylphenyl | Me | N | C | 2,6-dimethyl-4-heptafluoro isopropylphenyl |
| 2085 | 2-fluorophenyl | Me | N | C | 2,6-dimethyl-4-heptafluoro isopropylphenyl |
| 2086 | 3-fluorophenyl | Me | N | C | 2,6-dimethyl-4-heptafluoro isopropylphenyl |
| 2087 | 4-fluorophenyl | Me | N | C | 2,6-dimethyl-4-heptafluoro isopropylphenyl |
| 2088 | 2-chlorophenyl | Me | N | C | 2,6-dimethyl-4-heptafluoro isopropylphenyl |

TABLE 4-continued

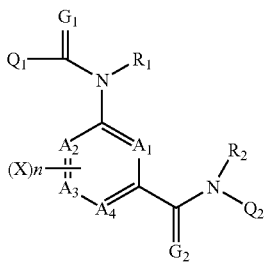

(A$_3$, A$_4$, = carbon atoms; X, R$_2$ = hydrogen atoms; G$_1$, G$_2$ = oxygen atoms; n = 0)

| Compound No. | Q$_1$ | R$_1$ | A$_1$ | A$_2$ | Q$_2$ |
|---|---|---|---|---|---|
| 2089 | 4-chlorophenyl | Me | N | C | 2,6-dimethyl-4-heptafluoroisopropylphenyl |
| 2090 | 2-bromophenyl | Me | N | C | 2,6-dimethyl-4-heptafluoroisopropylphenyl |
| 2091 | 2-iodophenyl | Me | N | C | 2,6-dimethyl-4-heptafluoroisopropylphenyl |
| 2092 | 3-cyanophenyl | Me | N | C | 2,6-dimethyl-4-heptafluoroisopropylphenyl |
| 2093 | 4-cyanophenyl | Me | N | C | 2,6-dimethyl-4-heptafluoroisopropylphenyl |
| 2094 | 2-nitrophenyl | Me | N | C | 2,6-dimethyl-4-heptafluoroisopropylphenyl |
| 2095 | 3-nitrophenyl | Me | N | C | 2,6-dimethyl-4-heptafluoroisopropylphenyl |
| 2096 | 4-nitrophenyl | Me | N | C | 2,6-dimethyl-4-heptafluoroisopropylphenyl |
| 2097 | 2-trifluoromethylphenyl | Me | N | C | 2,6-dimethyl-4-heptafluoroisopropylphenyl |
| 2098 | 4-trifluoromethylphenyl | Me | N | C | 2,6-dimethyl-4-heptafluoroisopropylphenyl |
| 2099 | 4-trifluoromethoxyphenyl | Me | N | C | 2,6-dimethyl-4-heptafluoroisopropylphenyl |
| 2100 | 2,3-difluorophenyl | Me | N | C | 2,6-dimethyl-4-heptafluoroisopropylphenyl |
| 2101 | 2,4-difluorophenyl | Me | N | C | 2,6-dimethyl-4-heptafluoroisopropylphenyl |
| 2102 | 2,5-difluorophenyl | Me | N | C | 2,6-dimethyl-4-heptafluoroisopropylphenyl |
| 2103 | 2,6-difluorophenyl | Me | N | C | 2,6-dimethyl-4-heptafluoroisopropylphenyl |
| 2104 | 2,4-dichlorophenyl | Me | N | C | 2,6-dimethyl-4-heptafluoroisopropylphenyl |
| 2105 | 2,6-dichlorophenyl | Me | N | C | 2,6-dimethyl-4-heptafluoroisopropylphenyl |
| 2106 | 3,4-dichlorophenyl | Me | N | C | 2,6-dimethyl-4-heptafluoroisopropylphenyl |
| 2107 | 2-chloro-4-nitrophenyl | Me | N | C | 2,6-dimethyl-4-heptafluoroisopropylphenyl |

TABLE 4-continued

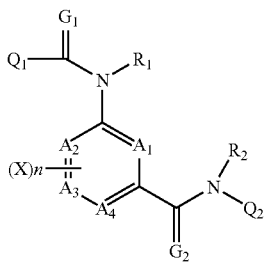

(A$_3$, A$_4$, = carbon atoms; X, R$_2$ = hydrogen atoms; G$_1$, G$_2$ = oxygen atoms; n = 0)

| Compound No. | Q$_1$ | R$_1$ | A$_1$ | A$_2$ | Q$_2$ |
|---|---|---|---|---|---|
| 2108 | 2-chloro-4-fluorophenyl | Me | N | C | 2,6-dimethyl-4-heptafluoroisopropylphenyl |
| 2109 | 2-chloro-6-fluorophenyl | Me | N | C | 2,6-dimethyl-4-heptafluoroisopropylphenyl |
| 2110 | 4-chloro-2-fluorophenyl | Me | N | C | 2,6-dimethyl-4-heptafluoroisopropylphenyl |
| 2111 | 4-chloro-2-nitrophenyl | Me | N | C | 2,6-dimethyl-4-heptafluoroisopropylphenyl |
| 2112 | 2,3,6-trifluorophenyl | Me | N | C | 2,6-dimethyl-4-heptafluoroisopropylphenyl |
| 2113 | pyridin-2-yl | Me | N | C | 2,6-dimethyl-4-heptafluoroisopropylphenyl |
| 2114 | pyridin-3-yl | Me | N | C | 2,6-dimethyl-4-heptafluoroisopropylphenyl |
| 2115 | 2-fluoropyridin-3-yl | Me | N | C | 2,6-dimethyl-4-heptafluoroisopropylphenyl |
| 2116 | 2-chloropyridin-3-yl | Me | N | C | 2,6-dimethyl-4-heptafluoroisopropylphenyl |
| 2117 | 2-chloropyridin-5-yl | Me | N | C | 2,6-dimethyl-4-heptafluoroisopropylphenyl |
| 2118 | 2-methylthiopyridin-3-yl | Me | N | C | 2,6-dimethyl-4-heptafluoroisopropylphenyl |
| 2119 | pyrazin-2-yl | Me | N | C | 2,6-dimethyl-4-heptafluoroisopropylphenyl |
| 2120 | furan-2-yl | Me | N | C | 2,6-dimethyl-4-heptafluoroisopropylphenyl |
| 2121 | thiophen-2-yl | Me | N | C | 2,6-dimethyl-4-heptafluoroisopropylphenyl |
| 2122 | phenyl | Me | N | C | 2,6-dibromo-4-(heptafluoro-n-propylthio)phenyl |
| 2123 | 2-methylphenyl | Me | N | C | 2,6-dibromo-4-(heptafluoro-n-propylthio)phenyl |
| 2124 | 4-methylphenyl | Me | N | C | 2,6-dibromo-4-(heptafluoro-n-propylthio)phenyl |
| 2125 | 2-fluorophenyl | Me | N | C | 2,6-dibromo-4-(heptafluoro-n-propylthio)phenyl |
| 2126 | 3-fluorophenyl | Me | N | C | 2,6-dibromo-4-(heptafluoro-n-propylthio)phenyl |

TABLE 4-continued

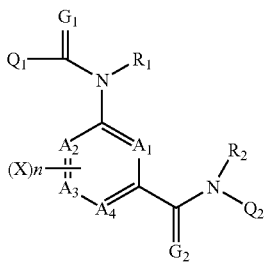

(A₃, A₄, = carbon atoms; X, R₂ = hydrogen atoms; G₁, G₂ = oxygen atoms; n = 0)

| Compound No. | Q₁ | R₁ | A₁ | A₂ | Q₂ |
|---|---|---|---|---|---|
| 2127 | 4-fluorophenyl | Me | N | C | 2,6-dibromo-4-(heptafluoro-n-propylthio)phenyl |
| 2128 | 2-chlorophenyl | Me | N | C | 2,6-dibromo-4-(heptafluoro-n-propylthio)phenyl |
| 2129 | 4-chlorophenyl | Me | N | C | 2,6-dibromo-4-(heptafluoro-n-propylthio)phenyl |
| 2130 | 2-bromophenyl | Me | N | C | 2,6-dibromo-4-(heptafluoro-n-propylthio)phenyl |
| 2131 | 2-iodophenyl | Me | N | C | 2,6-dibromo-4-(heptafluoro-n-propylthio)phenyl |
| 2132 | 3-cyanophenyl | Me | N | C | 2,6-dibromo-4-(heptafluoro-n-propylthio)phenyl |
| 2133 | 4-cyanophenyl | Me | N | C | 2,6-dibromo-4-(heptafluoro-n-propylthio)phenyl |
| 2134 | 2-nitrophenyl | Me | N | C | 2,6-dibromo-4-(heptafluoro-n-propylthio)phenyl |
| 2135 | 3-nitrophenyl | Me | N | C | 2,6-dibromo-4-(heptafluoro-n-propylthio)phenyl |
| 2136 | 4-nitrophenyl | Me | N | C | 2,6-dibromo-4-(heptafluoro-n-propylthio)phenyl |
| 2137 | 2-trifluoromethyl phenyl | Me | N | C | 2,6-dibromo-4-(heptafluoro-n-propylthio)phenyl |
| 2138 | 4-trifluoromethyl phenyl | Me | N | C | 2,6-dibromo-4-(heptafluoro-n-propylthio)phenyl |
| 2139 | 4-trifluoromethoxy phenyl | Me | N | C | 2,6-dibromo-4-(heptafluoro-n-propylthio)phenyl |
| 2140 | 2,3-difluorophenyl | Me | N | C | 2,6-dibromo-4-(heptafluoro-n-propylthio)phenyl |
| 2141 | 2,4-difluorophenyl | Me | N | C | 2,6-dibromo-4-(heptafluoro-n-propylthio)phenyl |
| 2142 | 2,5-difluorophenyl | Me | N | C | 2,6-dibromo-4-(heptafluoro-n-propylthio)phenyl |
| 2143 | 2,6-difluorophenyl | Me | N | C | 2,6-dibromo-4-(heptafluoro-n-propylthio)phenyl |
| 2144 | 2,4-dichlorophenyl | Me | N | C | 2,6-dibromo-4-(heptafluoro-n-propylthio)phenyl |
| 2145 | 2,6-dichlorophenyl | Me | N | C | 2,6-dibromo-4-(heptafluoro-n-propylthio)phenyl |
| 2146 | 3,4-dichlorophenyl | Me | N | C | 2,6-dibromo-4-(heptafluoro-n-propylthio)phenyl |
| 2147 | 2-chloro-4-nitro phenyl | Me | N | C | 2,6-dibromo-4-(heptafluoro-n-propylthio)phenyl |
| 2148 | 2-chloro-4-fluoro phenyl | Me | N | C | 2,6-dibromo-4-(heptafluoro-n-propylthio)phenyl |
| 2149 | 2-chloro-6-fluoro phenyl | Me | N | C | 2,6-dibromo-4-(heptafluoro-n-propylthio)phenyl |
| 2150 | 4-chloro-2-fluoro phenyl | Me | N | C | 2,6-dibromo-4-(heptafluoro-n-propylthio)phenyl |
| 2151 | 4-chloro-2-nitro phenyl | Me | N | C | 2,6-dibromo-4-(heptafluoro-n-propylthio)phenyl |
| 2152 | 2,3,6-trifluoro phenyl | Me | N | C | 2,6-dibromo-4-(heptafluoro-n-propylthio)phenyl |
| 2153 | pyridin-2-yl | Me | N | C | 2,6-dibromo-4-(heptafluoro-n-propylthio)phenyl |
| 2154 | pyridin-3-yl | Me | N | C | 2,6-dibromo-4-(heptafluoro-n-propylthio)phenyl |
| 2155 | 2-fluoropyridin-3-yl | Me | N | C | 2,6-dibromo-4-(heptafluoro-n-propylthio)phenyl |
| 2156 | 2-chloropyridin-3-yl | Me | N | C | 2,6-dibromo-4-(heptafluoro-n-propylthio)phenyl |
| 2157 | 2-chloropyridin-5-yl | Me | N | C | 2,6-dibromo-4-(heptafluoro-n-propylthio)phenyl |
| 2158 | 2-methylthio pyridin-3-yl | Me | N | C | 2,6-dibromo-4-(heptafluoro-n-propylthio)phenyl |
| 2159 | pyrazin-2-yl | Me | N | C | 2,6-dibromo-4-(heptafluoro-n-propylthio)phenyl |
| 2160 | furan-2-yl | Me | N | C | 2,6-dibromo-4-(heptafluoro-n-propylthio)phenyl |
| 2161 | thiophen-2-yl | Me | N | C | 2,6-dibromo-4-(heptafluoro-n-propylthio)phenyl |
| 2162 | phenyl | H | C | N | 2,6-dimethyl-4-heptafluoro isopropylphenyl |
| 2163 | phenyl | H | C | N-oxide | 2,6-dimethyl-4-heptafluoro isopropylphenyl |
| 2164 | phenyl | H | N-oxide | C | 2,6-dimethyl-4-heptafluoro isopropylphenyl |

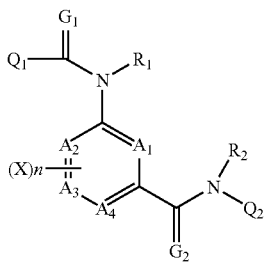

TABLE 4-continued

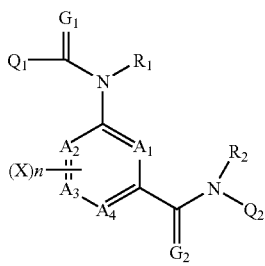

($A_3$, $A_4$, = carbon atoms; X, $R_2$ = hydrogen atoms; $G_1$, $G_2$ = oxygen atoms; n = 0)

| Compound No. | $Q_1$ | $R_1$ | $A_1$ | $A_2$ | $Q_2$ |
|---|---|---|---|---|---|
| 2165 | 2-fluorophenyl | H | N-oxide | C | 2,6-dimethyl-4-heptafluoro isopropylphenyl |
| 2166 | phenyl | H | N-oxide | C | 2,6-dibromo-4-(heptafluoro-n-propylthio)phenyl |
| 2167 | 2-fluorophenyl | H | N-oxide | C | 2,6-dibromo-4-(heptafluoro-n-propylthio)phenyl |
| 2168 | phenyl | Me | N-oxide | C | 2,6-dimethyl-4-heptafluoro isopropylphenyl |
| 2169 | 2-fluorophenyl | Me | N-oxide | C | 2,6-dimethyl-4-heptafluoro isopropylphenyl |
| 2170 | phenyl | Me | N-oxide | C | 2,6-dibromo-4-(heptafluoro-n-propylthio)phenyl |
| 2171 | 2-fluorophenyl | Me | N-oxide | C | 2,6-dibromo-4-(heptafluoro-n-propylthio)phenyl |

TABLE 5

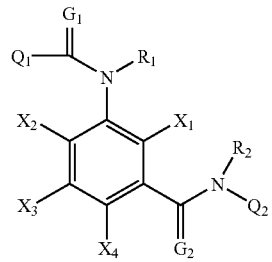

($R_1$, $R_2$, $X_1$, $X_2$, $X_3$, $X_4$ = hydrogen atoms; $Q_1$ = phenyl)

| Compound No. | $G_1$ | $G_2$ | $Q_2$ |
|---|---|---|---|
| 2201 | O | S | 2,6-dimethyl-4-heptafluoroisopropylphenyl |
| 2202 | S | O | 2,6-dimethyl-4-heptafluoroisopropylphenyl |
| 2203 | S | S | 2,6-dimethyl-4-heptafluoroisopropylphenyl |
| 2204 | O | S | 2,6-dibromo-4-(heptafluoro-n-propylthio)phenyl |
| 2205 | S | O | 2,6-dibromo-4-(heptafluoro-n-propylthio)phenyl |
| 2206 | S | S | 2,6-dibromo-4-(heptafluoro-n-propylthio)phenyl |
| 2207 | O | S | 2,6-dimethyl-4-(nonafluoro-2-butyl)phenyl |
| 2208 | S | O | 2,6-dimethyl-4-(nonafluoro-2-butyl)phenyl |
| 2209 | S | S | 2,6-dimethyl-4-(nonafluoro-2-butyl)phenyl |
| 2210 | O | S | 2-bromo-4-(heptafluoroisopropyl)-6-(methylsulfonyl)phenyl |
| 2211 | S | O | 2-bromo-4-(heptafluoroisopropyl)-6-(methylsulfonyl)phenyl |
| 2212 | S | S | 2-bromo-4-(heptafluoroisopropyl)-6-(methylsulfonyl)phenyl |
| 2213 | O | S | 2-n-propyl-6-iodo-4-(heptafluoroisopropyl)phenyl |
| 2214 | S | O | 2-n-propyl-6-iodo-4-(heptafluoroisopropyl)phenyl |
| 2215 | S | S | 2-n-propyl-6-iodo-4-(heptafluoroisopropyl)phenyl |
| 2216 | O | S | 2,6-dibromo-4-(heptafluoro-n-propylsulfinyl)phenyl |
| 2217 | S | O | 2,6-dibromo-4-(heptafluoro-n-propylsulfinyl)phenyl |
| 2218 | S | S | 2,6-dibromo-4-(heptafluoro-n-propylsulfinyl)phenyl |
| 2219 | O | S | 2,6-dichloro-4-(heptafluoro-n-propylthio)phenyl |
| 2220 | S | O | 2,6-dichloro-4-(heptafluoro-n-propylthio)phenyl |
| 2221 | S | S | 2,6-dichloro-4-(heptafluoro-n-propylthio)phenyl |

The physical properties of the compound represented by the general formula (1) of the present invention are shown in Table 6 below. Tetramethylsilane is used as an internal standard substance to record shift values of $^1$H-NMR as shown herein, unless otherwise particularly mentioned.

TABLE 6

| Compound No. | $^1$H-NMR (DMSO-$d_6$, ppm) |
|---|---|
| 1 | (CDCl$_3$) δ 2.36 (6H, s), 7.36 (2H, s), 7.51-7.65 (5H, m), 7.73 (1H, d, J = 7.8 Hz), 7.86 (1H, d, J = 7.8 Hz), 7.89 (2H, d, J = 7.8 Hz), 8.01 (1H, s), 8.33 (1H, s). |
| 2 | δ 7.52-7.63 (4H, m), 7.77 (1H, d, J = 7.8 Hz), 7.98-8.09 (5H, m), 8.39 (1H, s), 10.48 (1H, s), 10.59 (1H, s). |
| 3 | δ 7.32-7.39 (2H, m), 7.54-7.63 (2H, m), 7.67-7.72 (1H, m), 7.77 (1H, d, J = 7.8 Hz), 7.98 (1H, d, J = 7.8 Hz), 8.03 (2H, s), 8.34 (1H, s), 10.61 (1H, s), 10.65 (1H, s). |
| 4 | δ 7.53-7.63 (4H, m), 7.79 (1H, d, J = 8.3 Hz), 7.99-8.02 (2H, m), 8.08 (1H, dd, J = 2.0, 8.3 Hz), 8.17 (2H, s), 8.39 (1H, d, J = 2.0 Hz), 10.50 (1H, s), 10.63 (1H, s). |
| 5 | δ 7.33-7.40 (2H, m), 7.54-7.63 (2H, m), 7.68-7.72 (1H, m), 7.79 (1H, d, J = 7.8 Hz), 7.99 (1H, d, J = 7.8 Hz), 8.17 (2H, s), 8.35 (1H, s), 10.65 (1H, s), 10.67 (1H, s). |
| 6 | δ 7.52-7.62 (4H, m), 7.75 (1H, d, J = 7.8 Hz), 7.91 (2H, s), 7.97 (2H, d, J = 7.8 Hz), 8.04 (1H, d, J = 7.8 Hz), 8.36 (1H, s), 10.50 (1H, s), 10.61 (1H, s). |
| 7 | δ 7.53-7.64 (4H, m), 7.78 (1H, d, J = 7.8 Hz), 7.99-8.01 (2H, m), 8.06 (2H, s), 8.09 (1H, dd, J = 2.0, 7.8 Hz), 8.39 (1H, s), 10.51 (1H, s), 10.63 (1H, s). |
| 8 | δ 7.33-7.40 (2H, m), 7.55-7.63 (2H, m), 7.68-7.72 (1H, m), 7.78 (1H, d, J = 7.8 Hz), 7.99 (1H, d, J = 7.8 Hz), 8.05 (2H, s), 8.34 (1H, s), 10.65 (1H, s), 10.69 (1H, s). |
| 9 | δ 2.29 (6H, s), 7.47 (2H, s), 7.51-7.62 (4H, m), 7.75 (1H, d, J = 7.8 Hz), 7.97-8.00 (2H, m), 8.03-8.06 (1H, m), 8.36 (1H, s), 10.00 (1H, s), 10.45 (1H, s). |
| 10 | δ 2.37 (6H, s), 7.34 (2H, s), 7.46-7.57 (4H, m), 7.75 (1H, d, J = 7.8 Hz), 7.98-8.01 (2H, m), 8.12 (1H, d, J = 7.3 Hz), 8.34 (1H, s), 8.87 (1H, s), 9.66 (1H, s). |

TABLE 6-continued

| Compound No. | ¹H-NMR (DMSO-d₆, ppm) |
|---|---|
| 11 | (CDCl₃) δ 2.35 (6H, s), 2.52 (3H, s), 7.26-7.31 (2H, m), 7.36 (2H, s), 7.37-7.42 (1H, m), 7.49-7.54 (2H, m), 7.68-7.73 (3H, m), 7.79 (1H, d, J = 7.3 Hz), 8.30 (1H, s). |
| 12 | δ 2.30 (6H, s), 2.41 (3H, s), 7.42-7.48 (4H, m), 7.54 (1H, d, J = 7.94 Hz), 7.74-7.82 (3H, m), 8.07 (1H, d, J = 7.94 Hz), 8.35 (1H, s), 9.99 (1H, s), 10.43 (1H, s). |
| 13 | δ 2.30 (6H, s), 2.40 (3H, s), 7.35 (2H, d, J = 8.3 Hz), 7.45 (2H, s), 7.53 (1H, t, J = 7.8 Hz), 7.74 (1H, d, J = 7.81 Hz), 7.92 (2H, d, J = 8.3 Hz), 8.07 (1H, d, J = 7.8 Hz), 8.36 (1H, s), 9.98 (1H, s), 10.39 (1H, s). |
| 14 | δ 1.18 (3H, t, J = 7.6 Hz), 2.30 (6H, s), 2.76 (2H, q, J = 7.6 Hz), 7.30-7.37 (2H, m), 7.42-7.46 (4H, m), 7.52 (1H, t, J = 8.0 Hz), 7.81 (1H, d, J = 8.0 Hz), 7.96 (1H, d, J = 8.0 Hz), 8.35 (1H, s), 9.98 (1H, s), 10.56 (1H, s). |
| 16 | δ 1.22 (3H, t, J = 7.6 Hz), 2.31 (6H, s), 2.69 (2H, q, J = 7.6 Hz), 7.39 (2H, d, J = 8.3 Hz), 7.45 (2H, t, J = 7.9 Hz), 7.53 (2H, d, J = 8.3 Hz), 7.74 (1H, d, J = 7.9 Hz), 7.94 (1H, d, J = 8.3 Hz), 8.07 (1H, d, J = 7.9 Hz), 8.36 (1H, s), 9.99 (1H, s), 10.40 (1H, s). |
| 17 | δ 2.30 (6H, s), 7.33-7.76 (8H, m), 7.97 (1H, d, J = 8.30 Hz), 8.30 (1H, s), 10.01 (1H, s), 10.65 (1H, s). |
| 18 | δ 2.30 (6H, s), 7.45-7.64 (5H, m), 7.76-8.05 (3H, m), 8.06 (1H, d, J = 8.3 Hz), 8.35 (1H, s), 10.00 (1H, s), 10.54 (1H, s). |
| 19 | δ 2.30 (6H, s), 7.37-7.45 (4H, m), 7.54 (1H, t, J = 7.8 Hz), 7.76 (1H, d, J = 7.8 Hz), 8.05-8.11 (3H, m), 8.34 (1H, s), 10.00 (1H, s), 10.49 (1H, s). |
| 20 | (CDCl₃) δ 2.35 (6H, s), 7.36 (2H, s), 7.37-7.54 (4H, m), 7.69-7.83 (4H, m), 8.13 (1H, s), 8.33 (1H, s). |
| 22 | δ 2.30 (6H, s), 7.45 (2H, s), 7.56 (1H, dd, J = 7.8, 6.8 Hz), 7.63 (1H, d, J = 8.8 Hz), 7.72 (1H, d, J = 8.8 Hz), 7.77 (1H, d, J = 6.8 Hz), 7.94 (1H, d, J = 8.3 Hz), 8.03 (1H, d, J = 8.8 Hz), 8.17 (1H, d, J = 7.8 Hz), 8.34 (1H, s), 9.99 (1H, s), 10.54 (1H, s). |
| 23 | (CDCl₃) δ 2.36 (6H, s), 7.34-7.38 (3H, m), 7.42-7.46 (1H, m), 7.53 (1H, t, J = 7.8 Hz), 7.62 (1H, s), 7.65-7.68 (2H, m), 7.73-7.75 (1H, m), 7.82-7.84 (1H, m), 7.89 (1H, s), 8.32 (1H, s). |
| 26 | (CDCl₃) δ 2.36 (6H, s), 7.19 (1H, dt, J = 2.0, 7.8 Hz), 7.36 (2H, s), 7.46 (1H, t, J = 7.8 Hz), 7.52-7.57 (3H, m), 7.66 (1H, s), 7.74 (1H, d, J = 7.8 Hz), 7.85 (1H, d, J = 7.8 Hz), 7.94 (1H, d, J = 7.8 Hz), 8.31 (1H, s) |
| 28 | δ 2.36 (6H, s), 7.33 (2H, s), 7.48 (1H, t, J = 7.8 Hz), 7.75-7.84 (5H, m), 8.14 (1H, d, J = 7.8 Hz), 8.31 (1H, s), 9.20 (1H, s), 10.04 (1H, s). |
| 29 | δ 2.30 (6H, s), 7.45 (2H, s), 7.57 (1H, d, J = 7.8 Hz), 7.75-7.80 (2H, m), 8.06-8.11 (2H, m), 8.29 (1H, d, J = 7.8 Hz), 8.34 (1H, s), 8.46 (1H, s), 10.02 (1H, s), 10.65 (1H, s). |
| 30 | δ 2.30 (6H, s), 7.45 (2H, s), 7.56 (1H, t, J = 7.8 Hz), 7.79 (1H, d, J = 7.8 Hz), 8.04-8.06 (3H, m), 8.16 (2H, d, J = 8.3 Hz), 8.36 (1H, s), 10.02 (1H, s), 10.72 (1H, s). |
| 31 | δ 2.30 (6H, s), 7.45 (2H, s), 7.56 (1H, d, J = 7.8 Hz), 7.76-7.81 (3H, m), 7.88-7.94 (2H, m), 8.17 (1H, d, J = 7.8 Hz), 8.24 (1H, s), 10.02 (1H, s), 10.90 (1H, s). |
| 32 | δ 2.32 (6H, s), 7.46 (2H, s), 7.58 (1H, t, J = 7.8 Hz), 7.80-7.89 (2H, m), 8.11 (1H, d, J = 7.8 Hz), 8.36 (1H, s), 8.44-8.48 (2H, m), 8.86 (1H, s), 10.04 (1H, s), 10.83 (1H, s). |
| 33 | δ 2.31 (6H, s), 7.45 (2H, s), 7.57 (1H, t, J = 8.1 Hz), 7.80 (1H, d, J = 8.1 Hz), 8.08 (1H, d, J = 8.1 Hz), 8.24 (1H, s), 8.36-8.41 (4H, m), 10.01 (1H, s), 10.79 (1H, s). |
| 34 | δ 2.30 (6H, s), 6.39 (2H, s), 6.58-6.62 (1H, m), 6.76 (1H, dd, J = 1.0, 8.3 Hz), 7.19-7.24 (1H, m), 7.45 (2H, s), 7.51 (1H, t, J = 7.8 Hz), 7.66-7.73 (2H, m), 7.94-7.97 (1H, m), 8.30 (1H, d, J = 2.0 Hz), 9.96 (1H, s), 10.20 (1H, s). |
| 35 | δ 2.30 (6H, s), 6.53-6.86 (1H, m), 7.20-7.21 (4H, m), 7.45 (2H, s), 7.52 (1H, t, J = 7.8 Hz), 7.73 (1H, d, J = 7.8 Hz), 8.02 (1H, d, J = 7.8 Hz), 8.35 (1H, s), 9.96 (1H, s), 10.32 (1H, s). |
| 37 | (CDCl₃) δ 2.34 (6H, s), 7.35 (2H, s), 7.51 (1H, t, J = 7.8 Hz), 7.62-7.80 (8H, m), 8.25 (1H, s). |
| 39 | δ 2.31 (6H, s), 7.45 (2H, s), 7.57 (1H, t, J = 7.8 Hz), 7.79 (1H, d, J = 7.8 Hz), 7.94 (2H, d, J = 8.3 Hz), 8.07 (1H, d, J = 7.8 Hz), 8.20 (2H, d, J = 8.3 Hz), 8.36 (1H, s), 10.01 (1H, s), 10.70 (1H, s). |
| 40 | δ 2.30 (6H, s), 6.96-7.01 (2H, m), 7.43-7.48 (3H, m), 7.56 (1H, t, J = 8.3 Hz), 7.78 (1H, d, J = 8.3 Hz), 7.97-8.00 (2H, m), 8.29 (1H, s), 10.01 (1H, s), 10.61 (1H, s). |
| 41 | δ 2.30 (6H, s), 3.90 (3H, s), 7.05-7.10 (1H, m), 7.19 (1H, d, J = 8.3 Hz), 7.45 (2H, s), 7.49-7.54 (2H, m), 7.63 (1H, dd, J = 2.0, 7.8 Hz), 7.72 (1H, d, J = 7.8 Hz), 7.96 (1H, d, J = 7.8 Hz), 8.33 (1H, s), 9.98 (1H, s), 10.33 (1H, s). |
| 45 | δ 1.33 (9H, s), 2.31 (6H, s), 7.45 (2H, s), 7.53 (1H, t, J = 7.8 Hz), 7.54 (2H, d, J = 8.3 Hz), 7.74 (1H, d, J = 7.8 Hz), 7.94 (2H, d, J = 8.3 Hz), 8.06 (1H, d, J = 7.8 Hz), 8.36 (1H, s), 9.99 (1H, s), 10.40 (1H, s). |
| 46 | δ 2.30 (6H, s), 2.98 (6H, s), 6.93-6.95 (1H, m), 7.25-7.35 (3H, m), 7.45 (2H, s), 7.53 (1H, t, J = 7.8 Hz), 7.74 (1H, d, J = 7.8 Hz), 8.06 (1H, d, J = 7.8 Hz), 8.35 (1H, s), 9.99 (1H, s), 10.35 (1H, s). |
| 47 | δ 2.30 (6H, s), 3.01 (6H, s), 6.77 (2H, d, J = 9.3 Hz), 7.45 (2H, s), 7.50 (1H, t, J = 7.8 Hz), 7.69 (1H, d, J = 7.8 Hz), 7.91 (2H, d, J = 9.3 Hz), 8.06 (1H, d, J = 7.8 Hz), 8.33 (1H, s), 9.96 (1H, s), 10.09 (1H, s). |
| 48 | δ 2.31 (6H, s), 7.45 (2H, s), 7.53-7.60 (3H, m), 7.77 (1H, d, J = 7.3 Hz), 8.06 (1H, d, J = 8.3 Hz), 8.13 (2H, d, J = 8.3 Hz), 8.35 (1H, s), 10.01 (1H, s), 10.59 (1H, s). |
| 52 | δ 2.21 (3H, s), 2.30 (6H, s), 7.27 (1H, d, J = 8.3 Hz), 7.39-7.44 (1H, m), 7.45 (2H, s), 7.50-7.62 (2H, m), 7.70-7.52 (2H, m), 7.92 (1H, d, J = 7.8 Hz), 8.29 (1H, s), 9.99 (1H, s), 10.57 (1H, s). |
| 54 | δ 2.30 (6H, s), 3.91 (3H, s), 7.45 (2H, s), 7.56 (1H, t, J = 7.8 Hz), 7.78 (1H, d, J = 7.8 Hz), 8.03-8.15 (5H, m), 8.36 (1H, s), 10.01 (1H, s), 10.67 (1H, s). |
| 56 | δ 2.27 (6H, s), 2.30 (6H, s), 7.18-7.22 (1H, m), 7.26-7.30 (2H, m), 7.45 (2H, s), 7.52 (1H, t, J = 7.8 Hz), 7.72 (1H, d, J = 7.8 Hz), 7.95 (1H, d, J = 7.8 Hz), 8.36 (1H, s), 9.98 (1H, s), 10.52 (1H, s). |
| 57 | δ 2.30 (6H, s), 2.33 (3H, s), 2.38 (3H, s), 7.11-7.13 (2H, m), 7.40 (1H, d, J = 7.8 Hz), 7.44 (2H, s), 7.51 (1H, t, J = 7.8 Hz), 7.72 (1H, d, J = 7.8 Hz), 7.95 (1H, d, J = 8.8 Hz), 8.34 (1H, s), 9.98 (1H, s), 10.43 (1H, s). |
| 58 | δ 2.30 (12H, s), 7.12 (2H, d, J = 7.8 Hz), 7.23-7.27 (1H, m), 7.45 (2H, s), 7.52 (1H, t, J = 8.3 Hz), 7.75 (1H, d, J = 8.3 Hz), 7.94-7.99 (1H, m), 8.35 (1H, s), 10.00 (1H, s), 10.61 (1H, s). |
| 59 | δ 2.30 (6H, s), 7.34-7.40 (1H, m), 7.45 (2H, s), 7.50-7.58 (2H, m), 7.60-7.68 (1H, m), 7.77 (1H, d, J = 7.8 Hz), 7.96 (1H, d, J = 8.3 Hz), 8.31 (1H, s), 10.02 (1H, s), 10.78 (1H, s). |

TABLE 6-continued

| Compound No. | $^1$H-NMR (DMSO-d$_6$, ppm) |
|---|---|
| 60 | δ 2.30 (6H, s), 7.22-7.28 (1H, m), 7.42-7.48 (3H, m), 7.53-7.57 (1H, m), 7.75-7.82 (2H, m), 7.96 (1H, d, J = 7.8 Hz), 8.30 (1H, s), 10.01 (1H, s), 10.65 (1H, s). |
| 61 | δ 2.30 (6H, s), 7.45 (2H, s), 7.46-7.49 (2H, m), 7.53-7.59 (2H, m), 7.77 (1H, d, J = 7.8 Hz), 7.96 (1H, d, J = 8.3 Hz), 8.30 (1H, s), 10.02 (1H, broad), 10.72 (1H, broad). |
| 62 | δ 2.30 (6H, s), 7.25-7.30 (2H, m), 7.45 (2H, s), 7.54-7.65 (2H, m), 7.77 (1H, d, J = 7.8 Hz), 7.93 (1H, d, J = 7.8 Hz), 8.29 (1H, s), 10.03 (1H, s), 11.04 (1H, s). |
| 66 | δ 2.30 (6H, s), 7.45 (2H, s), 7.52-7.62 (2H, m), 7.66 (1H, d, J = 8.3 Hz), 7.75-7.80 (2H, m), 7.94 (1H, d, J = 7.8 Hz), 8.30 (1H, s), 10.02 (1H, s), 10.77 (1H, s). |
| 68 | δ 2.30 (6H, s), 7.45 (2H, s), 7.50-7.62 (4H, m), 7.78 (1H, d, J = 7.8 Hz), 7.94 (1H, d, J = 7.8 Hz), 8.28 (1H, s), 10.03 (1H, s), 10.99 (1H, s). |
| 69 | δ 2.30 (6H, s), 7.45 (2H, s), 7.56 (1H, t, J = 7.8 Hz), 7.79 (1H, d, J = 7.8 Hz), 7.85 (1H, d, J = 8.3 Hz), 7.97-8.00 (1H, m), 8.05-8.08 (1H, m), 8.27 (1H, d, J = 2.0 Hz), 8.33 (1H, s), 10.00 (1H, s), 10.61 (1H, s). |
| 70 | δ 2.74 (6H, s), 7.34 (2H, s), 7.52 (1H, t, J = 7.8 Hz), 7.81 (1H, d, J = 7.8 Hz), 7.93 (1H, d, J = 8.3 Hz), 8.13-8.15 (2H, m), 8.58 (1H, d, J = 8.3 Hz), 8.94 (1H, s), 9.27 (1H, s), 10.67 (1H, s). |
| 71 | (CDCl$_3$) δ 1.6-2.4 (6H, broad-s), 6.5-7.7 (3H, broad), 7.8-8.0 (4H, broad), 8.10 (1H, broad-s), 8.28 (1H, d, J = 8.8 Hz). |
| 72 | δ 2.30 (6H, s), 3.78 (6H, s), 6.66-6.75 (2H, m), 7.34-7.50 (4H, m), 7.67 (1H, d, J = 7.8 Hz), 7.91 (1H, d, J = 7.8 Hz), 8.34 (1H, s), 9.98 (1H, s), 10.44 (1H, s). |
| 73 | δ 2.30 (6H, s), 3.83 (6H, s), 6.73 (1H, t, J = 2.4 Hz), 7.15 (2H, d, J = 2.4 Hz), 7.45 (2H, s), 7.54 (1H, t, J = 8.3 Hz), 7.75 (1H, d, J = 8.3 Hz), 8.06 (1H, d, J = 8.3 Hz), 8.33 (1H, s), 9.99 (1H, s), 10.39 (1H, s). |
| 74 | (CDCl$_3$) δ 2.34 (6H, s), 2.68 (3H, s), 7.36 (2H, s), 7.55 (1H, t, J = 7.8 Hz), 7.62 (1H, s), 7.72 (1H, d, J = 7.8 Hz), 7.81 (1H, d, J = 8.3 Hz), 7.88 (1H, s), 7.92 (1H, d, J = 7.8 Hz), 8.05 (1H, d, J = 8.3 Hz), 8.17 (1H, s), 8.26 (1H, s). |
| 75 | δ 2.30 (6H, s), 5.22 (2H, broad-s), 6.67-6.72 (1H, m), 6.78-6.81 (1H, m), 6.97-7.02 (1H, m), 7.45 (2H, s), 7.52 (1H, t, J = 7.8 Hz), 7.72 (1H, d, J = 7.8 Hz), 7.94 (1H, d, J = 7.8 Hz), 8.32 (1H, s), 9.98 (1H, s), 10.46 (1H, s). |
| 77 | δ 2.30 (6H, s), 7.45 (2H, s), 7.58 (1H, t, J = 7.8 Hz), 7.70 (1H, t, J = 8.8 Hz), 7.80 (1H, d, J = 7.8 Hz), 7.99 (1H, d, J = 7.8 Hz), 8.29 (1H, s), 8.45-8.50 (1H, m), 8.57-8.60 (1H, m), 10.03 (1H, s), 10.91 (1H, s). |
| 81 | δ 2.30 (6H, s), 7.56 (1H, t), 7.73-7.80 (6H, m), 7.92 (1H, d, J = 7.81 Hz), 8.22 (1H, s), 10.03 (1H, s), 11.05 (1H, s). |
| 82 | δ 2.30 (6H, s), 7.45 (2H, s), 7.57 (1H, t, J = 7.8 Hz), 7.80 (1H, d, J = 7.8 Hz), 7.92-7.96 (2H, m), 8.29-8.45 (2H, m), 8.45 (1H, m), 10.03 (1H, s), 10.98 (1H, s). |
| 83 | δ 2.28 (6H, s), 7.33-7.38 (1H, m), 7.43 (2H, s), 7.53 (1H, t, J = 7.9 Hz), 7.58 (1H, d, J = 2.4 Hz), 7.61-7.71 (1H, m), 7.75 (1H, d, J = 7.9 Hz), 7.93 (1H, d, J = 7.9 Hz), 8.28 (1H, s), 9.98 (1H, s), 10.71 (1H, s). |
| 84 | δ 2.30 (6H, s), 7.38-7.48 (4H, m), 7.54-7.60 (2H, m), 7.78 (1H, d, J = 7.8 Hz), 7.93 (1H, d, J = 7.8 Hz), 8.28 (1H, s), 10.03 (1H, s), 11.03 (1H, s). |
| 86 | δ 2.30 (6H, s), 7.42-7.47 (3H, m), 7.55 (1H, t, J = 8.0 Hz), 7.64 (1H, d, J = 2.0 Hz), 7.66-7.77 (2H, m), 7.96 (1H, d, J = 8.0 Hz), 8.29 (1H, s), 10.01 (1H, s), 10.69 (1H, s). |
| 87 | δ 2.30 (6H, s), 7.45 (2H, s), 7.56 (1H, t, J = 7.9 Hz), 7.79 (1H, d, J = 7.9 Hz), 7.87 (1H, d, J = 7.9 Hz), 7.92 (1H, dd, J = 8.2, 1.6 Hz), 8.00 (1H, dd, J = 8.2, 1.6 Hz), 8.22 (1H, t, J = 1.6 Hz), 8.29 (1H, d, J = 1.6 Hz), 10.03 (1H, s), 10.94 (1H, s). |
| 88 | (CDCl$_3$) δ 2.37 (6H, s), 4.06 (3H, s), 7.37 (2H, s), 7.44 (1H, d, J = 9.7 Hz), 7.52 (1H, s), 7.58 (1H, t, J = 7.8 Hz), 7.70 (1H, s), 7.74 (1H, d, J = 7.8 Hz), 7.93 (1H, s), 7.95 (1H, s), 8.02 (1H, s), 8.26 (1H, s). |
| 89 | (CDCl$_3$) δ 2.37 (6H, s), 4.22 (3H, s), 7.37 (2H, s), 7.55 (1H, t, J = 7.8 Hz), 7.56 (1H, s), 7.72 (1H, d, J = 7.8 Hz), 7.94-7.97 (2H, m), 8.00 (1H, d, J = 7.8 Hz), 8.28 (1H, s), 8.47 (1H, d, J = 8.8 Hz), 9.83 (1H, s). |
| 91 | δ 2.25 (6H, s), 2.27 (3H, s), 2.29 (6H, s), 6.94 (2H, s), 7.45 (2H, s), 7.51 (1H, t, J = 7.8 Hz), 7.73 (1H, d, J = 7.8 Hz), 7.94 (1H, d, J = 7.8 Hz), 8.34 (1H, s), 9.97 (1H, s), 10.53 (1H, s). |
| 92 | δ 2.33 (6H, s), 7.32-7.40 (1H, m), 7.45 (2H, s), 7.58 (1H, t, J = 8.06 Hz), 7.67-7.75 (1H, m), 7.80 (1H, d, J = 7.81 Hz), 7.92 (1H, d, J = 8.29 Hz), 8.27 (1H, s), 10.04 (1H, s), 11.14 (1H, s). |
| 95 | δ 2.30 (6H, s), 7.45 (2H, s), 7.59 (1H, t, J = 7.8 Hz), 7.83 (1H, d, J = 7.8 Hz), 7.91-7.94 (1H, dd, J = 1.5, 7.8 Hz), 8.25 (1H, d, J = 1.5 Hz), 10.06 (1H, s), 11.27 (1H, s). |
| 96 | δ 2.30 (6H, s), 7.28-7.55 (10H, m), 7.57-7.61 (2H, m), 7.69 (1H, d, J = 7.8 Hz), 7.74 (1H, d, J = 7.8 Hz), 8.13 (1H, s), 9.94 (1H, s), 10.47 (1H, s). |
| 97 | δ 2.32 (6H, s), 7.41-7.57 (6H, m), 7.72-7.82 (3H, m), 7.85-7.88 (2H, m), 8.09-8.13 (3H, m), 8.40 (1H, s), 10.01 (1H, s), 10.53 (1H, s). |
| 98 | δ 2.31 (6H, s), 7.45 (2H, s), 7.54-7.65 (4H, m), 7.76-7.80 (2H, m), 8.01-8.06 (2H, m), 8.10 (1H, d, J = 8.3 Hz), 8.21-8.23 (1H, m), 8.43 (1H, s), 10.01 (1H, s), 10.80 (1H, s). |
| 99 | δ 2.32 (6H, s), 7.46 (2H, s), 7.57 (1H, t, J = 7.8 Hz), 7.61-7.72 (2H, m), 7.78 (1H, d, J = 7.8 Hz), 7.99-8.17 (5H, m), 8.41 (1H, t, J = 2.0 Hz), 8.65 (1H, s), 10.01 (1H, s), 10.66 (1H, s). |
| 100 | δ 2.31 (6H, s), 7.45 (2H, s), 7.55 (1H, t, J = 7.8 Hz), 7.69-7.76 (2H, m), 8.07-8.14 (2H, m), 8.19 (1H, d, J = 7.8 Hz), 8.54 (1H, s), 8.77 (1H, d, J = 4.9 Hz), 9.99 (1H, s), 10.86 (1H, s). |
| 101 | δ 2.30 (6H, s), 7.45 (2H, s), 7.54-7.61 (2H, m), 7.78 (1H, d, J = 8.3 Hz), 8.06 (1H, d, J = 7.3 Hz), 8.32-8.35 (2H, m), 8.77-8.79 (1H, m), 9.14 (1H, d, J = 1.5 Hz), 10.00 (1H, s), 10.66 (1H, s). |
| 102 | δ 2.30 (6H, s), 7.45 (2H, s), 7.57 (1H, t, J = 7.8 Hz), 7.80 (1H, d, J = 7.8 Hz), 7.91 (2H, d, J = 5.6 Hz), 8.06 (1H, d, J = 7.8 Hz), 8.35 (1H, s), 8.81 (2H, d, J = 5.6 Hz), 10.01 (1H, s), 10.72 (1H, s). |
| 103 | δ 2.27 (3H, s), 2.30 (6H, s), 7.45 (2H, s), 7.54-8.07 (6H, m), 8.35 (1H, s), 10.02 (1H, s), 10.77 (1H, s). |
| 105 | δ 2.30 (6H, s), 7.45 (2H, s), 7.52-7.58 (2H, m), 7.78 (1H, d, J = 8.30 Hz), 7.97 (1H, d, J = 8.29 Hz), 8.26-8.31 (2H, m), 8.42 (1H, d, J = 4.39 Hz), 10.02 (1H, s), 10.80 (1H, s). |

TABLE 6-continued

| Compound No. | ¹H-NMR (DMSO-d$_6$, ppm) |
|---|---|
| 106 | δ 2.30 (6H, s), 7.45 (2H, s), 7.54-7.60 (2H, m), 7.77-7.81 (1H, m), 7.95 (1H, d, J = 7.8 Hz), 8.10-8.13 (1H, m), 8.30 (1H, s), 8.54-8.59 (1H, m), 10.03 (1H, s), 10.88 (1H, s). |
| 108 | δ 2.31 (6H, s), 7.45 (2H, s), 7.56 (1H, t, J = 7.8 Hz), 7.78 (1H, d, J = 7.8 Hz), 7.82 (1H, dd, J = 6.3, 2.4 Hz), 8.11-8.16 (3H, m), 8.47 (1H, s), 10.01 (1H, s), 10.69 (1H, s). |
| 109 | δ 2.31 (6H, s), 7.46 (2H, s), 7.57 (1H, t, J = 8.3 Hz), 7.74 (1H, d, J = 8.3 Hz), 7.80 (1H, d, J = 8.3 Hz), 8.06 (1H, dd, J = 8.3, 1.7 Hz), 8.34 (1H, t, J = 1.7 Hz), 8.40 (1H, dd, J = 8.3, 1.7 Hz), 9.00 (1H, d, J = 1.7 Hz), 10.02 (1H, s), 10.71 (1H, s). |
| 110 | δ 2.31 (6H, s), 7.45 (2H, s), 7.56 (1H, d, J = 8.1 Hz), 7.78 (1H, d, J = 8.1 Hz), 7.86 (1H, d, J = 2.1 Hz), 8.11 (1H, dd, J = 8.1, 2.1 Hz), 8.19 (1H, d, J = 2.1 Hz), 8.53 (1H, t, J = 2.1 Hz), 8.75 (1H, d, J = 5.4 Hz), 10.01 (1H, s), 10.96 (1H, s). |
| 111 | (CDCl$_3$) δ 2.36 (6H, s,), 7.34 (2H, s,), 7.47-8.94 (7H, m,), 9.63 (1H, s,), 10.73 (1H, s,). |
| 113 | (CDCl$_3$) δ 2.36 (6H, s,), 7.34-8.73 (15H, m,), 10.01 (1H, s,) |
| 114 | δ 2.30 (6H, s), 2.42 (3H, s), 7.25-7.28 (1H, m), 7.44 (2H, s), 7.55 (1H, t, J = 7.8 Hz), 7.77 (1H, d, J = 7.8 Hz), 7.94-7.97 (2H, m), 8.30 (1H, s), 8.61 (1H, dd, J = 4.9, 1.5 Hz), 10.01 (1H, s), 10.67 (1H, s). |
| 115 | δ 2.29 (6H, s), 3.94 (3H, s), 4.06 (3H, s), 6.53 (1H, d, J = 8.3 Hz), 7.44 (2H, s), 7.51 (1H, t, J = 7.9 Hz), 7.72 (1H, d, J = 7.9 Hz), 7.95 (1H, d, J = 7.9 Hz), 8.12 (1H, d, J = 8.3 Hz), 8.28 (1H, s), 9.96 (1H, s), 10.07 (1H, s). |
| 116 | δ 2.29 (6H, s), 7.44 (2H, s), 7.57 (1H, t, J = 7.9 Hz), 7.80 (1H, d, J = 7.9 Hz), 8.05 (1H, d, J = 7.9 Hz), 8.30 (1H, s), 8.67 (1H, d, J = 2.2 Hz), 8.93 (1H, d, J = 2.2 Hz), 10.01 (1H, s), 10.73 (1H, s). |
| 117 | (CDCl$_3$) δ 2.36 (6H, s), 7.37-8.50 (9H, m,), 8.97 (1H, s). |
| 118 | δ 2.28 (6H, s), 7.43 (2H, s), 7.56 (1H, t, J = 8.0 Hz), 7.74-7.79 (2H, m), 7.92 (1H, d, J = 8.0 Hz), 8.20 (1H, d, J = 8.3 Hz), 8.25 (1H, s), 10.01 (1H, s), 10.88 (1H, s). |
| 119 | (CDCl$_3$) δ 2.36 (6H, s), 7.36-8.60 (10H, m,). |
| 120 | δ 2.31 (6H, s), 7.46 (2H, s), 7.57 (1H, t, J = 7.8 Hz), 7.80 (1H, d, J = 7.8 Hz), 8.02 (1H, d, J = 7.8 Hz), 8.08 (2H, d, J = 1.2 Hz), 8.33 (1H, t, J = 2.0 Hz), 8.40 (2H, d, J = 7.3 Hz), 10.02 (1H, s), 10.63 (1H, s). |
| 121 | δ 2.30 (6H, s), 3.89 (3H, s), 6.11 (1H, dd, J = 2.0, 3.9 Hz), 7.03 (1H, t, J = 2.0 Hz), 7.10 (1H, dd, J = 2.0, 3.9 Hz), 7.45 (2H, s), 7.49 (1H, t, J = 7.8 Hz), 7.69 (1H, d, J = 7.8 Hz), 7.99 (1H, d, J = 7.8 Hz), 8.28 (1H, s), 9.95 (2H, s). |
| 122 | δ 2.31 (6H, s), 7.45 (2H, s), 7.57 (1H, t, J = 7.8 Hz), 7.78 (1H, d, J = 7.8 Hz), 8.11 (1H, d, J = 7.8 Hz), 8.53 (1H, s), 8.84 (1H, dd, J = 1.5, 2.4 Hz), 8.95 (1H, d, J = 2.4 Hz), 9.33 (1H, d, J = 1.5 Hz), 10.00 (1H, s), 10.97 (1H, s). |
| 124 | δ 2.28 (6H, s), 7.44 (2H, s), 7.58 (1H, t, J = 7.9 Hz), 7.81 (1H, d, J = 7.9 Hz), 7.92 (1H, d, J = 7.9 Hz), 8.20 (1H, s), 9.43 (1H, s), 9.59 (1H, s), 10.03 (1H, s), 11.06 (1H, s). |
| 125 | δ 2.30 (6H, s), 7.45 (2H, s), 7.50-7.62 (4H, m), 7.78 (1H, d, J = 7.8 Hz), 7.94 (1H, d, J = 7.8 Hz), 8.28 (1H, s), 10.03 (1H, s), 10.99 (1H, s). |
| 126 | δ 2.30 (6H, s), 7.04 (1H, t, J = 1.5 Hz), 7.45 (2H, s), 7.53 (1H, t, J = 8.0 Hz), 7.74-7.82 (2H, m), 8.04 (1H, d, J = 1.5 Hz), 8.25 (1H, d, J = 1.5 Hz), 8.43 (1H, t, J = 1.5 Hz), 9.98 (1H, s), 10.14 (1H, s). |
| 127 | δ 1.86-1.91 (2H, m), 2.00-2.02 (1H, m), 2.19-2.29 (7H, m), 3.81-3.87 (1H, m), 3.98-4.03 (1H, m), 4.40-4.43 (1H, m), 7.44-7.50 (3H, m), 7.77 (1H, d, J = 7.8 Hz), 7.94 (1H, d, J = 7.8 Hz), 8.26 (1H, s), 9.89 (1H, s), 9.94 (1H, s). |
| 128 | (CDCl$_3$) δ 2.02-2.10 (2H, m), 2.28 (6H, s), 3.15-3.22 (1H, m), 3.80-3.98 (4H, m), 7.44 (2H, s), 7.48 (1H, t, J = 7.8 Hz), 7.68 (1H, t, J = 7.8 Hz), 7.87 (1H, d, J = 7.8 Hz), 8.16 (1H, s), 9.96 (1H, s), 10.3 (1H, s). |
| 129 | (CDCl$_3$) δ 2.22 (6H, s), 7.17-7.28 (3H, m), 7.33-7.39 (2H, m), 7.42-7.48 (2H, m), 7.58-7.65 (2H, m), 7.79 (1H, dd, J = 1.5, 8.3 Hz), 7.91 (1H, s), 8.27 (1H, s), 8.51 (1H, s). |
| 130 | (CDCl$_3$) δ 1.48-2.17 (6H, m), 2.34 (6H, s), 3.52-3.60 (1H, m), 3.92 (1H, dd, J = 2.5, 11.2 Hz), 4.11-4.18 (1H, m), 7.35 (2H, s), 7.47 (1H, t, J = 7.8 Hz), 7.60 (1H, broad), 7.69 (1H, d, J = 7.8 Hz), 7.77 (1H, dd, J = 1.0, 7.8 Hz), 8.26 (1H, s), 8.54 (1H, s). |
| 131 | δ 1.97-2.07 (2H, m), 2.15-2.31 (9H, m), 2.97-3.07 (2H, m), 3.99-3.98 (2H, m), 7.46 (2H, s), 7.55 (1H, t, J = 8.0 Hz), 7.65 (1H, d, J = 8.0 Hz), 7.87 (1H, d, J = 8.0 Hz), 8.20 (1H, s), 9.60 (1H, s), 9.91 (1H, s). |
| 132 | (CDCl$_3$) δ 2.35 (6H, s), 7.16 (1H, dd, J = 3.9, 4.9 Hz), 7.36 (2H, s), 7.51 (1H, t, J = 7.8 Hz), 7.59 (1H, dd, J = 1.0, 4.9 Hz), 7.67 (1H, dd, J = 1.0, 3.9 Hz), 7.70-7.74 (2H, m), 7.80-7.83 (1H, m), 7.95 (1H, s), 8.27 (1H, s). |
| 133 | δ 2.30 (6H, s), 7.45 (2H, s), 7.54 (1H, t, J = 8.0 Hz), 7.67 (2H, d, J = 2.4 Hz), 7.75 (1H, d, J = 7.8 Hz), 8.07 (1H, d, J = 7.8 Hz), 8.31 (1H, s), 8.41 (1H, t, J = 2.2 Hz), 9.99 (1H, s), 10.28 (1H, s). |
| 134 | δ 2.30 (6H, s), 2.47 (3H, s), 7.04 (1H, d, J = 4.2 Hz), 7.45 (2H, s), 7.52 (1H, t, J = 7.8 Hz), 7.69 (1H, d, J = 4.2 Hz), 7.74 (1H, d, J = 7.8 Hz), 7.93 (1H, d, J = 7.8 Hz), 8.27 (1H, s), 9.97 (1H, s), 10.17 (1H, s). |
| 135 | δ 2.30 (6H, s), 7.45 (2H, s), 7.56 (1H, t, J = 7.8 Hz), 7.79 (1H, d, J = 7.8 Hz), 8.08 (1H, d, J = 7.8 Hz), 8.30 (1H, s), 8.71 (1H, d, J = 2.0 Hz), 8.74 (1H, d, J = 2.0 Hz), 10.01 (1H, s), 10.54 (1H, s). |
| 136 | δ 2.30 (6H, s), 2.50 (3H, s), 6.94 (1H, d, J = 3.4 Hz), 7.45 (2H, s), 7.52 (1H, t, J = 7.9 Hz), 7.74 (1H, d, J = 7.9 Hz), 7.88 (1H, d, J = 3.4 Hz), 8.02 (1H, d, J = 7.9 Hz), 8.27 (1H, s), 9.97 (1H, s), 10.32 (1H, s). |
| 137 | δ 2.29 (6H, s), 7.22 (1H, d, J = 5.1 Hz), 7.43 (2H, s), 7.53 (1H, t, J = 8.0 Hz), 7.76 (1H, d, J = 8.0 Hz), 7.91-7.93 (2H, m), 8.26 (1H, s), 9.98 (1H, s), 10.42 (1H, s). |
| 138 | δ 2.30 (6H, s), 7.45 (2H, s), 7.57 (1H, t, J = 8.1 Hz), 7.79 (1H, d, J = 8.1 Hz), 8.05 (1H, d, J = 8.1 Hz), 8.52 (1H, s), 9.97 (1H, s), 11.11 (1H, s). |
| 139 | δ 2.30 (6H, s), 7.26 (1H, d, J = 5.4 Hz), 7.45 (2H, s), 7.54 (1H, t, J = 8.0 Hz), 7.77 (1H, d, J = 8.0 Hz), 7.90-7.94 (2H, m), 8.27 (1H, s), 9.99 (1H, s), 10.50 (1H, s). |
| 140 | δ 2.30 (6H, s), 7.39 (1H, d, J = 4.6 Hz), 7.45 (2H, s), 7.54 (1H, t, J = 8.1 Hz), 7.77 (1H, d, J = 8.1 Hz), 7.92 (1H, d, J = 4.6 Hz), 8.02 (1H, d, J = 8.1 Hz), 8.26 (1H, s), 9.99 (1H, s), 10.50 (1H, s). |
| 141 | δ 2.30 (6H, s), 7.29 (1H, d, J = 4.9 Hz), 7.45 (2H, s), 7.55 (1H, t, J = 7.9 Hz), 7.77 (1H, d, J = 7.9 Hz), 7.81 (1H, d, J = 4.9 Hz), 7.92 (1H, d, J = 7.9 Hz), 8.29 (1H, s), 10.00 (1H, s), 10.50 (1H, s). |
| 142 | δ 2.27 (6H, s), 7.25-7.52 (10H, m), 7.70-7.73 (1H, m), 7.81-7.20 (1H, m), 8.12 (1H, s), 9.94 (1H, s), 10.27 (1H, s). |
| 143 | δ 2.28 (6H, s), 2.40 (3H, s), 2.45 (3H, s), 6.74 (1H, s), 7.43 (2H, s), 7.49 (1H, t, J = 8.1 Hz), 7.71 (1H, d, J = 8.1 Hz), 7.90 (1H, d, J = 8.1 Hz), 8.24 (1H, s), 9.94 (1H, s), 9.98 (1H, s). |

TABLE 6-continued

| Compound No. | ¹H-NMR (DMSO-d₆, ppm) |
|---|---|
| 144 | δ 2.31 (6H, s), 7.41-7.59 (5H, m), 7.78 (1H, d, J = 7.8 Hz), 8.00-8.09 (3H, m), 8.34 (1H, d, J = 2.0 Hz), 8.43 (1H, s), 10.02 (1H, s), 10.75 (1H, s). |
| 146 | δ 0.86 (3H, 7.2), 2.30 (6H, s), 4.34 (2H, q, J = 7.2 Hz), 7.45 (2H, s), 7.77-7.79 (3H, m), 7.84 (1H, s), 8.24 (1H, s), 8.37 (1H, s), 10.05 (1H, s), 11.11 (1H, s). |
| 147 | δ 2.30 (6H, s), 3.89 (3H, s), 7.45 (2H, s), 7.52 (1H, t, J = 7.9 Hz), 7.73 (1H, d, J = 7.9 Hz), 7.97 (1H, d, J = 7.9 Hz), 8.23 (1H, s), 8.45 (1H, s), 9.98 (1H, s), 10.08 (1H, s). |
| 148 | δ 2.35 (6H, s), 3.92 (3H, s), 7.26 (1H, s), 7.36 (2H, s), 7.48-7.55 (2H, m),, 7.70 (1H, d, J = 7.7 Hz), 7.83 (1H, d, J = 7.7 Hz), 8.26 (1H, s), 8.47 (1H, s). |
| 149 | δ 2.36 (6H, s), 3.95 (3H, s), 7.26 (1H, s), 7.36 (2H, s), 7.50 (1H, t, J = 7.7 Hz), 7.70 (1H, d, J = 7.7 Hz), 7.83 (1H, d, J = 7.7 Hz), 8.00 (1H, s), 8.26 (1H, s), 8.58 (1H, s). |
| 150 | (CDCl₃) δ 2.35 (6H, s), 4.01 (3H, s), 7.36 (2H, s), 7.51 (1H, t, J = 7.8 Hz), 7.68-7.73 (3H, m), 7.92 (1H, s), 8.05 (1H, s), 8.25 (1H, s). |
| 151 | δ 2.29 (6H, s), 4.06 (3H, s), 7.44 (2H, s), 7.53 (1H, t, J = 7.9 Hz), 7.77 (1H, d, J = 7.9 Hz), 7.96 (1H, d, J = 7.9 Hz), 8.11 (1H, s), 8.26 (1H, s), 10.02 (1H, s), 10.58 (1H, s). |
| 152 | δ 2.30 (6H, s), 7.32 (1H, d, J = 2.0 Hz), 7.45 (2H, s), 7.58 (1H, t, J = 7.8 Hz), 7.81 (1H, d, J = 7.8 Hz), 8.04 (1H, d, J = 7.8 Hz), 8.35 (1H, s), 8.84 (1H, d, J = 2.0 Hz), 10.03 (1H, s), 10.97 (1H, s). |
| 153 | δ 2.29 (6H, s), 7.46 (2H, s), 7.64 (1H, t), 7.72 (1H, d, J = 1.0 Hz), 7.81 (1H, s), 7.97 (1H, d, J = 8.0 Hz), 8.17 (1H, s), 8.34 (1H, s), 10.04 (1H, s). |
| 154 | δ 2.29 (6H, s), 2.51 (3H, s), 2.56 (3H, s), 7.46 (2H, s), 7.53 (1H, t, J = 8.03 Hz), 7.75 (1H, d, J = 8.03 Hz), 7.92 (1H, d, J = 8.03 Hz), 8.24 (1H, s), 9.79 (1H, s), 10.30 (1H, s). |
| 155 | δ 1.36 (3H, t, J = 7.3 Hz), 2.30 (6H, s), 2.73 (3H, s), 3.05 (2H, q, J = 7.3 Hz), 7.45 (2H, s), 7.55 (1H, t, J = 8.3 Hz), 7.78 (1H, d, J = 8.3 Hz), 7.98 (1H, d, J = 8.3 Hz), 8.29 (1H, s), 10.01 (1H, s), 10.69 (1H, s). |
| 156 | δ 2.28 (6H, s), 2.57 (3H, s), 7.43 (2H, s), 7.53 (1H, t, J = 7.8 Hz), 7.77 (1H, d, J = 7.8 Hz), 7.91 (1H, d, J = 7.8 Hz), 8.21 (1H, s), 9.98 (1H, s), 10.47 (1H, s). |
| 157 | δ 2.31 (6H, s), 7.45 (2H, s), 7.57 (1H, t, J = 7.8 Hz), 7.79 (1H, d, J = 7.8 Hz), 8.06 (1H, d, J = 7.8 Hz), 8.53 (1H, s), 10.00 (1H, s), 11.12 (1H, s). |
| 158 | δ 2.36 (6H, s), 7.45 (2H, s), 7.57 (1H, t, J = 8.1 Hz), 7.79 (1H, d, J = 8.1 Hz), 8.06 (1H, d, J = 8.1 Hz), 8.53 (1H, s), 10.01 (1H, s), 11.11 (1H, s). |
| 159 | δ 2.30 (6H, s), 7.45 (2H, s), 7.56-7.66 (3H, m), 7.80 (1H, d, J = 8.3 Hz), 7.94-7.98 (2H, m), 8.16-8.20 (1H, m), 8.32 (1H, s), 10.04 (1H, s), 10.79 (1H, s). |
| 160 | δ 2.31 (6H, s), 7.45 (2H, s), 7.53-7.61 (2H, m), 7.78 (1H, d, J = 7.8 Hz), 7.92-7.95 (1H, m), 8.02-8.07 (2H, m), 8.34 (1H, s), 9.99 (1H, s), 10.50 (1H, s). |
| 161 | δ 2.30 (6H, s), 7.37 (1H, t, J = 7.8 Hz), 7.45 (2H, s), 7.57 (1H, t, J = 7.8 Hz), 7.62-7.65 (2H, m), 7.79 (1H, d, J = 7.8 Hz), 7.99 (1H, d, J = 7.8 Hz), 8.30 (1H, s), 10.01 (1H, s), 10.65 (1H, s). |
| 163 | δ 2.38 (3H, s), 7.53-7.63 (4H, m), 7.70 (1H, m), 7.77 (1H, d, J = 7.8 Hz), 7.81 (1H, s), 7.99-8.01 (2H, m), 8.08 (1H, d, J = 7.8 Hz), 8.37 (1H, s), 10.28 (1H, s), 10.50 (1H, s). |
| 164 | (CDCl₃) δ 1.20 (3H, t, J = 7.3 Hz), 2.32 (3H, s), 2.67 (2H, q, J = 7.3 Hz), 7.36 (2H, s), 7.46-7.51 (3H, m), 7.55-7.59 (1H, m), 7.67-7.72 (2H, m), 7.85-7.88 (3H, m), 8.15 (1H, s), 8.28 (1H, s). |
| 165 | δ 1.13 (3H, t, J = 7.3 Hz), 2.29 (3H, s), 2.67 (2H, q, J = 7.3 Hz), 7.33-7.41 (3H, m), 7.47 (1H, s), 7.52-7.63 (2H, m), 7.67-7.76 (2H, m), 7.97 (1H, d, J = 7.8 Hz), 8.32 (1H, s), 10.01 (1H, s), 10.65 (1H, s). |
| 166 | δ 2.36 (3H, s), 7.53-7.63 (4H, m), 7.68 (1H, s), 7.79 (1H, d, J = 7.8 Hz), 7.96 (1H, s), 7.99-8.01 (2H, m), 8.08 (1H, dd, J = 1.5, 7.8 Hz), 8.38 (1H, d, J = 1.5 Hz), 10.27 (1H, s), 10.50 (1H, s). |
| 167 | (CDCl₃) δ 2.48 (3H, s), 7.05 (1H, s), 7.23 (1H, s), 7.50-7.62 (4H, m), 7.69 (1H, d, J = 7.8 Hz), 7.84 (1H, dd, J = 2.0, 7.8 Hz), 7.89 (2H, d, J = 6.8 Hz), 8.13 (1H, s), 8.16 (1H, d, J = 6.8 Hz), 8.39 (1H, t, J = 1.9 Hz), 8.89 (1H, s). |
| 168 | δ 1.15 (3H, t, J = 7.3 Hz), 2.73 (2H, q, J = 7.3 Hz), 7.50-7.63 (5H, m), 7.71-7.77 (2H, m), 7.94-8.01 (2H, m), 8.08 (1H, d, J = 7.8 Hz), 8.37 (1H, s), 10.28 (1H, s), 10.50 (1H, s). |
| 169 | δ 1.14 (3H, t, J = 7.3 Hz), 2.73 (2H, q, J = 7.3 Hz), 7.52-7.64 (5H, m), 7.76 (1H, d, J = 7.8 Hz), 7.83 (1H, d, J = 2.0 Hz), 7.98-8.01 (2H, m), 8.06-8.09 (1H, m), 8.37 (1H, s), 10.29 (1H, s), 10.48 (1H, s). |
| 170 | δ 1.14 (3H, t, J = 7.3 Hz), 2.72 (2H, q, J = 7.3 Hz), 7.33-7.39 (2H, m), 7.53-7.64 (2H, m), 7.67-7.72 (1H, m), 7.76 (1H, d, J = 7.8 Hz), 7.82 (1H, s), 7.98 (1H, d, J = 8.8 Hz), 8.32 (1H, s), 10.30 (1H, s), 10.65 (1H, s). |
| 171 | δ 1.13 (3H, t, J = 7.3 Hz), 2.71 (2H, q, J = 7.3 Hz), 7.52-7.63 (5H, m), 7.78 (1H, d, J = 7.8 Hz), 7.97-8.01 (3H, m), 8.07-8.09 (1H, m), 8.37 (1H, d, J = 2.0 Hz), 10.28 (1H, s), 10.48 (1H, s). |
| 172 | δ 1.13 (3H, t, J = 7.3 Hz), 2.71 (2H, q, J = 7.3 Hz), 7.33-7.39 (2H, m), 7.54-7.63 (3H, m), 7.67-7.72 (1H, m), 7.78 (1H, d, J = 7.8 Hz), 7.97-8.00 (2H, m), 8.33 (1H, s), 10.30 (1H, s), 10.66 (1H, s). |
| 173 | δ 1.13 (3H, t, J = 7.3 Hz), 2.72 (2H, q, J = 7.3 Hz), 7.57-7.64 (2H, m), 7.83 (1H, d, J = 7.8 Hz), 7.98 (1H, s), 8.10 (1H, d, J = 7.8 Hz), 8.24 (2H, d, J = 8.8 Hz), 8.37 (1H, s), 8.40 (2H, d, J = 8.8 Hz), 10.32 (1H, s), 10.81 (1H, s). |
| 174 | δ 1.13 (3H, t, J = 7.3 Hz), 2.71 (2H, q, J = 7.3 Hz), 7.56-7.63 (2H, m), 7.82 (1H, d, J = 7.8 Hz), 7.98 (1H, s), 8.04-8.10 (3H, m), 8.15 (2H, d, J = 8.3 Hz), 8.36 (1H, s), 10.31 (1H, s), 10.72 (1H, s). |
| 175 | δ 0.85 (3H, t, J = 7.3 Hz), 1.49-1.59 (2H, m), 2.30 (3H, s), 2.65 (2H, t, J = 6.8 Hz), 7.40 (1H, s), 7.47 (1H, s), 7.58 (1H, t, J = 7.8 Hz), 7.79 (1H, d, J = 7.8 Hz), 8.08 (1H, s), 8.22-8.25 (2H, m), 8.36-8.41 (3H, m), 10.03 (1H, s), 10.79 (1H, s). |
| 176 | δ 1.18 (6H, d, J = 6.8 Hz), 2.29 (3H, s), 3.23 (1H, septet, J = 6.8 Hz), 7.41 (1H, s), 7.47 (1H, s), 7.52-7.63 (4H, m), 7.75 (1H, d, J = 7.8 Hz), 7.99-8.01 (2H, m), 8.06-8.09 (1H, m), 8.36 (1H, t, J = 2.0 Hz), 10.00 (1H, s), 10.48 (1H, s). |
| 177 | δ 1.17 (6H, d, J = 6.8 Hz), 2.30 (3H, s), 3.24 (1H, septet, J = 6.8 Hz), 7.28-7.41 (3H, m), 7.47 (1H, s), 7.55-7.63 (2H, m), 7.65-7.78 (2H, m), 7.99 (1H, d, J = 7.8 Hz), 8.33 (1H, s), 10.02 (1H, s), 10.66 (1H, s). |
| 178 | δ 0.85 (3H, t, J = 7.3 Hz), 1.47-1.60 (2H, m), 2.70 (2H, t, J = 7.3 Hz), 7.53-7.63 (5H, m), 7.75 (1H, d, J = 7.8 Hz), 7.83 (1H, d, J = 2.0 Hz), 7.98-8.01 (2H, m), 8.08 (1H, d, J = 7.8 Hz), 8.36 (1H, s), 10.29 (1H, s), 10.49 (1H, s). |
| 179 | δ 0.85 (3H, t, J = 7.3 Hz), 1.50-1.60 (2H, m), 2.69 (2H, t, J = 6.8 Hz), 7.29-7.40 (2H, m), 7.53-7.62 (3H, m), 7.67-7.76 (2H, m), 7.83 (1H, d, J = 2.0 Hz), 7.98 (1H, d, J = 7.8 Hz), 8.32 (1H, s), 10.31 (1H, s), 10.66 (1H, s). |

TABLE 6-continued

| Compound No. | $^1$H-NMR (DMSO-$d_6$, ppm) |
|---|---|
| 180 | δ 0.85 (3H, t, J = 7.3 Hz), 1.50-1.58 (2H, m), 2.70 (2H, t, J = 7.8 Hz), 7.57-7.63 (2H, m), 7.78-7.84 (2H, m), 8.09 (1H, d, J = 7.8 Hz), 8.18-8.24 (2H, m), 8.35-8.41 (3H, m), 10.32 (1H, s), 10.80 (1H, s). |
| 181 | δ 0.85 (3H, t, J = 7.3 Hz), 1.50-1.60 (2H, m), 2.69 (2H, t, J = 7.3 Hz), 7.56-7.62 (2H, m), 7.79 (1H, d, J = 7.8 Hz), 7.83 (1H, d, J = 2.0 Hz), 8.04-8.09 (3H, m), 8.15 (2H, d, J = 8.8 Hz), 8.35 (1H, s), 10.31 (1H, s), 10.72 (1H, s). |
| 182 | δ 0.84 (3H, t, J = 7.3 Hz), 1.49-1.59 (2H, m), 2.68 (2H, t, J = 7.3 Hz), 7.53-7.63 (5H, m), 7.77 (1H, d, J = 7.8 Hz), 7.97-8.01 (3H, m), 8.08 (1H, d, J = 7.8 Hz), 8.37 (1H, s), 10.29 (1H, s), 10.49 (1H, s). |
| 183 | δ 0.84 (3H, t, J = 7.3 Hz), 1.49-1.59 (2H, m), 2.67 (2H, t, J = 7.3 Hz), 7.28-7.40 (2H, m), 7.51-7.63 (3H, m), 7.68-7.72 (1H, m), 7.77 (1H, d, J = 8.3 Hz), 7.97-8.00 (2H, m), 8.33 (1H, s), 10.31 (1H, s), 10.67 (1H, s). |
| 184 | δ 0.84 (3H, t, J = 7.3 Hz), 1.49-1.59 (2H, m), 2.68 (2H, t, J = 6.8 Hz), 7.57-7.62 (2H, m), 7.82 (1H, d, J = 7.8 Hz), 7.98 (1H, d, J = 2.0 Hz), 8.08-8.10 (1H, m), 8.15-8.41 (5H, m), 10.32 (1H, s), 10.80 (1H, s). |
| 185 | δ 0.84 (3H, t, J = 7.3 Hz), 1.49-1.57 (2H, m), 2.68 (2H, broad), 7.56-7.61 (2H, m), 7.81 (1H, d, J = 7.8 Hz), 7.98 (1H, s), 8.05 (2H, d, J = 8.3 Hz), 8.09 (1H, s), 8.15 (2H, d, J = 8.3 Hz), 8.35 (1H, s), 10.31 (1H, s), 10.72 (1H, s). |
| 186 | δ 0.84 (3H, t, J = 7.3 Hz), 1.49-1.57 (2H, m), 2.68 (2H, t, J = 6.8 Hz), 7.56-7.61 (2H, m), 7.80 (1H, d, J = 7.8 Hz), 7.94 (2H, d, J = 8.3 Hz), 7.98 (1H, s), 8.09 (1H, d, J = 7.8 Hz), 8.20 (2H, d, J = 8.3 Hz), 8.36 (1H, s), 10.31 (1H, s), 10.71 (1H, s). |
| 187 | δ 0.83 (3H, t, J = 7.3 Hz), 1.21-1.31 (2H, m), 1.47-1.55 (2H, m), 2.72 (2H, t, J = 7.8 Hz), 7.53-.63 (5H, m), 7.70-7.75 (2H, m), 7.99-8.01 (2H, m), 8.06-8.09 (1H, m), 8.37 (1H, t, J = 2.0 Hz), 10.27 (1H, s), 10.49 (1H, s). |
| 188 | δ 0.83 (3H, t, J = 7.3 Hz), 1.21-1.31 (2H, m), 1.47-1.55 (2H, m), 2.72 (2H, t, J = 7.8 Hz), 7.33-7.40 (2H, m), 7.53-7.63 (3H, m), 7.67-7.75 (3H, m), 7.98 (1H, d, J = 7.8 Hz), 8.32 (1H, s), 10.29 (1H, s), 10.66 (1H, s). |
| 189 | δ 0.83 (3H, t, J = 7.3 Hz), 1.21-1.31 (2H, m), 1.47-1.55 (2H, m), 2.72 (2H, t, J = 7.3 Hz), 7.52-7.63 (5H, m), 7.75 (1H, d, J = 7.8 Hz), 7.82 (1H, d, J = 1.5 Hz), 7.99-8.01 (2H, m), 8.08 (1H, dd, J = 1.5, 7.8 Hz), 8.37 (1H, t, J = 1.5 Hz), 10.29 (1H, s), 10.49 (1H, s). |
| 190 | δ 0.83 (3H, t, J = 7.3 Hz), 1.21-1.31 (2H, m), 1.47-1.55 (2H, m), 2.71 (2H, t, J = 7.3 Hz), 7.28-7.37 (2H, m), 7.53-7.62 (3H, m), 7.72 (1H, t, J = 7.3 Hz), 7.75 (1H, d, J = 7.8 Hz), 7.82 (1H, s), 7.98 (1H, d, J = 7.8 Hz), 8.62 (1H, s), 10.31 (1H, s), 10.66 (1H, s). |
| 191 | δ 0.82 (3H, t, J = 7.3 Hz), 1.22-1.30 (2H, m), 1.46-1.54 (2H, m), 2.70 (2H, t, J = 7.8 Hz), 7.53-7.63 (5H, m), 7.78 (1H, d, J = 7.8 Hz), 7.93-8.02 (3H, m), 8.07-8.09 (1H, m), 8.37 (1H, s), 10.29 (1H, s), 10.49 (1H, s). |
| 192 | δ 0.83 (3H, t, J = 7.3 Hz), 1.21-1.31 (2H, m), 1.47-1.55 (2H, m), 2.71 (2H, t, J = 7.8 Hz), 7.28-7.40 (2H, m), 7.55-7.65 (3H, m), 7.69-7.73 (1H, m), 7.79 (1H, d, J = 7.8 Hz), 7.98-8.02 (2H, m), 8.35 (1H, s), 10.33 (1H, s), 10.68 (1H, s). |
| 193 | δ 0.75 (3H, t, J = 7.3 Hz), 1.18 (3H, d, J = 6.8 Hz), 1.55-1.60 (2H, m), 3.00-3.05 (1H, m), 7.49-7.67 (5H, m), 7.72-7.77 (2H, m), 7.99-8.02 (2H, m), 8.09 (1H, d, J = 7.8 Hz), 8.36 (1H, s), 10.29 (1H, s), 10.49 (1H, s). |
| 194 | δ 0.75 (3H, t, J = 7.3 Hz), 1.17 (3H, d, J = 6.8 Hz), 1.55-1.60 (2H, m), 2.98-3.04 (1H, m), 7.52-7.63 (5H, m), 7.77 (1H, d, J = 8.3 Hz), 7.84 (1H, s), 7.99-8.10 (3H, m), 8.36 (1H, s), 10.30 (1H, s), 10.49 (1H, s). |
| 195 | δ 0.74 (3H, t, J = 7.3 Hz), 1.17 (3H, d, J = 6.8 Hz), 1.55-1.63 (2H, m), 2.98-3.04 (1H, m), 7.33-7.40 (2H, m), 7.52-7.63 (3H, m), 7.67-7.77 (2H, m), 7.83 (1H, d, J = 1.5 Hz), 7.99 (1H, d, J = 8.3 Hz), 8.32 (1H, s), 10.32 (1H, s), 10.66 (1H, s). |
| 196 | δ 0.74 (3H, t, J = 6.8 Hz), 1.15 (3H, d, J = 6.8 Hz), 1.53-1.64 (2H, m), 2.94-3.04 (1H, m), 7.51-7.63 (5H, m), 7.79 (1H, d, J = 7.3 Hz), 7.98-8.02 (3H, m), 8.09 (1H, dd, J = 1.5, 7.8 Hz), 8.37 (1H, s), 10.30 (1H, s), 10.50 (1H, s). |
| 197 | δ 7.33-7.41 (2H, m), 7.56-7.64 (2H, m), 7.68-7.73 (2H, m), 7.93-8.03 (2H, m), 8.38-8.40 (1H, m), 8.45 (1H, d, J = 2.0 Hz), 10.72 (1H, s), 10.98 (1H, s). |
| 198 | δ 2.50 (3H, s), 7.39 (1H, s), 7.48-7.63 (4H, m), 7.73 (1H, d, J = 7.8 Hz), 7.99-8.01 (2H, m), 8.08 (1H, d, J = 7.8 Hz), 8.35 (1H, s), 10.36 (1H, s), 10.50 (1H, s). |
| 199 | δ 2.50 (3H, s), 7.33-7.39 (3H, m), 7.53-7.63 (2H, m), 7.67-7.77 (3H, m), 7.98 (1H, d, J = 7.8 Hz), 8.30 (1H, s), 10.38 (1H, s), 10.67 (1H, s). |
| 200 | δ 2.81 (3H, s), 7.53-7.64 (4H, m), 7.75 (1H, d, J = 8.3 Hz), 7.99-8.01 (2H, m), 8.08-8.11 (2H, m), 8.25 (1H, d, J = 2.0 Hz), 8.40 (1H, t, J = 2.0 Hz), 10.52 (1H, s), 10.61 (1H, s). |
| 201 | δ 3.40 (3H, s), 7.33-7.40 (2H, m), 7.56-7.63 (2H, m), 7.67-7.78 (2H, m), 7.99 (1H, d, J = 8.3 Hz), 8.17 (1H, d, J = 1.5 Hz), 8.35 (1H, s), 8.39 (1H, d, J = 1.5 Hz), 10.63 (1H, s), 10.69 (1H, s). |
| 202 | δ 3.40 (3H, s), 7.57-7.62 (2H, m), 7.79 (1H, d, J = 7.8 Hz), 7.96 (1H, dd, J = 1.5, 8.3 Hz), 8.12 (1H, dd, J = 1.5, 8.3 Hz), 8.17 (1H, d, J = 2.0 Hz), 8.32 (1H, d, J = 2.0 Hz), 8.40 (1H, d, J = 2.0 Hz), 8.54-8.56 (1H, m), 10.65 (1H, s), 10.92 (1H, s). |
| 203 | δ 3.40 (3H, s), 7.53-7.63 (4H, m), 7.78 (1H, d, J = 7.8 Hz), 7.98-8.01 (2H, m), 8.07-8.10 (1H, m), 8.21 (1H, s), 8.39 (1H, s), 8.48 (1H, d, J = 1.5 Hz), 10.51 (1H, s), 10.63 (1H, s). |
| 204 | δ 3.39 (3H, s), 7.33-7.40 (2H, m), 7.56-7.63 (2H, m), 7.68-7.72 (2H, m), 7.78 (1H, d, J = 7.8 Hz), 8.00 (1H, d, J = 7.8 Hz), 8.21 (1H, d, J = 1.5 Hz), 8.35 (1H, s), 8.48 (1H, d, J = 1.5 Hz), 10.66 (1H, s), 10.69 (1H, s). |
| 205 | δ 3.39 (3H, s), 7.36-7.42 (2H, m), 7.58 (1H, t, J = 7.8 Hz), 7.78 (1H, d, J = 7.8 Hz), 8.06-8.10 (3H, m), 8.21 (1H, s), 8.36 (1H, s), 8.48 (1H, s), 10.52 (1H, s), 10.63 (1H, s). |
| 206 | δ 3.39 (3H, s), 7.61 (1H, t, J = 7.8 Hz), 7.82 (1H, d, J = 7.8 Hz), 8.09 (1H, d, J = 7.8 Hz), 8.20-8.24 (3H, m), 8.37-8.41 (3H, m), 8.48 (1H, s), 10.67 (1H, s), 10.83 (1H, s). |
| 207 | δ 3.39 (3H, s), 7.60 (1H, t, J = 7.8 Hz), 7.81 (1H, d, J = 7.8 Hz), 7.97-8.10 (3H, m), 8.14-8.21 (3H, m), 8.37 (1H, t, J = 2.0 Hz), 8.48 (1H, d, J = 2.0 Hz), 10.65 (1H, s), 10.74 (1H, s). |
| 208 | δ 3.39 (3H, s), 7.57-7.62 (2H, m), 7.80 (1H, d, J = 7.8 Hz), 7.96 (1H, dd, J = 1.5, 7.8 Hz), 8.11 (1H, dd, J = 1.5, 7.8 Hz), 8.20 (1H, s), 8.31 (1H, s), 8.51 (1H, s), 8.55 (1H, dd, J = 1.5, 4.9 Hz), 10.68 (1H, s), 10.92 (1H, s). |
| 209 | δ 1.96 (3H, s), 3.84 (2H, broad), 7.53-7.63 (4H, m), 7.73 (1H, d, J = 7.8 Hz), 7.89 (1H, s), 7.99-8.01 (2H, m), 8.07 (1H, dd, J = 1.5, 7.8 Hz), 8.19 (1H, s), 8.33 (1H, t, J = 2.0 Hz), 10.43 (1H, s), 10.49 (1H, s). |

TABLE 6-continued

| Compound No. | ¹H-NMR (DMSO-d$_6$, ppm) |
|---|---|
| 210 | δ 7.53-7.64 (4H, m), 7.81 (1H, d, J = 7.8 Hz), 8.00-8.05 (3H, m), 8.11 (1H, d, J = 7.8 Hz), 8.31 (1H, d, J = 1.5 Hz), 8.41 (1H, s), 10.52 (1H, s), 10.93 (1H, s). |
| 211 | δ 2.29 (6H, s), 7.47 (2H, s), 7.50-7.62 (4H, m), 7.75 (1H, d, J = 7.8 Hz), 7.97-8.00 (2H, m), 8.05 (1H, dd, J = 1.5, 7.8 Hz), 8.36 (1H, s), 10.01 (1H, s), 10.46 (1H, s). |
| 212 | δ 2.30 (6H, s), 7.45 (2H, s), 7.51-7.63 (4H, m), 7.76 (1H, d, J = 7.8 Hz), 7.98-8.07 (3H, m), 8.37 (1H, d, J = 2.0 Hz), 9.99 (1H, s), 10.48 (1H, s). |
| 255 | δ 7.25-7.29 (2H, m), 7.54-7.65 (2H, m), 7.78 (1H, d, J = 7.8 Hz), 7.92-7.95 (1H, m), 8.03 (2H, s), 8.30 (1H, s), 10.58 (1H, s), 11.05 (1H, s). |
| 256 | δ 7.53-7.63 (4H, m), 7.78 (1H, d, J = 7.3 Hz), 7.99-8.01 (2H, m), 8.06-8.09 (1H, m), 8.17 (2H, s), 8.38 (1H, s), 10.50 (1H, s), 10.55 (1H, s). |
| 257 | δ 7.25-7.29 (2H, m), 7.55-7.63 (2H, m), 7.79 (1H, d, J = 7.3 Hz), 7.94 (1H, d, J = 8.3 Hz), 8.17 (2H, s), 8.30 (1H, s), 10.60 (1H, s), 11.05 (1H, s). |
| 258 | (CDCl$_3$) δ 7.45-7.61 (4H, m), 7.76 (1H, d, J = 7.8 Hz), 7.84-7.91 (3H, m), 7.93 (2H, s), 8.02 (1H, s), 8.08 (1H, d, J = 6.8 Hz), 8.31 (1H, s). |
| 259 | (CDCl$_3$) δ 7.22 (1H, dd, J = 7.8, 12.2 Hz), 7.35 (1H, t, J = 7.8 Hz), 7.52-7.60 (2H, m), 7.77 (1H, d, J = 7.8 Hz), 7.88 (1H, s), 7.92 (1H, s), 7.93 (2H, d), 8.19 (1H, dt, J = 1.9, 7.8 Hz), 8.33 (1H, s), 8.64 (1H, d, J = 15.6 Hz). |
| 260 | (CDCl$_3$) δ 2.31 (6H, s), 7.41 (2H, s), 7.50-7.67 (5H, m), 7.71 (1H, d, J = 7.8 Hz), 7.87-7.90 (3H, m), 8.07 (1H, s), 8.31 (1H, s). |
| 261 | (CDCl$_3$) δ 2.33 (6H, s), 7.20-7.25 (1H, m), 7.35 (1H, t, J = 7.3 Hz), 7.44 (2H, s), 7.52-7.60 (3H, m), 7.73 (1H, d, J = 7.8 Hz), 7.88 (1H, dd, J = 1.0, 7.8 Hz), 8.18 (1H, dt, J = 2.0, 7.8 Hz), 8.33 (1H, s), 8.63 (1H, d, J = 7.3 Hz). |
| 262 | (CDCl$_3$) δ 7.44-7.57 (5H, m), 7.72 (2H, s), 7.78 (1H, d, J = 7.8 Hz), 8.00 (1H, d, J = 6.8 Hz), 8.18 (1H, d, J = 8.3 Hz), 8.34 (1H, t, J = 2.0 Hz), 9.46 (1H, s), 9.83 (1H, s). |
| 263 | (CDCl$_3$) δ 7.47-7.57 (4H, m), 7.78 (1H, d, J = 7.8 Hz), 7.93 (2H, s), 7.99-8.01 (2H, m), 8.18 (1H, d, J = 7.8 Hz), 8.33 (1H, t, J = 2.0 Hz), 9.27 (1H, s), 9.65 (1H, s). |
| 266 | δ 7.20-7.25 (1H, m), 7.35 (1H, t, J = 7.8 Hz), 7.53-7.60 (2H, m), 7.76-7.79 (2H, m), 7.95 (2H, s), 7.96 (1H, s), 8.19 (1H, dt, J = 2.0, 7.8 Hz), 8.32 (1H, s), 8.63 (1H, d, J = 15.7 Hz). |
| 276 | (CDCl$_3$) δ 7.56 (1H, t, J = 7.8 Hz), 7.71 (1H, d, J = 7.8 Hz), 7.75 (1H, d, J = 7.8 Hz), 7.87-7.90 (3H, m), 8.04 (1H, d, J = 7.8 Hz), 8.28 (2H, s), 8.42 (1H, dd, J = 1.0, 7.3 Hz), 8.46 (1H, s), 8.76 (1H, t, J = 2.0 Hz). |
| 284 | (CDCl$_3$) δ 7.03 (2H, t, J = 7.8 Hz), 7.42-7.49 (1H, m), 7.54 (1H, t, J = 7.8 Hz), 7.78 (1H, d, J = 7.8 Hz), 7.81 (1H, s), 7.87-7.92 (2H, m), 7.93 (2H, s), 8.28 (1H, t, J = 2.0 Hz). |
| 285 | δ 6.86 (1H, d, J = 8.8 Hz), 7.24 (1H, t, J = 7.8 Hz), 7.30-7.32 (2H, m), 7.47 (1H, t, J = 7.8 Hz), 7.77 (1H, d, J = 7.8 Hz), 7.93 (2H, s), 8.14 (1H, d, J = 7.3 Hz), 8.31 (1H, s), 9.32 (1H, s), 9.46 (1H, s). |
| 286 | δ 2.17 (3H, s), 7.40 (1H, t, J = 7.8 Hz), 7.49 (1H, t, J = 7.8 Hz), 7.80 (1H, d, J = 7.8 Hz), 7.78 (1H, d, J = 7.8 Hz), 7.94-7.95 (3H, m), 8.06 (1H, s), 8.16 (1H, d, J = 7.8 Hz), 8.31 (1H, s), 9.50 (1H, s), 9.58 (1H, s), 9.79 (1H, s). |
| 287 | δ 3.00 (3H, s), 7.42 (1H, t, J = 7.8 Hz), 7.50 (1H, t, J = 7.8 Hz), 7.48 (1H, s), 7.74 (1H, d, J = 7.8 Hz), 7.79 (1H, d, J = 7.8 Hz), 7.88 (1H, t, J = 2.0 Hz), 7.93 (2H, s), 8.17 (1H, d, J = 7.8 Hz), 8.29 (1H, t, J = 2.0 Hz), 9.37 (1H, s), 9.49 (1H, s), 9.72 (1H, s). |
| 288 | (CDCl$_3$) δ 7.51 (1H, t, J = 7.8 Hz), 7.69 (1H, d, J = 7.8 Hz), 7.86-7.91 (3H, m), 7.95 (2H, s), 8.07 (1H, s), 8.39 (1H, s), 8.53-8.55 (1H, m), 8.90 (1H, s). |
| 289 | (CDCl$_3$) δ 7.54 (1H, t, J = 8.3 Hz), 7.80 (1H, d, J = 7.8 Hz), 7.94 (2H, s), 8.02 (1H, d, J = 8.3 Hz), 8.26-8.27 (2H, m), 8.52 (1H, d, J = 8.3 Hz), 8.74 (1H, s), 8.87 (1H, s), 10.56 (1H, s). |
| 290 | δ 2.68 (3H, s), 7.52 (1H, t, J = 7.8 Hz), 7.81 (1H, d, J = 7.8 Hz), 7.93 (2H, s), 8.03 (2H, s), 8.07 (1H, s), 8.24 (1H, d, J = 7.8 Hz), 8.29 (1H, s), 9.34 (1H, s), 10.13 (1H, s). |
| 291 | (CDCl$_3$) δ 4.17 (2H, s), 6.80-6.84 (1H, m), 6.98 (1H, dd, J = 7.8, 11.2 Hz), 7.33 (1H, dd, J = 2.9, 6.4 Hz), 7.51 (1H, t, J = 7.8 Hz), 7.82 (1H, d, J = 7.8 Hz), 7.94 (2H, s), 8.10 (1H, d, J = 8.2 Hz), 8.22 (1H, s), 9.06 (1H, d, J = 13.2 Hz), 9.48 (1H, s). |
| 292 | (CDCl$_3$) δ 7.44 (1H, dd, J = 8.8, 10.7 Hz), 7.58 (1H, t, J = 7.8 Hz), 7.80 (1H, d, J = 7.8 Hz), 7.85 (1H, s), 7.95 (2H, s), 7.98 (1H, d, J = 7.8 Hz), 8.27 (1H, s), 8.43-8.47 (1H, m), 8.55 (1H, d, J = 14.2 Hz), 9.09 (1H, dd, J = 3.0, 6.4 Hz). |
| 293 | δ 2.97 (3H, s), 7.16 (1H, dd, J = 8.8, 10.8 Hz), 7.49 (1H, t, J = 7.8 Hz), 7.51 (1H, s), 7.83 (1H, d, J = 7.8 Hz), 7.90-7.93 (1H, m), 7.94 (2H, s), 8.10 (1H, d, J = 7.8 Hz), 8.24 (1H, s), 9.15 (1H, d, J = 11.2 Hz), 9.38 (1H, s), 9.58 (1H, s). |
| 294 | (CDCl$_3$) δ 4.22 (3H, s), 7.56 (1H, t, J = 7.8 Hz), 7.75 (1H, t, J = 7.8 Hz), 7.83 (1H, s), 7.94 (1H, s), 7.95 (2H, s), 7.99-8.05 (2H, m), 8.25 (1H, s), 8.47 (1H, d, J = 7.8 Hz), 9.83 (1H, s). |
| 295 | δ 4.06 (3H, s), 7.52 (1H, t, J = 7.3 Hz), 7.73 (1H, d, J = 8.3 Hz), 7.82-7.88 (2H, m), 7.89 (1H, d, J = 8.3 Hz), 7.93 (2H, s), 8.25-8.29 (2H, m), 9.48 (1H, s), 10.23 (1H, s). |
| 296 | (CDCl$_3$) δ 2.16 (3H, s), 7.14 (1H, dd, J = 9.3, 11.2 Hz), 7.52 (1H, t, J = 7.8 Hz), 7.80 (1H, d, J = 7.8 Hz), 7.94 (2H, s), 7.96 (1H, d, J = 2.9 Hz), 8.01 (1H, s), 8.13-8.16 (1H, m), 8.27 (1H, s), 8.86 (1H, s), 8.90 (1H, d, J = 14.2 Hz), 9.00 (1H, s). |
| 306 | (CDCl$_3$) δ 7.52-7.58 (2H, m), 7.77 (1H, d, J = 7.8 Hz), 7.90 (1H, s), 7.94 (2H, s), 7.95 (1H, d, J = 7.8 Hz), 8.01-8.03 (1H, m), 8.31 (1H, d, J = 7.8 Hz), 8.47 (1H, s), 8.65 (1H, dd, J = 1.0, 4.9 Hz), 10.25 (1H, s). |
| 307 | (CDCl$_3$) δ 7.57 (1H, t, J = 7.8 Hz), 7.73-7.77 (3H, m), 7.84 (1H, s), 7.89 (2H, s), 8.05 (1H, d, J = 7.8 Hz), 8.26 (1H, s), 8.32 (1H, s), 8.81 (1H, s), 8.83 (1H, s). |
| 309 | (CDCl$_3$) δ 7.44 (1H, dd, J = 4.8, 7.8 Hz), 7.56 (1H, t, J = 7.8 Hz), 7.80 (1H, d, J = 7.8 Hz), 7.86 (1H, s), 7.92 (1H, d, J = 7.3 Hz), 7.95 (2H, s), 8.23 (1H, dd, J = 20., 7.9 Hz), 8.30 (1H, s), 8.41 (1H, s), 8.55 (1H, dd, J = 2.0, 4.5 Hz). |
| 310 | (CDCl$_3$) δ 7.46 (1H, d, J = 8.3 Hz), 7.55 (1H, t, J = 8.3 Hz), 7.74 (1H, d, J = 8.3 Hz), 7.88 (3H, s), 8.03 (1H, d, J = 7.8 Hz), 8.18 (1H, dd, J = 3.0, 8.2 Hz), 8.24 (1H, s), 8.41 (1H, s), 8.90 (1H, d, J = 2.4 Hz). |
| 312 | (CDCl$_3$) δ 7.57 (1H, t, J = 7.8 Hz), 7.70 (2H, s), 7.75 (1H, d, J = 7.8 Hz), 7.83 (1H, s), 7.88 (2H, s), 8.04 (1H, d, J = 7.8 Hz), 8.21 (1H, s), 8.47 (1H, s). |
| 313 | (CDCl$_3$) δ 7.33 (1H, t, J = 7.8 Hz), 7.46 (1H, d, J = 8.3 Hz), 7.60 (1H, s), 7.76 (1H, s), 7.80 (1H, d, J = 7.8 Hz), 7.95 (2H, s), 8.18-8.23 (2H, m), 8.40 (1H, s). |
| 314 | (CDCl$_3$) δ 2.62 (3H, s), 7.29 (1H, s), 7.56 (1H, t, J = 7.8 Hz), 7.77-7.79 (2H, m), 7.91 (1H, s), 7.94 (2H, s), 8.16 (1H, d, J = 7.8 Hz), 8.29 (1H, s), 8.48 (1H, s). |

TABLE 6-continued

| Compound No. | ¹H-NMR (DMSO-d₆, ppm) |
|---|---|
| 315 | (CDCl₃) δ 7.47-7.59 (3H, m), 7.80 (1H, d, J = 7.8 Hz), 7.93 (1H, s), 7.94 (2H, s), 8.26 (1H, s), 8.34 (1H, d, J = 6.5 Hz), 8.47 (1H, t, J = 2.0 Hz), 8.52-8.55 (1H, m), 13.91 (1H, s). |
| 316 | (CDCl₃) δ 7.59 (1H, t, J = 7.8 Hz), 7.79 (1H, d, J = 7.8 Hz), 7.84 (1H, s), 7.95 (2H, s), 8.04 (1H, d, J = 7.8 Hz), 8.41 (1H, t, J = 2.0 Hz), 8.63 (1H, t, J = 2.5 Hz), 8.86 (1H, d, J = 2.4 Hz), 9.54 (1H, d, J = 1.5 Hz), 9.87 (1H, s). |
| 317 | (CDCl₃) δ 3.93 (3H, s), 7.53 (1H, t, J = 7.8 Hz), 7.74 (1H, d, J = 7.8 Hz), 7.84 (1H, s), 7.87 (1H, d, J = 7.8 Hz), 7.94 (2H, s), 8.03 (1H, s), 8.26 (1H, t, J = 2.0 Hz), 8.48 (1H, s). |
| 318 | (CDCl₃) δ 4.02 (3H, s), 7.53 (1H, t, J = 7.8 Hz), 7.45 (1H, d, J = 7.8 Hz), 7.80 (1H, d, J = 7.8 Hz), 7.85 (1H, s), 7.89 (1H, s), 7.94 (2H, s), 8.05 (1H, s), 8.24 (1H, s). |
| 319 | (CDCl₃) δ 4.10 (3H, s), 7.53 (1H, t, J = 7.8 Hz), 7.67 (1H, s), 7.76 (1H, d, J = 7.8 Hz), 7.70-7.86 (3H, m), 7.94 (2H, s), 8.21 (1H, s). |
| 320 | (CDCl₃) δ 1.94-2.04 (2H, m), 2.17-2.22 (1H, m), 2.37-2.42 (1H, m), 3.95-4.00 (1H, m), 4.05-4.09 (1H, m), 4.49 (1H, dd, J = 5.9, 8.3 Hz), 7.50 (1H, t, J = 7.8 Hz), 7.72 (1H, d, J = 7.8 Hz), 7.83 (1H, dd, J = 2.0, 7.8 Hz), 7.87 (1H, s), 7.94 (2H, s), 8.23 (1H, t, J = 2.0 Hz), 8.67 (1H, s). |
| 321 | (CDCl₃) δ 7.51-7.53 (3H, m), 7.57 (1H, t, J = 8.3 Hz), 7.76 (1H, d, J = 7.3 Hz), 7.83 (1H, s), 7.95 (2H, s), 8.01-8.07 (3H, m), 8.23 (1H, s), 8.38 (1H, s), 9.51 (1H, s). |
| 327 | (CDCl₃) δ 7.45-7.61 (4H, m), 7.77 (1H, d, J = 7.8 Hz), 7.84-7.91 (3H, m), 7.97-8.18 (4H, m), 8.31 (1H, s). |
| 328 | (CDCl₃) δ 7.24 (1H, d, J = 7.8 Hz), 7.35 (1H, t, J = 7.8 Hz), 7.54-7.60 (2H, m), 7.78 (1H, d, J = 7.8 Hz), 7.89 (1H, s), 7.96 (1H, d, J = 7.8 Hz), 8.15-8.19 (3H, m), 8.33 (1H, s), 8.64 (1H, d, J = 15.6 Hz). |
| 329 | (CDCl₃) δ 7.44-7.57 (4H, m), 7.70 (2H, s), 7.78 (1H, d, J = 7.8 Hz), 8.01 (2H, d, J = 6.8 Hz), 8.17 (1H, dd, J = 1.0, 7.8 Hz), 8.34 (1H, t, J = 2.0 Hz), 9.45 (1H, s), 9.81 (1H, s). |
| 330 | (CDCl₃) δ 7.22 (1H, dd, J = 8.3, 12.2 Hz), 7.34 (1H, t, J = 7.3 Hz), 7.52-7.67 (2H, m), 7.72 (2H, s), 7.76 (1H, d, J = 7.9 Hz), 7.90 (1H, s), 7.92 (1H, s), 8.18 (1H, dt, J = 1.4, 7.8 Hz), 8.33 (1H, t, J = 2.0 Hz), 8.64 (1H, d, J = 16.6 Hz). |
| 331 | (CDCl₃) δ 7.44 (1H, dd, J = 4.4, 7.8 Hz), 7.57 (1H, t, J = 7.8 Hz), 7.73 (2H, s), 7.78 (1H, d, J = 7.8 Hz), 7.84 (1H, s), 7.90 (1H, d, J = 7.8 Hz), 8.23 (1H, dd, J = 2.0, 7.8 Hz), 8.29 (1H, s), 8.41 (1H, s), 8.55 (1H, dd, J = 2.0, 4.9 Hz). |
| 332 | δ 7.43-7.57 (4H, m), 7.79 (1H, d, J = 7.8 Hz), 7.92 (2H, s), 8.00 (2H, d, J = 6.9 Hz), 8.18 (1H, d, J = 8.3 Hz), 8.35 (1H, t, J = 2.0 Hz), 8.59 (1H, s), 9.86 (1H, s). |
| 333 | (CDCl₃) δ 7.30-7.62 (4H, m), 7.75 (1H, d, J = 7.8 Hz), 7.84 (1H, d, J = 7.8 Hz), 7.89-7.92 (3H, m), 7.93 (2H, s), 8.03 (1H, s), 8.31 (1H, s). |
| 334 | (CDCl₃) δ 7.20-7.25 (1H, m), 7.35 (1H, t, J = 6.3 Hz), 7.54-7.58 (2H, m), 7.79 (1H, d, J = 6.3 Hz), 7.90-7.94 (2H, m), 7.95 (2H, s), 8.19 (1H, d, J = 8.3 Hz), 8.33 (1H, t, J = 2.0 Hz), 8.64 (1H, d, J = 16.1 Hz). |
| 335 | (CDCl₃) δ 7.51-7.62 (4H, m), 7.77 (1H, d, J = 7.3 Hz), 7.89-7.93 (3H, m), 8.02 (2H, s), 8.08 (1H, s), 8.26 (1H, s), 8.37 (1H, d, J = 14.6 Hz). |
| 338 | (CDCl₃) δ 7.22 (1H, t, J = 7.8 Hz), 7.36 (1H, t, J = 7.8 Hz), 7.54-7.60 (2H, m), 7.78 (1H, d, J = 7.8 Hz), 7.90 (1H, d, J = 7.8 Hz), 8.03-8.04 (2H, m), 8.19 (1H, t, J = 7.8 Hz), 8.26 (1H, s), 8.41 (1H, s), 8.65 (1H, d, J = 16.6 Hz). |
| 369 | (CDCl₃) δ 7.46 (1H, dd, J = 4.4, 7.8 Hz), 7.59 (1H, t, J = 8.3 Hz), 7.81 (1H, d, J = 8.3 Hz), 7.89-7.92 (1H, m), 8.04 (2H, s), 8.24 (1H, dd, J = 2.0, 7.8 Hz), 8.27 (1H, s), 8.35 (1H, d, J = 13.7 Hz), 8.42 (1H, s), 8.56 (1H, dd, J = 1.4, 4.4 Hz). |
| 375 | δ 7.25 (1H, d, J = 8.3 Hz), 7.27 (1H, d, J = 7.8 Hz), 7.56-7.64 (2H, m), 7.79 (1H, d, J = 7.8 Hz), 7.94 (1H, d, J = 8.3 Hz), 8.32 (1H, s), 8.42 (2H, s), 10.87 (1H, s), 11.05 (1H, s). |
| 376 | δ 7.53-7.64 (4H, m), 7.80 (1H, d, J = 7.8 Hz), 7.99-8.01 (2H, m), 8.09 (1H, dd, J = 1.5, 7.8 Hz), 8.41 (1H, d, J = 1.5 Hz), 8.54 (2H, s), 10.52 (1H, s), 10.83 (1H, s). |
| 377 | δ 7.19-7.30 (2H, m), 7.57-7.66 (2H, m), 7.81 (1H, d, J = 7.8 Hz), 7.95 (1H, dd, J = 1.5, 7.8 Hz), 8.33 (1H, t, J = 1.5 Hz), 8.53 (2H, s), 10.89 (1H, s), 11.08 (1H, s). |
| 378 | (CDCl₃) δ 7.21-7.23 (1H, m), 7.36 (1H, t, J = 6.9 Hz), 7.55-7.59 (2H, m), 7.79 (1H, d, J = 8.3 Hz), 7.84 (1H, d, J = 8.0 Hz), 8.05 (2H, s), 8.17-8.21 (2H, m), 8.43 (1H, t, J = 2.0 Hz), 8.65 (1H, d, J = 6.9 Hz). |
| 379 | (CDCl₃) δ 7.46-7.63 (4H, m), 7.77 (1H, d, J = 7.8 Hz), 7.84-7.91 (3H, m), 8.00 (1H, s), 8.07 (2H, s), 8.14 (1H, s), 8.40 (1H, t, J = 2.0 Hz). |
| 380 | (CDCl₃) δ 7.52-7.63 (4H, m), 7.77 (1H, d, J = 7.8 Hz), 7.89 (1H, s), 7.90 (2H, d, J = 7.8 Hz), 7.99 (1H, s), 8.03 (1H, s), 8.26 (2H, s), 8.39 (1H, t, J = 2.0 Hz). |
| 383 | (CDCl₃) δ 7.21 (1H, d, J = 8.3 Hz), 7.36 (1H, t, J = 7.8 Hz), 7.55-7.61 (2H, m), 7.78 (1H, d, J = 7.8 Hz), 7.90 (1H, d, J = 8.3 Hz), 8.02 (1H, s), 8.19 (1H, dt, J = 1.9, 8.3 Hz), 8.27 (2H, s), 8.41 (1H, s), 8.65 (1H, d, J = 16.6 Hz). |
| 414 | (CDCl₃) δ 7.44 (1H, dd, J = 4.9, 7.8 Hz), 7.59 (1H, t, J = 8.3 Hz), 7.81 (1H, d, J = 7.8 Hz), 7.89 (1H, d, J = 8.3 Hz), 8.04 (1H, s), 8.23 (1H, dd, J = 1.9, 7.8 Hz), 8.27 (2H, s), 8.37 (1H, s), 8.43 (1H, s), 8.55 (1H, dd, J = 1.9, 4.3 Hz). |
| 460 | δ 7.25 (1H, d, J = 8.3 Hz), 7.27 (1H, d, J = 7.8 Hz), 7.56-7.64 (2H, m), 7.79 (1H, d, J = 7.8 Hz), 7.94 (1H, d, J = 8.3 Hz), 8.32 (1H, s), 8.42 (2H, s), 10.87 (1H, s), 11.05 (1H, s). |
| 461 | (CDCl₃) δ 2.47 (3H, s), 7.51-7.62 (5H, m), 7.75 (1H, d, J = 7.8 Hz), 7.89-7.93 (4H, m), 8.00 (1H, broad-s), 8.35 (1H, t, J = 2.0 Hz). |
| 462 | (CDCl₃) δ 2.47 (3H, s), 7.20-7.23 (1H, m), 7.36 (1H, t, J = 7.8 Hz), 7.55-7.60 (3H, m), 7.76 (1H, d, J = 7.8 Hz), 7.89 (1H, s), 7.92 (1H, s), 8.18-8.22 (1H, m), 8.39 (1H, s), 8.62 (1H, broad-s). |
| 463 | (CDCl₃) δ 2.27 (3H, s), 2.41 (3H, s), 6.59 (1H, septet, J = 6.4 Hz), 6.72 (1H, s), 7.49-7.61 (5H, m), 7.70 (1H, d, J = 7.8 Hz), 7.83-7.89 (3H, m), 8.05 (1H, broad-s), 8.33 (1H, t, J = 1.5 Hz). |
| 464 | (CDCl₃) δ 2.38 (3H, s), 6.34 (1H, septet, J = 6.4 Hz), 6.87 (1H, s), 7.50-7.63 (5H, m), 7.72 (1H, d, J = 7.8 Hz), 7.88-7.90 (3H, m), 7.99 (1H, brs), 8.31 (1H, broad-s). |
| 465 | (CDCl₃) δ 2.37 (3H, s), 6.36 (1H, septet, J = 5.9 Hz), 6.87 (1H, s), 7.50-7.61 (4H, m), 7.72-7.73 (2H, m), 7.88-7.90 (3H, m), 8.06 (1H, s), 8.32 (1H, s). |
| 466 | (CDCl₃) δ 2.39 (3H, s), 6.36 (1H, septet, J = 5.9 Hz), 6.89 (1H, s), 7.20-7.25 (1H, m), 7.35 (1H, t, J = 6.8 Hz), 7.52-7.60 (2H, m), 7.70 (1H, broad-s), 7.75 (1H, d, J = 7.8 Hz), 7.89 (1H, d, J = 7.8 Hz), 8.17-8.21 (1H, m), 8.36 (1H, s), 8.64 (1H, broad-d, J = 16.1 Hz). |
| 467 | (CDCl₃) δ 2.53 (3H, s), 6.35 (1H, septet, J = 5.9 Hz), 6.83 (1H, s), 7.49-7.61 (4H, m), 7.66 (1H, s), 7.74 (1H, d, J = 8.3 Hz), 7.88-7.92 (3H, m), 8.32 (1H, broad-s), 8.33 (1H, t, J = 1.9 Hz). |

TABLE 6-continued

| Compound No. | ¹H-NMR (DMSO-$d_6$, ppm) |
|---|---|
| 601 | δ 2.34 (6H, s), 7.37 (1H, t, J = 7.8 Hz), 7.45 (2H, s), 7.53-7.65 (4H, m), 7.77-7.82 (1H, m), 8.00-8.02 (2H, m), 10.10 (1H, s), 10.29 (1H, s). |
| 602 | δ 2.36 (6H, s), 2.56 (3H, s), 7.29-7.43 (7H, m), 7.55-7.57 (1H, m), 7.75-7.78 (1H, m), 7.84-7.88 (1H, m), 8.64-8.66 (1H, m). |
| 603 | δ 2.37 (6H, s), 2.46 (3H, s), 7.34-7.42 (5H, m), 7.69-7.85 (4H, m), 8.11 (1H, s), 8.59-8.63 (1H, s). |
| 604 | δ 2.38 (6H, s), 2.45 (3H, s), 7.33-7.38 (5H, m), 7.78-7.85 (4H, m), 8.10 (1H, s), 8.61-8.65 (1H, m). |
| 605 | δ 2.34 (6H, s), 7.39 (1H, t, J = 7.4 Hz), 7.44 (2H, s), 7.50-7.54 (1H, m), 7.76-7.80 (2H, m), 7.88 (1H, t, J = 7.4 Hz), 8.12 (1H, t, J = 7.4 Hz), 8.20 (1H, d, J = 1.0 Hz), 10.12 (1H, s), 10.73 (1H, s). |
| 606 | δ 2.35 (6H, s), 7.40 (1H, t, J = 7.8 Hz), 7.45 (2H, s), 7.59-7.62 (1H, m), 7.82-7.90 (2H, m), 8.44-8.50 (2H, m), 8.86 (1H, d, J = 2.0 Hz), 10.12 (1H, s), 10.72 (1H, s). |
| 607 | δ 2.34 (6H, s), 7.40 (1H, t, J = 7.8 Hz), 7.45 (2H, s), 7.57-7.62 (1H, m), 7.81-7.85 (1H, m), 8.22-8.25 (2H, m), 8.39-8.42 (2H, m), 10.12 (1H, s), 10.66 (1H, s). |
| 609 | δ 2.34 (6H, s), 7.39 (1H, t, J = 6.9 Hz), 7.45 (2H, s), 7.58 (1H, t, J = 6.9 Hz), 7.82 (1H, t, J = 6.9 Hz), 8.06 (2H, d, J = 8.8 Hz), 8.15 (2H, d, J = 8.8 Hz), 10.12 (1H, s), 10.58 (1H, s). |
| 610 | δ 2.34 (6H, s), 7.33-7.40 (3H, m), 7.45 (2H, s), 7.52-7.56 (1H, m), 7.59-7.65 (1H, m), 7.72-7.77 (1H, m), 8.00 (1H, t, J = 7.8 Hz), 10.12 (1H, s), 10.35 (1H, s). |
| 611 | δ 2.34 (6H, s), 7.38 (1H, t, J = 7.6 Hz), 7.45-7.65 (5H, m), 7.78-7.83 (2H, m), 7.87 (1H, d, J = 7.6 Hz), 10.10 (1H, s), 10.39 (1H, s). |
| 612 | δ 2.34 (6H, s), 7.35-7.45 (5H, m), 7.55-7.59 (1H, m), 7.77-7.81 (1H, m), 8.07-8.12 (2H, m), 10.09 (1H, s), 10.32 (1H, s). |
| 616 | δ 2.34 (6H, s), 7.22-7.27 (1H, m), 7.38 (1H, t, J = 7.8 Hz), 7.46 (2H, s), 7.50-7.55 (3H, m), 7.95 (1H, d, J = 7.8 Hz), 7.99-8.03 (1H, m), 10.12 (1H, s), 10.50 (1H, s). |
| 618 | δ 2.34 (6H, s), 7.39 (1H, t, J = 7.7 Hz), 7.45 (2H, s), 7.60 (1H, t, J = 7.7 Hz), 7.83 (1H, t, J = 7.7 Hz), 7.95 (2H, d, J = 8.3 Hz), 8.20 (2H, d, J = 8.3 Hz), 10.12 (1H, s), 10.56 (1H, s). |
| 619 | δ 2.34 (6H, s), 7.38 (1H, t, J = 7.4 Hz), 7.45 (2H, s), 7.55-7.60 (3H, m), 7.81 (1H, t, J = 7.4 Hz), 8.14 (2H, d, J = 8.8 Hz), 10.11 (1H, s), 10.40 (1H, s). |
| 620 | δ 2.34 (6H, s), 3.01 (6H, s), 6.77 (2H, d, J = 9.0 Hz), 7.33 (1H, t, J = 7.0 Hz), 7.45 (2H, s), 7.52 (1H, t, J = 7.0 Hz), 7.78 (1H, t, J = 7.0 Hz), 7.90 (2H, d, J = 9.0 Hz), 9.86 (1H, s), 10.07 (1H, s). |
| 624 | δ 2.34 (6H, s), 7.23-7.28 (2H, m), 7.38 (1H, t, J = 7.8 Hz), 7.45 (2H, s), 7.52-7.64 (2H, m), 8.05-8.10 (1H, m), 10.13 (1H, s), 10.88 (1H, s). |
| 628 | δ 2.34 (6H, s), 7.37-7.42 (1H, m), 7.40 (2H, s), 7.55-7.58 (1H, m), 7.95-8.07 (2H, m), 8.21 (1H, dd, J = 8.9, 2.1 Hz), 8.30 (1H, dd, J = 8.9, 2.1 Hz), 10.13 (1H, s), 10.75 (1H, s). |
| 629 | δ 2.34 (6H, s), 7.39 (1H, t, J = 7.4 Hz), 7.45 (2H, s), 7.52 (1H, 7.4), 7.81 (1H, dd, J = 8.3, 2.7 Hz), 7.88 (1H, dd, J = 8.3, 5.6 Hz), 8.10-8.16 (2H, m), 10.13 (1H, s), 10.75 (1H, s). |
| 630 | δ 2.33 (6H, s), 7.34-7.38 (2H, m), 7.43 (2H, s), 7.51-7.54 (1H, m), 7.58-7.60 (1H, m), 7.67-7.71 (1H, m), 8.00-8.04 (1H, m), 10.10 (1H, s), 10.54 (1H, s). |
| 631 | δ 2.34 (6H, s), 7.37 (1H, t, J = 7.9 Hz), 7.45-7.47 (3H, m), 7.52-7.56 (1H, m), 7.65 (1H, dd, J = 10.2, 2.0 Hz), 7.77 (1H, t, J = 7.9 Hz), 7.99-8.02 (1H, m), 10.11 (1H, s), 10.41 (1H, s). |
| 633 | δ 2.34 (6H, s), 7.40 (1H, t, J = 8.1 Hz), 7.45 (2H, s), 7.55 (1H, t, J = 6.5 Hz), 7.92 (1H, d, J = 8.1 Hz), 8.10 (1H, t, J = 6.5 Hz), 8.32 (1H, d, J = 8.1 Hz), 8.43 (1H, s), 10.13 (1H, s), 10.84 (1H, s). |
| 634 | δ 2.34 (6H, s), 7.39 (1H, t, J = 8.0 Hz), 7.45 (2H, s), 7.51-7.55 (1H, m), 7.83 (1H, d, J = 8.0 Hz), 7.99 (1H, dd, J = 7.7, 2.2 Hz), 8.12 (1H, t, J = 7.7 Hz), 8.30 (1H, d, J = 2.2 Hz), 10.13 (1H, s), 10.78 (1H, s). |
| 638 | δ 2.33 (6H, s), 7.37 (1H, t, J = 8.1 Hz), 7.44 (2H, s), 7.50-7.55 (2H, m), 8.03-8.07 (1H, m), 8.26-8.31 (1H, m), 8.41-8.42 (1H, m), 10.10 (1H, s), 10.54 (1H, s). |
| 639 | (CDCl$_3$) δ 2.38 (6H, s), 7.38 (2H, s), 7.41-7.49 (2H, m), 7.80 (1H, broad-d, J = 11.4 Hz), 7.90-7.94 (1H, m), 8.32-8.35 (1H, m), 8.57-8.59 (1H, m), 8.62-8.65 (1H, m), 8.74 (1H, s). |
| 648 | δ 1.80-1.86 (2H, m), 2.05 (3H, s), 2.33-2.38 (8H, m), 3.99 (2H, t, J = 5.1 Hz), 7.29 (1H, t, J = 7.4 Hz), 7.44-7.48 (3H, m), 7.79 (1H, d, J = 7.4 Hz), 9.25 (1H, s), 10.04 (1H, s). |
| 649 | δ 2.29 (6H, s), 7.45 (2H, s), 7.54-7.66 (3H, m), 7.77 (1H, d, J = 8.8 Hz), 7.94 (1H, dd, J = 2.0, 8.1 Hz), 8.00-8.03 (2H, m), 8.19 (1H, d, J = 2.0 Hz), 10.10 (1H, s), 10.29 (1H, s). |
| 650 | δ 2.29 (6H, s), 7.45 (2H, s), 7.48-7.65 (4H, m), 7.93-8.02 (3H, m), 8.23 (1H, dd, J = 2.4, 7.3 Hz), 10.03 (1H, s), 10.32 (1H, s). |
| 651 | δ 2.29 (6H, s), 7.45 (2H, s), 7.54 (1H, dd, J = 8.8, 9.8 Hz), 7.96-8.01 (1H, m), 8.23 (2H, d, J = 8.8 Hz), 8.26 (1H, dd, J = 2.4, 8.8 Hz), 8.40 (2H, d, J = 8.8 Hz), 10.05 (1H, s), 10.70 (1H, s). |
| 652 | δ 2.29 (6H, s), 7.45 (2H, s), 7.51-7.56 (1H, m), 7.96-8.00 (1H, m), 8.06 (2H, d, J = 8.3 Hz), 8.15 (2H, d, J = 8.3 Hz), 8.25 (1H, dd, J = 2.0, 7.3 Hz), 10.05 (1H, s), 10.61 (1H, s). |
| 653 | δ 2.29 (6H, s), 7.33-7.40 (2H, m), 7.45 (2H, s), 7.49-7.54 (1H, m), 7.59-7.65 (1H, m), 7.73-7.77 (1H, m), 7.91-7.95 (1H, m), 8.42 (1H, d, J = 6.3 Hz), 10.05 (1H, s), 10.35 (1H, s). |
| 654 | δ 2.29 (6H, s), 7.37-7.45 (4H, m), 7.51 (1H, dd, J = 8.8, 9.8 Hz), 7.93-7.98 (1H, m), 8.06-8.10 (2H, m), 8.22 (1H, dd, J = 2.0, 7.3 Hz), 10.03 (1H, s), 10.37 (1H, s). |
| 655 | δ 2.29 (6H, s), 7.45 (2H, s), 7.51-7.56 (1H, m), 7.94-8.00 (3H, m), 8.20 (2H, d, J = 8.3 Hz), 8.25 (1H, dd, J = 2.0, 7.3 Hz), 10.05 (1H, s), 10.59 (1H, s). |
| 656 | δ 2.29 (6H, s), 7.23-7.28 (1H, m), 7.42-7.54 (4H, m), 7.80-7.87 (1H, m), 7.91-7.95 (1H, m), 8.41 (1H, d, J = 5.9 Hz), 10.05 (1H, s), 10.36 (1H, s). |
| 657 | δ 2.30 (6H, s), 7.46 (2H, s), 7.50-7.59 (2H, m), 7.92-7.96 (1H, m), 8.10 (1H, dd, J = 2.0, 7.3 Hz), 8.52-8.56 (2H, m), 10.07 (1H, s), 10.73 (1H, s). |
| 658 | δ 2.31 (6H, s), 7.47 (2H, s), 7.55-7.59 (2H, m), 7.62-7.66 (1H, m), 8.01-8.04 (2H, m), 8.09 (1H, s), 8.54 (1H, s), 8.66 (1H, s), 10.27 (1H, s), 10.79 (1H, s). |
| 659 | δ 2.34 (6H, s), 7.40 (1H, t, J = 9.3 Hz), 7.45 (2H, s), 7.53-7.64 (3H, m), 7.97-8.05 (3H, m), 8.14 (1H, dd, J = 2.9, 6.3 Hz), 10.03 (1H, s), 10.48 (1H, s). |
| 660 | δ 2.40 (6H, s), 7.45 (2H, s), 7.54-7.65 (4H, m), 7.97-8.03 (3H, m), 8.09 (1H, d, J = 2.4 Hz), 10.20 (1H, s), 10.56 (1H, s). |
| 661 | δ 2.41 (6H, s), 7.45 (2H, s), 7.54-7.65 (3H, m), 7.72 (1H, d, J = 8.8 Hz), 7.94-7.99 (3H, m), 8.08 (1H, d, J = 2.9 Hz), 10.20 (1H, s), 10.56 (1H, s). |
| 662 | δ 2.44 (6H, s), 7.45 (2H, s), 7.53-7.65 (3H, m), 7.79 (1H, dd, J = 2.4, 8.3 Hz), 7.90-7.98 (3H, m), 8.05 (1H, d, J = 2.4 Hz), 10.15 (1H, s), 10.53 (1H, s). |
| 663 | δ 2.35 (6H, s), 7.32 (1H, t, J = 8.3), 7.46 (2H, s), 7.54-7.77 (4H, m), 8.00 (2H, dd, J = 1.5, J = 8.3), 10.3 (1H, s), 10.6 (1H, s). |

TABLE 6-continued

| Compound No. | ¹H-NMR (DMSO-d₆, ppm) |
|---|---|
| 664 | (CDCl₃) δ 2.53 (6H, s), 7.35 (2H, s), 7.52-7.63 (5H, m), 7.92 (2H, d, J = 8.8 Hz), 8.46 (1H, d, J = 8.8 Hz), 8.57 (1H, s). |
| 665 | δ 2.34 (6H, s), 7.37 (1H, t, J = 7.8 Hz), 7.44 (2H, s), 7.53-7.65 (4H, m), 7.77-7.81 (1H, m), 7.99-8.02 (2H, m), 10.09 (1H, broad), 10.29 (1H, broad). |
| 668 | δ 2.34 (6H, s), 7.33-7.40 (3H, m), 7.44 (2H, s), 7.51-7.56 (1H, m), 7.58-7.65 (1H, m), 7.72-7.77 (1H, m), 8.00 (1H, t, J = 8.3 Hz), 10.10 (1H, s), 10.34 (1H, s). |
| 670 | δ 2.28 (6H, s), 7.31-7.44 (5H, m), 7.57 (1H, t, J = 6.3 Hz), 7.79 (1H, t, J = 7.3 Hz), 8.07-8.09 (2H, m), 10.09 (1H, s), 10.32 (1H, s). |
| 676 | δ 7.34 (6H, s), 7.39 (1H, t, J = 7.2 Hz), 7.44 (2H, s), 7.59 (1H, t, J = 7.2 Hz), 7.83 (1H, t, J = 7.2 Hz), 7.99 (2H, d, J = 8.8 Hz), 8.15 (2H, d, J = 8.8 Hz), 10.1 (1H, s), 10.57 (1H, s). |
| 679 | δ 2.35 (6H, s), 7.4 (1H, t, J = 7.3 Hz), 7.44 (2H, s), 7.61 (1H, t, J = 7.3 Hz), 7.84 (1H, t, J = 7.3 Hz), 8.24 (1H, d, J = 8.8 Hz), 8.41 (2H, d, J = 8.8 Hz), 10.11 (1H, s), 10.66 (1H, s). |
| 682 | δ 2.35 (6H, s), 7.38 (1H, t, J = 8.1 Hz), 7.44 (2H, s), 7.49 (1H, d, J = 8.1 Hz), 7.56 (1H, d, J = 8.1 Hz), 8.07 (2H, d, J = 8.8 Hz), 8.14 (2H, d, J = 8.8 Hz), 10.1 (1H, s), 10.43 (1H, s). |
| 686 | δ 2.34 (6H, s), 7.23-7.28 (2H, m), 7.38 (1H, t, J = 7.8 Hz), 7.44 (2H, s), 7.52-7.65 (2H, m), 8.05-8.10 (1H, m), 10.12 (1H, s), 10.88 (1H, s). |
| 699 | δ 2.34 (6H, s), 3.39 (3H, s), 7.39 (1H, t, J = 7.8 Hz), 7.44 (2H, s), 7.49-7.59 (2H, m), 8.08-8.13 (2H, m), 8.55 (1H, dd, J = 4.9, 2.0 Hz), 10.12 (1H, s), 10.73 (1H, s). |
| 708 | (CDCl₃) δ 7.39 (1H, t, J = 7.8 Hz), 7.48-7.64 (3H, m), 7.88-7.96 (4H, m), 8.09-8.13 (2H, m), 8.69 (1H, t, J = 7.8 Hz), 8.75 (1H, d, J = 7.8 Hz). |
| 711 | (CDCl₃) δ 7.22 (1H, d, J = 8.3 Hz), 7.35-7.40 (2H, m), 7.56-7.62 (1H, m), 7.91 (1H, t, J = 7.3 Hz), 7.96 (2H, s), 8.15 (1H, d, J = 13.3 Hz), 8.22 (1H, dt, J = 1.9, 8.3 Hz), 8.73 (1H, dt, J = 1.5, 8.3 Hz), 8.92 (1H, dt, J = 17.1 Hz). |
| 719 | (CDCl₃) δ 7.41 (1H, t, J = 8.3 Hz), 7.85 (2H, d, J = 8.3 Hz), 7.92 (1H, d, J = 6.9 Hz), 7.96 (2H, s), 8.03 (2H, d, J = 8.3 Hz), 8.06 (1H, s), 8.10 (1H, s), 8.63 (1H, dt, J = 1.5, 8.3 Hz). |
| 722 | (CDCl₃) δ 7.42 (1H, t, J = 8.3 Hz), 7.93 (1H, d, J = 5.3 Hz), 7.96 (2H, s), 8.06 (1H, d, J = 12.2 Hz), 8.10 (2H, d, J = 8.8 Hz), 8.13 (1H, s), 8.40 (2H, d, J = 8.8 Hz), 8.64 (1H, dt, J = 1.5, 8.3 Hz). |
| 791 | (CDCl₃) δ 2.34 (6H, s), 7.37 (1H, t, J = 7.8 Hz), 7.45 (2H, s), 7.54 (2H, t, J = 7.8 Hz), 7.61 (1H, d, J = 7.8 Hz), 7.80 (1H, d, J = 11.7 Hz), 7.82-7.87 (1H, m), 7.92 (2H, d, J = 7.8 Hz), 8.12 (1H, s), 8.62 (1H, dt, J = 2.0, 7.8 Hz). |
| 831 | (CDCl₃) δ 7.46-7.64 (6H, m), 7.93-7.96 (4H, m), 8.61 (1H, s), 7.75 (1H, dd, J = 1.9, 8.3 Hz). |
| 832 | (CDCl₃) δ 7.24 (1H, d, J = 8.3 Hz), 7.36 (1H, t, J = 8.3 Hz), 7.47 (1H, t, J = 8.3 Hz), 7.55-7.62 (3H, m), 7.96 (2H, s), 8.21 (1H, dt, J = 2.0, 8.3 Hz), 8.77 (1H, dd, J = 2.0, 8.3 Hz), 9.33 (1H, d, J = 16.6 Hz). |
| 833 | (CDCl₃) δ 7.45-7.52 (3H, m), 7.60 (1H, d, J = 8.8 Hz), 7.96 (2H, s), 8.29 (1H, d, J = 7.8 Hz), 8.57 (1H, dd, J = 2.0, 4.4 Hz), 8.72 (1H, d, J = 7.8 Hz), 9.00 (1H, s). |
| 1001 | δ 2.20 (6H, s), 3.45 (3H, s), 7.23-7.30 (5H, m), 7.43-7.45 (4H, m), 7.73-7.76 (2H, m), 9.88 (1H, s). |
| 1013 | δ 2.20 (6H, s), 3.48 (3H, s), 7.39-7.97 (8H, m), 7.43 (2H, s), 9.90 (1H, s). |
| 1016 | δ 2.21 (6H, s), 3.46 (3H, s), 7.40-8.03 (10H, m), 9.91 (1H, s). |
| 1032 | δ 2.08 (3H, s), 2.30 (6H, s), 7.45 (2H, s), 7.47 (1H, d, J = 7.8 Hz), 7.54 (1H, t, J = 7.8 Hz), 7.66 (1H, d, J = 7.8 Hz), 7.75 (1H, d, J = 7.8 Hz), 7.82 (1H, d, J = 7.8 Hz), 8.04 (1H, dd, J = 2.0, 7.8 Hz), 8.13 (1H, s), 8.35 (1H, s), 9.99 (1H, s), 10.16 (1H, s), 10.48 (1H, s). |
| 1043 | (CDCl₃) δ 1.38 (6H, m), 2.37 (6H, s), 3.13 (1H, broad), 3.33 (3H, broad), 3.78 (1H, broad), 3.89 (1H, broad), 7.37 (2H, s), 7.48 (1H, d, J = 7.8 Hz), 7.58 (1H, t, J = 7.8 Hz), 7.77 (1H, s), 7.90 (1H, s), 7.93 (1H, broad). |
| 1089 | (CDCl₃) δ 0.89 (3H, t, J = 7.3 Hz), 1.53-1.62 (2H, m), 2.61 (2H, t, J = 7.3 Hz), 3.50 (3H, broad), 6.80 (1H, broad), 7.03 (1H, broad), 7.22 (1H, broad), 7.34 (3H, broad), 7.47 (1H, s), 7.67-7.76 (3H, broad-m), 7.93 (1H, s). |
| 1091 | (CDCl₃) δ 0.88 (3H, t, J = 7.3 Hz), 1.53-1.63 (2H, m), 2.62 (2H, t, J = 7.8 Hz), 3.52 (3H, s), 6.83-6.89 (2H, m), 7.26-7.32 (3H, m), 7.41 (1H, t, J = 7.8 Hz), 7.48 (1H, s), 7.66 (1H, s), 7.76 (2H, d, J = 8.8 Hz), 7.93 (1H, d, J = 1.5 Hz). |
| 1097 | (CDCl₃) δ 0.90 (3H, t, J = 7.3 Hz), 1.55-1.65 (2H, m), 2.64 (2H, t, J = 7.8 Hz), 3.55 (3H, s), 7.27 (1H, s), 7.40-7.44 (3H, m), 7.49-7.51 (3H, m), 7.59 (1H, s), 7.76 (1H, d, J = 7.8 Hz), 7.95 (1H, s). |
| 1100 | (CDCl₃) δ 0.88 (3H, t, J = 7.3 Hz), 1.54-1.64 (2H, m), 2.63 (2H, t, J = 7.8 Hz), 3.56 (3H, s), 7.29 (1H, s), 7.40-7.50 (4H, m), 7.59 (1H, s), 7.71 (1H, s), 7.76 (1H, d, J = 7.3 Hz), 7.94 (1H, d, J = 1.5 Hz), 8.06 (2H, d, J = 8.8 Hz). |
| 1125 | (CDCl₃) δ 2.25 (6H, s), 3.54 (3H, s), 6.84 (1H, broad-s), 7.00-7.10 (2H, m), 7.20-7.40 (6H, m), 7.50-7.60 (1H, broad), 7.60-7.70 (1H, broad). |
| 1126 | (CDCl₃) δ 3.57 (3H, s), 7.20-7.24 (2H, m), 7.29-7.32 (3H, m), 7.34 (1H, t, J = 7.8 Hz), 7.40-7.44 (2H, m), 7.57 (1H, d, J = 7.8 Hz), 7.86-7.91 (1H, m), 7.92 (2H, s). |
| 1206 | δ 1.17 (3H, broad), 2.22 (6H, s), 3.94 (2H, broad), 7.01-7.08 (2H, m), 7.29-7.43 (6H, m), 7.72-7.77 (2H, m), 9.90 (1H, s). |
| 1207 | δ 1.26 (3H, t, J = 6.8 Hz), 2.04 (6H, s), 4.11 (2H, q, J = 6.8 Hz), 7.16-7.70 (12H, m). |
| 1208 | δ 2.28 (6H, s), 3.36 (3H, s), 7.27-7.32 (6H, m), 7.43 (2H, s), 7.55-7.57 (2H, broad), 9.96 (1H, s). |
| 1209 | δ 2.28 (6H, s), 3.47 (3H, s), 6.98 (1H, broad), 7.11 (2H, broad), 7.19 (1H, broad), 7.37 (1H, broad), 7.44 (2H, s), 7.51 (1H, broad), 7.74 (1H, broad), 9.94 (1H, s). |
| 1210 | δ 2.23 (3H, s), 2.29 (6H, s), 7.07-7.26 (5H, m), 7.44 (2H, s), 7.56-7.77 (2H, m), 9.98 (1H, s). |
| 1211 | δ 2.24 (3H, s), 2.28 (6H, s), 7.08-7.09 (2H, m), 7.22-7.28 (2H, m), 7.44 (2H, s), 7.51-7.58 (3H, m), 9.99 (1H, s). |
| 1212 | δ 2.29 (6H, s), 3.12 (3H, s), 7.17-8.02 (9H, m), 9.95 (1H, s). |
| 1213 | δ 2.26 (6H, s), 3.41 (3H, s), 7.12-8.34 (9H, m), 9.92 (1H, s). |
| 1214 | δ 2.26 (6H, s), 3.40 (3H, s), 7.29 (1H, broad), 7.44 (2H, s), 7.59-7.81 (4H, m), 8.12 (2H, broad), 9.91 (1H, s). |
| 1215 | δ 2.26 (6H, s), 3.40 (3H, s), 7.31-7.39 (7H, m), 7.50-7.56 (1H, m), 7.81-7.83 (1H, m), 9.94 (1H, s). |
| 1216 | δ 2.27 (6H, s), 3.39 (3H, s), 7.31 (1H, m), 7.47 (2H, s), 7.60-7.67 (3H, m), 7.72-7.80 (3H, m), 9.96 (1H, s). |
| 1217 | δ 2.27 (6H, s), 3.37 (3H, s), 7.29 (2H, broad), 7.44-7.48 (3H, m), 7.59-7.64 (2H, m), 7.76 (2H, broad), 9.94 (1H, s). |

TABLE 6-continued

| Compound No. | $^1$H-NMR (DMSO-d$_6$, ppm) |
|---|---|
| 1218 | δ 2.27 (6H, s), 3.39 (3H, s), 7.03-7.72 (9H, m), 9.94 (1H, s). |
| 1219 | δ 2.28 (6H, s), 3.36 (3H, s), 7.18-8.04 (9H, m), 9.98 (1H, m). |
| 1220 | δ 2.28 (6H, s), 3.34 (3H, s), 7.12-7.56 (9H, m), 9.97 (1H, s). |
| 1229 | δ 2.28 (6H, s), 3.39 (3H, s), 7.02-7.28 (2H, m), 7.35-7.43 (2H, m), 7.55-7.70 (2H, m), 7.93-7.99 (2H, m), 9.95 (1H, m). |
| 1235 | δ 2.26 (6H, s), 3.43 (3H, s), 7.27 (1H, t, J = 7.8 Hz), 7.44 (2H, s), 7.58-7.65 (2H, m), 7.71 (1H, t, J = 7.8), 8.00 (1H, dd, J = 8.3, 2.0 Hz), 8.04 (1H, dd, J = 9.3, 2.0 Hz), 9.91 (1H, s). |
| 1236 | δ 2.29 (6H, s), 3.41 (3H, s), 7.44-7.46 (3H, m), 7.59-7.61 (2H, m), 7.72-7.77 (1H, m), 7.88 (1H, d, J = 6.8 Hz), 7.95-7.99 (1H, m), 9.95 (1H, s). |
| 1237 | δ 2.29 (6H, s), 3.40 (3H, s), 7.08-7.91 (8H, m), 9.94 (1H, s). |
| 1238 | δ 2.28 (6H, s), 3.39 (3H, s), 7.21-7.28 (1H, m), 7.34-7.44 (3H, m), 7.54-7.60 (2H, m), 7.79-7.91 (2H, m), 9.95 (1H, m). |
| 1244 | (CDCl$_3$) δ 2.29 (6H, s), 3.52 (3H, s), 7.21-7.23 (1H, m), 7.28-7.30 (1H, m), 7.35 (2H, m), 7.41 (1H, m), 7.72 (2H, m), 8.01 (1H, t, J = 6.8 Hz), 8.53 (2H, m). |
| 1245 | δ 2.28 (6H, s), 3.41 (3H, s), 7.25 (1H, t, J = 7.6 Hz), 7.36 (1H, d, J = 4.7 Hz), 7.44 (2H, s), 7.57-7.64 (2H, m), 7.92 (1H, d, J = 7.6 Hz), 8.32 (1H, dd, J = 4.7, 1.9 Hz), 9.97 (1H, s). |
| 1246 | δ 2.31 (6H, s), 3.60 (3H, s), 7.25-7.31 (2H, m), 7.44 (2H, s), 7.57-7.59 (2H, m), 7.97-8.01 (1H, m), 8.17-8.18 (1H, m), 9.97 (1H, s). |
| 1247 | δ 2.28 (6H, s), 3.39 (3H, s), 7.33 (1H, d, J = 7.6 Hz), 7.44 (2H, s), 7.61-7.69 (3H, m), 7.80 (1H, broad), 8.30 (1H, broad), 10.01 (1H, s). |
| 1255 | δ 2.29 (6H, s), 3.35 (3H, s), 7.19-7.70 (10H, m), 9.98 (1H, s). |
| 1256 | δ 2.28 (6H, s), 2.30 (3H, s), 3.32 (3H, s), 6.98-7.72 (9H, m), 9.93 (1H, s). |
| 1257 | δ 2.23 (3H, s), 2.29 (6H, s), 3.34 (3H, s), 7.07-7.38 (5H, m), 7.53-7.76 (2H, m), 7.43 (2H, s), 9.98 (1H, s). |
| 1258 | δ 2.27 (6H, s), 2.33 (3H, s), 3.31 (3H, s), 6.98-7.51 (9H, s), 9.93 (1H, s). |
| 1259 | δ 2.29 (6H, s), 3.41 (3H, s), 7.18 (1H, J = 7.3 Hz), 7.44 (2H, s), 7.46-7.57 (2H, m), 7.67 (1H, t, J = 7.3 Hz), 7.73-7.82 (2H, m), 8.01 (1H, d, J = 7.8 Hz), 9.95 (1H, s). |
| 1260 | δ 2.26 (6H, s), 3.36 (3H, s), 7.42 (2H, s), 7.59 (1H, broad), 7.7 (1H, broad), 7.82 (1H, t, J = 7.9 Hz), 8.2 (1H, broad), 8.34-8.37 (1H, m), 8.48 (1H, dd, J = 7.9, 1.7 Hz), 8.62 (1H, t, J = 2.0 Hz), 9.92 (1H, s). |
| 1261 | δ 2.27 (6H, s), 3.37 (3H, s), 7.43 (2H, s), 7.59-7.65 (2H, m), 8.11 (1H, broad), 8.18 (2H, d, J = 8.8 Hz), 8.29 (2H, d, J = 8.8 Hz), 9.91 (1H, s). |
| 1262 | δ 2.33 (6H, s), 3.35 (3H, s), 7.30-7.83 (9H, m), 9.93 (1H, s). |
| 1263 | δ 2.27 (6H, s), 3.37 (3H, s), 7.18-7.80 (9H, m), 9.96 (1H, s). |
| 1264 | δ 2.27 (6H, s), 3.35 (3H, s), 7.43 (2H, s), 7.48 (1H, broad), 7.58 (1H, broad), 7.75 (1H, broad), 7.99 (2H, d, J = 8.5 Hz), 8.08 (2H, d, J = 8.5 Hz), 9.95 (1H, s). |
| 1265 | δ 2.27 (6H, s), 3.36 (3H, s), 7.03-7.73 (9H, m), 9.93 (1H, s). |
| 1266 | δ 2.28 (6H, s), 3.35 (2H, s), 7.18-7.61 (9H, m), 9.99 (1H, s). |
| 1267 | δ 2.28 (6H, s), 3.39 (3H, s), 7.11-7.18 (3H, m), 7.26-7.30 (1H, t, J = 7.8 Hz), 7.40-7.47 (3H, m), 7.58 (2H, t, J = 7.6 Hz), 9.96 (1H, s). |
| 1274 | δ 2.27 (6H, s), 3.37 (3H, s), 7.29 (3H, broad), 7.41-7.47 (4H, m), 7.59-7.61 (2H, m), 9.95 (1H, s). |
| 1293 | δ 2.28 (6H, s), 3.41 (3H, s), 7.25 (1H, t, J = 7.6 Hz), 7.35 (1H, dd, J = 7.3, 4.9 Hz), 7.43 (2H, s), 7.57-7.63 (2H, m), 7.91 (1H, d, J = 7.6 Hz), 8.32 (1H, dd, J = 4.9, 2.0 Hz), 9.96 (1H, s). |
| 1294 | δ 2.28 (6H, s), 3.39 (3H, s), 7.31-7.35 (1H, m), 7.42 (2H, s), 7.43-7.48 (1H, m), 7.61-7.75 (2H, m), 7.80 (1H, s), 8.32 (1H, broad), 10.01 (1H, s). |
| 1463 | δ 2.25 (6H, s), 3.38 (3H, s), 7.27-7.41 (6H, m), 7.45 (2H, s), 7.90 (1H, broad), 8.05 (1H, d, J = 6.8 Hz), 9.96 (1H, s). |
| 1464 | δ 2.23 (6H, s), 3.42 (3H, s), 7.41 (1H, broad), 7.45 (2H, s), 7.60 (2H, broad), 7.90 (1H, broad), 8.08-8.13 (3H, broad), 9.93 (1H, s). |
| 1465 | δ 2.25 (6H, s), 3.40 (3H, s), 7.39-7.42 (1H, m), 7.45 (2H, s), 7.50 (1H, broad), 7.78 (1H, broad), 7.91 (1H, broad), 7.97-8.10 (3H, m), 9.94 (1H, s). |
| 1478 | δ 2.29 (6H, s), 3.24 (3H, s), 6.84 (1H, d, J = 7.8 Hz), 7.12 (1H, t, J = 7.8 Hz), 7.33 (2H, s), 7.50-7.64 (4H, m), 7.85-7.88 (2H, m), 7.98-8.03 (1H, m), 10.22 (1H, s). |
| 1479 | δ 2.41 (3H, s), 3.25 (3H, s), 6.95 (1H, dd, J = 1.5, 7.8 Hz), 7.16 (1H, t, J = 7.8 Hz), 7.50-7.64 (4H, m), 7.68 (1H, s), 7.86-7.88 (2H, m), 7.93 (1H, t, J = 1.5 Hz), 7.98-8.00 (1H, m), 10.24 (1H, s). |
| 1480 | (CDCl$_3$) δ 3.34 (3H, s), 7.13-7.19 (2H, m), 7.49-7.58 (3H, m), 7.70-7.73 (2H, m), 7.78-7.91 (4H, m), 8.12 (1H, s). |
| 1481 | (CDCl$_3$) δ 3.35 (3H, s), 7.15-7.20 (3H, m), 7.32 (1H, t, J = 7.8 Hz), 7.51-7.55 (1H, m), 7.71 (1H, d, J = 2.9 Hz), 7.72 (1H, d, J = 2.0 Hz), 7.80 (2H, s), 8.14 (1H, dt, J = 2.0, 7.8 Hz), 8.37 (1H, d, J = 16.1 Hz). |
| 1482 | δ 1.18 (3H, t, J = 7.3 Hz), 2.30 (6H, s), 3.76 (2H, q, J = 7.3 Hz), 6.81 (1H, d, J = 7.8 Hz), 7.11 (1H, t, J = 7.8 Hz), 7.33 (2H, s), 7.50-7.62 (4H, m), 7.84-7.88 (2H, m), 7.95-8.00 (1H, m), 10.20 (1H, s). |
| 1483 | δ 1.44 (6H, d, J = 6.3 Hz), 2.07 (6H, s), 5.35 (1H, septet, J = 6.3 Hz), 6.84 (1H, d, J = 7.8 Hz), 7.21 (1H, t, J = 7.8 Hz), 7.21 (2H, s), 7.50-7.61 (3H, m), 7.75 (1H, dd, J = 1.5, 7.8 Hz), 7.86-7.89 (3H, m), 10.29 (1H, s). |
| 1484 | δ 2.18 (3H, s), 2.32 (6H, s), 7.37-7.59 (11H, m), 10.42 (1H, s). |
| 1485 | δ 2.34 (3H, s), 2.35 (6H, s), 7.34-8.02 (10H, m), 10.33 (1H, s). |
| 1486 | δ 2.33 (3H, s), 2.36 (6H, s), 7.29-8.12 (9H, m), 10.37 (1H, s). |
| 1487 | δ 2.20 (6H, s), 3.08 (3H, s), 3.20 (3H, s), 6.93-7.39 (10H, m), 7.45-7.51 (1H, m). |
| 1607 | (CDCl$_3$) δ 3.31 (3H, s), 3.35 (3H, s), 6.81 (1H, dt, J = 6.8, 1.0 Hz), 6.94 (1H, t, J = 7.8 Hz), 7.10-7.24 (5H, m), 7.35-7.40 (1H, m), 7.41 (1H, s), 7.78 (2H, s). |
| 1617 | (CDCl$_3$) δ 3.30 (3H, s), 3.33 (3H, s), 6.76-7.00 (4H, m), 7.19-7.23 (3H, m), 7.37 (1H, s), 7.77 (2H, s). |
| 1645 | (CDCl$_3$) δ 3.30 (3H, s), 3.36 (3H, s), 6.96-7.06 (3H, m), 7.12-7.16 (1H, m), 7.39-7.42 (2H, m), 7.95 (2H, s), 8.24 (1H, s). |
| 1654 | (CDCl$_3$) δ 3.30 (3H, s), 3.42 (3H, s), 7.01 (1H, d, J = 7.3 Hz), 7.10 (1H, t, J = 7.8 Hz), 7.16 (1H, dd, J = 1.4, 7.8 Hz), 7.41 (1H, t, J = 1.4 Hz), 7.54 (1H, dd, J = 1.9 Hz), 7.56 (1H, d, J = 1.9 Hz), 7.80 (1H, s), 7.81 (2H, s). |

TABLE 6-continued

| Compound No. | $^1$H-NMR (DMSO-$d_6$, ppm) |
|---|---|
| 1655 | (CDCl$_3$) δ 3.29 (3H, s), 3.38 (3H, s), 3.78 (3H, s), 6.73 (1H, d, J = 8.3 Hz), 6.96 (1H, d, J = 8.3 Hz), 7.04 (1H, t, J = 7.8 Hz), 7.08 (1H, d, J = 1.5 Hz), 7.14 (1H, d, J = 7.8 Hz), 7.40 (1H, s), 7.54 (1H, d, J = 8.3 Hz), 7.81 (2H, s). |
| 1697 | δ 2.23 (6H, s), 3.32 (3H, s), 3.39 (3H, s), 7.15-7.43 (10H, m). |
| 2001 | (CDCl$_3$) δ 2.36 (6H, s), 7.36 (2H, s), 7.53-7.57 (2H, m), 7.61-7.65 (1H, m), 7.95-8.03 (3H, m), 8.08 (1H, dd, J = 7.3, 1.0 Hz), 8.52 (1H, broad-s), 8.62 (1H, dd, J = 8.3, 1.0 Hz), 9.19 (1H, broad-s). |
| 2004 | δ 2.30 (6H, s), 7.37-7.43 (2H, m), 7.46 (2H, s), 7.65 (1H, d, J = 8.1 Hz), 7.83 (1H, dd, J = 7.5, 5.6 Hz), 7.88 (1H, d, J = 7.5 Hz), 8.13 (1H, t, J = 8.1 Hz), 8.40 (1H, d, J = 8.1 Hz), 10.08 (1H, s), 10.62 (1H, s). |
| 2032 | δ 2.30 (6H, s), 7.46 (2H, s), 7.75-7.78 (1H, m), 7.91 (1H, dd, J = 7.3, 1.0 Hz), 8.13-8.18 (2H, m), 8.27 (1H, d, J = 8.0 Hz), 8.56 (1H, d, J = 8.0 Hz), 8.77 (1H, d, J = 1.0 Hz), 10.62 (1H, s), 10.75 (1H, s). |
| 2033 | δ 2.27 (6H, s), 6.16 (2H, s), 6.71 (1H, d, J = 7.6 Hz), 7.01 (2H, d, J = 1.0 Hz), 7.24 (1H, d, J = 6.9 Hz), 7.42 (2H, s), 7.59 (1H, dd, J = 7.6, 6.9 Hz), 7.65 (1H, s), 9.94 (1H, s). |
| 2034 | δ 2.32 (6H, s), 7.47 (2H, s), 7.90-7.93 (3H, m), 8.15 (1H, t, J = 8.0 Hz), 8.37 (1H, d, J = 8.0 Hz), 8.83 (2H, dd, J = 4.6, 1.7 Hz), 10.12 (1H, s), 10.92 (1H, s). |
| 2035 | δ 2.30 (6H, s), 7.46 (2H, s), 7.55-7.56 (1H, m), 7.89 (1H, d, J = 7.4 Hz), 8.14 (1H, t, J = 7.8 Hz), 8.34-8.41 (2H, m), 8.45 (1H, dd, J = 5.4, 1.2 Hz), 10.03 (1H, s), 10.90 (1H, s). |
| 2036 | δ 2.29 (6H, s), 7.45 (2H, s), 7.59 (1H, t, J = 6.3 Hz), 7.88 (1H, d, J = 6.3 Hz), 8.12-8.16 (2H, m), 8.39 (1H, m), 8.55 (1H, m), 9.93 (1H, s), 11.25 (1H, s). |
| 2037 | δ 2.32 (6H, s), 7.47 (2H, s), 7.67 (1H, d, J = 7.6 Hz), 7.75 (1H, d, J = 8.3 Hz), 7.90 (1H, d, J = 7.6 Hz), 8.14 (1H, t, J = 7.6 Hz), 8.29 (1H, dd, J = 8.3 Hz, 2.0 Hz), 8.89 (1H, d, J = 2.0 Hz), 10.07 (1H, s), 10.97 (1H, s). |
| 2082 | δ 2.20 (6H, s), 3.58 (3H, s), 7.29-7.39 (5H, m), 7.43 (2H, s), 7.50 (1H, d, J = 7.4 Hz), 7.83 (1H, t, J = 7.4 Hz), 7.94 (1H, t, J = 7.4 Hz), 9.91 (1H, s). |
| 2085 | δ 2.22 (6H, s), 3.57 (3H, s), 7.12 (1H, t, J = 9.2 Hz), 7.20 (1H, t, J = 7.3 Hz), 7.28-7.30 (1H, m), 7.44 (2H, s), 7.55 (1H, t, J = 7.2 Hz), 7.63 (1H, broad), 7.87 (1H, d, J = 7.2 Hz), 7.98 (1H, t, J = 7.2 Hz), 9.90 (1H, s). |
| 2093 | δ 2.14 (6H, s), 3.57 (3H, s), 7.42 (2H, s), 7.66-7.87 (3H, m), 7.96-8.09 (4H, m), 9.77 (1H, s). |
| 2116 | δ 2.23 (6H, s), 3.55 (3H, s), 7.45 (3H, s), 7.89-9.91 (2H, m), 8.03-8.10 (3H, m), 9.82 (1H, s). |
| 2117 | δ 2.13 (6H, s), 3.58 (3H, s), 7.42 (2H, s), 7.46 (1H, d, J = 8.2 Hz), 7.72-7.75 (2H, m), 7.90 (1H, d, J = 8.2 Hz), 8.08 (1H, t, J = 8.2 Hz), 8.35 (1H, d, J = 2.0 Hz), 9.83 (1H, s). |
| 2162 | (CDCl$_3$) δ 2.38 (6H, s), 7.38 (2H, s), 7.53-7.57 (2H, m), 7.62 (1H, d, J = 7.8 Hz), 7.68 (1H, dd, J = 4.9, 1.5 Hz), 7.85 (1H, broad-s), 7.95 (2H, d, J = 7.8 Hz), 8.52 (1H, d, J = 4.9 Hz), 8.22 (1H, broad-s), 8.88 (1H, s). |
| 2163 | (CDCl$_3$) δ 2.36 (6H, s), 7.38 (2H, s), 7.55-7.59 (2H, m), 7.64-7.72 (2H, m), 7.75 (1H, broad-s), 8.01 (2H, d, J = 7.3 Hz), 8.41 (1H, d, J = 6.8 Hz), 9.14 (1H, d, J = 2.4 Hz), 10.9 (1H, broad-s). |
| 2164 | (CDCl$_3$) δ 2.34 (6H, s), 7.47 (2H, s), 7.62-7.65 (2H, m), 7.70-7.81 (2H, m), 8.04-8.04 (3H, m), 8.64 (1H, dd, J = 8.3, 1.5 Hz), 10.9 (1H, broad-s), 12.3 (1H, broad-s). |
| 2165 | δ 2.35 (6H, s), 7.29-8.03 (10H, m), 8.75 (1H, d, J = 2.0 Hz). |
| 2168 | δ 2.25 (6H, s), 3.32 (3H, s), 7.26 (1H, d, J = 7.7 Hz), 7.38 (1H, d, J = 7.7 Hz), 7.44 (2H, s), 7.55 (1H, t, J = 7.7 Hz), 7.90 (3H, m), 8.11 (2H, m), 12.40 (1H, s). |
| 2201 | (CDCl$_3$) δ 2.38 (6H, s), 7.25-8.00 (1H, m), 8.34 (1H, s), 8.85 (1H, broad.). |
| 2202 | (CDCl$_3$) δ 2.36 (6H, s), 7.37 (2H, s), 7.47-7.61 (5H, m), 7.85-8.03 (4H, m), 8.57 (1H, s), 9.18 (1H, s). |
| 2203 | (CDCl$_3$) δ 2.38 (6H, s), 7.41 (2H, s), 7.45-7.55 (4H, m), 7.90-7.96 (4H, m), 8.57 (1H, broad), 8.74 (1H, broad), 9.18 (1H, broad). |

An agent containing the composition for preventing harmful organisms of the present invention as an active ingredient is suitable for controlling harmful organisms such as various agricultural, forest harmful insects and horticultural harmful insects, stored grain harmful insects, hygienic harmful insects, nematodes or the like which are injurious to paddy rice, fruit trees, vegetables, other crops, flowers and the like. Examples of the harmful insects include LEPIDOPTERA such as swift moth (Endoclyta excrescens), grape tree-borer (Endoclyta sinensis), swift moth (Palpifer sexnotata), strawberry tortrix moth (Acleris comariana), summer fruit tortrix moth (Adoxophyes orana fasciata), small tea tortrix moth (Adoxophyes sp.), Asiatic leaf roller (Archips breviplicanus), apple tortrix (Archips fuscocupreanus), brown oak tortrix (Archips xylosteanus), tortrix moth (Bactra furfurana), tobacco leaf worm (Cnephasia cinereipalpana), nut fruit tortrix (Cydia kurokoi), greenish chestnut moth (Eucoenogenes aestuosa), Manchurian fruit moth (Grapholita inopinata), oriental fruit moth (Grapholita molesta), oriental tea tortrix moth (Homona magnanima), leaf roller (Hoshinoa adumbratana), soybean pod borer (Leguminivora glycinivorella), adzuki bean pod worm (Matsumuraeses azukivora), soybean pod worm (Matsumuraeses falcana), soybean pod worm (Matsumuraeses phaseoli), mulberry leaf roller (Olethreutes mori), apple fruit licker (Spilonota lechriaspis), eye-spotted bud moth (Spilonota ocellana), European grape berry moth (Eupoecillia ambiguella), arrowhead moth (Phalonidia mesotypa), mugwort moth (Phtheochroides clandestina), codling moth (Cydia pomonella), grape berry moth (Endopiza viteana), mulberry bagworm (Bambalina sp.), giant bagworm (Eumeta japonica), tea bagworm (Eumeta minuscula), European grain moth (Nemapogon granellus), case making clothes moth (Tinea translucens), pear leaf miner (Bucculatrix pyrivorella), peach leaf miner (Lyonetia clerkella), apple leaf miner (Lyonetia prunifoliella), soybean leaf roller (Caloptilia soyella), tea leaf roller (Caloptilia theivora), apple leaf miner (Caloptilia zachrysa), persimmon leaf miner (Cuphodes diospyrosella), apple leaf miner (Phyllonorycter ringoniella), pear bark miner (Spulerina astaurota), citrus leaf miner (Phyllocnistis citrella), grape leaf miner (Phyllocnistis toparcha), allium leaf miner (Acrolepiopsis sapporensis), yam leaf miner (Acrolepiopsis suzukiella), diamondback moth (Plutella xylostella), apple fruit moth (Argyresthia conjugella), grape clearwing moth (Paranthrene regalis), cherry tree borer (Synanthedon hector), persimmon fruit moth (Stathmopoda masinissa), sweet potato leaf folder (Brachmia triannulella), pink bollworm (Pectinophora gossypiella), potato tuber moth (Phthorimaea operculella), peach fruit moth (Carposina niponensis), pear leaf worm (Illiberis pruni), Chinese cochlid (Latoia sinica), oriental moth (*Monema flavescens*), pear stinging caterpillar (*Narosoideus flavidorsalis*), green stinging caterpillar (*Parasa consocia*), persimmon cochlid (*Scopelodes contracus*), rice striped stem borer (*Chilo suppressalis*), rice leaf-folder (*Cnaphalocrocis medinalis*), yellow peach moth (*Conogethes punctiferalis*), cucumber moth (*Diaphania indica*), pear fruit moth (*Ectomyelois pyrivorella*), tobacco moth (*Ephestia elutella*), Mediterranean flour moth (*Ephestia kuehniella*), limabean pod borer (*Etiella zinckenella*), persimmon bark borer (*Euzophera batangensis*), mulberry pyralid (*Glyphodes pyloalis*), cabbage webworm (*Hellulla undalis*), rice leaf roller (*Marasmia exigua*), legume pod borer (*Maruca testulalis*), cotton leaf roller (*Notarcha derogata*), Asian corn borer (*Ostrinia furnacalis*), adzuki bean borer (*Ostrinia scapulalis*), butterbur borer (*Ostrinia zaguliaevi*), bluegrass webworm moth (*Parapediasia teterrella*), peppered moth (*Pleuroptya ruralis*), Indian-meal moth (*Plodia interpunctella*), yellow stem borer (*Scirpophaga incertulas*), common straight swift butterfly (*Parnara guttata*), large swallowtail butterfly (*Papilio helenus*), papilionid butterfly (*Papilio machaon hippocrates*), citrus swallowtail butterfly (*Papilio xuthus*), Eastern pale clouded yellow (*Colias erate poliographus*), small white butterfly (*Pieris rapae crucivora*), long-tailed pea-blue (*Lampides boeticus*), orange moth (*Angerona prunaria*), Japanese giant looper (*Ascotis selenaria*), giant geometrid moth (*Biston robustum*), plum cankerworm (*Cystidia couaggaria*), pine moth (*Dendrolimus spectabilis*), tent moth (*Malacosoma neustria testacea*), apple caterpillar (*Odonestis pruni japonensis*), coffee hawk moth (*Cephonodes hylas*), hawk moth (*Acosmeryx castanea*), scarce chocolate-tip (*Clostera anachoreta*), poplar tip moth (*Clostera anastomosis*), black-marked prominent (*Phalera flavescens*), drab-brown moth (*Phalerodonta manleyi*), lobster moth (*Stauropus fagi persimilis*), tea tussock moth (*Euproctis pseudoconspersa*), brown tail moth (*Euproctis similis*), oriental tussock moth (*Euproctis subflava*), Asian gypsy moth (*Lymantria dispar*), white-spotted tussock moth (*Orgyia thyellina*), fall webworm moth (*Hyphantria cunea*), mulberry tiger moth (*Spilosoma imparilis*), three-spotted plusia (*Acanthoplusia agnata*), sweet potato leaf worm (*Aedia leucomelas*), black cutworm (*Agrotis ipsilon*), turnip moth (*Agrotis segetum*), cotton looper (*Anomis flava*), hibiscus leaf caterpillar (*Anomis mesogona*), beet semi-looper (*Autographa nigrisigna*), tiger moth (*Trichoplusia ni*), American boll worm (*Helicoverpa armigera*), oriental tobacco budworm (*Helicoverpa assulta*), flax budworm (*Heliothis maritima*), cabbage moth (*Mamestra brassicae*), green rice semi-looper (*Naranga aenescens*), growth-blocking peptide (*Pseudaletia separata*), pink stem borer (*Sesamia inferens*), Japanese lawn grass cutworm (*Spodoptera depravata*), beet armyworm (*Spodoptera exigua*), oriental leafworm moth (*Spodoptera litura*), apple dagger moth (*Triaena intermedia*), sorrel cutworm (*Viminia rumicis*), spotted cutworm moth (*Xestia c-nigrum*) and the like;

Heteroptera of HEMIPTERA such as globular stink bug (*Megacopta punctatissimum*), black-shouldered shield bug (*Carpocoris purpureipennis*), sloe bug (*Dolycoris baccarum*), cabbage bug (*Eurydema pulchrum*), cabbage bug (*Eurydema rugosum*), 2-spotted sesame bug (*Eysarcoris guttiger*), white-spotted larger spined bug (*Eysarcoris lewisi*), white-spotted bug (*Eysarcoris parvus*), white-spotted stink bug (*Eysarcoris ventralis*), fruit-piercing stink bug (*Glaucias subpunctatus*), red-striped stink bug (*Graphosoma rubrolineatum*), brown marmorated stink bug (*Halyomorpha mista*), rice stink bug (*Lagynotomus elongatus*), eastern green stink bug (*Nezara antennata*), southern green stink bug (*Nezara viridula*), redbanded shield bug (*Piezodorus hybneri*), brownwinged green bug (*Plautia stali*), black rice bug (*Scotinophara lurida*), shield bug (*Starioides iwasakii*), winter cherry bug (*Acanthocoris sordidus*), Coreid bug (*Anacanthocoris striicornis*), narrow squash bug (*Cletus punctiger*), slender rice bug (*Cletus trigonus*), leaf-footed bug (*Molipteryx fulginosa*), paddy bug (*Leptocorisa acuta*), rice bug (*Leptocorisa chinensis*), rice bug (*Leptocorisa oratorius*), bean bug (*Riptortus clavatus*), carrot bug (*Aeschynteles maculatus*), plant bug (*Liorhyssus hyalinus*), oriental chinch bug (*Cavelerius saccharivorus*), chinch bug (*Macropes obnubilus*), ground bug (*Pachybrachius luridus*), lygaeid bug (*Paromius exguus*), seed bug (*Togo hemipterus*), red cotton bug (*Dysdercus cingulatus*), red bug (*Dysdercus poecilus*), chrysanthemum lace bug (*Galeatus spinifrons*), lace bug (*Metasalis populi*), silver magnolia lace bug (*Stephanitis fasciicarina*), pear lace bug (*Stephanitis nashi*), azalea lace bug (*Stephanitis pyrioides*), chestnut lace bug (*Uhlerites debile*), walnut lace bug (*Uhlerites latius*), alfalfa plant bug (*Adelphocoris lineolatus*), plant bug (*Adelphocoris triannulatus*), green leaf bug (*Apolygus lucorum*), pale green plant bug (*Apolygus spinolai*), sweet potato yellow bug (*Creontiades pallidifer*), tobacco leaf bug (*Cyrtopeltis tennuis*), plant bug (*Ectometopterus micantulus*), plant bug (*Halticiellus insularis*), apple leaf bug (*Heterocordylus flavipes*), mirid bug (*Lygus disponsi*), lygus bug (*Lygus saundersi*), mirid bug (*Orthotylus flavosparsus*), plant bug (*Stenodema calcaratum*), mired plant bug (*Stenotus binotatus*), sorghum plant bug (*Stenotus rubrovittatus*), broken back bug (*Taylorilygus pallidulus*), rice leaf bug (*Trigonotylus coelestialium*) and the like;

Homoptera such as large brown cicada (*Graptopsaltria nigrofuscata*), spittle bug (*Aphrophora costalis*), pine spittle bug (*Aphrophora flavipes*), grape spittle bug (*Aphrophora vitis*), spittle bug (*Clovia punctata*), meadow spittle bug (*Philaenus spumarius*), black-tipped leafhopper (*Bothrogonia japonica*), green leafhopper (*Cicadella viridis*), white leafhopper (*Cofana spectra*), oak leafhopper (*Aguriahana quercus*), polyphagous leafhopper (*Alnetoidia alneti*), citrus leafhopper (*Apheliona ferruginea*), grape leafhopper (*Arboridia apicalis*), small green leafhopper (*Edwardsiana flavescens*), rose leafhopper (*Edwardsiana rosae*), spruce leafhopper (*Empoasca abietis*), tea green leafhopper (*Empoasca onukii*), yellow rice leafhopper (*Thaia subrufa*), small citrus leafhopper (*Zyginella citri*), aster leafhopper (*Macrosteles fascifrons*), green rice leafhopper (*Nephotettix cincticeps*), green rice leafhopper (*Nephotettix nigropictus*), green leafhopper (*Nephotettix virescens*), apple leafhopper (*Orientus ishidai*), zigzag leafhopper (*Recilia dorsalis*), wheat leafhopper (*Sorhoanus tritici*), leafhopper (*Speusotettix subfusculus*), small brown plant hopper (*Laodelphax striatellus*), brown plant hopper (*Nilaparvata lugens*), planthopper (*Numata muiri*), maize planthopper (*Peregrinus maidis*), sugarcane planthopper (*Perkinsiella saccharicida*), white backed planthopper (*Sogatella furcifera*), panicum planthopper (*Sogatella panicicola*), mulberry psyllid (*Anomoneura mori*), psyllid (*Calophya nigridorsalis*), Asian citrus psyllid (*Diaphorina citri*), psyllid (*Mesohomotoma camphorae*), abies sucker (*Psylla abieti*), jumping plant louse (*Psylla alni*), Japanese louse (*Psylla jamatonica*), apple psyllid (*Psylla mali*), black apple sucker (*Psylla malivorella*), larger pear sucker (*Psylla pyrisuga*), Tobira sucker (*Psylla tobirae*), camphor sucker (*Trioza camphorae*), sucker (*Trioza quercicola*), spiny whitefly (*Aleurocanthus spiniferus*), grape whitefly (*Aleurolobus taonabae*), sweet potato whitefly (*Bemisia tabaci*), citrus whitefly (*Dialeurodes citri*), greenhouse whitefly (*Trialeurodes vaporariorum*), silver leaf whitefly (*Bemisia argentifolii*), grape phylloxera (*Viteus vitifolii*), root aphid (*Aphidounguis mali*), woolly apple aphid (*Eriosoma*

*lanigerum*), sugarcane root aphid (*Geoica lucifuga*), pea aphid (*Acyrthosiphon pisum*), spiraea aphid (*Aphis citricola*), cowpea aphid (Aphis craccivora), willow aphid (*Aphis farinose yanagicola*), cotton-melon aphid (*Aphis gossypii*), foxglove aphid (*Aulacorthum solani*), leafcurl plum aphid (*Brachycaudus helichrysi*), cabbage aphid (*Brevicoryne brassicae*), tulip bulb aphid (*Dysaphis tulipae*), European birch aphid (*Euceraphis punctipennis*), mealy plum aphid (*Hyalopterus pruni*), mustard aphid (*Lipaphis erysimi*), chrysanthemum aphid (*Macrosiphoniella sanborni*), potato aphid (*Macrosiphum euphorbiae*), bean aphid (*Megoura crassicauda*), pear aphid (*Melanaphis siphonella*), apple leaf-curling aphid (*Myzus malisuctus*), plum aphid (*Myzus mumecola*), green peach aphid (*Myzus persicae*), onion aphid (*Neotoxoptera formosana*), apple aphid (*Ovatus malicolens*), waterlily aphid (*Rhopalosiphum nymphaeae*), wheat aphid (*Rhopalosiphum padi*), rice root aphid (*Rhopalosiphum rufiabdominalis*), wormwood root aphid (*Sappaphis piri*), pear aphid (*Schizaphis piricola*), corn leaf aphid (*Sitobion akebiae*), rose aphid (*Sitobion ibarae*), black citrus aphid (*Toxoptera aurantii*), black citrus aphid (*Toxoptera citricidus*), peach aphid (*Tuberocephalus momonis*), Formosan lettuce aphid (*Uroleucon formosanum*), greenbug aphid (*Schizaphis graminum*), giant mealybug (*Drosicha corpulenta*), cottony cushion scale (*Icerya purchasi*), Matsumoto mealybug (*Crisicoccus matsumotoi*), pine mealybug (*Crisicoccus pini*), pear mealybug (*Dysmicoccus wistariae*), citrus mealybug (*Planococcus citri*), Japanese mealybug (*Planococcus kraunhiae*), citrus mealybug (*Pseudococcus citriculus*), comstock mealybug (*Pseudococcus comstocki*), Indian white wax scale (*Ceroplastes ceriferus*), pink wax scale (*Ceroplastes rubens*), soft scale (*Coccus discrepans*), brown soft scale (*Coccus hesperidum*), citricola scale (*Coccus pseudomagnoliarum*), Chinese white-wax scale (*Ericerus pela*), European fruit scale (*Lecanium corni*), European peach scale (*Lecanium persicae*), citrus cottony scale (*Pulvinaria aurantii*), cottony citrus scale (*Pulvinaria citricola*), cottony mulberry scale (*Pulvinaria kuwacola*), black scale (*Saissetia oleae*), citrus scale (*Andaspis kashicola*), California red scale (*Aonidiella aurantii*), citrus yellow scale (*Aonidiella citrina*), coconut scale (*Aspidiotus destructor*), oleander scale (*Aspidiotus hederae*), Florida red scale (*Chrysomphalus ficus*), San Jose scale (*Comstockaspis perniciosa*), dupla scale (*Duplaspidiotus claviger*), purple scale (*Lepidosaphes beckii*), oystershell scale (*Lepidosaphes ulmi*), pear scale (*Lepholeucaspis japonica*), pear scale (*Parlatoreopsis pyri*), armored scale (*Parlatoria camelliae*), tea black scale (*Parlatoria theae*), black parlatoria scale (*Parlatoria ziziphi*), fern scale (*Pinnaspis aspidistrae*), camphor scale (*Pseudaonidia duplex*), Japanese camellia scale (*Pseudaonidia paeoniae*), white peach scale (*Pseudaulacaspis pentagona*), white prunicola Scale (*Pseudaulacaspis prunicola*), arrowhead scale (*Unaspis yanonensis*) and the like;

COLEOPTERA such as brown chafer (*Adoretus tenuimaculatus*), cupreous chafer (*Anomala cuprea*), soybean beetle (*Anomala rufocuprea*), flower chafer (*Eucetonia pilifera*), flower beetle (*Eucetonia roelofsi*), yellowish elongate chafer (*Heptophylla picea*), cockchafer (*Melolontha japonica*), Japanese cockchafer (*Mimela splendens*), smaller green flower chafer (*Oxycetonia jucunda*), Japanese beetle (*Popillia japonica*), variegated carpet beetle (*Anthrenus verbasci*), black carpet beetle (*Attagenus unicolor japonicus*), cigarette beetle (*Lasioderma serricorne*), powder post beetle (*Lyctus brunneus*), corn sap beetle (*Carpophilus dimidiatus*), dried fruit beetle (*Carpophilus hemipterus*), herbivorous ladybird beetle (*Epilachna vigintioctomaculata*), spotted ladybird beetle (*Epilachna vigintioctopunctata*), Mexican bean beetle (*Epilachna varivestis*), black fungus beetle (*Alphitobius laevigatus*), beetle (*Neatus picipes*), flour beetle (*Palorus ratzeburgii*), depressed flour beetle (*Palorus subdepressus*), yellow mealworm beetle (*Tenebrio molitor*), rust red flour beetle (*Tribolium castaneum*), red flour beetle (*Tribolium confusum*), Japanese blister beetle (*Epicauta gorhami*), long-horn beetle (*Aeolesthes chrysothrix*), whitespotted longicorn beetle (*Anoplophora malasiaca*), Japanese pine sawyer beetle (*Monochamus alternatus*), yellow-spotted longicorn beetle (*Psacothea hilaris*), grape borer (*Xylotrechus pyrrhoderus*), monkeypod roundheaded borer (*Xystrocera globosa*), bean weevil (*Acanthoscelides obtectus*), Chinese bean weevil (*Callosobruchus chinensis*), southern cowpea weevil (*Callosobruchus maculatus*), cucurbit leaf beetle (*Aulacophora femoralis*), leaf beetle (*Basilepta balyi*), tortoise beetle (*Cassida nebulosa*), brown-blackish beetle (*Chaetocnema concinna*), chrysomelid leaf beetle (*Colasposoma dauricum*), asparagus leaf beetle (*Crioceris quatuordecimpunctata*), rice rootworm (*Donacia provosti*), alder chrysomelid beetle (*Linaeidea aenea*), leaf beetle (*Luperomorpha tunebrosa*), two-striped leaf beetle (*Medythia nigrobilineata*), rice leaf beetle (*Oulema oryzae*), tropical legume leaf beetle (*Pagria signata*), daikon leaf beetle (*Phaedon brassicae*), crucifer flea beetle (*Phyllotreta striolata*), Colorado potato beetle (*Leptinotarsa decemlineata*), corn root worm (*Diabrotica* sp.), weevil (*Involvulus cupreus*), peach curculio (*Rhynchites heros*), sweet potato weevil (*Cylas formicarius*), apple blossom weevil (*Anthonomus pomorum*), weevil (*Ceuthorhynchidius albosuturalis*), chestnut weevil (*Curculio sikkimensis*), rice-plant weevil (*Echinocnemus squameus*), West Indian sweet potato weevil (*Euscepes postfasciatus*), lesser clover leaf weevil (*Hypera nigrirostris*), Alfalfa weevil (*Hypera postica*), rice water weevil (*Lissorhoptrus oryzophilus*), Australian tomato weevil (*Listroderes costirostris*), common leaf weevil (*Phyllobius armatus*), Japanese weevil (*Sitona japonicus*), boll weevil (*Anthonomus grandis*), rice weevil (*Sitophilus oryzae*), maize weevil (*Sitophilus zeamais*), hunting billbug (*Sphenophrus venatus vestitus*), pine shoot beetle (*Tomicus piniperda*) and the like;

THYSANOPTERA such as grass thrips (*Anaphothrips obscurus*), cocksfoot thrips (*Chirothrips manicatus*), black tea thrips (*Dendrothrips minowai*), flower thrips (*Frankliniella intonsa*), thrips (*Frankliniella lilivora*), greenhouse thrips (*Heliothrips haemorrhoidalis*), composite thrips (*Microcephalothrips abdominalis*), oriental soybean thrips (*Mycterothrips glycines*), mulberry thrips (*Pseudodendrothrips mori*), yellow tea thrips (*Scirtothrips dorsalis*), redbanded thrips (*Selenothrips rubrocinctus*), oriental rice thrips (*Stenchaetothrips biformis*), thrips (*Thrips alliorum*), loquat thrips (*Thrips coloratus*), Eurasian yellow flower thrips (*Thrips flavus*), banana flower thrips (*Thrips hawaiiensis*), chrysanthemum thrips (*Thrips nigropilosus*), melon thrips (*Thrips palmi*), western flower thrips (*Frankliniella occidentalis*), light brown soybean thrips (*Thrips setosus*), gladiolus thrips (*Thrips simplex*), onion thrips (*Thrips tabaci*), rye thrips (*Haplothrips aculeatus*), Chinese thrips (*Haplothrips chinensis*), predatory thrips (*Haplothrips kurdjumovi*), red clover thrips (*Haplothrips niger*), thrips (*Leeuwenia pasanii*), camphor thrips (*Liothrips floridensis*), lily thrips (*Liothrips vaneeckei*), thrips (*Litotetothrips pasaniae*), Japanese gallforming thrips (*Ponticulothrips diospyrosi*) and the like;

ORTHOPTERA such as American cockroach (*Periplaneta americana*), smokybrown cockroach (*Periplaneta fuliginosa*), Japanese cockroach (*Periplaneta japonica*), German cockroach (*Blattella germanica*), wild cockroach (*Blattella lituricollis*), Northern cone-headed long horn grasshopper (*Homorocoryphus jezoensis*), walker (*Homorocoryphus line-*

*osus*), mole cricket (*Gryllotalpa* sp.), small rice grasshopper (*Oxya hyla intricata*), rice grasshopper (*Oxya yezoensis*), migratory locust (*Locusta migratoria*) and the like;

DIPTERA such as rice crane fly (*Tipula aino*), fungus gnat (*Bradysia agrestis*), soybean pod gall midge (*Asphondylia* sp.), melon fly (*Dacus cucurbitae*), oriental fruit fly (*Dacus dorsalis*), Japanese orange fly (*Dacus tsuneonis*), Japanese cherry fruit fly (*Rhacochlaena japonica*), rice leaf miner (*Hydrellia griseola*), rice whorl maggot (*Hydrellia sasakii*), fruit fly (*Drosophila suzukii*), rice stem maggot (*Chlorops oryzae*), wheat stem maggot (*Meromyza nigriventris*), rice leaf miner (*Agromyza oryzae*), garden pea leaf miner (*Chromatomyia horticola*), tomato leaf miner (*Liriomyza bryoniae*), stone leek leaf miner (*Liriomyza chinensis*), American serpentine leaf miner (*Liriomyza trifolii*), vegetable leaf miner (*Liriomyza sativae*), pea leaf miner (*Liriomyza huidobrensis*), onion maggot (*Delia antiqua*), onion maggot (*Delia platura*), beet leaf miner (*Pegomya cunicularia*), green bottle fly (*Phormia regina*), house fly (*Musca domestica*), mosquito (*Culex pipiens pallens*), malaria vector (*Anopheles sinensis*), Asian tiger mosquito (*Aedes albopictus*), mosquito (*Culex pipiens molestus*) and the like;

HYMENOPTERA such as cabbage sawfly (*Athalia japonica*), turnip sawfly (*Athalia rosae ruficornis*), apple argid sawfly (*Arge mali*), large rose sawfly (*Arge pagana*), oriental chestnut gall wasp (*Dryocosmus kuriphilus*), wood ant (*Formica japonica*) and the like;

ACARINA such as broad mite (*Polyphagotarsonemus latus*), cyclamen mite (*Steneotarsonemus pallidus*), fungus mite (*Tarsonemus waitei*), straw itch mite (*Pyemotes ventricosus*), blue oat mite (*Penthaleus major*), citrus flat mite (*Brevipalpus lewisi*), privet mite (*Brevipalpus obovatus*), pineapple flat mite (*Dolichotetranychus floridanus*), persimmon false spider mite (*Tenuipalpus zhizhilashviliae*), flat mite (*Brevipalpus phoenicis*), Tuckerellid mite (*Tuckerella pavoniformis*), clover mite (*Bryobia praetiosa*), brown almond mite (*Bryobia rubrioculus*), apricot spider mite (*Eotetranychus boreus*), spider mite (*Eotetranychus geniculatus*), spider mite (*Eotetranychus pruni*), 6-spotted mite (*Eotetranychus sexmanaculatus*), tetranychid mite (*Eotetranychus smithi*), red spider mite (*Eotetranychus uncatus*), sugi spider mite (*Oligonychus hondoensis*), southern red mite (*Oligonychus ilicis*), larch mite (*Oligonychus karamatus*), citrus red mite (*Panonychus citri*), European red mite (*Panonychus ulmi*), carmine spider mite (*Tetranychus cinnabarinus*), tea red spider mite (*Tetranychus kanzawai*), 2-spotted spider mite (*Tetranychus urticae*), hawthorn spider mite (*Tetranychus viennensis*), pink tea rust mite (*Acaphylla theae*), tulip bulb mite (*Aceria tulipae*), pink citrus rust mite (*Aculops pelekassi*), plum rust mite (*Aculus fockeui*), apple rust mite (*Aculus schlechtendali*), ribbed tea mite (*Calacarus carinatus*), grape leaf rust mite (*Calepitrimerus vitis*), pear rust mite (*Epitrimerus pyri*), Japanese pear rust mite (*Eriophyes chibaensis*), flour mite (*Acarus siro*), brown legged grain mite (*Aleuroglyphus ovatus*), bulb mite (*Rhizoglyphus robini*), mould mite (*Tyrophagus putrescentiae*), tropical rat mite (*Ornithonyssus bacoti*), scrub typhus mite (*Leptotrombidium akamushi*), moth (*Leptotrombidium scutellaris*), chigger mite (*Leptotrombidium pallidum*) and the like;

TYLENCHIDA such as bent grass nematode (*Anguina agrostis*), ear-cockle nematode (*Anguina tritici*), potato rot nematode (*Ditylenchus destructor*), tobacco stunt nematode (*Tylenchorhynchus claytoni*), sugar cane stylet nematode (*Tylenchorhynchus martini*), stunt nematode (*Tylenchorhynchus* sp.), rice root nematode (*Hirschmanniella imamuri*), rice root nematode (*Hirschmanniella oryzae*), coffee root-lesion nematode (*Pratylenchus coffeae*), lesion nematode (*Pratylenchus convallariae*), root lesion nematode (*Pratylenchus fallax*), root lesion nematode of tea (*Pratylenchus loosi*), California root lesion nematode (*Pratylenchus neglectus*), Cobb's root lesion nematode (*Pratylenchus penetrans*), plant root lesion nematode (*Pratylenchus* sp.), Steiner's spiral nematode (*Helicotylenchus dihystera*), grass spiral nematode (*Helicotylenchus erythrinae*), spiral nematode (*Helicotylenchus* sp.), lance nematode (*Hoplolaimus* sp.), reniform nematode (*Rotylenchulus reniformis*), British spiral nematode (*Scutellonema brachyurum*), oat nematode (*Bidera avenae*), cactus cyst nematode (*Cactodera cacti*), cyst nematode (*Cryphodera* sp.), gold-plated nematode (*Globodera rostochiensis*), Japanese cyst nematode (*Heterodera elachista*), soybean cyst nematode (*Heterodera glycines*), clover cyst nematode (*Heterodera trifolii*), peanut root-knot nematode (*Meloidogyne arenaria*), camellia root-knot nematode (*Meloidogyne camelliae*), root-knot nematode (*Meloidogyne graminis*), northern root-knot nematode (*Meloidogyne hapla*), southern root-knot nematode (*Meloidogyne incognita*), root-knot nematode (*Meloidogyne* sp.), citrus root nematode (*Tylenchulus semipenetrans*), fungivorous nematode (*Aphelenchus avenae*) and the like;

DORYLAIMIDA such as needle nematode (*Longidorus martini*), needle nematode (*Longidorus* sp.), American dagger nematode (*Xiphinema americanum*), dagger nematode (*Xiphinema* sp.), stubby root nematode (*Trichodorus* sp.) and the like;

THYSANURA such as oriental silverfish (*Ctenolepisma villosa*), silverfish (*Lepisma saccharina*), firebrat (*Thermobia domestica*) and the like;

ISOPTERA such as drywood termite (*Cryptotermes domesticus*), Formosan subterranean termite (*Coptotermes formosanus*), Japanese subterranean termite (*Reticulitermes speratus*), fungus-growing termite (*Odontotermes formosanus*) and the like;

PSOCOPTERA such as booklouse (*Liposcelis bostrychophilus*) and the like;

SIPHONAPTERA such as dog flea (*Ctenocephalides canis*) and the like;

ANOPLURA such as body louse (*Pediculus humanus humanus*) and the like;

CHILOPODA such as house centipede (*Thereuronema tuberculata*) and the like;

DIPLOPODA such as flat-backed millipede (*Oxidus gracilis*) and the like; and

MOLLUSCA such as terrestrial slug (*Incilaria bilineata*) and the like.

Meanwhile, the composition for preventing harmful organisms of the present invention is effective against plant diseases of the following species. Concrete examples of the diseases and pathogens thereof which are the targets to control are illustrated below.

Examples thereof include rice diseases such as rice blast (*Pyricularia oryzae*), sheath blight (*Rhizoctonia solani*), helminthosporium leaf spot (*Cochliobolus miyabeanus*) and "bakanae" disease (*Gibberela fujikuroi*); wheat diseases such as powdery mildew (*Erysiphe graminis* f.sp.hordei; f.sp. tritici), stripe rust (*Puccinia striiformis; P. graminis; P. recondita; P. hordei*), leaf stripe (*Pyrenophora graminea*), net blotch (*Pyrenophora teres*), fusarium blight (*Fusarium calmorum; F. anenaceum; F. graminearum; Microdochium nivale*), snow rot (*Typhula* sp.; *Micronectriella nivale*), loose smut (*Ustilago tritici; U. nuda*), bunt (*Tilletia caries*), eye spot (*Pseudocercosporella herpotrichoides*), foot rot (*Rhizoctonia cerealis*), rhynchosporium leaf blotch (*Rhynchosporium secalis*), septoria leaf blotch (*Septoria tritici*) and glume blotch (*Leptosphaeria nodorum*); kidney bean, cucumber, tomato, strawberry, grape, potato, soybean, cabbage, Japanese eggplant and lettuce diseases such as gray mold (*Botrytis cinerea*); rice, cabbage, Japanese mustard spinach, tomato and Japanese eggplant diseases such as black scurf (*Rhizoctonia solani*); grape diseases such as downy mildew (*Plasmopora viticola*), rust (*Phakopsora ampelopsidis*), powdery mildew (*Uncinula necator*), anthracnose (*Elsinoe ampelina*) and ripe rot (*Glomerella cingulata*); apple diseases such as powdery mildew (*Podosphaera leucotricha*), scab (*Venturia inaequalis*), alternaria leaf spot (*Alternaria mali*), rust (*Gymnosporangium yamadae*), blossom blight (*Sclerotinia mali*) and canker (*Valsa mali*); pear diseases such as black spot (*Alternaria kikuchiana*), scab (*Venturia nashicola*), rust (*Gymnosporangium haraeanum*) and physalospora canker (*Physalospora piricola*); peach diseases such as brown rot (*Sclerotinia cinerea*), scab (*Cladosporium carpophilum*) and phomopsis rot (*Phomopsis sp.*); persimmon diseases such as anthracnose (*Gloeosporium kaki*), angular leaf spot (*Cercoapora kaki; Mycosphaerella nawae*) and powdery mildew (*Phyllactinia kakikora*); cucumber diseases such as downy mildew (*Pseudoperonospora cubensis*) and brown leaf spot (*Corynospora melonis*); gourd family diseases such as take-all disease (*Rizoctonia solani*), powdery mildew (*Sphaerotheca fuliginea*), anthracnose (*Colletotrichum lagenarium*) and gummy stem blight (*Mycosphaerella melonis*); tomato diseases such as early blight (*Alternaria solani*), leaf mold (*Cladosporium fulvam*) and late blight (*Phytophthora infestans*); eggplant diseases such as powdery mildew (*Erysiphe cichoracorum*) and mycovellosiella leaf spot (*Mycovellosiella nattrassii*); brassicaceae vegetable diseases such as alternaria leaf spot (*Alternaria japonica*), white spot (*Cercosporella barassicae*), clubroot (*Plasmodiophora brassicae*) and root rot (*Phoma lingam*); leek diseases such as rust (*Puccinia allii*) and alternaria leaf spot (*Alternaria porri*); spinach and Welsh onion diseases such as filamentous fungus (*Fusarium oxysporum*); soybean diseases such as purple speck (*Cercospora kikukuchii*), sphaceloma scab (*Elsinoe glycinnes*), pod and stem blight (*Diaporthe phaseololum*) and soybean rust (*Phakopsora pachyrhizi*); kidney bean diseases such as anthracnose (*Colletotrichum lindemuthianum*); peanut diseases such as leaf spot (*Mycosphaerella personatum*) and brown leaf spot (*Cercospora arachidicola*); pea diseases such as powdery mildew (*Erysiphe pisi*) and downy mildew (*Peronospora pisi*); potato diseases such as early blight (*Alternaria solani*), black scurf (*Rhizoctonia solani*) and late blight (*Phytophthora infestans*); broad bean diseases such as downy mildew (*Peronospora viciae*) and phytophthora rot (*Phytophthora nicotianae*); tea diseases such as net blister blight (*Exobasidium reticulatum*), white scab (*Elsinoe leucospila*) and anthracnose (*Colletotrichum theae-sinensis*); tobacco diseases such as brown spot (*Alternaria longipes*), powdery mildew (*Erysiphe cichoracearum*), anthracnose (*Colletotrichum tabacum*) and *Phytophthora* blight (*Phytophthora parasitica*); beat diseases such as cercospora leaf spot (*Cercospora beticola*); rose diseases such as black spot (*Diplocarpon rosae*), powdery mildew (*Sphaerotheca pannosa*) and wilt (*Phytophthora megasperma*); chrysanthemum diseases such as leaf blotch (*Septoria chrysanthemi-indici*) and rust (*Puccinia horiana*); strawberry diseases such as powdery mildew (*Sphaerotheca humuli*) and root rot (*Phytophthora nicotianae*); kidney bean, cucumber, tomato, potato, strawberry, soybean, cabbage, Japanese eggplant and lettuce diseases such as sclerotinia rot (*Sclerotinia sclerotiorum*); citrus diseases such as pod and stem blight (*Diaporthe citri*) and citrus scab (*Elsinoe fawcettii*); carrot diseases such as leaf bright (*Alternaria dauci*); grass diseases such as brown patch (*Rhizoctonia solani*), dollar spot (*Sclerotinia homoeocarpa*) and large patch disease (*Rhizoctonia solani*), and the like.

In order to control various kinds of harmful organisms, the composition for preventing harmful organisms of the present invention may be used in the plants which are expected to create harmful organisms in an amount effective in controlling harmful organisms as intact, as appropriately diluted with water and the like, or as suspended. For example, the composition may be dispersed on the stem and leaf against harmful organisms caused in fruit trees, grain, vegetables and the like. In addition thereto, the composition for preventing harmful organisms can be used by being applied to the soil and the like for letting the root to absorb it. Examples of such treatment include seed treatment such as soaking a seed into a chemical solution, dressing for seeds, treatment by oxygen supplier and the like, soil treatment, row application, seedbed soil incorporation, nursery pot application, planting pit treatment, plant foot treatment, top dressing, nursery box application for rice, submerged application or the like. In addition, it can be applied to nutrient solution in the nutrient solution culture (hydroponic culture), and it can be used by means of smoking or trunk injection as well. Furthermore, the composition can be dispersed into, for example, stored grain harmful insects, house and household harmful insects, hygienic harmful insects, forest harmful organisms and the like. In addition thereto, it can also be used for coating on residential building materials, smoking, bait casting or the like.

The composition for preventing harmful organisms of the present invention is generally used as formulated in a useful manner according to the usual method of formulation in agricultural and horticultural chemicals. That is, it may be mixed with an appropriate inert carrier, or as needed, adjuvant in a suitable proportion, and may be prepared in a suitable formulation form such as a suspension, emulsifiable concentrate, soluble concentrate, wettable powder, granules, dust, tablets or the like through dissolution, separation, suspension, mixing, impregnation, absorption or adhering, prior to use.

The inert carrier which can be used in the present invention may be either solid or liquid. Such a material which can be an inert solid carrier includes, for example, soybean flour, cereal flour, wood flour, bark flour, saw dust, powdered tobacco stalks, powdered walnut shells, bran, cellulose powder, residue after plant extraction, synthetic polymers such as ground synthetic resins or the like, inorganic mineral powder such as clays (for example, kaolin, bentonite, acid clay and the like), talcs (for example, talc, pyrophyllite and the like), silica powders or flakes (for example, diatomaceous earth, silica sand, mica, white carbon [synthetic, high-dispersion silicic acid, also called finely divided hydrated silicon, hydrated silicic acid, some of commercially available products contain calcium silicate as the major component]), activated carbon, powdered sulfur, pumice stone, calcined diatomite, brick groats, fly ash, sand, calcium carbonate powder, calcium phosphate powder; chemical fertilizers such as ammonium sulfate, ammonium phosphate, ammonium nitrate, urea, ammonium chloride and the like; compost and the like. These carriers can be used singly or in combination of two or more kinds.

A material which can be an inert liquid carrier is selected from such a material which itself has solvency or which does not have such solvency but is capable of dispersing an active ingredient compound with the aid of an adjuvant. The following are typical examples of the carrier and can be used singly or in combination of two or more kinds. Examples thereof include water, alcohols (for example, methanol, ethanol, isopropanol, butanol, ethylene glycol and the like), ketones (for example, acetone, methylethyl ketone, methylisobutyl ketone, diisobutyl ketone, cyclohexanone and the like), ethers (for example, diethyl ether, dioxane, cellosolve, diisopropyl ether, tetrahydrofuran and the like), aliphatic hydrocarbons (for example, kerosene, mineral oil and the like), aromatic hydrocarbons (for example, benzene, toluene, xylene, solvent naphtha, alkyl naphthalene and the like), halogenated hydrocarbons (for example, dichloromethane, chloroform, carbon tetrachloride, chlorobenzene and the like), esters (for example, ethyl acetate, butyl acetate, ethyl propionate, diisobutyl phthalate, dibutyl phthalate, dioctyl phthalate and the like), amides (for example, dimethylformamide, diethylformamide, dimethylacetamide and the like) and nitriles (for example, acetonitrile and the like).

As an adjuvant, representative adjuvants mentioned below can be exemplified. These adjuvants can be used depending on purposes and used singly or in combination of two or more kinds or cannot be used at all in some cases.

When aiming at emulsification, dispersion, solubilization and/or moistening of an active ingredient compound, a surfactant can be used. Examples thereof include surfactants such as polyoxyethylene alkyl ethers, polyoxyethylene alkylaryl ethers, polyoxyethylene higher fatty acid esters, polyoxyethylene resin acid asters, polyoxyethylene sorbitan monolaurate, polyoxyethylene sorbitan monooleate, alkylarylsulfonates, naphthalenesulfonates, lignin sulfonates, higher alcohol sulfate esters and the like.

Furthermore, when aiming at dispersion stabilization, adhesion and/or binding of an active ingredient compound, the following adjuvants can be used. Examples thereof include casein, gelatin, starch, methyl cellulose, carboxymethyl cellulose, gum arabic, polyvinyl alcohols, pine oil, bran oil, bentonite, xanthan gum, lignin sulfonates and the like.

In order to improve fluidity of a solid product, the following adjuvants can be used. Examples thereof include waxes, stearates, alkyl phosphates and the like. Adjuvants such as naphthalenesulfonic acid condensation products and polycondensates of phosphates may be used as a peptizer for suspendible products. As a defoaming agent, adjuvants such as silicon oils can also be used.

Incidentally, the composition for preventing harmful organisms of the present invention is stable to light, heat, oxidation and the like. However, an anti-oxidant or an ultraviolet absorber including a phenol derivative, for example, BHT (2,6-di-t-butyl-4-methylphenol) and BHA (butylated hydroxyanisole), a bisphenol derivative or arylamines such as phenyl-α-naphthylamine, phenyl-β-naphthylamine, condensates of phenetidine and acetone or a benzophenone-based compound is added as a stabilizer in a proper amount when necessary, whereby it is possible to obtain a composition with much stabilized effect.

The composition for preventing harmful organisms of the present invention contains one or more compounds of other insecticides, miticides or fungicides in an amount of 0.001 to 95 weight % and preferably in 0.01 to 80 weight %.

Furthermore, the amount of the active ingredient of the composition for preventing harmful organisms of the present invention is usually from 0.5 weight % to 20 weight % for dust formulation, from 5 weight % to 50 weight % for emulsifiable concentrate, from 10 weight % to 90 weight % for wettable powder, from 0.1 weight % to 20 weight % for granule, and from 10 weight % to 90 weight % for flowable formulation. On the other hand, the amount of the carrier in each formulation is usually from 60 weight % to 99 weight % for dust formulation, from 40 weight % to 95 weight % for emulsifiable concentrate, from 10 weight % to 90 weight % for wettable powder, from 80 weight % to 99 weight % for granule, and from 10 weight % to 90 weight % for flowable formulation. Meanwhile, the amount of the adjuvant is usually from 0.1 weight % to 20 weight % for dust formulation, from 1 weight % to 20 weight % for emulsifiable concentrate, from 0.1 weight % to 20 weight % for wettable powder, from 0.1 weight % to 20 weight % for granule, and from 0.1 weight % to 20 weight % for flowable formulation.

In order to control various kinds of harmful organisms, the composition for preventing harmful organisms of the present invention may be applied to crops which are expected to create harmful organisms or places where such creation is not desired in an amount effective in controlling harmful organisms as intact, as appropriately diluted with water or the like, or as suspended, and used accordingly. The amount thereof is varied according to various factors such as purpose, target harmful organisms, reared status of crops, occurrence trend of harmful organisms, weather, environmental conditions, type of formulation, method of application, place of application, time of application and the like. However, usually, the amount may be properly selected in a range of 0.1 g to 1000 g and preferably in a range of 1 g to 500 g as an active ingredient per 1 are.

Insecticides, miticides and nematicides which can be used in combination with the compound represented by the general formula (1) of the present invention include, for example, organophosphate-based insecticides such as azinphos-methyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridaphenthion, pirimiphos-methyl, fenitrothion, fenthion, phenthoate, flupyrazofos, prothiofos, propaphos, profenofos, phoxim, phosalone, phosmet, formothion, phorate, malathion, mecarbam, mesulfenfos, methamidophos, methidathion, parathions, parathion-methyl, monocrotophos, trichlorfon, EPN, isazofos, isamidofos, cadusafos, diamidafos, dichlofenthion, thionazin, fenamiphos, fosthiazate, fosthietan, phosphocarb, DSP, ethoprophos and the like; carbamate-based insecticides such as alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl and the like; synthetic pyrethroid-based insecticides such as acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox and the like, and various isomers thereof; nereistoxin-based insecticides such as cartap, thiocyclam, bensultap and the like; neonicotinoid-based insecticides such as acetamiprid, imidacloprid, clothianidin, dinotefuran, thiacloprid, thiamethoxam, nitenpyram and the like; insect growth regulators such as chlorfluazuron, diflubenzuron, teflubenzuron, triflumuron, novaluron, noviflumuron, bistrifluoron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate and the like; organochlorine-based insecticides such as endosulfan, chlorfenson, chlorobenzilate, dicofol, bromopropylate and the like; phenylpyrazole-based insecticides such as acetoprole, fipronil, ethiprole and the like; natural insecticidal products such as pyrethrins, rotenone, nicotine sulfate, BT agent, spinosad and the like; miticides such as abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pylimidifen, fenazaquin, fenothiocarb, fenpyroximate, fluacrypyrim, fluazinam, flufenzine, hexythiazox, propargite, benzomate, polynactin complex, milbemectin, lufenuron, mecarbam, methiocarb, mevinphos, halfenprox and the like; azadirachtin, diafenthiuron, indoxacarb, emamectin benzoate, potassium oleate, sodium oleate, chlorfenapyl, tolfenpyrad, pymetrozine, fenoxycarb, hydramethylnon, hydroxy propyl starch, pyridalyl, flufenerim, flubendiamide, flonicamid, metaflumizole, lepimectin, TPIC (tripropylisocyanurate), albendazole, oxibendazole, oxfendazole, trichlamide, fensulfothion, fenbendazole, levamisol hydrochloride, morantel tartrate, dazomet, metamsodium and compounds represented by the aforementioned general formulae (A) and (B).

Fungicides which can be used in combination with the compound represented by the general formula (1) of the present invention include, for example, azole-based fungicides such as triadimefon, hexaconazole, propiconazole, ipconazole, prochloraz, triflumizole, tebconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazol, imazalil, furametpyr, thifluzamide, etridiazole, oxpoconazole, oxpoconazole-fumarate, pefurazoate, prothioconazole and the like; pyrimidine-based fungicides such as pyrifenox, fenarimol, nuarimol, bupirimate and the like; anilinopyrimidine-based fungicides such as mepanipyrim, cyprodinil, pyrimethanil and the like; acylalanine-based fungicides such as metalaxyl, oxadinil, benalaxyl and the like; benzimidazole-based fungicides such as thiophanate, thiophanate-methyl, benomyl, carbendazim, fuberidazole, thiabendazole and the like; dithiocarbamate-based fungicides such as mancozeb, propineb, zineb, metiram, maneb, ziram, thiram and the like; organochlorine-based fungicides such as chlorothalonil and the like; carboxamide-based fungicides such as ethaboxam, oxycarboxin, carboxin, flutolanil, silthiofam, mepronil and the like; morpholine-based fungicides such as dimethomorph, fenpropidin, fenpropimorph, spiroxamine, tridemorph, dodemorph, flumorph and the like; strobilurin-based fungicides such as azoxystrobin, kresoxim-methyl, metominostrobin, orysastrobin, fluoxastrobin, trifloxystrobin, dimoxystrobin, pyraclostrobin, picoxystrobin and the like; dicarboximide-based fungicides such as iprodione, procymidone, vinclozolin, chlozolinate and the like; soil fungicides such as flusulfamide, dazomet, methyl isothiocyanate, chloropicrin, methasulfocarb, hydroxyisoxazole, hydroisoxazole-potassium, echlomezole, D-D (1,3-dichloropropene), carbam (metam-sodium) and the like; copper fungicides such as basic copper chloride, basic copper sulfate, copper nonylphenol sulfonate, copper-oxinate, DBEDC, copper sulfate anhydride, copper sulfate pentahydrate, copper hydroxide and the like; inorganic fungicides such as sulfur, wettable sulfur, calcium polysulfide, zinc sulfate, fentin, sodium hydrogen carbonate, potassium hydrogen carbonate, sodium hypochlorote, silver and the like; organophosphate-based fungicides such as edifenphos, tolclofos-methyl, fosetyl, iprobenfos, dinocap, pyrazophos and the like; melanin biosynthesis inhibitor-based fungicides such as carpropamid, fthalide, tricyclazole, pyroquilon, diclocymet, fenoxanil and the like; antibiotic fungicides such as kasugamycin, validamycinA, polyoxins, blastcidin-S, oxytetracycline, mildiomycin, streptomycin and the like; natural product-based fungicides such as rape seed oil, machine oil and the like; carbamate-based fungicides such as benthiavalicarb-isopropyl, iprovalicarb, propamocarb, diethofencarb and the like; pyrrole-based fungicides such as fluoroimide, fludioxonil, fenpiclonil and the like; quinoline-based fungicides such as quinoxyfen, oxolinic acid and the like; phthalimide-phthalonitrile-based fungicides such as chlorothalonil, captan, folpet and the like; plant activators for leading resistance to plant diseases such as probenazole, acibenzolar-5-methyl, tiadinil and the like; cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanid, triforine, isoprothiolane, ferimzone, diclomezine, tecloftalam, pencycuron, quinomethionate, iminoctadine-triacetate, iminoctadine-albesilate, amobam, polycarbamate, thiadiazin, chloroneb, nickel dimethyldithiocarbamate, guazatine, dodecylguanidine-acetate, quintozene, tolylfluanid, anilazine, nitrothal-isopropyl, fenitropan, dimethirimol, benthiazole, harpin protein, flumetover, mandipropamide, penthiopyrad and the like. Of the compounds cited above, there are compounds capable of obtaining stereoisomers, whereas these isomers are also included in the present invention.

The composition for preventing harmful organisms of the present invention can be used as a mixture with a plant protectant such as a herbicide, a fertilizer, a soil conditioner, a plant growth regulator and the like, or a material, whereby it is possible to prepare a multi-purpose composition with a more excellent effect cam be prepared as well.

EXAMPLES

The typical examples are illustrated with reference to the following Examples for preparing the compound represented by the general formula (1) of the present invention. However, the present invention is not restricted to these Examples.

Example 1-1

Preparation of
N-(2,6-dimethyl-4-heptafluoroisopropyl)phenyl
3-nitrobenzamide

To a solution of 20.0 g of 2,6-dimethyl-4-heptafluoroisopropylaniline and 11.0 g of pyridine added to 100 ml of tetrahydrofuran and stirred at room temperature was introduced dropwise 13.0 g of 3-nitrobenzoyl chloride dissolved in 20 ml of tetrahydrofuran little by little. The reaction solution was stirred at room temperature for 10 hours, and then ethyl acetate and water were added thereto. Solution separation was performed for taking out an organic layer. The organic layer was dried over anhydrous magnesium sulfate. The solution was filtered off, the filtrate was collected, and the solvent was removed under a reduced pressure to obtain a residue. The resulting residue was washed with a mixed solvent of hexane and diisopropyl ether to obtain 26.0 g of the desired product (Yield: 85%) as a white solid.

$^1$H-NMR (CDCl$_3$, ppm) δ 2.33 (6H, s), 7.37 (2H, s), 7.68 (1H, s), 7.72 (1H, t, J=8.1 Hz), 8.28 (1H, d, J=8.1 Hz), 8.44 (1H, dd, J=1.2, 8.1 Hz), 8.75 (1H, t, J=1.2 Hz)

Example 1-2

Preparation of
N-(2,6-dimethyl-4-heptafluoroisopropyl)phenyl
3-aminobenzamide

To a solution of 0.90 g of N-(2,6-dimethyl-4-heptafluoroisopropyl)phenyl 3-nitrobenzamide and 1.56 g of anhydrous stannous chloride added to 25 ml of ethanol and stirred at room temperature was added 2 ml of concentrated hydrochloric acid, and the resulting mixture was stirred at 60 degree centigrade for 1 hour. The reaction solution was returned to room temperature, poured into water, and then neutralized with potassium carbonate. Ethyl acetate was added thereto, the insoluble substance was filtered off, and then the organic layer was separated and dried over anhydrous magnesium sulfate. The solution was filtered off, the filtrate was collected, and the solvent was removed under a reduced pressure to obtain a residue. The resulting residue was washed with hexane to obtain 0.44 g of the desired product (Yield: 53%) as a white solid.

$^1$H-NMR (CDCl$_3$, ppm) δ 2.34 (6H, s), 3.87 (2H, broad), 6.86-6.89 (1H, m), 7.20-7.35 (6H, m)

Example 1-3

Preparation of N-(2,6-dimethyl-4-heptafluoroisopropyl)phenyl 3-(benzoylamino)benzamide (Compound No. 10)

To a solution of 0.25 g of N-(2,6-dimethyl-4-heptafluoroisopropyl)phenyl 3-aminobenzamide and 0.06 g of pyridine added to 5 ml of tetrahydrofuran and stirred at room temperature was introduced dropwise 0.09 g of benzoyl chloride dissolved in 1 ml of tetrahydrofuran. The reaction solution was stirred at room temperature for 1 hour, and then ethyl acetate and 1N hydrochloric acid were added thereto for separating an organic layer. The organic layer was washed with saturated baking soda solution one time and then dried over anhydrous magnesium sulfate. The solution was filtered off, the filtrate was collected and the solvent was removed under a reduced pressure to precipitate a solid. The precipitated solid was washed with diisopropyl ether to obtain 0.29 g of the desired product (Yield: 92%) as a white solid.

$^1$H-NMR (DMSO-d$_6$, ppm) δ2.37 (6H, s), 7.34 (2H, s), 7.46-7.57 (4H, m), 7.75 (1H, d, J=7.8 Hz), 7.98-8.01 (2H, m), 8.12 (1H, d, J=7.3 Hz), 8.34 (1H, s), 8.87 (1H, s), 9.66 (1H, s).

Example 2-1

Preparation of N-(2,6-dimethyl-4-heptafluoroisopropyl)phenyl-N-methyl 3-nitrobenzamide To a solution of 0.18 g of 60% sodium hydride suspended in 15 ml of tetrahydrofuran was introduced dropwise 2.0 g of N-(2,6-dimethyl-4-heptafluoroisopropyl)phenyl 3-nitrobenzamide dissolved in 5 ml of tetrahydrofuran at room temperature. The reaction solution was stirred at room temperature for 30 minutes, and then 0.65 g of methyl iodide dissolved in 5 ml of tetrahydrofuran was introduced dropwise. Subsequently, the reaction solution was heated to 50 degree centigrade and stirred for 4 hours and then returned to room temperature, and ethyl acetate and water were added thereto. An organic layer was separated, washed with water one time, and then dried over anhydrous magnesium sulfate. The solvent was removed under a reduced pressure. The resulting residue was purified by silica gel column chromatography using an eluent (development solvent; hexane:ethyl acetate=6:1) to obtain 1.73 g of the desired product (Yield: 84%) as a white solid.

$^1$H-NMR (CDCl$_3$, ppm) δ2.31 (6H, s), 3.38 (3H, s), 7.27 (2H, s), 7.37 (1H, t, J=7.8 Hz), 7.62-7.65 (1H, m), 8.05 (1H, t, J=2.0 Hz), 8.11-8.14 (1H, m).

Example 2-2

Preparation of N-(2,6-dimethyl-4-heptafluoroisopropyl)phenyl-N-methyl 3-aminobenzamide A solution of 1.50 g of N-(2,6-dimethyl-4-heptafluoroisopropyl)phenyl-N-methyl 3-nitrobenzamide and 0.15 g of 10% palladium carbon added to 20 ml of methanol was stirred in an ordinary pressure, in a hydrogen atmosphere for 2 hours. The catalyst was filtered out and then the solvent was removed under a reduced pressure. Subsequently, the precipitated solid was washed with hexane to obtain 1.24 g of the desired product (Yield: 88%) as a white solid.

$^1$H-NMR (CDCl$_3$, ppm) δ2.27 (6H, s), 3.31 (3H, s), 3.80 (2H, broad), 6.40-6.43 (1H, m), 6.54-6.58 (1H, m), 6.71 (1H, t, J=2.0 Hz), 6.76-6.86 (1H, m), 7.22 (2H, s).

Example 2-3

Preparation of N-(2,6-dimethyl-4-heptafluoroisopropyl)phenyl-N-methyl 3-(benzoylamino)benzamide (Compound No. 1478)

A desired title product was prepared according to the conditions as described in Example 1-3 as a white solid.

$^1$H-NMR (DMSO-d$_6$, ppm) δ2.29 (6H, s), 3.24 (3H, s), 6.84 (1H, d, J=7.8 Hz), 7.12 (1H, t, J=7.8 Hz), 7.33 (2H, s), 7.50-7.64 (4H, m), 7.85-7.88 (2H, m), 7.98-8.03 (1H, m), 10.22 (1H, s).

Example 3

Preparation of N-(2,6-dimethyl-4-heptafluoroisopropyl)phenyl 3-[(2-chloropyridin-3-yl)carbonylamino]benzamide (Compound No. 106)

To a solution of 0.6 g of N-(2,6-dimethyl-4-heptafluoroisopropyl)phenyl 3-aminobenzamide and 0.4 g of pyridine added to 10 ml of tetrahydrofuran was added 0.35 g of 2-chloronicotic acid chloride hydrochloride, and the resulting solution was stirred at room temperature for 4 hours. Ethyl acetate was added thereto and then the reaction solution was washed with saturated baking soda solution two times, and the solvent was removed under a reduced pressure. The precipitated solid was washed with a mixed solvent of hexane and diisopropyl ether and dried to obtain 0.64 g of the desired product (Yield: 75%) as a white solid.

$^1$H-NMR (DMSO-d$_6$, ppm) δ2.30 (6H, s), 7.45 (2H, s), 7.54-7.60 (2H, m), 7.77-7.80 (1H, m), 7.95 (1H, d, J=7.8 Hz), 8.10-8.12 (1H, m), 8.30 (1H, s), 8.54-8.59 (1H, m), 10.03 (1H, s), 10.88 (1H, s).

Example 4

Preparation of N-(2,6-dimethyl-4-heptafluoroisopropyl)phenyl 3-[(pyridin-3-yl)carbonylamino]benzamide (Compound No. 101)

A solution of 99 mg of nicotic acid and 153 mg of 1,1'-oxalyldiimidazole added to 10 ml of acetonitrile was stirred at room temperature for 15 minutes and at 40 degree centigrade for 40 minutes. The reaction solution was returned to room temperature, and then 300 mg of N-(2,6-dimethyl-4-heptafluoroisopropyl)phenyl 3-aminobenzamide was added thereto and stirred at 60 degree centigrade for 5 hours. Subsequently, the solvent was removed under a reduced pressure to obtain a residue. While ethyl was added to the resulting residue, the organic solvent was washed with saturated baking soda solution two times, and the solvent was removed under a reduced pressure again. The obtained residue was purified by silica gel column chromatography using an eluent (development solvent; hexane:ethyl acetate=1:3) to obtain 70 mg of the desired product (Yield: 18%) as a white solid.

$^1$H-NMR (DMSO-d$_6$, ppm) δ2.30 (6H, s), 7.45 (2H, s), 7.54-7.61 (2H, m), 7.78 (1H, d, J=8.3 Hz), 8.06 (1H, d, J=7.3 Hz), 8.32-8.35 (2H, m), 8.77-8.79 (1H, m), 9.15 (1H, d, J=1.5 Hz), 10.00 (1H, s), 10.66 (1H, s).

Example 5-1

Preparation of N-methyl-2-bromo-4-heptafluoroisopropyl-6-methylaniline

To a solution of 1.0 g of N-methyl-4-heptafluoroisopropyl-2-methylaniline added to 5 ml of N,N-dimethylformamide was introduced dropwise 0.8 g of N-bromosuccinic acid imide dissolved in 3 ml of N,N-dimethylformamide. The resulting solution was stirred at room temperature for 5 hours, and then ethyl acetate and water were added thereto for separating an organic layer. The organic layer was washed with water two times, and then dried over anhydrous magnesium sulfate and the solvent was removed under a reduced pressure to obtain a residue. The resulting residue was purified by silica gel column chromatography using an eluent (development solvent; hexane:ethyl acetate=9:1) to obtain 0.86 g of the desired product (Yield: 68%) as red oil.

$^1$H-NMR (CDCl$_3$, ppm) δ2.41 (3H, s), 2.93 (3H, s), 3.90 (1H, broad), 7.23 (1H, s), 7.54 (1H, s).

Example 5-2

Preparation of N-(2-bromo-4-heptafluoroisopropyl-6-methyl)phenyl-N-methyl 3-(benzoylamino)benzamide (Compound No. 1479)

A desired title product was prepared from N-methyl-2-bromo-4-heptafluoroisopropyl-6-methylaniline according to the conditions as described in Example 1 as a white solid.

$^1$H-NMR (DMSO-d$_6$, ppm) δ2.41 (3H, s), 3.25 (3H, s), 6.95 (1H, dd, J=1.5, 7.8 Hz), 7.16 (1H, t, J=7.8 Hz), 7.50-7.64 (4H, m), 7.68 (1H, s), 7.86-7.88 (2H, m), 7.93 (1H, t, J=1.5 Hz), 7.98-8.00 (1H, m), 10.24 (1H, s).

Example 6

Preparation of N-(2,6-dimethyl-4-heptafluoroisopropyl)phenyl-N-methyl 3-(N-methylbenzoylamino)benzamide (Compound No. 1487)

To a solution of 40 mg of 60% sodium hydride suspended in 10 ml of tetrahydrofuran was introduced dropwise 0.3 g of N-(2,6-dimethyl-4-heptafluoroisopropyl)phenyl-N-methyl 3-(benzoylamino)benzamide dissolved in 5 ml of tetrahydrofuran at room temperature. The reaction solution was stirred at room temperature for 1 hour, and then 0.16 g of methyl iodide dissolved in 5 ml of tetrahydrofuran was introduced dropwise. Subsequently, the reaction solution was heated to 50 degree centigrade, stirred for 4 hours and then returned to room temperature, and ethyl acetate and water were added thereto. An organic layer was separated and washed with water one time, and then dried over anhydrous magnesium sulfate. The solvent was removed under a reduced pressure. The resulting residue was washed with diisopropyl ether to obtain 1.73 g of the desired product (Yield: 84%) as a white solid.

$^1$H-NMR (DMSO-d$_6$, ppm) δ2.20 (6H, s), 3.08 (3H, s), 3.20 (3H, s), 6.93-7.39 (10H, m), 7.45-7.51 (1H, m).

Example 7-1

Preparation of N-(2,6-dimethyl-4-heptafluoroisopropyl)phenyl 3-aminobenzthioamide 0.35 g of N-(2,6-dimethyl-4-heptafluoroisopropyl)phenyl 3-aminobenzamide and 0.19 g of a Lawson reagent were added to 10 ml of toluene, and the resulting solution was heated and stirred at a reflux temperature for 6 hours. The reaction solution was concentrated under a reduced pressure for removing the solvent, and then the obtained residue was purified by silica gel column chromatography using an eluent (development solvent; hexane:ethyl acetate=3:1) to obtain 0.07 g of the desired product (Yield: 20%).

$^1$H-NMR (CDCl$_3$, ppm) δ2.36 (6H, s), 3.87 (2H, broad-s), 6.84-6.87 (1H, m), 7.18-7.24 (2H, m), 7.33 (1H, s), 7.39 (2H, s), 8.56 (1H, broad-s).

Example 7-2

Preparation of N-(2,6-dimethyl-4-heptafluoroisopropyl)phenyl 3-(benzoylamino)benzthioamide (Compound No. 2201)

A desired title product was prepared from N-(2,6-dimethyl-4-heptafluoroisopropyl)phenyl 3-aminobenzthioamide according to the conditions as described in Example 1-3.

$^1$H-NMR (CDCl$_3$, ppm) δ2.38 (6H, s), 7.25-8.00 (11H, m), 8.34 (1H, s), 8.85 (1H, broad.).

Example 8

Preparation of N-(2,6-dimethyl-4-heptafluoroisopropyl)phenyl 3-(phenylthiocarbonylamino)benzamide (Compound No. 2202) and N-(2,6-dimethyl-4-heptafluoroisopropyl)phenyl 3-(phenylthiocarbonylamino)benzthioamide (Compound No. 2203)

A solution of 0.37 g of N-(2,6-dimethyl-4-heptafluoroisopropyl)phenyl 3-(benzoylamino)benzamide and 0.30 g of a Lawson reagent added to 10 ml of toluene was stirred at 70 degree centigrade for 6 hours. The reaction solution was concentrated under a reduced pressure, and the resulting residue was purified by silica gel column chromatography using an eluent (development solvent; hexane ethyl acetate=3:1) to prepare 0.18 g of N-(2,6-dimethyl-4-heptafluoroisopropyl)phenyl 3-(phenylthiocarbonylamino)benzamide (Yield: 47%) and 0.05 g of N-(2,6-dimethyl-4-heptafluoroisopropyl)phenyl 3-(phenylthiocarbonylamino)benzthioamide (Yield: 13%) respectively.

Physical properties of Compound No. 2202

$^1$H-NMR (CDCl$_3$, ppm) δ2.36 (6H, s), 7.37 (2H, s), 7.47-7.61 (5H, m), 7.85-8.03 (4H, m), 8.57 (1H, s), 9.18 (1H, s).

Physical properties of Compound No. 2203

$^1$H-NMR (CDCl$_3$, ppm) δ2.38 (6H, s), 7.41 (2H, s), 7.45-7.55 (4H, m), 7.90-7.96 (4H, m), 8.57 (1H, broad), 8.74 (1H, broad), 9.18 (1H, broad).

Example 9-1

Preparation of N-benzyl-N-(2,6-dimethyl-4-heptafluoroisopropyl)phenyl 3-nitrobenzamide A desired title product was prepared according to the method as described in Example 6 using N-(2,6-dimethyl-4-heptafluoroisopropyl)phenyl 3-nitrobenzamide and benzyl bromide.

Example 9-2

Preparation of N-benzyl-N-(2,6-dimethyl-4-heptafluoroisopropyl)phenyl 3-(2-fluorobenzoylamino)benzamide A desired title product was prepared according to the method as described in Examples 1-2 and 1-3 using N-benzyl-N-(2,6-dimethyl-4-heptafluoroisopropyl)phenyl 3-nitrobenzamide and 2-fluorobenzoyl chloride.

Example 9-3

Preparation of N-benzyl-N-(2,6-dimethyl-4-heptafluoroisopropyl)phenyl

3-[N-ethyl-N-(2-fluorobenzoyl)amino]benzamide desired title product was prepared according to the method as described in Example 6 using N-benzyl-N-(2,6-dimethyl-4-heptafluoroisopropyl)phenyl 3-(2-fluorobenzoylamino)benzamide and ethyl iodide.

Example 9-4

Preparation of N-(2,6-dimethyl-4-heptafluoroisopropyl)phenyl 3-[N-ethyl-N-(2-fluorobenzoyl)amino]benzamide (Compound No. 1206)

A solution of 1.07 g of N-benzyl-N-(2,6-dimethyl-4-heptafluoroisopropyl)phenyl 3-[N-ethyl-N-(2-fluorobenzoyl)amino]benzamide and 0.15 g of 10% palladium carbon added to 10 ml of methanol was stirred at 45 degree centigrade in a hydrogen atmosphere for 6 hours. The catalyst was filtered out and then the solvent was removed under a reduced pressure. Subsequently, the obtained residue was purified by silica gel (NH Silica by Fuji Silysia Chemical Ltd.) column chromatography (development solvent; hexane:ethyl acetate=1:1) to obtain 0.30 g of the desired product (Yield: 32%) as a white solid.

$^1$H-NMR (DMSO-d$_6$, ppm) δ 1.17 (3H, broad), 2.22 (6H, s), 3.99 (2H, broad), 7.01-7.08 (2H, m), 7.29-7.43 (6H, m), 7.72-7.77 (2H, m), 9.90 (1H, s).

Example 10-1

Preparation of N-(2,6-dimethyl-4-heptafluoroisopropyl)phenyl 2-fluoro-3-nitrobenzamide 2.35 g of N-(2,6-dimethyl-4-heptafluoroisopropyl)phenyl 2-chloro-3-nitrobenzamide prepared in accordance with the method as described in Example 1-1 and 0.87 g of potassium fluoride (spray drying product) were added to 25 ml of N,N-dimethylformamide dried using molecular sieves, and the mixture was heated and stirred at 150 degree centigrade for 3 hours. The reaction solution was returned to room temperature, and then ethyl acetate and water were added thereto for solution separation. An organic layer was separated, washed with water two times, and dried over anhydrous magnesium sulfate. The solution was filtered off, the filtrate was collected and the solvent was removed under a reduced pressure to obtain a residue. The resulting residue was purified by silica gel column chromatography using an eluent (development solvent; hexane:ethyl acetate=4:1) to obtain 1.02 g of the desired product (Yield: 45%) as a solid.

$^1$H-NMR (CDCl$_3$, ppm) δ 2.37 (6H, s), 7.39 (2H, s), 7.48-7.53 (1H, m), 7.87 (1H, d, J=11.5 Hz), 8.23-8.28 (1H, m), 8.42-8.46 (1H, m).

Example 10-2

Preparation of N-(2,6-dimethyl-4-heptafluoroisopropyl)phenyl 3-(benzoylamino)-2-fluorobenzamide (Compound No. 601)

A desired title product was prepared according to the method as described in Examples 1-2 and 1-3.

$^1$H-NMR (DMSO-d$_6$, ppm) δ 2.34 (6H, s), 7.37 (1H, t, J=7.8 Hz), 7.45 (2H, s), 7.53-7.65 (4H, m), 7.77-7.82 (1H, m), 8.00-8.02 (2H, m), 10.10 (1H, s), 10.29 (1H, s).

Example 11-1

Preparation of N-(2,6-dimethyl-4-heptafluoroisopropyl)phenyl 4-fluoro-3-nitrobenzamide 5.22 g of 4-fluoro-3-nitrobenzoic acid and 0.1 g of N,N-dimethylformamide were introduced to 30 ml of toluene, and then 3.7 g of thionyl chloride was added thereto. The resulting solution was stirred at 80 degree centigrade for 1 hour and then stirred under a reflux condition for 2 hours. The solution was cooled down to room temperature, the solvent was removed under a reduced pressure, the resulting residue was dissolved in 10 ml of tetrahydrofuran, and added dropwise to a mixed solution of 8.1 g of 2,6-dimethyl-4-heptafluoroisopropylaniline, 4.4 g of pyridine and 20 ml of tetrahydrofuran. The solution was stirred at room temperature for 2 hours, and then ethyl acetate was introduced thereinto. The organic layer was washed successively with water and saturated baking soda solution, and dried over anhydrous magnesium sulfate. Then, the solvent was removed under a reduced pressure to obtain a residue. The resulting residue was purified by silica gel column chromatography using an eluent (development solvent; hexane:ethyl acetate=4:1) to obtain 5.9 g of the desired product (Yield: 46%) as a white solid.

$^1$H-NMR (CDCl$_3$, ppm) δ 2.11 (6H, s), 7.26-7.31 (3H, m), 8.12-8.15 (1H, m), 8.60-8.62 (1H, m), 8.70 (1H, s).

Example 11-2

Preparation of N-(2,6-dimethyl-4-heptafluoroisopropyl)phenyl 3-amino-4-fluorobenzamide A desired title product was obtained according to the conditions as described in Example 1-2 as a white solid.

$^1$H-NMR (DMSO-d$_6$, ppm) δ 2.26 (6H, s), 5.42 (2H, broad-s), 7.10-7.19 (2H, m), 7.37 (1H, dd, J=2.0, 8.8 Hz), 7.42 (2H, s), 9.78 (1H, s).

Example 11-3

Preparation of N-(2,6-dimethyl-4-heptafluoroisopropyl)phenyl 4-fluoro-3-(methylamino)benzamide 18 ml of 98% sulfuric acid was cooled from 0 to 5 degree centigrade and stirred, and 2.50 g of N-(2,6-dimethyl-4-heptafluoroisopropyl)phenyl 3-amino-4-fluorobenzamide was added thereto. The reaction solution was stirred for 15 minutes, and then 18 ml of 37% aqueous formaldehyde solution was added dropwise thereto. The solution was stirred at 0 degree centigrade for 1 hour and at room temperature for 3 hours. To the reaction solution cooled down to 0 degree centigrade again was added 28% ammonia water for neutralization and ethyl acetate was added thereto for separating an organic layer. The organic layer was dried over anhydrous magnesium sulfate and the solvent was removed under a reduced pressure to obtain a residue. The resulting residue was purified by silica gel column chromatography using an eluent (development solvent; hexane:ethyl acetate=4:1) to obtain 1.74 g of the desired product (Yield: 67%) as an amorphous substance.

$^1$H-NMR (CDCl$_3$, ppm) δ 2.32 (6H, s), 2.94 (3H, d, J=4.9 Hz), 4.14 (1H, broad), 7.03 (1H, dd, J=8.3, 11.2 Hz), 7.10-7.13 (1H, m), 7.24 (1H, s), 7.34 (2H, s), 7.42 (1H, s).

The following compounds can be prepared in accordance with the method as described in Example 11-3.

N-(2,6-dimethyl-4-heptafluoroisopropyl)phenyl 2-fluoro-3-(methylamino)benzamide $^1$H-NMR (DMSO-d$_6$) δ 2.32 (6H, s), 2.76 (3H, d, J=4.9 Hz), 5.84 (1H, broad), 6.77-6.81 (2H, m), 7.10 (1H, t, J=7.8 Hz), 7.43 (2H, s), 9.90 (1H, s).

N-[2,6-dimethyl-4-(nonafluoro-2-butyl)]phenyl 2-fluoro-3-(methylamino)benzamide $^1$H-NMR (DMSO-d$_6$) δ 2.32 (6H, s), 2.77 (3H, d, J=4.9 Hz), 5.82 (1H, broad), 6.79 (1H, t, J=7.8 Hz), 7.08-7.21 (2H, m), 7.42 (2H, s), 9.88 (1H, s).

N-(2,6-dimethyl-4-heptafluoroisopropyl)phenyl-N-methyl 2-fluoro-3-(methylamino)benzamide $^1$H-NMR (DMSO-d$_6$) δ 2.33 (6H, s), 2.76 (3H, d, J=4.9 Hz), 4.55 (3H, s), 6.58-6.62 (1H, m), 6.70-6.78 (1H, m), 7.13 (1H, t, J=7.8 Hz), 7.31 (1H, s), 7.50 (2H, s).

Example 11-4

Preparation of N-(2,6-dimethyl-4-heptafluoroisopropyl)phenyl 4-fluoro-3-[N-methyl-N-(4-nitrobenzoyl)amino]benzamide (Compound No. 1464)

A desired title product was obtained as a white solid according to the conditions as described in Example 1-3 using 4-nitrobenzoyl chloride.

$^1$H-NMR (DMSO-d$_6$, ppm) δ 2.23 (6H, s), 3.42 (3H, s), 7.41 (1H, broad), 7.45 (2H, s), 7.60 (2H, broad), 7.90 (1H, broad), 8.08-8.13 (3H, broad), 9.93 (1H, s).

Example 12-1

Preparation of N-(2,6-dimethyl-4-heptafluoroisopropyl)phenyl 6-chloropyridine-2-carboxylic acid amide 2.2 g of 6-chloropyridine-2-carboxylic acid and 0.1 g of N,N-dimethylformamide were introduced to 10 ml of toluene, and then 2.0 g of thionyl chloride was added thereto. The resulting solution was stirred at 80 degree centigrade for 1 hour, and then stirred under a reflux condition for 2 hours. The solution was cooled down to room temperature, the solvent was removed under a reduced pressure, the resulting residue was added dropwise to a mixed solution of 3.67 g of 2,6-dimethyl-4-heptafluoroisopropylaniline, 1.22 g of pyridine and 20 ml of tetrahydrofuran. The solution was stirred at room temperature for 2 hours, and then ethyl acetate was introduced thereto. An organic layer was washed successively with water and saturated baking soda solution, and dried over anhydrous magnesium sulfate. Then, the solvent was removed under a reduced pressure to obtain a residue. The resulting residue was washed with hexane cooled down to 5 degree centigrade to obtain 4.42 g of the desired product (Yield: 77%) as a white solid.

$^1$H-NMR (CDCl$_3$, ppm) δ 2.36 (6H, s), 7.36 (2H, s), 7.56 (1H, dd, J=1.0, 8.1 Hz), 7.88 (1H, dd, J=7.6, 8.1 Hz), 8.23 (1H, dd, J=1.0, 7.6 Hz), 9.27 (1H, broad-s).

Example 12-2

Preparation of N-(2,6-dimethyl-4-heptafluoroisopropyl)phenyl 6-aminopyridine-2-carboxylic acid amide 3.08 g of N-(2,6-dimethyl-4-heptafluoroisopropyl)phenyl 6-chloropyridine-2-carboxylic acid amide, 30 ml of 28% ammonia water, 0.20 g of copper sulfate and 70 ml of methanol were introduced into a 200-ml autoclave, and heated and stirred at 150 degree centigrade for 2 hours. The reaction solution was cooled down to room temperature, and then ammonia was removed at 60 degree centigrade in an ordinary pressure and methanol was removed under a reduced pressure. Ethyl acetate and water were added to the reaction solution for solution separation. An organic layer was separated and dried over anhydrous magnesium sulfate. The solution was filtered off, the filtrate was collected and the solvent was removed under a reduced pressure to obtain a residue. The resulting residue was purified by silica gel column chromatography using an eluent (development solvent; hexane:ethyl acetate=3:2 to 2:3) to obtain 2.90 g of the desired product (Yield: 98%) as oil.

$^1$H-NMR (CDCl$_3$, ppm) δ2.35 (6H, s), 4.57 (2H, broad-s), 6.69-6.74 (1H, m), 7.34 (2H, s), 7.62-7.66 (2H, m), 9.39 (1H, broad-s).

Example 12-3

Preparation of N-(2,6-dimethyl-4-heptafluoroisopropyl)phenyl 6-(benzoylamino)pyridine-2-carboxylic acid amide (Compound No. 2001)

0.16 g of N-(2,6-dimethyl-4-heptafluoroisopropyl)phenyl 6-aminopyridine-2-carboxylic acid amide and 62 mg of pyridine were introduced to 3 ml of tetrahydrofuran, and 63 mg of benzoyl chloride was added thereto. The resulting solution was stirred at room temperature for 3 hours. Ethyl acetate was introduced thereto, an organic layer was washed with water and then washed with saturated baking soda solution. After the organic layer was dried over anhydrous magnesium sulfate, the solvent was removed under a reduced pressure to obtain a residue. The resulting residue was purified by silica gel column chromatography using an eluent (development solvent; hexane:ethyl acetate=6:4) to obtain 0.13 g of the desired product (Yield: 65%) as a white solid.

$^1$H-NMR (CDCl$_3$, ppm) δ 2.36 (6H, s), 7.36 (2H, s), 7.53-7.57 (2H, m), 7.61-7.65 (1H, m), 7.95-8.03 (3H, m), 8.08 (1H, dd, J=1.0, 7.3 Hz), 8.52 (1H, broad-s), 8.62 (1H, dd, J=1.0, 8.3 Hz), 9.19 (1H, broad-s).

Example 12-4

Preparation of N-(2,6-dimethyl-4-heptafluoroisopropyl)phenyl 6-(benzoylamino)-1-oxopyridine-2-carboxylic acid amide (Compound No. 2164)

65 mg of N-(2,6-dimethyl-4-heptafluoroisopropyl)phenyl 6-(benzoylamino)pyridine-2-carboxylic acid amide and 0.11 g of m-chloroperbenzoic acid were introduced to 5 ml of benzene, and the resulting solution was stirred at 80 degree centigrade for 4 hours. After the solution was cooled down to room temperature, an organic layer was washed successively with water and saturated baking soda solution, and dried over anhydrous magnesium sulfate. The solvent was removed under a reduced pressure, and then the resulting residue was purified by silica gel column chromatography using an eluent (development solvent; hexane:ethyl acetate=4:1) to obtain 52 mg of the desired product (Yield: 52%) as a white solid.

$^1$H-NMR (CDCl$_3$, ppm) δ 2.34 (6H, s), 7.47 (2H, s), 7.62-7.65 (2H, m), 7.70-7.81 (2H, m), 8.00-8.04 (3H, m), 8.64 (1H, dd, J=1.5, 8.3 Hz), 10.90 (1H, broad-s), 12.30 (1H, broad-s).

Example 13-1

Preparation of 2,6-dibromo-4-heptafluoroisopropylaniline

To a solution of 2.0 g of 4-heptafluoroisopropylaniline added to 5 ml of N,N-dimethylformamide was introduced 2.73 g of N-bromosuccinic acid imide dissolved in 10 ml of N,N-dimethylformamide at 5 degree centigrade. The reaction solution was returned to room temperature and stirred for 2 hours, and then ethyl acetate and water were added thereto for separating an organic layer. The organic layer was further washed with water one time. After the solvent was removed under a reduced pressure, the resulting residue was purified by silica gel column chromatography using an eluent (development solvent; hexane ethyl acetate=20:1) to obtain 2.20 g of the desired product (Yield: 69%) as orange oil.

$^1$H-NMR (CDCl$_3$, ppm) δ 4.89 (2H, broad-s), 7.59 (2H, s)

Example 13-2

Preparation of N-(2,6-dibromo-4-heptafluoroisopropyl)phenyl 3-nitrobenzamide

A mixed solution of 2.20 g of 2,6-dibromo-4-heptafluoroisopropylaniline, 1.46 g of 3-nitrobenzoyl chloride and 10 ml of pyridine was stirred at 70 degree centigrade for 20 hours. The resulting solution was returned to room temperature, and ethyl acetate and 1N hydrochloric acid were added thereto. An organic layer was separated and then washed with saturated baking soda solution. The solvent was removed under a reduced pressure and the resulting residue was dissolved in a mixed solvent of 8 ml of tetrahydrofuran and 2 ml of methanol. Subsequently, the reaction solution was cooled down to 5 degree centigrade, 0.30 g of sodium hydroxide was added thereto, the mixture was stirred for 2 hours, and then ethyl acetate and water were added thereto. An organic layer was separated and washed with saturated baking soda solution, and then dried over anhydrous magnesium sulfate. The solvent was removed under a reduced pressure and the resulting residue was washed with hexane to obtain 2.19 g of the desired product (Yield: 73%) as a light brown solid.

$^1$H-NMR (DMSO-d$_6$, ppm) δ7.92 (1H, t, J=7.8 Hz), 8.08 (2H, s), 8.45 (1H, d, J=7.8 Hz), 8.53 (1H, dd, J=1.5, 7.8 Hz), 8.85 (1H, d, J=1.5 Hz), 11.08 (1H, s).

Example 13-3

Preparation of N-(2,6-dibromo-4-heptafluoroisopropyl)phenyl 3-aminobenzamide

A desired title product was obtained according to the conditions as described in Example 1-2 as a white solid.

$^1$H-NMR (DMSO-d$_6$, ppm) δ 5.39 (2H, broad-s), 6.77-6.80 (1H, m), 7.13-7.20 (3H, m), 8.02 (2H, s), 10.35 (1H, s).

Example 13-4

Preparation of N-(2,6-dibromo-4-heptafluoroisopropyl)phenyl 3-(2-fluorobenzoyl)aminobenzamide (Compound No. 8)

A desired title product was obtained according to the conditions as described in Example 1-3 as a white solid using 2-fluorobenzoyl chloride.

$^1$H-NMR (DMSO-d$_6$, ppm) δ 7.33-7.40 (2H, m), 7.55-7.63 (2H, m), 7.68-7.72 (1H, m), 7.78 (1H, d, J=7.8 Hz), 7.99 (1H, d, J=7.8 Hz), 8.05 (2H, s), 8.34 (1H, s), 10.65 (1H, s), 10.69 (1H, s).

Example 14-1

Preparation of 4-(heptafluoro-n-propylthio) aniline

To 20 ml of an acetonitrile solution of 1.25 g of 4-aminothiophenol and 1.11 g of triethylamine was added 5.91 g of 1-iodoheptafluoro-n-propane. The resulting mixture was stirred at room temperature for 3 hours, diluted with ether, and then washed with aqueous 1N sodium hydroxide solution, purified by silica gel column chromatography using an eluent (development solvent; hexane:ethyl acetate=4:1) to obtain 1.85 g of the desired product (Yield: 63%).

$^1$H-NMR (CDCl$_3$, ppm) δ 3.95 (2H, s), 6.66 (2H, d, J=8.8 Hz), 7.40 (2H, d, J=8.8 Hz).

Example 14-2

Preparation of 2,6-dibromo-4-(heptafluoro-n-propylthio)aniline

To a solution of 0.77 g of 4-(heptafluoro-n-propylthio) aniline added to 15 ml of N,N-dimethylformamide was introduced 0.98 g of N-bromosuccinic acid imide. The resulting solution was stirred at 60 degree centigrade for 2 hours, and then ether and water were added thereto for separating an organic layer. The organic layer was washed with water two times, and then dried over anhydrous magnesium sulfate. The solvent was removed under a reduced pressure and the resulting residue was purified by silica gel column chromatography using an eluent (development solvent; hexane:ethyl acetate=9:1) to obtain 1.19 g of the desired product (Yield: 100%) as red oil.

$^1$H-NMR (CDCl$_3$, ppm) δ 4.98 (2H, broad-s), 7.66 (2H, s).

Example 14-3

Preparation of N-{2,6-dibromo-4-(heptafluoro-n-propylthio)}phenyl 3-nitrobenzamide To a solution of 1.08 g of 2,6-dibromo-4-(heptafluoro-n-propylthio)aniline and 0.4 g of pyridine added to 20 ml of tetrahydrofuran and stirred at room temperature was introduced dropwise 0.55 g of 3-nitrobenzoyl chloride dissolved in 20 ml of tetrahydrofuran little by little. The reaction solution was stirred at room temperature for 10 hours, and then ethyl acetate and water were added thereto. An organic layer was separated and dried over anhydrous magnesium sulfate. The solution was filtered out, the filtrate was collected, and the solvent was removed under a reduced pressure to obtain a residue. The resulting residue was purified by silica gel column chromatography using an eluent (development solvent; hexane ethyl acetate=4:1) to obtain 0.86 g of the desired product (Yield: 48%) as a white solid.

$^1$H-NMR (CDCl$_3$, ppm) δ 7.73 (1H, s, J=7.8 Hz), 7.77 (1H, t, J=7.8 Hz), 7.96 (2H, s), 8.31 (1H, s), 8.47-8.50 (1H, m), 8.79 (1H, t, J=2.0 Hz).

Example 14-4

Preparation of N-{2,6-dibromo-4-(heptafluoro-n-propylthio)}phenyl 3-aminobenzamide To a solution of 0.97 g of N-{2,6-dibromo-4-(heptafluoro-n-propylthio)}phenyl 3-nitrobenzamide and 0.95 g of anhydrous stannous chloride added to 20 ml of ethanol and stirred at room temperature was added 2 ml of concentrated hydrochloric acid, and the resulting mixture was heated and stirred at 60 degree centigrade for 1 hour. The reaction solution was returned to room temperature, poured into water, and then neutralized with potassium carbonate. Ethyl acetate was added thereto, the insoluble substance was filtered out, and then an organic layer was separated and dried over anhydrous magnesium sulfate. The solution was filtered off, the filtrate was collected, and the solvent was removed under a reduced pressure to obtain a residue. The resulting residue was washed with hexane to obtain 0.75 g of the desired product (Yield: 81%) as a white solid.

$^1$H-NMR (CDCl$_3$, ppm) δ 3.89 (2H, broad-s), 6.90 (1H, dt, J=2.5, 6.4 Hz), 7.28-7.30 (3H, m), 7.60 (1H, s), 7.93 (2H, s).

Example 14-5

Preparation of N-(2,6-dibromo-4-heptafluoro-n-propylthio)phenyl 3-(benzoylamino)benzamide (Compound No. 263)

To a solution of 0.10 g of N-(2,6-dibromo-4-heptafluoro-n-propylthio)phenyl 3-aminobenzamide and 0.02 g of pyridine added to 5 ml of tetrahydrofuran and stirred at room temperature was introduced dropwise 0.03 g of benzoyl chloride dissolved in 1 ml of tetrahydrofuran. After the mixture was stirred at room temperature for 1 hour, ethyl acetate and 1N hydrochloric acid were added thereto for separating an organic layer. The organic layer was washed with saturated baking soda solution one time and then dried over anhydrous magnesium sulfate. The solution was filtered off, the filtrate was collected, and the solvent was removed under a reduced pressure to obtain a residue. The resulting residue was purified by silica gel column chromatography using an eluent (development solvent; hexane:ethyl acetate=3:1) to obtain 0.10 g of the desired product (Yield: 67%) as a white solid.

$^1$H-NMR (DMSO-d$_6$, ppm) δ 7.47-7.57 (4H, m), 7.78 (1H, d, J=7.8 Hz), 7.93 (2H, s), 7.99-8.01 (2H, m), 8.18 (1H, d, J=7.8 Hz), 8.33 (1H, t, J=2.0 Hz), 9.27 (1H, s), 9.65 (1H, s).

Example 14-6

Preparation of N-(2,6-dibromo-4-heptafluoro-n-propylthio)phenyl 3-[(2-chloropyridin-3-yl)carbonylamino]benzamide (Compound No. 309)

To a solution of 0.15 g of N-(2,6-dibromo-4-heptafluoro-n-propylthio)phenyl 3-aminobenzamide and 0.03 g of pyridine added to 5 ml of tetrahydrofuran was added 0.05 g of 2-chloronicotic acid chloride hydrochloride, and the mixture was stirred at room temperature for 4 hours. Ethyl acetate was added thereto, and then the solution was washed with saturated baking soda solution two times, and the solvent was removed under a reduced pressure. The precipitated solid was purified by silica gel column chromatography using an eluent (development solvent; hexane:ethyl acetate=3:1) to obtain 0.17 g of the desired product (Yield: 92%) as an amorphous substance.

$^1$H-NMR (CDCl$_3$, ppm) δ 7.44 (1H, dd, J=4.8, 7.8 Hz), 7.56 (1H, t, J=7.8 Hz), 7.80 (1H, d, J=7.8 Hz), 7.86 (1H, s), 7.92 (1H, d, J=7.8 Hz), 7.95 (2H, s), 8.23 (1H, dd, J=2.0., 7.8 Hz), 8.30 (1H, s), 8.41 (1H, s), 8.55 (1H, dd, J=2.0, 4.8 Hz).

Example 14-7

Preparation of N-(2,6-dibromo-4-heptafluoro-n-propylsulfinyl)phenyl 3-nitrobenzamide To a solution of 0.5 g of N-(2,6-dibromo-4-heptafluoro-n-propylthio)phenyl 3-nitrobenzamide added to 15 ml of chloroform and stirred at room temperature was introduced 0.5 g of m-chloroperbenzoic acid. The mixture was stirred at room temperature for 2 days, and then an aqueous solution of sodium sulfite was added thereto and stirred. While solution separation was performed, the reaction solution was washed with aqueous sodium hydroxide solution and saturated salt water, and the solvent was removed under a reduced pressure to obtain a residue. The resulting residue was purified by silica gel column chromatography using an eluent (development solvent; hexane:ethyl acetate=4:1) to obtain 0.36 g of the desired product (Yield: 70%) as a white solid.

$^1$H-NMR (CDCl$_3$, ppm) δ 7.76-7.82 (2H, m), 8.06 (1H, s), 8.29 (1H, s), 8.33-8.35 (1H, m), 8.49-8.53 (1H, m), 8.81 (1H, s).

Example 14-8

Preparation of N-(2,6-dibromo-4-heptafluoro-n-propylsulfinyl)phenyl 3-aminobenzamide A desired title product was obtained according to the method as described in Example 1-2 using N-(2,6-dibromo-4-heptafluoropropyl-n-sulfinyl)phenyl 3-nitrobenzamide.

$^1$H-NMR (CDCl$_3$, ppm) δ 6.90-6.94 (1H, m), 7.28-7.33 (3H, m), 7.73 (1H, s), 8.02 (1H, s), 8.25 (1H, s).

Example 14-9

Preparation of N-(2,6-dibromo-4-heptafluoro-n-propylsulfinyl)phenyl 3-(benzoylamino)benzamide (Compound No. 335)

A desired title product was obtained according to the method as described in Example 1-3 using N-(2,6-dibromo-4-heptafluoro-n-propylsulfinyl)phenyl 3-aminobenzamide.
$^1$H-NMR (CDCl$_3$, ppm) δ 7.45-7.61 (4H, m), 7.77-7.79 (1H, m), 7.87-7.91 (3H, m), 8.01 (1H, s), 8.07-8.10 (1H, m), 8.15 (1H, s), 8.25 (1H, s), 8.38 (1H, s)

Example 14-10

Preparation of 2,6-dimethyl-4-(heptafluoro-n-propylthio)aniline 3.0 g (1.3 mmole) of 2,6-dibromo-4-heptafluoro-n-propylthioaniline, 3.0 g (21.9 mmole) of potassium carbonate, 0.75 g (0.65 mmole) of tetrakis(triphenylphosphine)palladium and 0.17 g (1.3 mmole) of trimethylboroxin were added to 20 ml of DMF, and the resulting solution was stirred at 135 degree centigrade for 6 hours. The reaction solution was returned to room temperature, and then the insoluble substance was removed with celite, and the filtrate was concentrated under a reduced pressure. The resulting residue was purified by silica gel column chromatography using an eluent (development solvent; hexane:ethyl acetate=12:1 to 4:1) to obtain 1.17 g of the desired product (Yield: 55%) as oil.
$^1$H-NMR (CDCl$_3$, ppm) δ 2.17 (6H, s), 3.86 (2H, broad-s), 7.22 (2H, s)

Example 15

Preparation of N-(2,6-dimethyl-4-heptafluoroisopropyl)phenyl 3-(methylamino)benzamide A mixture of 20.0 g of N-(2,6-dimethyl-4-heptafluoroisopropyl)phenyl 3-aminobenzamide, 4.40 g of 37% aqueous formaldehyde solution, 2.0 g of 10% palladium carbon and 200 ml of ethyl acetate was stirred in an ordinary pressure, in a hydrogen atmosphere at room temperature. An insoluble substance of the reaction solution was filtered out and the filtered product was washed with ethyl acetate. The filtrate was collected and the solvent was removed under a reduced pressure to obtain a residue. The resulting residue was washed with diisopropyl ether to obtain 13.5 g of the desired product (Yield: 65%) as a white solid.
$^1$H-NMR (CDCl$_3$, ppm) δ 2.35 (6H, s), 2.91 (3H, s), 6.82 (1H, d, J=7.3 Hz), 7.18-7.52 (7H, m).

Example 16-1

Preparation of 3-(benzoylamino)benzoic acid

To a solution of 1.37 g of 3-aminobenzoic acid and 0.4 g of sodium hydroxide added to 50 ml of water was added dropwise a solution of 1.41 g of benzoyl chloride and 0.4 g of sodium hydroxide dissolved in 5 ml of water under an ice bath at the same time, and the resulting mixture was stirred at room temperature for 6 hours. 1N hydrochloric acid was added to the reaction solution which was adjusted to pH 1, and then the precipitated solid was filtered off and collected to obtain 1.92 g of the desired product (Yield: 80%) as a white solid.
$^1$H-NMR (CDCl$_3$, ppm) δ 7.40-7.56 (5H, m), 7.78 (1H, d, J=7.8 Hz), 8.00 (2H, d, J=8.3 Hz), 8.15 (1H, d, J=7.8 Hz), 8.35 (1H, t, J=2.0 Hz), 9.89 (1H, s).

Example 16-2

Preparation of 3-(benzoylamino)benzoic acid chloride

To a solution of 1.5 g of 3-(benzoylamino)benzoic acid suspended in 10 ml of toluene was added 2 ml of thionyl chloride and the resulting mixture was stirred under a reflux condition for 2 hours. The reaction solution was returned to room temperature, and then the solvent was removed under a reduced pressure to obtain 1.53 g of the desired product (Yield: 95%) as a white solid.
$^1$H-NMR (CDCl$_3$, ppm) δ 7.51-7.62 (4H, m), 7.90 (2H, d, J=7.3 Hz), 7.93 (1H, s), 7.97 (1H, s), 8.15 (1H, dt, J=1.0, 5.9 Hz), 8.28 (1H, t, J=2.0 Hz).

Using benzoic acids which can be easily available, the following compounds can be prepared in accordance with the method as described in Examples 16-1 and 16-2.

3-[(2-fluorobenzoyl)amino]benzoic acid chloride
3-[(3-fluorobenzoyl)amino]benzoic acid chloride
3-[(4-fluorobenzoyl)amino]benzoic acid chloride
3-[(2-chlorobenzoyl)amino]benzoic acid chloride
3-[(3-chlorobenzoyl)amino]benzoic acid chloride
3-[(4-chlorobenzoyl)amino]benzoic acid chloride
3-[(3-cyanobenzoyl)amino]benzoic acid chloride
3-[(4-cyanobenzoyl)amino]benzoic acid chloride
3-[(2-methylbenzoyl)amino]benzoic acid chloride
3-[(3-methylbenzoyl)amino]benzoic acid chloride
3-[(4-methylbenzoyl)amino]benzoic acid chloride
3-[(2-nitrobenzoyl)amino]benzoic acid chloride
3-[(3-nitrobenzoyl)amino]benzoic acid chloride
3-[(4-nitrobenzoyl)amino]benzoic acid chloride
3-[(2-trifluoromethylbenzoyl)amino]benzoic acid chloride
3-[(3-trifluoromethylbenzoyl)amino]benzoic acid chloride
3-[(4-trifluoromethylbenzoyl)amino]benzoic acid chloride
3-[(2-trifluoromethoxybenzoyl)amino]benzoic acid chloride
3-[(3-trifluoromethoxybenzoyl)amino]benzoic acid chloride
3-[(4-trifluoromethoxybenzoyl)amino]benzoic acid chloride
3-[(2,3-difluorobenzoyl)amino]benzoic acid chloride
3-[(2,4-difluorobenzoyl)amino]benzoic acid chloride
3-[(2,5-difluorobenzoyl)amino]benzoic acid chloride
3-[(2,6-difluorobenzoyl)amino]benzoic acid chloride
3-[(3,4-difluorobenzoyl)amino]benzoic acid chloride
3-[(pyridin-3-yl)carbonylamino]benzoic acid chloride
3-[(2-fluoropyridin-3-yl)carbonylamino]benzoic acid chloride
3-[(2-chloropyridin-3-yl)carbonylamino]benzoic acid chloride
3-[(2,4-dichlorobenzoyl)amino]benzoic acid chloride
3-[(2,6-dichlorobenzoyl)amino]benzoic acid chloride
3-[(3,4-dichlorobenzoyl)amino]benzoic acid chloride
3-[(2-chloro-4-fluorobenzoyl)amino]benzoic acid chloride
3-[(4-chloro-2-fluorobenzoyl)amino]benzoic acid chloride
3-[(2-chloro-6-fluorobenzoyl)amino]benzoic acid chloride
3-[(2,3,6-trifluorobenzoyl)amino]benzoic acid chloride

Example 16-3

Preparation of N-(2,6-dimethyl-4-heptafluoro-n-propylthio)phenyl 3-(benzoylamino)benzamide (Compound No. 260)

To a solution of 0.1 g of 2,6-dimethyl-4-(heptafluoro-n-propylthio)aniline and 0.03 g of pyridine added to 5 ml of tetrahydrofuran and stirred at room temperature was introduced dropwise 0.09 g of 3-(benzoylamino)benzoic acid chloride dissolved in 1 ml of tetrahydrofuran. The resulting mixture was stirred at room temperature for 1 hour, and then ethyl acetate and 1N hydrochloric acid were added thereto for separating an organic layer. The organic layer was washed with saturated baking soda solution one time and then dried over anhydrous magnesium sulfate. The solution was filtered off, the filtrate was collected, and the solvent was removed under a reduced pressure to obtain a residue. The resulting residue was purified by silica gel column chromatography using an eluent (development solvent; hexane:ethyl acetate=3:1) to obtain 0.10 g of the desired product (Yield: 53%) as a white solid.

$^1$H-NMR (DMSO-d$_6$, ppm) δ 2.31 (6H, s), 7.41 (2H, s), 7.50-7.67 (5H, m), 7.71 (1H, d, J=7.8 Hz), 7.87-7.90 (3H, m), 8.07 (1H, s), 8.31 (1H, s).

Example 17-1

Preparation of 2,6-dimethyl-4-[1-hydroxy-2,2,2-trifluoro-1-(trifluoromethyl)ethyl]aniline While 24.4 g of 2,6-dimethylaniline and 50.0 g of hexafluoroacetone hydrate were mixed at room temperature, 0.5 g of p-toluenesulfonic acid monohydrate was added thereto. The reaction solution was stirred at 100 degree centigrade. After disappearance of the starting raw material was confirmed by means of TLC, to the reaction solution were added ethyl acetate and 1N aqueous sodium hydroxide solution for solution separation and extraction. Anhydrous magnesium sulfate was added to an organic layer, and the organic layer was dried and then filtered off. The filtrate was concentrated under a reduced pressure, and then hexane was added to the residue for washing. The suspension was filtered and the resulting filtered product was vacuum-dried at room temperature to obtain 24.3 g of the desired product (Yield: 69%) in the form of powder.

$^1$H-NMR (CDCl$_3$, ppm) δ 2.20 (6H, s), 3.26 (1H, broad-s), 3.76 (2H, broad-s), 7.25 (2H, s).

Example 17-2

Preparation of N-[2,6-dimethyl-4-{1-hydroxy-2,2,2-trifluoro-1-(trifluoromethyl)ethyl}phenyl]3-nitrobenzamide At room temperature, 5.0 g of 2,6-dimethyl-4-[1-hydroxy-2,2,2-trifluoro-1-(trifluoromethyl)ethyl]aniline, 3.9 g of 3-nitrobenzoyl chloride and 2.1 g of pyridine were introduced to 50 ml of tetrahydrofuran in a reaction vessel, and the resulting mixture was stirred at room temperature. After disappearance of the starting raw material was confirmed by means of TLC, to the reaction solution was added saturated baking soda solution and stirred for a while. Subsequently, ethyl acetate and water were added to the reaction solution for solution separation. Anhydrous magnesium sulfate was added to a separated organic layer, the organic layer was dried and filtered off. The filtrate was evaporated to be dried and the resulting solid was pulverized to obtain 7.5 g of the desired product (Yield: 95%) in the form of powder.

$^1$H-NMR (DMSO-d$_6$, ppm) δ 2.26 (6H, s), 7.46 (2H, s), 7.88 (1H, t, J=7.8 Hz), 8.43-8.48 (2H, m), 8.73 (1H, s), 8.81 (1H, s), 10.27 (1H, s).

Example 17-3

Preparation of N-[2,6-dimethyl-4-{1-hydroxy-2,2,2-trifluoro-1-(trifluoromethyl)ethyl}phenyl]3-aminobenzamide A solution of 8.0 g of N-[2,6-dimethyl-4-{1-hydroxy-2,2,2-trifluoro-1-(trifluoromethyl)ethyl}phenyl]3-nitrobenzamide and 0.8 g of 10% palladium carbon added to 50 ml of methanol was stirred in a hydrogen atmosphere at room temperature. After disappearance of the starting raw material was confirmed by means of TLC, the reaction solution was filtered and the obtained filtrate was concentrated under a reduced pressure. The resulting residue was purified by silica gel column chromatography using an eluent (development solvent; hexane:ethyl acetate=3:1) to obtain 6.3 g of the desired product (Yield: 85%) in the form of powder.

$^1$H-NMR (DMSO-d$_6$, ppm) δ 2.35 (6H, s), 4.31 (2H, broad), 6.84-6.87 (1H, m), 7.21-7.25 (1H, m), 7.29-7.31 (2H, m), 7.47-7.49 (2H, m), 7.83 (1H, s), 8.94 (1H, s).

Example 17-4

Preparation of N-[2,6-dimethyl-4-{1-hydroxy-2,2,2-trifluoro-1-(trifluoromethyl)ethyl}phenyl]3-(benzoylamino)benzamide At room temperature, 6.0 g of N-[2,6-dimethyl-4-{1-hydroxy-2,2,2-trifluoro-1-(trifluoromethyl)ethyl}phenyl]3-aminobenzamide, 2.5 g of benzoyl chloride and 1.8 g of pyridine were introduced to 50 ml of tetrahydrofuran. After disappearance of the starting raw material was confirmed by means of TLC, the reaction solution was filtered off, and the obtained filtrate was concentrated under a reduced pressure. The resulting residue was purified by silica gel column chromatography using an eluent (development solvent; hexane:ethyl acetate=3:1) to obtain 6.3 g of the desired product (Yield: 85%) in the form of powder.

$^1$H-NMR (DMSO-d$_6$, ppm) δ 2.26 (6H, s), 7.44 (2H, s), 7.51-7.63 (4H, m), 7.74 (1H, d, J=7.8 Hz), 7.98-8.07 (3H, m), 8.35 (1H, s), 8.71 (1H, s), 9.90 (1H, s), 10.47 (1H, s).

N-[2,6-dimethyl-4-{1-hydroxy-2,2,2-trifluoro-1-(trifluoromethyl)ethyl}phenyl]3-[(2-fluorobenzoyl)amino]benzamide was prepared according to Example 17-4 using 2-fluorobenzoyl chloride instead of benzoyl chloride.

$^1$H-NMR (DMSO-d$_6$, ppm) δ 2.34 (6H, s), 7.21 (1H, dd, J=8.2, 11.2 Hz), 7.32 (1H, t, J=7.8 Hz), 7.49-7.56 (4H, m), 7.78 (1H, d, J=7.8 Hz), 8.04-8.08 (2H, m), 8.23 (1H, s), 8.71 (1H, s), 9.08 (1H, d, J=11.2 Hz).

Example 17-5

Preparation of N-[2,6-dimethyl-4-{1-chloro-2,2,2-trifluoro-1-(trifluoromethyl)ethyl}phenyl]3-(benzoylamino)benzamide At room temperature, 8.0 g of N-[2,6-dimethyl-4-{1-hydroxy-2,2,2-trifluoro-1-(trifluoromethyl)ethyl}phenyl]3-(benzoylamino)benzamide and 1.0 g of pyridine were introduced to 40 ml of thionyl chloride. Thereafter, the mixture was heated and stirred under a reflux condition. After disappearance of the starting raw material was confirmed by means of TLC, the reaction solution was cooled down and concentrated under a reduced pressure. The resulting residue was purified by silica gel column chromatography using an eluent (development solvent; hexane:ethyl acetate=3:1) to obtain 6.2 g of the desired product (Yield: 75%) in the form of powder.

$^1$H-NMR (DMSO-$d_6$, ppm) δ 2.34 (6H, s), 7.49-7.63 (6H, m), 7.76 (1H, d, J=7.8 Hz), 7.99-8.08 (3H, m), 8.37 (1H, s), 9.99 (1H, s), 10.48 (1H, s).

Example 17-6

Preparation of N-(2,6-dimethyl-4-heptafluoroisopropyl)phenyl 3-(benzoylamino)benzamide (Compound No. 10)

At room temperature, 300 mg of N-[2,6-dimethyl-4-{1-chloro-2,2,2-trifluoro-1-(trifluoromethyl)ethyl}phenyl]3-(benzoylamino)benzamide and 165 mg of potassium fluoride were introduced to 20 ml of N,N-dimethylformamide. Thereafter, the mixture was heated to 120 degree centigrade and stirred for 4 hours. After the reaction solution was cooled down to room temperature, ethyl acetate and water were added thereto for separating an organic layer. Anhydrous magnesium sulfate was added, the organic layer was dried and filtered off, and the filtrate was concentrated under a reduced pressure. The resulting residue was washed with diisopropyl ether. The suspension was filtered off and the obtained filtered product was vacuum-dried at room temperature to obtain 250 mg of the desired product (Yield: 85%) in the form of powder.

The physical properties were described in Example 1-3.

Example 17-7

Preparation of N-[2,6-dimethyl-4-{1-hydroxy-2,2,2-trifluoro-1-(trifluoromethyl)ethyl}phenyl]3-(benzoylamino)benzamide At room temperature, 2.0 g of 2,6-dimethyl-4-[1-hydroxy-2,2,2-trifluoro-1-(trifluoromethyl)ethyl]aniline, 2.7 g of 3-(benzoylamino)benzoyl chloride and 1.2 g of pyridine were introduced to 50 ml of tetrahydrofuran, and the resulting solution was stirred at room temperature. After disappearance of the starting raw material was confirmed by means of TLC, saturated baking soda solution was added to the reaction solution which was stirred for a while. Ethyl acetate and water were added to the reaction solution for solution separation. To a separated organic layer was added anhydrous magnesium sulfate, and the organic layer was dried and filtered off. The filtrate was evaporated to be dried under a reduced pressure and the resulting solid was pulverized to obtain 3.4 g of the desired product (Yield: 95%) in the form of powder.

The physical properties were described in Example 17-4.

Example 17-8

Preparation of N-(2,6-dimethyl-4-heptafluoroisopropyl)phenyl 3-(benzoylamino)benzamide (Compound No. 10)

At room temperature, 300 mg of N-[2,6-dimethyl-4-{1-hydroxy-2,2,2-trifluoro-1-(trifluoromethyl)ethyl}phenyl]3-(benzoylamino)benzamide was introduced to 20 ml of methylene chloride. Next, 480 mg of 2,2-difluoro-1,3-dimethyl-2-imidazolidinone was added dropwise thereto and stirred at room temperature for 8 hours. Water was added to the reaction solution and an organic layer was separated. Anhydrous magnesium sulfate was added to the organic layer which was dried and filtered off. The obtained filtrate was evaporated to be dried under a reduced pressure and the resulting solid was pulverized to obtain 180 mg of the desired product (Yield: 60%) in the form of powder.

The physical properties were described in Example 1-3.

Example 18-1

Preparation of 4-methyl-5-nitro-2-(2,2,2-trifluoro-1-trifluoromethylethoxy)pyridine 1.33 g of 60% sodium hydride was introduced to 15 ml of tetrahydrofuran, the mixture was cooled down to 5 degree centigrade, and then 5.84 g of 1,1,1,3,3,3-hexafluoro-2-propanol wad added dropwise thereto. The resulting solution was stirred at 5 degree centigrade for 30 minutes, and then 3.0 g of 2-chloro-4-methyl-5-nitropyridine dissolved in 10 ml of tetrahydrofuran was added dropwise thereto, and stirred at room temperature for 3 hours. The solution was allowed to stand at room temperature for 3 days, and then ethyl acetate and water were added thereto. An organic layer was separated, washed with saturated salt water, and dried over anhydrous magnesium sulfate. Then, the solvent was removed under a reduced pressure to obtain a residue. The resulting residue was purified by silica gel column chromatography using an eluent (development solvent; hexane ethyl acetate=10:1) to obtain 4.5 g of the desired product (Yield: 80%) as yellow oil.

$^1$H-NMR (CDCl$_3$, ppm) δ 2.69 (3H, s), 6.54 (1H, septet, J=6.8 Hz), 6.95 (1H, s), 8.90 (1H, s).

Example 18-2

Preparation of 5-amino-4-methyl-2-(2,2,2-trifluoro-1-trifluoromethylethoxy)pyridine A desired title product was prepared according to the conditions as described in Example 1-2 using 4-methyl-5-nitro-2-(2,2,2-trifluoro-1-trifluoromethylethoxy)pyridine $^1$H-NMR (CDCl$_3$, ppm) δ 2.04 (3H, s), 3.49 (2H, broad-s), 6.40 (1H, septet, J=6.3 Hz), 6.69 (1H, s), 7.54 (1H, s).

Example 18-3

Preparation of 3-amino-2-chloro-4-methyl-6-(2,2,2-trifluoro-1-trifluoromethyl ethoxy)pyridine 1.0 g of 5-amino-4-methyl-2-(2,2,2-trifluoro-1-trifluoromethylethoxy)pyridine was introduced to 10 ml of N,N-dimethylformamide, and 0.56 g of N-chlorosuccinic acid imide was added thereto at room temperature. The resulting solution was heated to 60 degree centigrade, stirred for 1 hour, and then poured into water and extracted with ethyl acetate. The solution was dried over anhydrous magnesium sulfate, and then the solvent was removed under a reduced pressure to obtain a residue. The resulting residue was purified by silica gel column chromatography using an eluent (development solvent; hexane:ethyl acetate=10:1) to obtain 0.50 g of the desired product (Yield: 44%) as brown oil.

$^1$H-NMR (CDCl$_3$, ppm) δ 2.23 (3H, s), 3.82 (2H, broad-s), 6.24 (1H, septet, J=6.3 Hz), 6.67 (1H, s).

Example 18-4

Preparation of N-[2-chloro-4-methyl-6-(2,2,2-trifluoro-1-trifluoromethylethoxy)pyridin-3-yl]3-(benzoylamino)benzamide (Compound No. 464)

A desired title product was prepared according to the method as described in Example 1 using 5-amino-4-methyl-2-(2,2,2-trifluoro-1-trifluoromethylethoxy)pyridine $^1$H-NMR (CDCl$_3$, ppm) δ 2.38 (3H, s), 6.34 (1H, septet, J=6.3 Hz), 6.87 (1H, s), 7.50-7.63 (5H, m), 7.72 (1H, d, J=7.8 Hz), 7.88-7.90 (3H, m), 7.99 (1H, broad-s), 8.31 (1H, broad-s).

Next, typical Formulation Examples of the present invention will be illustrated. However, the present invention is not restricted to these Formulation Examples. Incidentally, in the Formulation Examples, part(s) refers to weight part(s).

Formulation Example 1

2 parts of the compound (106), 10 parts of probenazole, 0.5 part of a wetting agent (trade name: AIRROLL CT-1, a product of Toho Chemical Industry, Co., Ltd.), 3 parts of a binder (GOHSENOL, a product of Nippon Synthetic Chemical Industry Co., Ltd.), 15 parts of talc (trade name: VICTORYLITE, a product of Shokozan Mining Co., Ltd.), 71.5 parts of clay (trade name: SP, a product of Shokozan Mining Co., Ltd.) were mixed, extruded with the addition of water, and granulated with a granulating machine. The thus-obtained product was dried and granulated to obtain a granule.

Formulation Example 2

2 parts of the compound (1246), 5 parts of orysastrobin, 0.5 part of a wetting agent (trade name: AIRROLL CT-1, a product of Toho Chemical Industry, Co., Ltd.), 3 parts of a binder (trade name: SEROGEN, Dai-ichi Kogyo Seiyaku K.K.), 15 parts of talc (trade name: VICTORYLITE, a product of Shokozan Mining Co., Ltd.) and 74.5 parts of clay (trade name: SP, a product of Shokozan Mining Co., Ltd.) were mixed, extruded with the addition of water, and granulated with a granulating machine. The thus-obtained product was dried and granulated to obtain a granule.

Formulation Example 3

0.5 part of the compound (1208), 0.2 part of kasugamycin, 0.3 part of a coagulant agent (trade name: Driless C, a product of Sankyo Co., Ltd.), 50 parts of clay (trade name: 0-4410, a product of Asahi Komatsu Co., Ltd.) and 49 parts of calcium carbonate (trade name: NN200, a product of Nitto Funka Kogyo K.K.) were mixed and pulverized with a pin mill to obtain a powder.

Formulation Example 4

0.5 part of the compound (601), 1.0 part of tricyclazole, 0.3 part of a coagulation agent (trade name: Driless A, a product of Sankyo Co., Ltd.), 50 parts of clay (trade name: 0-4410, a product of Asahi Komatsu Co., Ltd.) and 48.2 parts of calcium carbonate (trade name: NN200, a product of Nitto Funka Kogyo K.K.) were mixed and pulverized with a pin mill to obtain a powder.

Formulation Example 5

0.5 part of the compound (105), 2.0 parts of flutolanil, 0.3 part of a coagulation agent (trade name: Driless A, a product of Sankyo Co., Ltd.), 50 parts of clay (trade name: 0-4410, a product of Asahi Komatsu Co., Ltd.), 47.2 parts of calcium carbonate (trade name: NN200, a product of Nitto Funka Kogyo K.K.) were mixed and pulverized with a pin mill to obtain a powder.

Formulation Example 6

0.5 part of the compound (639), 0.3 part of flusulfamide, 0.3 part of a coagulation agent (trade name: Driless A, a product of Sankyo Co., Ltd.), 50 parts of clay (trade name: 0-4410, a product of Asahi Komatsu Co., Ltd.) and 48.9 parts of calcium carbonate (trade name: Driless A, a product of Nitto Funka Kogyo K.K.) were mixed and pulverized with a pin mill to obtain a powder.

Formulation Example 7

0.5 part of the compound (1244), 3.0 parts of fenitrothion, 0.3 part of a coagulation agent (Driless A, a product of Sankyo Co., Ltd.), 2.0 parts of amorphous, water-containing silicic acid (trade name: CARPREX #80D, a product of Degussa Japan), 50 parts of clay (trade name: 0-4410, a product of Asahi Komatsu Co., Ltd.) and 44.2 parts of calcium carbonate (trade name: NN200, a product of Nitto Funka Kogyo K.K.) were mixed and pulverized with a pin mill to obtain a powder.

Formulation Example 8

5 parts of the compound (1208), 10 parts of imidacloprid, 1.5 parts of a wetting and dispersing agent (trade name: Sorpol 3074, a product of Toho Chemical Industry, Co., Ltd.), 2.5 parts of a dispersing agent (trade name: DEMOL N, a product of Kao Corporation), 0.08 part of a thickening agent (trade name: RHODOPOL, a product of Rhodia Nicca, Ltd.) and 80.92 parts of water were mixed, and then pulverized with a wet grinder and filtered off to obtain a flowable formulation.

Formulation Example 9

10 parts of the compound (1217), 15 parts of pyridaben, 2.5 parts of a wetting and dispersing agent (trade name: Sorpol 3074, a product of Toho Chemical Industry, Co., Ltd.), 3.0 parts of a dispersing agent (trade name: DEMOL N, a product of Kao Corporation), 0.08 part of a thickening agent (trade name: RHODOPOL, a product of Rhodia Nicca, Ltd.) and 69.42 parts of water were mixed, and then pulverized with a wet grinder and filtered off to obtain a flowable formulation.

Formulation Example 10

10 parts of the compound (210), 5 parts of chlorfenapyr, 1.5 parts of a wetting and dispersing agent (trade name: Sorpol 3074, a product of Toho Chemical Industry, Co., Ltd.), 2.5 parts of a dispersing agent (trade name: DEMOL N, a product of Kao Corporation), 0.08 part of a thickening agent (trade name: RHODOPOL, a product of Rhodia Nicca, Ltd.) and 80.92 parts of water were mixed, and then pulverized with a wet grinder and filtered off to obtain a flowable formulation.

Formulation Example 11

10 parts of the compound (178), 20 parts of buprofezin, 1.5 parts of a wetting agent (trade name: Sorpol 5050, a product of Toho Chemical Industry, Co., Ltd.), 2.5 parts of a dispersing agent (trade name: EMAL, a product of Kao Corporation), 2.0 parts of a dispersing agent (trade name: DEMOL N, a product of Kao Corporation) and 64 parts of diatomaceous earth were mixed, and then pulverized with a jet mill to obtain a wettable powder.

Formulation Example 12

10 parts of the compound (1247), 20 parts of pymetrozine, 1.5 parts of a wetting agent (trade name: Sorpol 5050, a product of Toho Chemical Industry, Co., Ltd.), 2.5 parts of a dispersing agent (trade name: EMAL, a product of Kao Corporation), 2.0 parts of a dispersing agent (trade name: DEMOL N, a product of Kao Corporation) and 64 parts of diatomaceous earth were mixed, and then pulverized with a jet mill to obtain a wettable powder.

Formulation Example 13

10 parts of the compound (601), 5 parts of fipronil, 2.0 parts of a wetting agent (trade name: Sorpol 5050, a product of Toho Chemical Industry, Co., Ltd.), 2.0 parts of a dispersing agent (trade name: EMAL, a product of Kao Corporation), 2.0 parts of a dispersing agent (trade name: DEMOL N, a product of Kao Corporation) and 79 parts of diatomaceous earth were mixed, and then pulverized with a jet mill to obtain a wettable powder.

Formulation Example 14

30 parts of isoxathion, 2.0 parts of a dispersing agent (trade name: Sorpol 7290P, a product of Toho Chemical Industry, Co., Ltd.) and 25 parts of hydrous amorphous silica (trade name: CARPREX 80D, a product of Degussa Japan) were mixed, and then 10 parts of the compound (1126), 1.5 parts of a wetting agent (trade name: Sorpol 5050, a product of Toho Chemical Industry, Co., Ltd.), 2.0 parts of a dispersing agent (trade name: EMAL, a product of Kao Corporation), 2.0 parts of a dispersing agent (trade name: DEMOL N, a product of Kao Corporation) and 27.5 parts of diatomaceous earth were mixed, and then pulverized with a jet mill to obtain a wettable powder.

Formulation Example 15

5 parts of the compound (1480), 5 parts of dinotefuran, 2.0 parts of a wetting agent (Sorpol 5050, a product of Toho Chemical Industry, Co., Ltd.), 2.0 parts of a dispersing agent (trade name: EMAL, a product of Kao Corporation) and 86 parts of diatomaceous earth were mixed, and then pulverized with a jet mill to obtain a wettable powder.

Furthermore, to make sure that the composition for preventing harmful organisms of the present invention has an excellent control activity against harmful organisms, the following Test Examples are illustrated. However, the present invention is not restricted to these Test Examples.

Test Example 1

Insecticidal Test on Green Peach Aphid (*Myzus persicae*)

Into a plastic pot having a diameter of 8 cm and a height of 8 cm were planted eggplants (cultivar: Senryo 2 Gou) and *Myzus persicae* was propagated. Then, a liquid chemical which was diluted and prepared to the prescribed concentration was sufficiently sprayed on the stem and leaf. After air-drying, the pot was allowed to stand in a greenhouse. After 5 days from spraying, the number of aphids which were parasitic on each eggplant was examined and the control rate was calculated according to the following equation (two replications of one pot per plot).

Control Rate=100−{($Ta \times Cb$)/($Tb \times Ca$)}×100

Ta: Number of parasitic insects after spraying on the treated area
Tb: Number of parasitic insects before spraying on the treated area
Ca: Number of parasitic insects after spraying on the untreated area
Cb: Number of parasitic insects before spraying on the untreated area The results are shown in Table 7.

TABLE 7

| Supplied chemical | Concentration (ppm) | Control rate (%) |
|---|---|---|
| Compound 1208 + acephate | 3 + 250 | 100 |
| Compound 1208 + methomyl | 3 + 250 | 100 |
| Compound 1208 + ethofenprox | 3 + 100 | 100 |
| Compound 1208 + dinotefuran | 3 + 100 | 100 |
| Compound 1208 + ethiprole | 3 + 100 | 100 |
| Compound 1208 + pymetrozine | 3 + 100 | 100 |
| Compound 1208 + flonicamid | 3 + 100 | 100 |
| Compound 1219 + acephate | 3 + 250 | 100 |
| Compound 1219 + methomyl | 3 + 250 | 100 |
| Compound 1219 + ethofenprox | 3 + 100 | 100 |
| Compound 1219 + dinotefuran | 3 + 100 | 100 |
| Compound 1219 + ethiprole | 3 + 100 | 100 |
| Compound 1219 + pymetrozine | 3 + 100 | 100 |
| Compound 1219 + flonicamid | 3 + 100 | 100 |
| Compound 1217 + acephate | 3 + 250 | 100 |
| Compound 1217 + methomyl | 3 + 250 | 100 |
| Compound 1217 + ethofenprox | 3 + 100 | 100 |
| Compound 1217 + dinotefuran | 3 + 100 | 100 |
| Compound 1217 + ethiprole | 3 + 100 | 100 |
| Compound 1217 + pymetrozine | 3 + 100 | 100 |
| Compound 1217 + flonicamid | 3 + 100 | 100 |
| Compound 210 + acephate | 3 + 250 | 100 |
| Compound 210 + methomyl | 3 + 250 | 100 |
| Compound 210 + ethofenprox | 3 + 100 | 100 |
| Compound 210 + dinotefuran | 3 + 100 | 100 |
| Compound 210 + ethiprole | 3 + 100 | 100 |
| Compound 210 + pymetrozine | 3 + 100 | 100 |
| Compound 210 + flonicamid | 3 + 100 | 100 |
| Compound 1245 + acephate | 3 + 250 | 100 |
| Compound 1245 + methomyl | 3 + 250 | 100 |
| Compound 1245 + ethofenprox | 3 + 100 | 100 |
| Compound 1245 + dinotefuran | 3 + 100 | 100 |
| Compound 1245 + ethiprole | 3 + 100 | 100 |
| Compound 1245 + pymetrozine | 3 + 100 | 100 |
| Compound 1245 + flonicamid | 3 + 100 | 100 |
| Compound 639 + acephate | 3 + 250 | 100 |
| Compound 639 + methomyl | 3 + 250 | 100 |
| Compound 639 + ethofenprox | 3 + 100 | 100 |
| Compound 639 + dinotefuran | 3 + 100 | 100 |
| Compound 639 + ethiprole | 3 + 100 | 100 |
| Compound 639 + pymetrozine | 3 + 100 | 100 |
| Compound 639 + flonicamid | 3 + 100 | 100 |
| Compound 1247 + acephate | 3 + 250 | 100 |
| Compound 1247 + methomyl | 3 + 250 | 100 |
| Compound 1247 + ethofenprox | 3 + 100 | 100 |
| Compound 1247 + dinotefuran | 3 + 100 | 100 |
| Compound 1247 + ethiprole | 3 + 100 | 100 |
| Compound 1247 + pymetrozine | 3 + 100 | 100 |
| Compound 1247 + flonicamid | 3 + 100 | 100 |
| Compound 1617 + acephate | 3 + 250 | 100 |
| Compound 1617 + methomyl | 3 + 250 | 100 |
| Compound 1617 + ethofenprox | 3 + 100 | 100 |
| Compound 1617 + dinotefuran | 3 + 100 | 100 |
| Compound 1617 + ethiprole | 3 + 100 | 100 |
| Compound 1617 + pymetrozine | 3 + 100 | 100 |

TABLE 7-continued

| Supplied chemical | Concentration (ppm) | Control rate (%) |
|---|---|---|
| Compound 1617 + flonicamid | 3 + 100 | 100 |
| Compound 1126 + acephate | 3 + 250 | 100 |
| Compound 1126 + methomyl | 3 + 250 | 100 |
| Compound 1126 + ethofenprox | 3 + 100 | 100 |
| Compound 1126 + dinotefuran | 3 + 100 | 100 |
| Compound 1126 + ethiprole | 3 + 100 | 100 |
| Compound 1126 + pymetrozine | 3 + 100 | 100 |
| Compound 1126 + flonicamid | 3 + 100 | 100 |
| Compound 1480 + acephate | 3 + 250 | 100 |
| Compound 1480 + methomyl | 3 + 250 | 100 |
| Compound 1480 + ethofenprox | 3 + 100 | 100 |
| Compound 1480 + dinotefuran | 3 + 100 | 100 |
| Compound 1480 + ethiprole | 3 + 100 | 100 |
| Compound 1480 + pymetrozine | 3 + 100 | 100 |
| Compound 1480 + flonicamid | 3 + 100 | 100 |
| Compound 1208 | 3 | 20 |
| Compound 1219 | 3 | 17 |
| Compound 1217 | 3 | 21 |
| Compound 210 | 3 | 7 |
| Compound 1245 | 3 | 12 |
| Compound 639 | 3 | 10 |
| Compound 1247 | 3 | 6 |
| Compound 1617 | 3 | 0 |
| Compound 1126 | 3 | 0 |
| Compound 1480 | 3 | 7 |
| acephate | 250 | 97 |
| methomyl | 250 | 96 |
| ethofenprox | 100 | 98 |
| dinotefuran | 100 | 99 |
| ethiprole | 100 | 98 |
| pymetrozine | 100 | 96 |
| flonicamid | 100 | 97 |

Test Example 2

Insecticidal Test on Resistant Cotton Melon Aphid (*Aphis gossypii*)

Into a plastic pot having a diameter of 8 cm and a height of 8 cm were planted cucumbers (cultivar: sagami-hanpaku) and resistant *Aphis gossypii* was propagated. Then, a liquid chemical which was diluted and prepared to the prescribed concentration was sufficiently sprayed on the stem and leaf. After air-drying, the pot was allowed to stand in a greenhouse. After 5 days from spraying, the number of aphids which were parasitic on each cucumber was examined and the control rate was calculated according to the following equation (two replications of a pot per plot).

Control Rate=$100-\{(Ta \times Cb)/(Tb \times Ca)\} \times 100$

Ta: Number of parasitic insects after spraying on the treated area
Tb: Number of parasitic insects before spraying on the treated area
Ca: Number of parasitic insects after spraying on the untreated area
Cb: Number of parasitic insects before spraying on the untreated area The results are shown in Table 8.

TABLE 8

| Supplied chemical | Concentration (ppm) | Control rate (%) |
|---|---|---|
| Compound 1208 + acephate | 3 + 250 | 20 |
| Compound 1208 + methomyl | 3 + 250 | 23 |
| Compound 1208 + ethofenprox | 3 + 100 | 87 |
| Compound 1208 + dinotefuran | 3 + 100 | 100 |
| Compound 1208 + ethiprole | 3 + 100 | 100 |
| Compound 1208 + pymetrozine | 3 + 100 | 100 |
| Compound 1208 + flonicamid | 3 + 100 | 100 |
| Compound 1219 + acephate | 3 + 250 | 18 |
| Compound 1219 + methomyl | 3 + 250 | 20 |
| Compound 1219 + ethofenprox | 3 + 100 | 84 |
| Compound 1219 + dinotefuran | 3 + 100 | 100 |
| Compound 1219 + ethiprole | 3 + 100 | 100 |
| Compound 1219 + pymetrozine | 3 + 100 | 100 |
| Compound 1219 + flonicamid | 3 + 100 | 100 |
| Compound 1217 + acephate | 3 + 250 | 16 |
| Compound 1217 + methomyl | 3 + 250 | 17 |
| Compound 1217 + ethofenprox | 3 + 100 | 85 |
| Compound 1217 + dinotefuran | 3 + 100 | 100 |
| Compound 1217 + ethiprole | 3 + 100 | 100 |
| Compound 1217 + pymetrozine | 3 + 100 | 100 |
| Compound 1217 + flonicamid | 3 + 100 | 100 |
| Compound 210 + acephate | 3 + 250 | 14 |
| Compound 210 + methomyl | 3 + 250 | 17 |
| Compound 210 + ethofenprox | 3 + 100 | 82 |
| Compound 210 + dinotefuran | 3 + 100 | 100 |
| Compound 210 + ethiprole | 3 + 100 | 100 |
| Compound 210 + pymetrozine | 3 + 100 | 100 |
| Compound 210 + flonicamid | 3 + 100 | 100 |
| Compound 1245 + acephate | 3 + 250 | 18 |
| Compound 1245 + methomyl | 3 + 250 | 19 |
| Compound 1245 + ethofenprox | 3 + 100 | 85 |
| Compound 1245 + dinotefuran | 3 + 100 | 100 |
| Compound 1245 + ethiprole | 3 + 100 | 100 |
| Compound 1245 + pymetrozine | 3 + 100 | 100 |
| Compound 1245 + flonicamid | 3 + 100 | 100 |
| Compound 639 + acephate | 3 + 250 | 15 |
| Compound 639 + methomyl | 3 + 250 | 17 |
| Compound 639 + ethofenprox | 3 + 100 | 81 |
| Compound 639 + dinotefuran | 3 + 100 | 100 |
| Compound 639 + ethiprole | 3 + 100 | 100 |
| Compound 639 + pymetrozine | 3 + 100 | 100 |
| Compound 639 + flonicamid | 3 + 100 | 100 |
| Compound 1247 + acephate | 3 + 250 | 11 |
| Compound 1247 + methomyl | 3 + 250 | 16 |
| Compound 1247 + ethofenprox | 3 + 100 | 81 |
| Compound 1247 + dinotefuran | 3 + 100 | 100 |
| Compound 1247 + ethiprole | 3 + 100 | 100 |
| Compound 1247 + pymetrozine | 3 + 100 | 100 |
| Compound 1247 + flonicamid | 3 + 100 | 100 |
| Compound 1617 + acephate | 3 + 250 | 7 |
| Compound 1617 + methomyl | 3 + 250 | 15 |
| Compound 1617 + ethofenprox | 3 + 100 | 79 |
| Compound 1617 + dinotefuran | 3 + 100 | 100 |
| Compound 1617 + ethiprole | 3 + 100 | 100 |
| Compound 1617 + pymetrozine | 3 + 100 | 100 |
| Compound 1617 + flonicamid | 3 + 100 | 100 |
| Compound 1126 + acephate | 3 + 250 | 5 |
| Compound 1126 + methomyl | 3 + 250 | 14 |
| Compound 1126 + ethofenprox | 3 + 100 | 77 |
| Compound 1126 + dinotefuran | 3 + 100 | 100 |
| Compound 1126 + ethiprole | 3 + 100 | 100 |
| Compound 1126 + pymetrozine | 3 + 100 | 100 |
| Compound 1126 + flonicamid | 3 + 100 | 100 |
| Compound 1480 + acephate | 3 + 250 | 4 |
| Compound 1480 + methomyl | 3 + 250 | 13 |
| Compound 1480 + ethofenprox | 3 + 100 | 78 |
| Compound 1480 + dinotefuran | 3 + 100 | 100 |
| Compound 1480 + ethiprole | 3 + 100 | 100 |
| Compound 1480 + pymetrozine | 3 + 100 | 100 |
| Compound 1480 + flonicamid | 3 + 100 | 100 |
| Compound 1208 | 3 | 18 |
| Compound 1219 | 3 | 15 |
| Compound 1217 | 3 | 15 |
| Compound 210 | 3 | 12 |
| Compound 1245 | 3 | 15 |
| Compound 639 | 3 | 12 |
| Compound 1247 | 3 | 10 |
| Compound 1617 | 3 | 5 |
| Compound 1126 | 3 | 3 |
| Compound 1480 | 3 | 3 |

TABLE 8-continued

| Supplied chemical | Concentration (ppm) | Control rate (%) |
|---|---|---|
| acephate | 250 | 0 |
| methomyl | 250 | 10 |
| ethofenprox | 100 | 75 |
| dinotefuran | 100 | 98 |
| ethiprole | 100 | 96 |
| pymetrozine | 100 | 95 |
| flonicamid | 100 | 97 |

Test Example 3

Insecticidal Test on Small Brown Planthopper (*Laodelphax striatellus*)

A liquid chemical which was diluted and prepared to the prescribed concentration was sprayed on rice seedlings (cultivar: koshihikari), air-dried, and then 10 three-stage insects of *Laodelphax striatellus* were put into a glass test tube having a diameter of 3 cm and a height of 10 cm along with the seedlings. The test tube was cotton plugged. After 6 days from the treatment, the number of surviving insects was examined and the mortality was calculated (two replications of 10 insects per plot). The results are shown in Table 9.

TABLE 9

| Supplied chemical | Concentration (ppm) | Mortality (%) |
|---|---|---|
| Compound 1208 + ethofenprox | 3 + 25 | 100 |
| Compound 1208 + fenitrothion | 3 + 100 | 100 |
| Compound 1208 + silafluofen | 3 + 25 | 100 |
| Compound 1208 + dinotefuran | 3 + 5 | 100 |
| Compound 1208 + buprofezin | 3 + 25 | 100 |
| Compound 1208 + pymetrozine | 3 + 25 | 100 |
| Compound 1208 + ethiprole | 3 + 25 | 100 |
| Compound 1208 + flonicamid | 3 + 20 | 100 |
| Compound 1219 + ethofenprox | 3 + 25 | 100 |
| Compound 1219 + fenitrothion | 3 + 100 | 100 |
| Compound 1219 + silafluofen | 3 + 25 | 100 |
| Compound 1219 + dinotefuran | 3 + 5 | 100 |
| Compound 1219 + buprofezin | 3 + 25 | 100 |
| Compound 1219 + pymetrozine | 3 + 25 | 100 |
| Compound 1219 + ethiprole | 3 + 25 | 100 |
| Compound 1219 + flonicamid | 3 + 20 | 100 |
| Compound 1217 + ethofenprox | 3 + 25 | 100 |
| Compound 1217 + fenitrothion | 3 + 100 | 100 |
| Compound 1217 + silafluofen | 3 + 25 | 100 |
| Compound 1217 + dinotefuran | 3 + 5 | 100 |
| Compound 1217 + buprofezin | 3 + 25 | 100 |
| Compound 1217 + pymetrozine | 3 + 25 | 100 |
| Compound 1217 + ethiprole | 3 + 25 | 100 |
| Compound 1217 + flonicamid | 3 + 20 | 100 |
| Compound 210 + ethofenprox | 3 + 25 | 100 |
| Compound 210 + fenitrothion | 3 + 100 | 100 |
| Compound 210 + silafluofen | 3 + 25 | 100 |
| Compound 210 + dinotefuran | 3 + 5 | 100 |
| Compound 210 + buprofezin | 3 + 25 | 100 |
| Compound 210 + pymetrozine | 3 + 25 | 100 |
| Compound 210 + ethiprole | 3 + 25 | 100 |
| Compound 210 + flonicamid | 3 + 20 | 100 |
| Compound 1245 + ethofenprox | 3 + 25 | 100 |
| Compound 1245 + fenitrothion | 3 + 100 | 100 |
| Compound 1245 + silafluofen | 3 + 25 | 100 |
| Compound 1245 + dinotefuran | 3 + 5 | 100 |
| Compound 1245 + buprofezin | 3 + 25 | 100 |
| Compound 1245 + pymetrozine | 3 + 25 | 100 |
| Compound 1245 + ethiprole | 3 + 25 | 100 |
| Compound 1245 + flonicamid | 3 + 20 | 100 |
| Compound 639 + ethofenprox | 3 + 25 | 100 |
| Compound 639 + fenitrothion | 3 + 100 | 100 |
| Compound 639 + silafluofen | 3 + 25 | 100 |

TABLE 9-continued

| Supplied chemical | Concentration (ppm) | Mortality (%) |
|---|---|---|
| Compound 639 + dinotefuran | 3 + 5 | 100 |
| Compound 639 + buprofezin | 3 + 25 | 100 |
| Compound 639 + pymetrozine | 3 + 25 | 100 |
| Compound 639 + ethiprole | 3 + 25 | 100 |
| Compound 639 + flonicamid | 3 + 20 | 100 |
| Compound 1247 + ethofenprox | 3 + 25 | 100 |
| Compound 1247 + fenitrothion | 3 + 100 | 100 |
| Compound 1247 + silafluofen | 3 + 25 | 100 |
| Compound 1247 + dinotefuran | 3 + 5 | 100 |
| Compound 1247 + buprofezin | 3 + 25 | 100 |
| Compound 1247 + pymetrozine | 3 + 25 | 100 |
| Compound 1247 + ethiprole | 3 + 25 | 100 |
| Compound 1247 + flonicamid | 3 + 20 | 100 |
| Compound 1617 + ethofenprox | 3 + 25 | 100 |
| Compound 1617 + fenitrothion | 3 + 100 | 100 |
| Compound 1617 + silafluofen | 3 + 25 | 100 |
| Compound 1617 + dinotefuran | 3 + 5 | 100 |
| Compound 1617 + buprofezin | 3 + 25 | 100 |
| Compound 1617 + pymetrozine | 3 + 25 | 100 |
| Compound 1617 + ethiprole | 3 + 25 | 100 |
| Compound 1617 + flonicamid | 3 + 20 | 100 |
| Compound 1126 + ethofenprox | 3 + 25 | 100 |
| Compound 1126 + fenitrothion | 3 + 100 | 100 |
| Compound 1126 + silafluofen | 3 + 25 | 100 |
| Compound 1126 + dinotefuran | 3 + 5 | 100 |
| Compound 1126 + buprofezin | 3 + 25 | 100 |
| Compound 1126 + pymetrozine | 3 + 25 | 100 |
| Compound 1126 + ethiprole | 3 + 25 | 100 |
| Compound 1126 + flonicamid | 3 + 20 | 100 |
| Compound 1480 + ethofenprox | 3 + 25 | 100 |
| Compound 1480 + fenitrothion | 3 + 100 | 100 |
| Compound 1480 + silafluofen | 3 + 25 | 100 |
| Compound 1480 + dinotefuran | 3 + 5 | 100 |
| Compound 1480 + buprofezin | 3 + 25 | 100 |
| Compound 1480 + pymetrozine | 3 + 25 | 100 |
| Compound 1480 + ethiprole | 3 + 25 | 100 |
| Compound 1480 + flonicamid | 3 + 20 | 100 |
| Compound 1208 | 3 | 10 |
| Compound 1219 | 3 | 10 |
| Compound 1217 | 3 | 15 |
| Compound 210 | 3 | 15 |
| Compound 1245 | 3 | 5 |
| Compound 639 | 3 | 0 |
| Compound 1247 | 3 | 5 |
| Compound 1617 | 3 | 5 |
| Compound 1126 | 3 | 10 |
| Compound 1480 | 3 | 10 |
| ethofenprox | 25 | 95 |
| fenitrothion | 100 | 85 |
| silafluofen | 25 | 95 |
| dinotefuran | 5 | 95 |
| buprofezin | 25 | 95 |
| pymetrozine | 25 | 95 |
| ethiprole | 25 | 90 |
| flonicamid | 20 | 95 |
| Untreated | — | 0 |

Test Example 4

Insecticidal Test on 2-spotted Spider Mite (*Tetranychus urticae*)

A plastic cup having a diameter of 8 cm was filled with water and covered by a lid with a hole having a diameter of 1 cm. Absorbent cotton was put on the top of the lid and dropped into water from the lid such that the absorbent cotton was always in a wet state due to a capillary phenomenon. A leaf disc having a diameter of 2 cm was prepared with primary leaves of kidney beans (cultivar: Green top) and placed on the aforementioned absorbent cotton. 4 adult female insects of *Tetranychus urticae* were inoculated thereon. Next day, the adult female insects were removed, and then the number of insect egg was examined. A liquid chemical which was prepared to the prescribed concentration was sprayed by using a vertical sprayer. After spraying, the resulting cup was allowed to stand in an isothermal chamber maintained at 25 degree centigrade. After 6 days from spraying, the number of hatched larvae that survived on the leaf disc was examined and the hatchability of larvae was calculated (two replications of one concentration per chemical). The results are shown in Table 10.

TABLE 10

| Supplied chemical | Concentration (ppm) | Hatchability of larvae (%) |
|---|---|---|
| Compound 1208 + pyridaben | 50 + 2 | 42 |
| Compound 1208 + acequinocyl | 50 + 5 | 23 |
| Compound 1208 + fenbutatin oxide | 50 + 25 | 37 |
| Compound 1208 + spirodiclofen | 50 + 3 | 44 |
| Compound 1208 + etoxazol | 50 + 0.1 | 27 |
| Compound 1208 + bifenazate | 50 + 5 | 53 |
| Compound 1208 + milbemectin | 50 + 5 | 12 |
| Compound 1219 + pyridaben | 50 + 2 | 43 |
| Compound 1219 + acequinocyl | 50 + 5 | 24 |
| Compound 1219 + fenbutatin oxide | 50 + 25 | 37 |
| Compound 1219 + spirodiclofen | 50 + 3 | 44 |
| Compound 1219 + etoxazol | 50 + 0.1 | 27 |
| Compound 1219 + bifenazate | 50 + 5 | 55 |
| Compound 1219 + milbemectin | 50 + 5 | 13 |
| Compound 1217 + pyridaben | 50 + 2 | 39 |
| Compound 1217 + acequinocyl | 50 + 5 | 21 |
| Compound 1217 + fenbutatin oxide | 50 + 25 | 35 |
| Compound 1217 + spirodiclofen | 50 + 3 | 42 |
| Compound 1217 + etoxazol | 50 + 0.1 | 25 |
| Compound 1217 + bifenazate | 50 + 5 | 52 |
| Compound 1217 + milbemectin | 50 + 5 | 9 |
| Compound 210 + pyridaben | 50 + 2 | 43 |
| Compound 210 + acequinocyl | 50 + 5 | 25 |
| Compound 210 + fenbutatin oxide | 50 + 25 | 38 |
| Compound 210 + spirodiclofen | 50 + 3 | 45 |
| Compound 210 + etoxazol | 50 + 0.1 | 28 |
| Compound 210 + bifenazate | 50 + 5 | 54 |
| Compound 210 + milbemectin | 50 + 5 | 13 |
| Compound 1245 + pyridaben | 50 + 2 | 45 |
| Compound 1245 + acequinocyl | 50 + 5 | 26 |
| Compound 1245 + fenbutatin oxide | 50 + 25 | 39 |
| Compound 1245 + spirodiclofen | 50 + 3 | 48 |
| Compound 1245 + etoxazol | 50 + 0.1 | 31 |
| Compound 1245 + bifenazate | 50 + 5 | 57 |
| Compound 1245 + milbemectin | 50 + 5 | 15 |
| Compound 639 + pyridaben | 50 + 2 | 44 |
| Compound 639 + acequinocyl | 50 + 5 | 24 |
| Compound 639 + fenbutatin oxide | 50 + 25 | 38 |
| Compound 639 + spirodiclofen | 50 + 3 | 47 |
| Compound 639 + etoxazol | 50 + 0.1 | 29 |
| Compound 639 + bifenazate | 50 + 5 | 56 |
| Compound 639 + milbemectin | 50 + 5 | 14 |
| Compound 1247 + pyridaben | 50 + 2 | 40 |
| Compound 1247 + acequinocyl | 50 + 5 | 21 |
| Compound 1247 + fenbutatin oxide | 50 + 25 | 35 |
| Compound 1247 + spirodiclofen | 50 + 3 | 41 |
| Compound 1247 + etoxazol | 50 + 0.1 | 25 |
| Compound 1247 + bifenazate | 50 + 5 | 51 |
| Compound 1247 + milbemectin | 50 + 5 | 10 |
| Compound 1617 + pyridaben | 50 + 2 | 42 |
| Compound 1617 + acequinocyl | 50 + 5 | 23 |
| Compound 1617 + fenbutatin oxide | 50 + 25 | 35 |
| Compound 1617 + spirodiclofen | 50 + 3 | 48 |
| Compound 1617 + etoxazol | 50 + 0.1 | 28 |
| Compound 1617 + bifenazate | 50 + 5 | 52 |
| Compound 1617 + milbemectin | 50 + 5 | 10 |

TABLE 10-continued

| Supplied chemical | Concentration (ppm) | Hatchability of larvae (%) |
|---|---|---|
| Compound 1126 + pyridaben | 50 + 2 | 39 |
| Compound 1126 + acequinocyl | 50 + 5 | 20 |
| Compound 1126 + fenbutatin oxide | 50 + 25 | 34 |
| Compound 1126 + spirodiclofen | 50 + 3 | 41 |
| Compound 1126 + etoxazol | 50 + 0.1 | 23 |
| Compound 1126 + bifenazate | 50 + 5 | 51 |
| Compound 1126 + milbemectin | 50 + 5 | 9 |
| Compound 1480 + pyridaben | 50 + 2 | 45 |
| Compound 1480 + acequinocyl | 50 + 5 | 27 |
| Compound 1480 + fenbutatin oxide | 50 + 25 | 39 |
| Compound 1480 + spirodiclofen | 50 + 3 | 48 |
| Compound 1480 + etoxazol | 50 + 0.1 | 30 |
| Compound 1480 + bifenazate | 50 + 5 | 57 |
| Compound 1480 + milbemectin | 50 + 5 | 15 |
| Compound 1208 | 50 | 78 |
| Compound 1219 | 50 | 80 |
| Compound 1217 | 50 | 74 |
| Compound 210 | 50 | 80 |
| Compound 1245 | 50 | 85 |
| Compound 639 | 50 | 82 |
| Compound 1247 | 50 | 74 |
| Compound 1617 | 50 | 78 |
| Compound 1126 | 50 | 73 |
| Compound 1480 | 50 | 85 |
| pyridaben | 2 | 48 |
| acequinocyl | 5 | 29 |
| fenbutatin oxide | 25 | 42 |
| spirodiclofen | 3 | 50 |
| etoxazol | 0.1 | 33 |
| bifenazate | 5 | 60 |
| milbemectin | 5 | 18 |
| Untreated | — | 88 |

Test Example 5

Control Test on Small Brown Planthopper (*Laodelphax striatellus*) and Rice Leafroller (*Cnaphalocrocis medinalis*) on Nursery Box Application of Paddy Rice Rice (cultivar: Nihonbare) cultured in a nursery box was treated with 50 g of a granule formulation per box, and then transplanted to the rice field. For the control effect against *Laodelphax striatellus*, the number of parasitic insects was examined for 30 stumps per plot after 40 days and 60 days from the transplantation. In addition, for the control effect against *Cnaphalocrocis medinalis*, the number of infected leaves was examined for 100 stumps per plot after 50 days from the transplantation, and the infected leaf rate was calculated. The results are shown in Table 11. In the Table, gai represents the amount of active ingredients (g).

TABLE 11

| | | *Laodelphax striatellus* Number of parasitic insects/ 30 stumps Days after spraying | | *Cnaphalocrocis medinalis* Infected leaf rate (%) |
|---|---|---|---|---|
| Supplied chemical | Amount of chemical (gai/box) | 40 | 60 | |
| Compound 1245 + imidacloprid | 5 + 1 | 0 | 7 | 0.30 |
| Compound 1245 + benfuracarb | 5 + 2.5 | 10 | 29 | 0.23 |

TABLE 11-continued

| Supplied chemical | Amount of chemical (gai/box) | Laodelphax striatellus Number of parasitic insects/ 30 stumps Days after spraying 40 | 60 | Cnaphalocrocis medinalis Infected leaf rate (%) |
|---|---|---|---|---|
| Compound 639 imidacloprid | 5 + 1 | 0 | 4 | 0.36 |
| Compound 639 + benfuracarb | 5 + 2.5 | 8 | 22 | 0.34 |
| Compound 1246 imidacloprid | 5 + 1 | 0 | 5 | 0.25 |
| Compound 1246 + benfuracarb | 5 + 2.5 | 11 | 29 | 0.21 |
| Compound 1247 imidacloprid | 5 + 1 | 0 | 4 | 0.23 |
| Compound 1247 + benfuracarb | 5 + 2.5 | 8 | 23 | 0.20 |
| Compound 1244 imidacloprid | 5 + 1 | 0 | 5 | 0.22 |
| Compound 1244 + benfuracarb | 5 + 2.5 | 9 | 26 | 0.19 |
| Compound 1245 | 5 | 82 | 140 | 0.32 |
| Compound 639 | 5 | 65 | 120 | 0.39 |
| Compound 1246 | 5 | 77 | 137 | 0.28 |
| Compound 1247 | 5 | 69 | 121 | 0.25 |
| Compound 1244 | 5 | 72 | 132 | 0.25 |
| imidacloprid | 1 | 0 | 9 | 1.77 |
| benfuracarb | 2.5 | 12 | 31 | 1.28 |
| Untreated | — | 95 | 142 | 1.62 |

Test Example 6

Insecticidal Test on Tiger Moth (*Trichoplusia ni*)

Cut leaves of cabbages (cultivar: shiki-kaku) were immersed in a liquid chemical which was diluted and prepared to the prescribed concentration for 30 seconds, air-dried, and then put into a plastic vessel having a diameter of 9 cm. Each of 10 second-stage insects of *Trichoplusia ni* was inoculated and the resulting vessel was allowed to stand in an isothermal chamber maintained at 25 degree centigrade. After 6 days from the treatment, the number of surviving insects was examined and the mortality was calculated (two replications of 10 insects per plot). The results are shown in Table 12.

TABLE 12

| Supplied chemical | Concentration (ppm) | Mortality (%) |
|---|---|---|
| Compound 1208 + ethofenprox | 0.5 + 3 | 80 |
| Compound 1208 + dinotefuran | 0.5 + 3 | 80 |
| Compound 1208 + fipronil | 0.5 + 0.5 | 85 |
| Compound 1208 + spinosad | 0.5 + 0.1 | 90 |
| Compound 1219 + ethofenprox | 0.5 + 3 | 75 |
| Compound 1219 + dinotefuran | 0.5 + 3 | 70 |
| Compound 1219 + fipronil | 0.5 + 0.5 | 75 |
| Compound 1219 + spinosad | 0.5 + 0.1 | 80 |
| Compound 1217 + ethofenprox | 0.5 + 3 | 75 |
| Compound 1217 + dinotefuran | 0.5 + 3 | 75 |
| Compound 1217 + fipronil | 0.5 + 0.5 | 75 |
| Compound 1217 + spinosad | 0.5 + 0.1 | 80 |
| Compound 210 + ethofenprox | 0.5 + 3 | 80 |
| Compound 210 + dinotefuran | 0.5 + 3 | 75 |
| Compound 210 + fipronil | 0.5 + 0.5 | 80 |
| Compound 210 + spinosad | 0.5 + 0.1 | 85 |
| Compound 1245 + ethofenprox | 0.5 + 3 | 75 |
| Compound 1245 + dinotefuran | 0.5 + 3 | 75 |
| Compound 1245 + fipronil | 0.5 + 0.5 | 80 |
| Compound 1245 + spinosad | 0.5 + 0.1 | 85 |
| Compound 639 + ethofenprox | 0.5 + 3 | 85 |
| Compound 639 + dinotefuran | 0.5 + 3 | 85 |
| Compound 639 + fipronil | 0.5 + 0.5 | 90 |
| Compound 639 + spinosad | 0.5 + 0.1 | 95 |
| Compound 1247 + ethofenprox | 0.5 + 3 | 75 |
| Compound 1247 + dinotefuran | 0.5 + 3 | 75 |
| Compound 1247 + fipronil | 0.5 + 0.5 | 80 |
| Compound 1247 + spinosad | 0.5 + 0.1 | 85 |
| Compound 1617 + ethofenprox | 0.5 + 3 | 85 |
| Compound 1617 + dinotefuran | 0.5 + 3 | 80 |
| Compound 1617 + fipronil | 0.5 + 0.5 | 90 |
| Compound 1617 + spinosad | 0.5 + 0.1 | 90 |
| Compound 1126 + ethofenprox | 0.5 + 3 | 80 |
| Compound 1126 + dinotefuran | 0.5 + 3 | 80 |
| Compound 1126 + fipronil | 0.5 + 0.5 | 85 |
| Compound 1126 + spinosad | 0.5 + 0.1 | 85 |
| Compound 1480 + ethofenprox | 0.5 + 3 | 85 |
| Compound 1480 + dinotefuran | 0.5 + 3 | 80 |
| Compound 1480 + fipronil | 0.5 + 0.5 | 85 |
| Compound 1480 + spinosad | 0.5 + 0.1 | 90 |
| Compound 1208 | 0.5 | 75 |
| Compound 1219 | 0.5 | 65 |
| Compound 1217 | 0.5 | 65 |
| Compound 210 | 0.5 | 70 |
| Compound 1245 | 0.5 | 70 |
| Compound 639 | 0.5 | 80 |
| Compound 1247 | 0.5 | 65 |
| Compound 1617 | 0.5 | 75 |
| Compound 1126 | 0.5 | 70 |
| Compound 1480 | 0.5 | 75 |
| ethofenprox | 3 | 45 |
| dinotefuran | 3 | 40 |
| fipronil | 0.5 | 55 |
| spinosad | 0.1 | 60 |
| Untreated | — | 0 |

Test Example 7

Insecticidal Test on Rice Striped Stem Borer (*Chilo suppressalis*) and Control Test on Rice Blast (*Pyricularia oryzae*) on Nursery Box Application of Paddy Rice Rice (cultivar: koshihikari) cultured in a nursery box was treated with a granule formulation of a prescribed amount, and then transplanted to a 1/5000a pot. After 14 days from the treatment, the parts of stem and leaf were cut and put into a plastic cup (diameter: 10 cm, height: 10 cm) along with 10 second-stage larvae of *Chilo suppressalis*. After 4 days, the mortality was examined. Furthermore, after 30 days from the treatment, a spore suspension of *Pyricularia oryzae* was spray-inoculated and allowed to stand under conditions of high humidity at a temperature of 25 degree centigrade for 1 week to examine the number of lesions. The control rate was calculated from the number of lesions according to the following equation (two replications). The results are shown in Table 13. In the Table, gai represents the amount of active ingredients (g).

Control Value=(1−number of lesions in the treated area number of lesions in the untreated area)×100

TABLE 13

| Supplied chemical | Amount of treated chemical (gai/box) | *Chilo suppressalis* Mortality (%) | *Pyricularia oryzae* Control value |
|---|---|---|---|
| Compound 106 + probenazole | 5 + 12 | 100 | 100 |
| Compound 106 + diclocymet | 5 + 1.5 | 100 | 100 |
| Compound 106 + orysastrobin | 5 + 3.5 | 100 | 100 |

TABLE 13-continued

| Supplied chemical | Amount of treated chemical (gai/box) | Chilo suppressalis Mortality (%) | Pyricularia oryzae Control value |
|---|---|---|---|
| Compound 106 + tricyclazole | 5 + 2 | 100 | 100 |
| Compound 106 + isoprothiolane | 5 + 6 | 100 | 100 |
| Compound 1217 + probenazole | 5 + 12 | 100 | 100 |
| Compound 1217 + diclocymet | 5 + 1.5 | 100 | 100 |
| Compound 1217 + orysastrobin | 5 + 3.5 | 100 | 100 |
| Compound 1217 + tricyclazole | 5 + 2 | 100 | 100 |
| Compound 1217 + isoprothiolane | 5 + 6 | 100 | 100 |
| Compound 1245 + probenazole | 5 + 12 | 100 | 100 |
| Compound 1245 + diclocymet | 5 + 1.5 | 100 | 100 |
| Compound 1245 + orysastrobin | 5 + 3.5 | 100 | 100 |
| Compound 1245 + tricyclazole | 5 + 2 | 100 | 100 |
| Compound 1245 + isoprothiolane | 5 + 6 | 100 | 100 |
| Compound 639 + probenazole | 5 + 12 | 100 | 100 |
| Compound 639 + diclocymet | 5 + 1.5 | 100 | 100 |
| Compound 639 + orysastrobin | 5 + 3.5 | 100 | 100 |
| Compound 639 + tricyclazole | 5 + 2 | 100 | 100 |
| Compound 639 + isoprothiolane | 5 + 6 | 100 | 100 |
| Compound 1246 + probenazole | 5 + 12 | 100 | 100 |
| Compound 1246 + diclocymet | 5 + 1.5 | 100 | 100 |
| Compound 1246 + orysastrobin | 5 + 3.5 | 100 | 100 |
| Compound 1246 + tricyclazole | 5 + 2 | 100 | 100 |
| Compound 1246 + isoprothiolane | 5 + 6 | 100 | 100 |
| Compound 106 | 5 | 90 | 5 |
| Compound 1217 | 5 | 90 | 7 |
| Compound 1245 | 5 | 95 | 0 |
| Compound 639 | 5 | 90 | 3 |
| Compound 1246 | 5 | 95 | 0 |
| probenazole | 12 | 5 | 94 |
| diclocymet | 1.5 | 0 | 95 |
| orysastrobin | 3.5 | 5 | 93 |
| tricyclazole | 2 | 5 | 95 |
| Isoprothiolane | 6 | 0 | 92 |
| Untreated | — | 5 | 0 |

Test Example 8

Control Test on Common Straight Swift Butterfly (*Parnara guttata*) and Rice Blast (*Pyricularia oryzae*) of Paddy Rice A powder of a prescribed concentration was sprayed on rice (cultivar: koshihikari) after 70 days from the transplantation (middle of May). Leaves on which *Parnara guttata* was parasitic before spraying were eliminated. After 20 days from spraying, the number of insects was examined for 100 stumps per plot. Furthermore, 10 days before spraying, infected rice seedlings of rice blast were placed in the middle of each plot. After 30 days from spraying, the number of panicles infected with panicle blast was examined by the degrees for 20 stumps in each plot, and the control value was calculated according to the following equation. The results are shown in Table 14. In the Table, gai represents the amount of active ingredients (g).

Degrees of Infection
a: panicle neck infected
b: 1/3 or more of rachis area infected
c: less than 1/3 of rachis area infected Severity index=incidence of $a$+incidence of $b \times 0.66$+ incidence of $c \times 0.26$ Control value=(1−severity in the treated plot/severity in the untreated plot)×100

TABLE 14

| Supplied chemical | Amount of treated chemical (gai/10a) | Number (insects/100 stumps) | Pyricularia oryzae Control value |
|---|---|---|---|
| Compound 601 + fthalide | 20 + 100 | 0 | 100 |
| Compound 601 + kasugamycin | 20 + 12 | 0 | 100 |
| Compound 601 + fenoxanil | 20 + 40 | 0 | 100 |
| Compound 1208 + fthalide | 20 + 100 | 0 | 100 |
| Compound 1208 + kasugamycin | 20 + 12 | 0 | 100 |
| Compound 1208 + fenoxanil | 20 + 40 | 0 | 100 |
| Compound 1245 + fthalide | 20 + 100 | 0 | 100 |
| Compound 1245 + kasugamycin | 20 + 12 | 0 | 100 |
| Compound 1245 + fenoxanil | 20 + 40 | 0 | 100 |
| Compound 210 + fthalide | 20 + 100 | 0 | 100 |
| Compound 210 + kasugamycin | 20 + 12 | 0 | 100 |
| Compound 210 + fenoxanil | 20 + 40 | 0 | 100 |
| Compound 601 | 20 | 1 | 7 |
| Compound 1208 | 20 | 1 | 5 |
| Compound 1245 | 20 | 2 | 0 |
| Compound 210 | 20 | 1 | 3 |
| fthalide | 100 | 150 | 90 |
| kasugamycin | 12 | 162 | 91 |
| fenoxanil | 40 | 155 | 88 |
| Untreated | — | 156 | 0 |

Test Example 9

Control Test on Common Straight Swift Butterfly (*Parnara guttata*) and Sheath Blight (*Rhizoctonia solani*) of Paddy Rice A powder of a prescribed amount was sprayed on rice (cultivar: koshihikari) after 70 days from the transplantation (middle of May) Leaves on which *Parnara guttata* was parasitic before spraying were eliminated. After 20 days from spraying, the number of insects was examined for 100 stumps in each plot. Furthermore, 7 days before spraying, *Rhizoctonia solani* cultured on a bran medium was inoculated into the base of the plant. After 30 days from spraying, the number of infected stumps was examined for 100 stumps in each plot and the rate of infected stumps was calculated. The results are shown in Table 15. In the Table, gai represents the amount of active ingredients (g).

TABLE 15

| Supplied chemical | Amount of treated chemical (gai/10a) | Number of insects (number/100 stumps) | Rate of infected stumps (%) |
|---|---|---|---|
| Compound 601 + flutolanil | 20 + 80 | 0 | 0 |
| Compound 601 + diclomezine | 20 + 48 | 0 | 0 |
| Compound 601 + pencycuron | 20 + 60 | 0 | 0 |
| Compound 601 + furametpyr | 20 + 20 | 0 | 0 |
| Compound 1208 + flutolanil | 20 + 80 | 0 | 0 |
| Compound 1208 + diclomezine | 20 + 48 | 0 | 0 |
| Compound 1208 + pencycuron | 20 + 60 | 0 | 0 |
| Compound 1208 + furametpyr | 20 + 20 | 0 | 0 |
| Compound 1245 + flutolanil | 20 + 80 | 0 | 0 |
| Compound 1245 + diclomezine | 20 + 48 | 0 | 0 |
| Compound 1245 + pencycuron | 20 + 60 | 0 | 0 |
| Compound 1245 + furametpyr | 20 + 20 | 0 | 0 |
| Compound 210 + flutolanil | 20 + 80 | 0 | 0 |
| Compound 210 + diclomezine | 20 + 48 | 0 | 0 |
| Compound 210 + pencycuron | 20 + 60 | 0 | 0 |
| Compound 210 + furametpyr | 20 + 20 | 0 | 0 |
| Compound 601 | 20 | 2 | 96 |
| Compound 1208 | 20 | 1 | 99 |
| Compound 1245 | 20 | 2 | 98 |
| Compound 210 | 20 | 1 | 98 |
| flutolanil | 80 | 153 | 2 |

TABLE 15-continued

| Supplied chemical | Amount of treated chemical (gai/10a) | Number of insects (number/100 stumps) | Rate of infected stumps (%) |
|---|---|---|---|
| diclomezine | 48 | 167 | 3 |
| pencycuron | 60 | 159 | 1 |
| furametpyr | 20 | 161 | 2 |
| Untreated | — | 160 | 98 |

Test Example 10

Control Test on Oriental Fruit Moth (*Grapholita molesta*) and Scab (*Venturia nashicola*) of Pear A liquid chemical which was prepared to the prescribed concentration was sufficiently sprayed on 17-year-old pears (cultivar: Hosui) (early June). After 40 days from spraying, the number of infected fruits due to *Grapholita molesta* was examined for all fruit in the plot, and the rate of infected fruit was calculated. Furthermore, after 14 days from spraying, infection of *Venturia nashicola* was examined by the degrees for optional 200 leaves in the plot and the severity index was calculated according to the following equation. The results are shown in Table 16.

Severity index=Σ(number of infected leaves by the degrees×index)×100/(number of examined leaves×5)

| Index: | |
|---|---|
| 0: No infection | 1: 1 to 3 lesion areas |
| 3: 4 to 7 lesion areas | 5: 8 or more lesion areas |

TABLE 16

| Supplied chemical | Treated concentration (ppm) | *Grapholita molesta* Infected fruit rate (%) | *Venturia nashicola* Severity index |
|---|---|---|---|
| Compound 601 + penthiopyrad | 50 + 75 | 2.1 | 3.1 |
| Compound 1208 + penthiopyrad | 50 + 75 | 1.3 | 3.0 |
| Compound 1245 + penthiopyrad | 50 + 75 | 2.5 | 2.7 |
| Compound 210 + penthiopyrad | 50 + 75 | 1.3 | 3.2 |
| Compound 178 + penthiopyrad | 50 + 75 | 3.0 | 2.9 |
| Compound 601 | 50 | 2.3 | 53.0 |
| Compound 1208 | 50 | 1.9 | 52.4 |
| Compound 1245 | 50 | 2.8 | 51.6 |
| Compound 210 | 50 | 1.7 | 50.6 |
| Compound 178 | 50 | 3.4 | 51.5 |
| penthiopyrad | 75 | 19.8 | 3.7 |
| Untreated | — | 20.6 | 52.2 |

Test Example 11

Insecticidal Test on Cucumber Moth (*Diaphania indica*) and Control Test on Powdery Mildew (*Sphaerotheca fuliginea*) of Cucumbers A liquid chemical which was prepared to the prescribed concentration was sufficiently sprayed on cucumbers (cultivar: sagami-hanpaku) cultured in a greenhouse. After 7 days from spraying, leaves were cut off and put into a plastic cup (diameter: 10 cm, height: 10 cm) along with 5 of second-stage larvae of *Diaphania indica*, and the mortality was examined 4 days thereafter. Furthermore, 1 day after spraying, the leaves of cucumbers which were previously arranged to be infected by pathogen were uniformly wiped with *Sphaerotheca fuliginea* thereon using a paintbrush for inoculation and examined after 10 days thereafter. The area occupied by lesion per leaf of cucumber was examined in accordance with the following index, and the control value was calculated from the average severity index of each plot according to the following equation (two replications). The results are shown in Table 17.

Severity Index
0: No lesion
1: Lesion area was not more than 5%
2: Lesion area was from 6 to 25%
3: Lesion area was from 26 to 50%
4: Lesion area was not less than 51%

Control Value=(1−average severity in the treated plot/average severity in the untreated plot)×100

TABLE 17

| Supplied chemical | Treated concentration (ppm) | *Diaphania indica* Mortality (%) | *Sphaerotheca fuliginea* Control value |
|---|---|---|---|
| Compound 601 + penthiopyrad | 10 + 3.15 | 100 | 100 |
| Compound 1208 + penthiopyrad | 10 + 3.15 | 100 | 100 |
| Compound 1245 + penthiopyrad | 10 + 3.15 | 100 | 100 |
| Compound 210 + penthiopyrad | 10 + 3.15 | 100 | 100 |
| Compound 178 + penthiopyrad | 10 + 3.15 | 100 | 100 |
| Compound 601 | 10 | 95 | 0 |
| Compound 1208 | 10 | 95 | 0 |
| Compound 1245 | 10 | 90 | 0 |
| Compound 210 | 10 | 95 | 0 |
| Compound 178 | 10 | 90 | 0 |
| penthiopyrad | 3.15 | 0 | 95 |
| Untreated | — | 0 | 0 |

Test Example 12

Control Test on Turnip Moth (*Agrotis segetum*) and Clubroot (*Plasmodiophora brassicae*) of Cabbage due to Soil Treatment A powder in a prescribed amount was mixed to soil and cabbages (cultivar: shiki-kaku) cultured on a cell medium were planted out. After 7 days from the treatment, the number of infected stumps due to *Agrotis segetum* was examined and the rate of infected stumps was calculated. Furthermore, after 60 days from the treatment, stumps were picked out, and lesion formation of *Plasmodiophora brassicase* was examined according to the degrees of severity. The control value was calculated from the average severity index of each plot according to the following equation. The results are shown in Table 18. In the Table, gai represents the amount of active ingredients (g).

Severity Index
0: No clubroot attached
1: Clubroot was attached at a portion of from 1 to 25% of the whole root
2: Clubroot was attached at a portion of from 25 to 50% of the whole root
3: Clubroot was attached at a portion of from 50 to 75% of the whole root 4: Clubroot was attached at a portion of from 75% or more of the whole root Control Value=(1−average severity in the treated plot/average severity in the untreated plot)×100

TABLE 18

| Supplied chemical | Amount of treated chemical (gai/10a) | *Agrotis segetum* Infected stump rate (%) | *Plasmodiophora brassicae* Control value |
|---|---|---|---|
| Compound 601 + flusulfamide | 100 + 60 | 0 | 95 |
| Compound 1208 + flusulfamide | 100 + 60 | 0 | 97 |
| Compound 1245 + flusulfamide | 100 + 60 | 0 | 98 |
| Compound 210 + flusulfamide | 100 + 60 | 0 | 95 |
| Compound 178 + flusulfamide | 100 + 60 | 0 | 96 |
| Compound 601 | 100 | 2.8 | 0 |
| Compound 1208 | 100 | 2.8 | 9 |
| Compound 1245 | 100 | 2.8 | 6 |
| Compound 210 | 100 | 2.8 | 0 |
| Compound 178 | 100 | 5.6 | 5 |
| flusulfamide | 60 | 36.1 | 91 |
| Untreated | — | 38.9 | 0 |

The invention claimed is:

1. A composition for preventing harmful organisms containing one or two or more compounds selected from compounds represented by the general formula (1), and one or two or more kinds selected from other insecticides, miticides or fungicides as active ingredients,

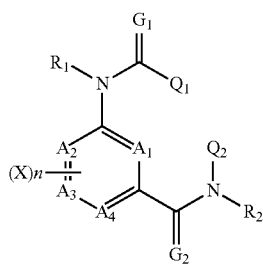

(1)

wherein, in the formula, $A_1$, $A_2$, $A_3$ and $A_4$ independently represent a carbon atom, a nitrogen atom or an oxidized nitrogen atom; $G_1$ and $G_2$ independently represent an oxygen atom or a sulfur atom; $R_1$ and $R_2$ independently represent a hydrogen atom or a C1-C4 alkyl group; Xs may be the same or different and represent a hydrogen atom, a halogen atom or a trifluoromethyl group; $Q_1$ represents a phenyl group, a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group, a heterocyclic group wherein the heterocyclic group herein represents a pyridyl group, a pyridine N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group or a tetrazolyl group, or a substituted heterocyclic group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group wherein the heterocyclic group represents the same as those described above, and $Q_2$ is represented by the general formula (2) or (3),

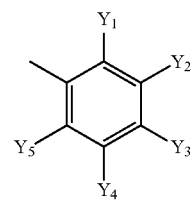

(2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_2$ and $Y_4$ represent a hydrogen atom, a halogen atom or a C1-C4 alkyl group; or

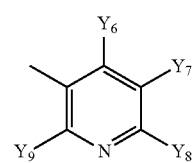

(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group, wherein the insecticides, miticides and fungicides are one or two or more compounds selected from azinphos-methyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafenthion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl, acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, diflubenzuron, teflubenzuron, triflumuron, novaluron, noviflumuron, bistrifluron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate, endosulfan, chlorfenson, chlorobenzilate, dicofol, bromopropylate, acetoprole, fipronil, ethiprole, pyrethrin, rotenone, nicotine sulphate, BT(Bacillus Thuringiensis) agent, spinosad, abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, fluazinam, flufenzin, hexythiazox, propargite, benzomate, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, a compound represented by the general formula (A),

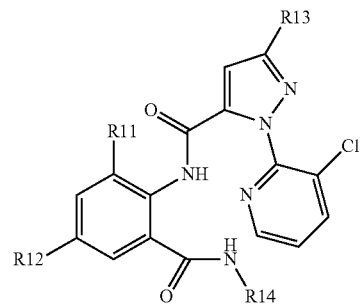

wherein, in the formula, R11 represents a methyl group or a chloro group; R12 represents a methyl group, a chloro group, a bromo group or a cyano group; R13 represents a chloro group, a bromo group, a trifluoromethyl group or a cyanomethoxy group; and R14 represents a methyl group or an isopropyl group, a compound represented by the general formula (B),

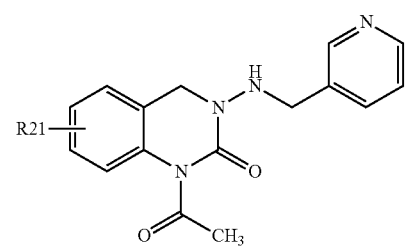

wherein, in the formula, R21 represents a 1,1,1,2,3,3,3-heptafluoro-2-propyl group or a 1,1,2,2,3,3,3-heptafluoro-1-propyl group, triadimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuarimol, bupirimate, mepanipyrim, cyprodinil, pyrimethanil, metalaxyl, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tiadinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichiofluanide, triforine, isoprothiolane, ferimzone, diclomezine, tecloftalam, pencycuron, chinomethionat, iminoctadine acetate, iminoctadine albesilate, ambam, poiycarbamate, thiadiazine, chloroneb, nickel dimethyldithiocarbamate, quazatine, dodecylguanidine-acetate, quintozene, tolylfluanid, anilazine, nitrothalisopropyl, fenitropan, dimethirimol, benthiazole, harpin protein, flumetover, mandipropamide and penthiopyrad.

2. The composition for preventing harmful organisms as set forth in claim 1 containing one or two or more compounds selected from compounds represented by the general formula (1a) in which all of $A_1$, $A_2$, $A_3$ and $A_4$ in the general formula (1) are carbon atoms, and one or two or more kinds selected from other insecticides, miticides or fungicides as active ingredients,

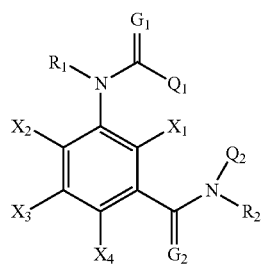

(1a)

wherein, in the formula, $G_1$ and $G_2$ independently represent an oxygen atom or a sulfur atom; $Q_1$ represents a phenyl group, a substituted phenyl group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group, a heterocyclic group wherein the heterocyclic group herein represents a pyridyl group, a pyridine N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrole group, a pyrazolyl group or a tetrazolyl group, or a substituted heterocyclic group having one or more substituents which may be the same or different and are selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di C1-C4 alkylamino group, a cyano group, a nitro group, a hydroxy group, a C1-C4 alkylcarbonyl group, a C1-C4 alkylcarbonyloxy group, a C1-C4 alkoxycarbonyl group, an acetylamino group and a phenyl group; $Q_2$ is represented by the general formula (2) or (3),

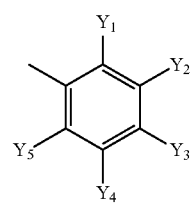

(2)

wherein, in the formula, $Y_1$ and $Y_5$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group; and $Y_2$ and $Y_4$ represent a hydrogen atom, a halogen atom or a C1-C4 alkyl group, or

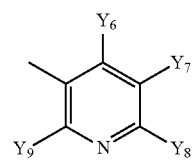

(3)

wherein, in the formula, $Y_6$ and $Y_9$ may be the same or different and represent a halogen atom, a C1-C4 alkyl group, a C1-C4 haloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C2-C6 perfluoroalkyl group; and $Y_7$ represents a hydrogen atom, a halogen atom or a C1-C4 alkyl group;

$X_1$ and $X_2$ independently represent a hydrogen atom or a fluorine atom; $X_3$ and $X_4$ are hydrogen atoms; and when any one of $R_1$ and $R_2$ is a hydrogen atom, the other one is a C1-C4 alkyl group, or both of $R_1$ and $R_2$ are C1-C4 alkyl groups.

3. The composition for preventing harmful organisms as set forth in claim 1, wherein insecticides, miticides and fungicides are one or two or more compounds selected from fenitrothion, fenthion, isoxathion, acephate, buprofezin, pyriproxyfen, silafluofen, dinotefuran, imidacloprid, ethofenprox, thiamethoxam, clothianidin, acetamiprid, nitenpyram, thiacloprid, benfuracarb, methomyl, fenobucarb, spinosad, pymetrozine, flonicamid, fipronil, ethiprole, abamectin, a compound represented by the general formula (B),

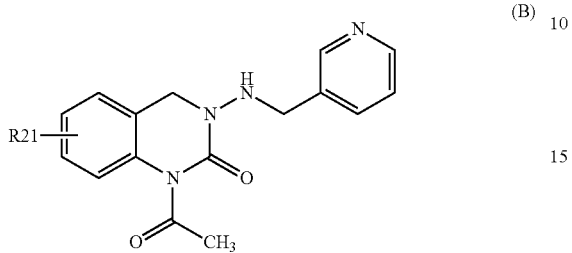
(B)

wherein, in the formula, R21 represents a 1,1,1,2,3,3,3-heptafluoro-2-propyl group or a 1,1,2,2,3,3,3-heptafluoro-1-propyl group, fenpyroximate, pyridaben, hexythiazox, fenbutatin oxide, tebufenpyrad, pyrimidifen, etoxazole, polynactins, milbemectin, acequinocyl, bifenazate, spirodiclofen, dienochlor, spiromesifen, tetradifon, chlorfenapyr, clofentezine, tolfenpyrad, fluacrypyrim, propargite, diafenthiuron, flufenoxuron, penthiopyrad, flusulfamide, iminoctadine acetate, iminoctadine albesilate, acibenzolar-S-methyl, ferimzone, pyroquilon, orysastrobin, azoxystrobin, carpropamid, diclocymet, probenazole, tiadinil, isoprothiolane, tricyclazole, fthalide, kasugamycin, fenoxanil, mepronil, diclomezine, pencycuron, validamycin, edifenphos, furametpyr, thifluzamide, flutolanil, metominostrobin, iprobenfos and oxolinic acid.

4. The composition for preventing harmful organisms as set forth in claim 1, wherein one or more compounds of other insecticides, miticides or fungicides are respectively contained in an amount of 0.001 to 95 weight %.

* * * * *